United States Patent
Zhang

(10) Patent No.: US 8,222,256 B2
(45) Date of Patent: Jul. 17, 2012

(54) METHODS OF USING IGF1R AND ABL KINASE MODULATORS

(75) Inventor: Wentao Zhang, Foster City, CA (US)

(73) Assignee: Exelixis, Inc., South San Francisco, CA (US)

( * ) Notice: Subject to any disclaimer, the term of this patent is extended or adjusted under 35 U.S.C. 154(b) by 180 days.

(21) Appl. No.: 12/306,606

(22) PCT Filed: Jul. 3, 2007

(86) PCT No.: PCT/US2007/015585

§ 371 (c)(1),
(2), (4) Date: Apr. 15, 2009

(87) PCT Pub. No.: WO2008/005538

PCT Pub. Date: Jan. 10, 2008

(65) Prior Publication Data

US 2009/0232828 A1    Sep. 17, 2009

Related U.S. Application Data

(60) Provisional application No. 60/818,568, filed on Jul. 5, 2006.

(51) Int. Cl.
*A61K 31/4965* (2006.01)

(52) U.S. Cl. ............... 514/255.05; 514/252.1; 514/247; 514/183; 544/405; 544/336; 544/224

(58) Field of Classification Search ........................ None
See application file for complete search history.

(56) References Cited

U.S. PATENT DOCUMENTS

| | | | | |
|---|---|---|---|---|
| 5,466,672 A * | 11/1995 | Kushnaryov et al. | ........ | 514/19.3 |
| 6,262,107 B1 * | 7/2001 | Li et al. | ........... | 514/449 |
| 6,835,726 B2 | 12/2004 | Cushing et al. | | |
| 2003/0078166 A1 | 4/2003 | Davies et al. | | |
| 2004/0127551 A1 * | 7/2004 | Zhang et al. | .................. | 514/449 |
| 2005/0054638 A1 * | 3/2005 | Barlaam et al. | ............ | 514/227.8 |
| 2006/0069110 A1 | 3/2006 | Andersen et al. | | |
| 2006/0135442 A1 * | 6/2006 | Khodadoust et al. | ........... | 514/26 |
| 2007/0093499 A1 * | 4/2007 | Lee et al. | ................. | 514/252.19 |

FOREIGN PATENT DOCUMENTS

| | | |
|---|---|---|
| WO | 00/39101 | 7/2000 |
| WO | 00/63182 | 10/2000 |
| WO | 00/71536 | 11/2000 |
| WO | 01/05783 | 1/2001 |
| WO | 01/47507 | 7/2001 |
| WO | 01/47507 A | 7/2001 |
| WO | 01/60816 | 8/2001 |
| WO | 01/64654 | 9/2001 |
| WO | 01/64654 A | 9/2001 |
| WO | 01/64655 | 9/2001 |
| WO | 02/22601 | 3/2002 |
| WO | 02/22602 | 3/2002 |
| WO | 02/22606 | 3/2002 |
| WO | 02/22607 | 3/2002 |
| WO | 02/50065 | 6/2002 |
| WO | 02/50066 | 6/2002 |
| WO | 02/057259 | 7/2002 |
| WO | 02/059112 | 8/2002 |
| WO | 02/062789 | 8/2002 |
| WO | 02/066461 | 8/2002 |
| WO | 02/068415 | 9/2002 |
| WO | 03/018021 | 3/2003 |
| WO | 03/018022 | 3/2003 |
| WO | 03/018022 A | 3/2003 |
| WO | 03/026664 | 4/2003 |
| WO | 03/026665 | 4/2003 |
| WO | 03/026666 | 4/2003 |
| WO | 03/026666 A | 4/2003 |
| WO | 03/030909 | 4/2003 |
| WO | 03/048133 | 6/2003 |
| WO | 04/000833 | 12/2003 |
| WO | 2004/043962 A | 5/2004 |
| WO | 2004/074244 | 9/2004 |
| WO | 2004/074244 A | 9/2004 |
| WO | 2004/089286 | 10/2004 |
| WO | 2005/007085 A | 1/2005 |
| WO | 2005/040159 | 5/2005 |
| WO | 2005/049033 | 6/2005 |
| WO | 2005/049033 A | 6/2005 |
| WO | 2005/068452 | 7/2005 |
| WO | 2005/090328 | 9/2005 |
| WO | 2006/017443 | 2/2006 |
| WO | 2006/017443 A | 2/2006 |
| WO | 2006/021454 | 3/2006 |
| WO | 2006/074057 A | 7/2006 |

OTHER PUBLICATIONS

"Paclitaxel and Docetaxel Combinations in Non-Small Cell Lung Cancer" by Belani, Chest 117, 114S-151S (2000).*
"Contemporary pre-clinical development of anticancer agents—What are the optimal preclinical models?" by Damia et al., Eur. J. Cancer 45, 2768-81 (2009).*
"Cancer Drug Design and Discovery" by Neidle (Ed.), Academic Press, pp. 427-431 (2008).*
"In Vitro Sensitivity Assays in Cancer: A Review, Analysis, and Prognosis" by Hoffman, J. Clin. Lab. Anal. 5, 133-43 (1991).*
"Lack of in vitro—in vivo correlation of a novel investigational anticancer agent, SH 30" by Poondru et al., Invest. New Drugs 20, 23-33 (2002).*
"Preclinical Modeling of Combination Treatments: Fantasy or Requirement?" by Decker et al., Ann. N. Y. Acad. Sci. 1059, 61-69 (2005).*
"Issues and Progress with Protein Kinase Inhibitors for Cancer Treatment" by Dancey et al., Nature Rev. Drug Discov. 2, 296-313 (2003).*
"Targeting cancer with small molecule kinase inhibitors" by Zhang et al., Nature Rev. Cancer 9, 28-39 (2009).*
Ghosh, D. et al., "2,4-Bis(arylamino)-5-methylpyrimidines as Antimicrobial Agents," Journal of Medicinal Chemistry, 10:974-975 (1967).
Ghosh, D. et al., "2,4-Bis(arylamino)pyrimidines as Antimicrobial Agents," Journal of Medicinal Chemistry, 9:423-424 (1966).

* cited by examiner

*Primary Examiner* — Anish Gupta
*Assistant Examiner* — Theodore R West
(74) *Attorney, Agent, or Firm* — McDonnell Boehnen Hulbert & Berghoff LLP

(57) ABSTRACT

The invention provides methods of treating cancer with a compound which inhibits kinases, more specifically IGF1R and Abl, in combination with treatments(s) selected from surgery, radiation, monoclonal antibody, bone marrow or peripheral blood stem cell transplantation, and one or more chemotherapeutic agent(s).

6 Claims, No Drawings

METHODS OF USING IGF1R AND ABL KINASE MODULATORS

CROSS REFERENCE

This application claims the benefit of U.S. Application No. 60/818,568, filed on Jul. 5, 2006, in the United States Patent and Trademark Office, which is herein incorporated by reference in its entirety.

BACKGROUND OF THE INVENTION

1. Field of the Invention

This invention relates to methods of treating cancer with a compound that modulates protein kinase enzymatic activity, and in particular, IGF1R and ABL kinase activity, and the resultant modulation of cellular activities (such as proliferation, differentiation, programmed cell death, migration, chemoinvasion and metabolism) in combination with anticancer agents.

2. State of the Art

Improvements in the specificity of agents used to treat various disease states such as cancer, metabolic, and inflammatory diseases is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins at the hydroxy groups of tyrosine, serine and threonine residues of proteins. The kinase complement of the human genome contains 518 putative protein kinase genes (Manning et al, Science, (2002), 298, 1912). The consequences of this activity include effects on cell differentiation, proliferation, transcription, translation, metabolism, cell cycle progression, apoptosis, metabolism, cytoskeletal rearrangement and movement; i.e., protein kinases mediate the majority of signal transduction in eukaryotic cells. Furthermore, abnormal protein kinase activity has been related to a host of disorders, ranging from relatively non-life threatening diseases such as psoriasis to cancer. Chromosomal mapping has revealed that over 200 kinases map to disease loci, including cancer, inflammatory and metabolic disease.

Tyrosine kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and -beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (Flt-1). The PDGF and FLK families are usually considered together due to the similarities of the two groups. For a detailed discussion of the receptor-type tyrosine kinases, see Plowman et al. (1994) DN&P 7(6): 334-339, which is hereby incorporated by reference.

The non-receptor type of tyrosine kinases is also comprised of numerous subfamilies, including Src, Frk, Btk, Csk, Abl, Syk/Zap70, Fes/Fps, Fak, Jak, and Ack. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen (1993) Oncogene, 8:2025-2031, which is hereby incorporated by reference.

Serine-threonine kinases play critical roles in intracellular signal transduction and include multiple families, such as STE, CKI, AGC, CAMK, and CMGC. Important subfamilies include, the MAP kinases, p38, JNK and ERK, which modulate signal transduction resulting from such diverse stimuli as mitogenic, stress, proinflammatory and antiapoptotic pathways. Members of the MAP kinase subfamily have been targeted for therapeutic intervention, including p38a, JNK isozymes and Raf.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases, such as immunological disorders, metabolic and cardiovascular diseases, inflammatory diseases, and degenerative diseases. Therefore, both receptor and non-receptor protein kinases are attractive targets for small molecule drug discovery.

One therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers. Gleevec® is a selective Abl kinase inhibitor.

Goals for development of small molecule drugs include modulation (particularly inhibition) of cell proliferation and angiogenesis, two key cellular processes needed for tumor growth and survival (Matter A. (2001) Drug Disc Technol 6, 1005-1024). Anti-angiogenic therapy represents a potentially important approach for the treatment of solid tumors and other diseases associated with dysregulated vascularization, including ischemic coronary artery disease, diabetic retinopathy (for IGF1R's role in diabetic retinopathy, see Poulaki, et. al. *American Journal of Pathology*. 2004, 165, 457-469), psoriasis and rheumatoid arthritis. Cell antiproliferative agents are also desirable to slow or stop the growth of tumors.

Insulin is the central hormone governing metabolism in vertebrates (reviewed in Steiner et al. (1989) in Endocrinology, DeGroot, eds. Philadelphia, Saunders: 1263-1289). In humans, insulin is secreted by the beta cells of the pancreas in response to elevated blood glucose levels, which normally occur following a meal. The immediate effect of insulin secretion is to induce the uptake of glucose by muscle, adipose tissue, and the liver. A longer-term effect of insulin is to increase the activity of enzymes that synthesize glycogen in the liver and triglycerides in adipose tissue. Insulin can exert other actions beyond these "classic" metabolic activities, including increasing potassium transport in muscle, promoting cellular differentiation of adipocytes, increasing renal retention of sodium, and promoting production of androgens by the ovary. Defects in the secretion and/or response to insulin are responsible for the disease diabetes mellitus, which is of enormous economic significance. Within the United States, diabetes mellitus is the fourth most common reason for physician visits by patients; it is the leading cause of end-stage renal disease, non-traumatic limb amputations, and blindness in individuals of working age (Warram et al. (1995) in "Joslin's Diabetes Mellitus", Kahn and Weir, eds., Philadelphia, Lea & Febiger, pp. 201-215; Kahn et al. (1996) Annu. Rev. Med. 47:509-531; Kahn (1998) Cell 92:593-596).

Beyond its role in diabetes mellitus, the phenomenon of insulin resistance has been linked to other pathogenic disorders including obesity, ovarian hyperandrogenism, and hypertension. Insulin resistance, hyperestrinism and the associated hyperandrogenism may play a role in the onset of some malignancies, such as endometrium cancer, breast cancer and prostate cancer (Guastamacchia E, et al. *Curr Drug Targets Immune Endocr Metabol Disord.* 2004, 4, 59-66). The physiologic effects of insulin are mediated by specific association of the peptide hormone with a cell surface receptor, the insulin receptor (INRS), with concomitant activation of a signal transduction pathway in responding tissues. The INRS has been well characterized at the molecular level; it is a member of a large family of tyrosine kinase receptors (Ulirich et al. (1985) Nature 313:756-761). INRS signaling has been shown to involve a number of intracellular participants (White and Kahn (1994) J. Biol. Chem. 269:1-4; Kahn et al. (1998) Supra.). These participants include the so-called insulin receptor substrate, or IRS-1, which is phosphorylated by an activated insulin receptor kinase. IRS-1 in turn associates with phosphatidyl-inositol-3-kinase (PI3K). A number of other protein kinases and signaling proteins have been implicated in this signal transduction mechanism and presumably participate in a "kinase cascade" that leads to the modification and regulation of a host of intracellular enzymes, structural proteins, and transcription factors.

In addition to the above, other diseases in which IGF1R may have a role include osteoarthritis ((IGFR-1 role in, Tardif, et. al. Arthritis Rheum 1996, 39(6), 968-78), Insulin-like Growth Factor 1 Receptor (IGF1R) is an integral membrane tyrosine kinase receptor that binds insulin-like growth factor with high affinity. IGF1R plays a critical role in transformation events and human cancer (LeRoith and Helman (2004) Cancer Cell 5:201-202). It is highly over-expressed in most malignant tissues where it functions as an anti-apoptotic agent by enhancing cell survival through the PI3K pathway, and also the p53 pathway. IGF1R has been linked to various disease states, such as breast and ovarian cancer (Maor et al. (2000) Molec. Genet. Metab. 69: 130-136), metastatic uveal melanoma (All-Ericsson, C. et al. (2002) *Invest. Ophthal. Vis. Sci.* 43: 1-8), macular degeneration (Lambooij, A. C. et al. *Invest. Ophthal. Vis. Sci.* 2003, 44, 2192-2198), and intrauterine growth retardation and poor postnatal growth (Roback, E. W. et al. *Am. J. Med. Genet.* 1991, 38, 74-79), among others.

Microtubules have a central role in the regulation of cell shape and polarity during differentiation, chromosome partitioning at mitosis, and intracellular transport. Microtubules undergo rearrangements involving rapid transitions between stable and dynamic states during these processes. Microtubule affinity regulating kinases (MARKs) are a novel family of protein kinases that phosphorylate microtubule-associated proteins and trigger microtubule disruption (Drewes, G., et al. (1997) Cell 89: 297-308). EMK1 (MARK2) is a serine/threonine protein kinase with 2 isoforms, which differ by the presence or absence of a 162-bp alternative exon (Espinosa, L. and Navarro, E. (1998) Cytogenet. Cell Genet. 81:278-282). Both human isoforms are co-expressed in a number of cell lines and tissues, with the highest expression found in heart, brain, placenta, skeletal muscle, and pancreas, and at lower levels in lung, liver, and kidney (Inglis, J. et al. (1993) Mammalian Genome 4: 401-403). EMK1 is a regulator of polarity and also a modulator of Wnt-beta-catenin signaling, indicating a link between two important developmental pathways (Sun T et al. (2001) Nature Cell Biology 3: 628-636). Due to the physical location of this gene, 11q12-q13, EMK1 is a candidate gene for carcinogenic events (Courseaux, A. et al. (1995) Mammalian Genome 6: 311-312), and has been associated with colon and prostate cancer (Moore, T. M., et al. (2000) Biol Chem 275:4311-22; Navarro, E., et al. (1999) Biochim Biophys Acta 1450: 254-64). Increased expression of EMK1 has been associated with increased inflammation in protocol biopsies of transplanted patients (Hueso M et al. (2004) Biochimica Et Biophysica Acta 1689: 58-65). Emk protein kinase is also essential for maintaining immune system homeostasis and its loss may contribute to autoimmune disease in mammals (Hurov J et al. (2001) Molecular and Cellular Biology 21: 3206-3219).

Cell motility is stimulated by extracellular stimuli and initiated by intracellular signaling proteins that localize to sites of cell contact with the extracellular matrix termed focal contacts. Focal adhesion kinase (FAK) is an intracellular protein-tyrosine kinase (PTK) that acts to regulate the cycle of focal contact formation and disassembly required for efficient cell movement. FAK is activated by a variety of cell surface receptors and transmits signals to a range of targets. FAKs are known to target paxillin and are substrates for Src family kinases (Calalb et al. (1995) Molec. Cell. Biol. 15: 954-963). Thus, FAK acts as an integrator of cell motility-associated signaling events. Activation of FAK may be an important early step in cell growth and intracellular signal transduction pathways triggered in response to certain neural peptides or to cell interactions with the extracellular matrix. FAK also functions in promoting cell invasion (Schlaepfer D D and Mitra S K (2004) Curr Opin Genet Dev. 14: 92-101). FAK2 is another member of the FAK subfamily of protein tyrosine kinases. The FAK2 gene encodes a cytoplasmic protein tyrosine kinase involved in calcium-induced regulation of ion channels and activation of the map kinase signaling pathway. FAK2 protein may represent an important signaling intermediate between neuropeptide-activated receptors or neurotransmitters that increase calcium flux and the downstream signals that regulate neuronal activity. FAK2 undergoes rapid tyrosine phosphorylation and activation in response to increases in the intracellular calcium concentration, nicotinic acetylcholine receptor activation, membrane depolarization, or protein kinase C activation. FAK2 binds CRK-associated substrate, nephrocystin, GTPase regulator associated with FAK, and the SH2 domain of GRB2.

Abl (Abelson murine leukemia viral oncogene homolog) is a protein tyrosine kinase involved in cellular proliferation, differentiation, adhesion and survival. Alterations of Abl by chromosomal translocation lead to malignant transformations. The t(9;22) translocation, resulting in a fusion protein Bcr-Abl with constitutive kinase activity, occurs in greater than 90% of chronic myeloid leukemia (CML), 25-30% of adult and 2-10% of childhood acute lymphoblastic leukemia (ALL), and rare cases of acute myelogenous leukemia (AML). The tyrosine kinase activity of Bcr-Abl is critical for malignant transformation. Gleevec® (Imatinib mesylate), a small-molecule inhibitor of Bcr-Abl kinase, was approved for the treatment of CML in 2001. Despite its early success, patients treated with Gleevec® have developed resistance to the therapy. Various mutations in the Abl kinase domain have been identified and are responsible for Gleevec®-resistant disease progression (Gorre M E, Mohammed M, Ellwood K, et al., *Science* 2001; 293:876-80). Molecular studies have demonstrated that these mutations modify the protein conformation of the kinase active site and thus interfere with the binding of Gleevec® (Shah N P, Nicoll J M, Nagar B, et al., *Cancer Cell* 2002; 2:117-25; Branford, S. et al., *Blood* 99, 3472-3475 (2002); Branford, S. et al., *Blood* 102, 276-283 (2003); Branford, S. et al., *Blood* 104, 2926-2932 (2004); Hochhaus, A. et al., *Leukemia* 16, 2190-2196 (2002); Roche-Lestienne, C. et al., *Blood* 100, 1014-1018 (2002); Roche-Lestienne, C., Lai, J. L., Darre, S., Facon, T. & Preudhomme, C., *N. Engl. J. Med.* 348, 2265-2266 (2003)). Second-generation Gleevec® analogs (e.g. AMN107) and other kinase inhibitors (e.g. Dasatinib) have been developed to inhibit many of the Gleevec®-resistant Abl mutants (Martinelli G, Soverini S, Rosti G, Cilloni D, Baccarani M., *Haematologica* 2005; 90:534-41). Both AMN107 and Dasatinib have shown improved response rates in CML patients, as compared to Gleevec®. However, neither compound can inhibit the T315I Abl mutant. It has been reported that a significant number of patients who relapsed in the treatment with Dasatinib have had or developed the T315I mutation (Shah N P, Sawyers C L, Kantajian H M, et al., "Correlation of Clinical Response to BMS-354825 with BCR-ABL Mutation Status in Imatinib-Resistant Patients with Chronic Myeloid Leukemia (CML) and Philadelphia Chromosome-Associated Acute Lymphoblastic Leukemia (Ph+ALL)"; ASCO Annual Meeting 2005; Abstract #6521).

Combination therapy has been commonly utilized to overcome drug resistance. Clinical trials of dasatinib or nilotinib (AMN-107) in combination with the current standard CML therapy, ie., imatinib (Gleevec®), are ongoing (ClinicalTrials.gov). Dasatinib in combination with Gleevec® has shown improved efficacy against various Abl mutants except for T315I in preclinical studies (O'Hare T, Walters D K, Stoffregen E P, et al., "Combined Abl inhibitor therapy for minimizing drug resistance in chronic myeloid leukemia: Src/Abl inhibitors are compatible with imatinib", *Clin Cancer Res.* 11, 6987-6993 (2005)). As T315I mutation emerges as the most prevalent resistant form in CML and Ph+ ALL patients for dasatinib, nilotinib and imatinib, a combination strategy that includes a T315I inhibitor with any existing standard therapy is necessary.

SUMMARY OF THE INVENTION

The compositions of the invention are used to treat diseases associated with abnormal and or unregulated cellular activities. Disease states which can be treated by the methods and compositions provided herein include cancer, ovarian hyperandrogenism, immunological disorders such as rheumatoid arthritis, graft-host diseases, multiple sclerosis, psoriasis; cardiovascular diseases such as artheroscrosis, hypertension, myocardioinfarction, ischemia, stroke and restenosis; metabolic disorders and diseases such as diabetes mellitus, obesity and hypercholesterolemia; and other inflammatory and degenerative diseases such as interbowel diseases, osteoarthritis, macular degeneration, and diabetic retinopathy.

It is appreciated that in some cases the cells may not be in a hyper- or hypo-proliferative and/or migratory state (abnormal state) but may still require treatment. For example, during wound healing, the cells may be proliferating "normally", but proliferation and migration enhancement may be desired. Alternatively, reduction in "normal" cell proliferation and/or migration rate may be desired.

One aspect of the invention relates to methods of treating cancer which method comprises administering to a patient a therapeutically effective amount of a compound of Formula I, II, III, IV, V, or VI, or a pharmaceutically acceptable composition thereof, in combination with one or more treatments(s) selected from surgery, radiation, and one or more chemotherapeutic agent(s).

A second aspect of the invention relates to a method of treating a disease mediated, at least in part, by inhibiting IGF1R, which method comprises administering to a patient a therapeutically effective amount of a compound of Formula I, II, III, IV, V, or VI or a pharmaceutically acceptable composition, thereof and which disease is acromegaly, benign prostatic hyperplasia, diarrhea associated with metastatic carcinoid, gigantism, atherosclerosis, inappropriate microvascular proliferation, Grave's disease, systemic lupus erythematosus, Hashimoto's Thyroiditis, Myasthenia Gravis, auto-immune thyroiditis, or Bechet's disease.

A third aspect of the invention is directed to a method of treating psoriasis which method comprises administering to a patient a therapeutically effective amount of a compound of Formula I, II, III, IV, V, or VI or a pharmaceutically acceptable composition, thereof, in combination with a topical agent such as anthralin, dovonex, salicylic acid, coal tar, tazorac, and a corticosteroid; phototherapy; a biologic such as amevive, raptiva, enbrel, humira, and remicade; cyclosporine; methotrexate; soriatane; accutane; hydrea; mycophenolate mofetil; sulfasalazine; and 6-Thioguanine.

A fourth aspect of the invention is directed to a method of treating rheumatoid arthritis, which method comprises administering to a patient a therapeutically effective amount of a compound of Formula I, II, III, IV, V, or VI or a pharmaceutically acceptable composition, thereof, in combination with a non-steroidal, anti-inflammatory drug (NSAID) including aspirin, ibuprofen, indomethacin and COX-2 inhibitors such as valdecoxib and celecoxib; an analgesic, including acetaminophen, propoxyphene, mepeidine, and morphine; glucocorticoids or prednisone; a disease modifying antirheumatic drug (DMARD) including methotrexate, injectable gold, penicillamine, azathioprine, chloroquine, hydroxychloroquine, sulfasalazine and oral gold; a biologic response modifiers including etanercept, infliximab, adaliumumab and anakinra; and Protein-A Immunoadsorption Therapy.

A fifth aspect of the invention is directed to a method of treating multiple sclerosis which method comprises administering to a patient a therapeutically effective amount of a compound of Formula I, II, III, IV, V, or VI or a pharmaceutically acceptable composition, thereof, in combination with Avonex® (interferon β 1-a), Betaseron® (interferon β 1-b), Copaxone® (glatiramer acetate), Rebif® (interferon β 1-a), Novatrone® (mitoxantrone), Tysabri, corticosteroid, and Solu-Medrol (methylprednisolone).

DETAILED DESCRIPTION OF THE INVENTION

One aspect of the invention is directed to a method of treating cancer which method comprises administering to a patient a therapeutically effective amount of a compound of Formula I, II, III, IV, V, or VI or a pharmaceutically acceptable composition, thereof, in combination with treatments(s) selected from surgery, radiation, monoclonal antibody, bone marrow or peripheral blood stem cell transplantation, and one or more chemotherapeutic agent(s). All of the following embodiments of the invention are intended to be non-limiting examples, whether this is explicitly stated or not.

In another embodiment, the cancer is mediated, at least in part by inhibiting IGF1R.

In another embodiment, the cancer is bladder cancer, Wilm's cancer, ovarian cancer, pancreatic cancer, gastrointestinal stroma cancer, breast cancer, prostate cancer, bone cancer, small cell lung cancer, non-small cell lung cancer, colorectal cancer, cervical cancer, endometrium cancer, synovial sarcoma, vasoactive intestinal peptide secreting tumors, or leukemia, including acute myelogenous leukemia (AML), acute lymphocytic leukemia (ALL), Philadelphia Chromosome-Associated Acute Lymphoblastic Leukemia (Ph+ ALL), chronic lymphocytic leukemia (CLL), and chronic myelogenous leukemia (CML). In another embodiment, the cancer is gastrointestinal stroma cancers, breast cancer, prostate cancer, small cell lung cancer, non-small cell lung cancer, or leukemia, including acute myelogenous leukemia (AML), acute lymphocytic leukemia (ALL), chronic lymphocytic leukemia (CLL), and chronic myclogenous leukemia (CML).

In another embodiment, the chemotherapeutic agent is selected from taxane, a topoisomerase inhibitor, a signal transduction inhibitor, a cell cycle inhibitor, an IGF/IGFR1 system modulator, a farnesyl protein transferase (FPT) inhibitor, an epidermal growth factor receptor (EGFR) inhibitor, a HER2 inhibitor, a vascular epidermal growth factor (VEGF) receptor inhibitor, a mitogen activated protein (MAP) kinase inhibitor, a MEK inhibitor, an AKT inhibitor, a, mTOR inhibitor, a p13 kinase inhibitor, a Raf inhibitor, a cyclin dependent kinase (CDK) inhibitor, a microtubule stabilizer, a microtubule inhibitor, a SERM/Antiestrogen, an aromatase inhibitor, an anthracycline, a proteasome inhibitor, an agent which inhibits insulin-like growth factor (IGF) production, an anti-sense inhibitor of IGFR1, IGF-1 or IGF2, and an alkylating agent.

Nonlimiting examples of taxane include paclitaxel and docetaxel. Nonlimiting examples of the microtubule inhibitor include vincristine, vinblastine, and a podophyllotoxin, epothilone B. Nonlimiting examples of, the epidermal growth factor receptor (EGFR) inhibitor include gefitinib, erlotinib, cetuximab, lapatanib, and canertinib. Nonlimiting examples of the farnesyl protein transferase inhibitor include lonafarnib and tipifarnib. Nonlimiting examples of the selective estrogen receptor modulator (SERM)/antiestrogen include tamoxifen, raloxifene, fulvestrant, acolbifene, pipendoxifene, arzoxifene, toremifene, lasofoxifene, bazedoxifene, and idoxifene. Non-limiting examples of the anthracycline include doxorubicin, daunorubicin and epirubicin. A non-limiting example of an HER2 inhibitor includes trastuzumab. Non-limiting examples of the topoisomerase inhibitor include etoposide, topotecan, camptothecin and irinotecan. Non-limiting examples of the alkylating agent include mitomycin C, adozelesin, cis-platinum, nitrogen mustard, 5-fluorouracil (5FU), etoposide (VP-16), camptothecin, actinomycin-D, and cisplatin (CDDP).

In another embodiment, the cancer is AML and one or more of the treatment(s) are selected from bone marrow or peripheral blood stem cell transplantation, radiation, monoclonal antibody, and one or more chemotherapeutic agent(s). In another embodiment, the monoclonal antibody is Gerntuzumab ozogamicin (Mylotarg); and the chemotherapeutic agent(s) are selected from daunorubicin, doxorubicin, cytarabine (ara-C), an anthracycline drug such as daunorubicin or idarubicin (Daunomycin, Idamycin), 6-thioguanine, and a granulocyte colony-stimulating factor such as Neupogen or Leukine.

In yet another embodiment, the cancer is ALL or Philadelphia Chromosome-Associated Acute Lymphoblastic Leukemia (Ph+ ALL) and the treatment(s) is selected from bone marrow or peripheral blood stem cell transplantation, monoclonal antibody, and one or more chemotherapeutic agent(s). In another embodiment, the monoclonal antibody is rituximab (Rituxan). In another embodiment, the chemotherapeutic agent(s) is selected from vincristine, prednisone, dexamethasone, anthracycline, L-asparaginase, Gleevec®, cyclophosphamide, doxorubicin (Adriamycin), daunorubicin, methotrexate, cytarabine (ara-C), etoposide, and 6-mercaptopurine (6-MP).

In yet another embodiment, the cancer is CLL and the treatment(s) is selected from bone marrow or peripheral blood stem cell transplantation, monoclonal antibody, radiation, and one or more chemotherapeutic agent(s). In another embodiment, the monoclonal antibody is Alemtuzumab (Campath) or Rituximab (Rituxan); and the chemotherapeutic agent(s) is selected from cyclophosphamide, chlorambucil, a corticosteroid such as prednisone, fludarabine, doxorubicin, vincristine, pentostatin, and cladribine (2-CdA).

In yet another embodiment, the cancer is CML and the treatment(s) is selected from bone marrow or peripheral blood stem cell transplantation, radiation, and one or more chemotherapeutic agent(s). Non-limiting examples of the chemotherapeutic agent(s) include interferon therapy such as interferon-$\alpha$, Gleevec®, hydroxyurea (Hydrea), cytosine, cytosine arabinoside, dasatinib, and cytarabine (ara-C).

In yet another embodiment, the cancer is gastrointestinal stromal cancer and the treatment(s) is selected from surgery, radiation, and one or more chemotherapeutic agents. In another embodiment, the surgical procedure is selected from cryosurgery, embolization, and ethanol ablation; and the chemotherapeutic agent is Gleevec®.

In yet another embodiment of the invention, the cancer is small cell lung cancer and the one or more of the treatment(s) is selected from surgery, radiation, and one or more chemotherapeutic agent(s) selected from a platin such as cisplatin or carboplatin, vinorelbine, docetaxel, paclitaxel, etoposide, ifosfamide, cyclophosphamide, doxorubicin, vincristine, gemcitabine, paclitaxel, vinorelbine, topotecan, irinotecan, methotrexate, and docetaxel.

In yet another embodiment, the cancer is non-small cell lung cancer and one or more of the treatment(s) is selected from surgery, radiation, and one or more chemotherapeutic agent(s) selected from gefitinib (Iressa) and erlotinib (Tarceva).

In yet another embodiment, the cancer is prostate cancer and one or more of the treatment(s) is selected from surgery (including cryosurgery), radiation, and one or more chemotherapeutic agent(s). Non-limiting examples of the chemotherapeutic agent(s) include hormone therapy (also called androgen deprivation therapy or androgen suppression therapy), mitoxantrone, prednisone, docetaxel (Taxotere), doxorubicin, etoposide, vinblastine, paclitaxel, and carboplatin.

In yet another embodiment, the cancer is breast cancer and one or more of the treatment(s) include surgery, radiation, a monoclonal antibody, and one or more chemotherapeutic agent(s). Non-limiting examples of the monoclonal antibody include Trastuzumab (Herceptin®). Non-limiting examples of the chemotherapeutic agent(s) include hormone therapy such as Tamoxifen, Raloxifene (Evista; Toremifene (Fareston), and Fulvestrant (Faslodex); luteinizing hormone-releasing hormone (LHRH) analogs including goserelin and leuprolide; Megestrol acetate (Megace); Aromatase inhibitors including etrozole (Femara), anastrozole (Arimidex), and exemestane (Aromasin); pamidronate or zoledronic acid (to treat bone weakness); CMF (cyclophosphamide, fluorouracil, and methotrexate); AC (adriamycin and Cyclophosphamide); axane (paclitaxel or Docetaxel); adriamyclin; and cyclophosphamide.

In yet another embodiment, the cancer is mediated, at least in part, by inhibiting wild-type Abl, including the T315I Abl mutant, and where the compound is of Formula I, II, V, or VI. Non-limiting examples of the cancer includes acute myelogenous leukemia (AML), chronic myelogenous leukemia (CML), and Philadelphia Chromosome-Associated Acute *Lymphoblastic Leukemia* (Ph+ ALL). In another embodiment, the cancer is Ph+ALL or CML. Non-limiting examples of the chemotherapeutic agent include Gleevec® (imatinib mesylate), dasatinib, and nilotinib.

A second aspect of the invention relates to a method of treating a disease mediated, at least in part, by inhibiting IGF1R, which method comprises administering to a patient a therapeutically effective amount of a compound of Formula I, II, III, IV, V, or VI, or a pharmaceutically acceptable composition thereof, and which disease is acromegaly, benign prostatic hyperplasia, diarrhea associated with metastatic carcinoid, gigantism, atherosclerosis, inappropriate microvascular proliferation, Grave's disease, systemic lupus erythematosus, Hashimoto's Thyroiditis, Myasthenia Gravis, auto-immune thyroiditis, or Bechet's disease.

A third aspect of the invention relates to a method of treating psoriasis which method comprises administering to a patient a therapeutically effective amount of a compound of Formula I, II, III, IV, V, or VI, or a pharmaceutically acceptable composition thereof, in combination with a topical agent such as anthralin, dovonex, salicylic acid, coal tar, tazorac, and a corticosteroid; phototherapy; a biologic such as amevive, raptiva, enbrel, humira, and remicade; cyclosporine; methotrexate; soriatane; accutane; hydrea; mycophenolate mofetil; sulfasalazine; or 6-Thioguanine.

A fourth aspect of the invention relates to a method of treating rheumatoid arthritis, which method comprises administering to a patient a therapeutically effective amount of a compound of Formula I, II, III, IV, V, or VI, or a pharmaceutically acceptable composition thereof, in combination with a non-steroidal, anti-inflammatory drug (NSAID) including aspirin, ibuprofen, indomethacin and COX-2 inhibitors such as valdecoxib and celecoxib; an analgesic, including acetaminophen, propoxyphene, mepeidine, and morphine; glucocorticoids or prednisone; a disease modifying antirheumatic drug (DMARD) including methotrexate, injectable gold, penicillamine, azathioprine, chloroquine, hydroxychloroquine, sulfasalazine and oral gold; a biologic response modifier including etanercept, infliximab, adaliumumab and anakinra; or Protein-A Immunoadsorption Therapy.

A fifth aspect of the invention relates to a method of treating multiple sclerosis which method comprises administering to a patient a therapeutically effective amount of a compound of Formula I, II, III, IV, V, or VI, or a pharmaceutically acceptable composition thereof, in combination with Avonex® (interferon β1-a), Betaseron® (interferon β 1-b), Copaxone® (glatiramer acetate), Rebif® (interferon β 1-a), Novatrone® (mitoxantrone), Tysabri, corticosteroid, or Solu-Medrol (methylprednisolone).

The compounds are Formula I, II, III, IV, V and VI that are referred to herein are defined below:

The compound of Formula I is of the formula:

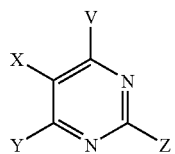

I or a pharmaceutically acceptable salt, hydrate, or prodrug thereof, wherein,

V is $NR_1R_{1a}$, or $O\!-\!R_1$, wherein $R_1$ is H, CN, halo, $-NR_{13}R_{14}$, $C(O)NR_{13}R_{14}$, $C_1$-$C_6$ alkyl, $-C(O)\!-\!C_1$-$C_6$ alkyl, $-C_0$-$C_6$ alkyl-$R_{20}$, wherein $R_{20}$ is aryl, heteroaryl, heterocyclyl, or a 5-12 membered fused bicyclical or tricyclic saturated, partially saturated, or unsaturated ring system containing 0-4 ring atoms selected from N, O, and S, wherein aryl, heteroaryl, $C_3$-$C_7$ heterocyclyl, or the 5-12 membered ring system are optionally substituted with one, two, or three groups independently selected from $C_1$-$C_6$ alkyl, and $-C_0$-$C_6$ alkyl-$R_{21}$;

$R_{1a}$ is H or $C_1$-$C_6$ alkyl; or when V is $NR_1R_{1a}$, $R_1$ and $R_{1a}$ together with the nitrogen to which they are attached form a 4-7 membered heterocyclyl or heteroaryl group containing, in addition to the nitrogen, up to two additional heteroatoms independently selected from O, N, and S, and wherein each heterocyclyl or heteroaryl group is optionally substituted with one or two of $C_1$-$C_6$ alkyl, $-NR_{13}R_{14}$ or $C_3$-$C_7$ cycloalkyl;

X is H, halo, $C_1$-$C_6$ alkyl, $NO_2$, mono-, di-, or tri-halo substituted methyl, $NR_{13}R_{14}$, $C(O)O\!-\!C_1$-$C_6$ alkyl, or $N(R_{13})\!-\!C(O)\!-\!C_1$-$C_6$ alkyl;

Y is H, halo, OH, $C_1$-$C_6$ alkyl, $C_0$-$C_6$ alkyl-$NR_{15}R_{16}$, $NR_{15}R_{16}$, $C_1$-$C_6$ alkoxy, $-N(R_{13})\!-\!(CH_2)_n\!-\!NR_{15}R_{16}$, $-C(O)O\!-\!C_1$-$C_6$ alkyl, $-O\!-\!(CH_2)_n\!-\!NR_{15}R_{16}$, $-C(O)\!-\!C_1$-$C_6$ alkyl, $-C_0$-$C_6$-alkyl-$R_{21}$, $-O\!-\!R_{21}$, $-C(O)\!-\!R_{21}$, $-O\!-\!(CH_2)_n\!-\!R_{21}$, $-C(O)\!-\!NR_{13}R_{14}$, $-C(O)\!-\!N(R_{13})$-aryl, $-C(O)\!-\!N(R_{13})\!-\!(CH_2)_n\!-\!NR_{15}R_{16}$, $-C(O)\!-\!N(R_{13})\!-\!(CH_2)_n$-aryl, $-C(O)\!-\!N(R_{13})\!-\!(CH_2)_n$-heterocyclyl;

or X and Y together with the atoms to which they are attached form a 4-7 membered heterocyclyl or heteroaryl group containing one or two heteroatoms independently selected from O, N, and S, wherein the heterocyclyl or heteroaryl group is optionally substituted with one or two moieties independently selected from halo, $C_1$-$C_6$ alkyl, aryl-$C_1$-$C_6$ alkyl-, aryl-$(CH_2)_n\!-\!O\!-\!(CH_2)_n$-aryl-, arylOH, $C_3$-$C_7$ cycloalkyl, heterocyclyl, -aryl-$N(R_{13})C(O)\!-\!C_3$-$C_7$ cycloalkyl-$C(O)\!-\!N(R_{14})$-aryl, or a group of the formula -L-M-Q, wherein:

L is a bond or $C_3$-$C_7$ cycloalkyl,

M is $C_1$-$C_6$ alkyl, $C_2$-$C_6$ alkenyl, or $C_2$-$C_6$ alkynyl,

Q is $NR_{13}R_{14}$, $N(R_{13})C(O)\!-\!C_1$-$C_6$ alkyl, heterocyclyl, or a saturated fused bicyclic ring containing one or two heteroatoms independently selected from O, N, and S, wherein each aryl, heteroaryl, or heterocyclyl substituent on the group formed by X and Y is optionally further substituted with one or two moieties independently selected from halo, $C(O)O\!-\!(CH_2)_n$-phenyl, and $C(O)\!-\!C_1$-$C_6$ alkyl;

Z is H, $NR_2R_3$, $-S\!-\!R_{2a}$, or $O\!-\!R_{2a}$, wherein $R_2$ is $-C_1$-$C_6$ alkyl, $-C_1$-$C_6$ alkyl-$NR_{13}R_{14}$, $-C(O)$-aryl, $-C_0$-$C_6$-alkyl-aryl, $-C_0$-$C_6$-alkyl-heteroaryl, $-C_0$-$C_6$-alkyl-($C_3$-$C_7$-cycloalkyl), $-C_0$-$C_6$-alkyl-heterocyclyl, or $-C_0$-$C_6$ alkyl-5-12 membered fused bicyclic or tricyclic saturated, partially saturated, or unsaturated ring system containing 0-4 ring atoms selected from N, O, and S, wherein each alkyl is optionally substituted with phenyl, and each aryl, heteroaryl, $C_3$-$C_7$ cycloalkyl, heterocyclyl, or 5-12 membered ring system is optionally substituted with one, two, or three groups independently selected from halo, mono-, di-, or tri-halo substituted methyl or methoxy, CN, $NO_2$, $NR_{13}R_{14}$, $C(O)O$—$C_1$-$C_6$ alkyl, $N(R_{13})C(O)$—$C_1$-$C_6$ alkyl, —$SO_2NR_{13}R_{14}$, —O—C(O)—$NR_{13}R_{14}$, —$C_0$-$C_6$ alkyl-$C(O)NR_{15}R_{16}$, $C_1$-$C_6$ alkoxy, $C_1$-$C_6$ thioalkoxy, —O—$(CH_2)_n$—$NR_{15}R_{16}$, —$C_1$-$C_6$ alkyl-$NR_{13}R_{14}$, —$N(R_{13})$—$C(O)$—$C_1$-$C_6$ alkyl, —$N(R_{13})$—$C(O)$-aryl, —$C_0$-$C_6$ alkyl-$C(O)$—N$(R_{13})$—$(CH_2)_n$—$NR_{15}R_{16}$, —$C_0$-$C_6$ alkyl-$C(O)$—N$(R_{13})$—$(CH_2)_n$-aryl, —O—$(CH_2)_n$—$C(O)$—$N(R_{13})$—$(CH_2)_n$—$NR_{15}R_{16}$, —O—$(CH_2)_n$—$C(O)$—$NR_{15}R_{16}$, —$C_0$-$C_6$ alkyl-$C(O)$—$N(R_{13})$—$(CH_2)_n$—O—$C_1$-$C_6$ alkyl, —$C_0$-$C_6$ alkyl-$N(R_{13})$—$C(O)O$—$C_1$-$C_6$ alkyl, —$C_0$-$C_6$alkyl-$C(O)$-heterocyclyl, —$C_0$-$C_6$alkyl-$C(O)$-heteroaryl, —$C_0$-$C_6$alkyl-$C(O)$-aryl, —$C_0$-$C_6$-alkyl-$R_{21}$, aryloxy, —O—$(CH_2)_n$—$R_{21}$, —$SO_2$-heterocyclyl, $N(R_{13})$—$C(O)$—$C_3$-$C_7$-cycloalkyl, —$C_0$-$C_6$alkyl $C(O)$ O—$R_{21}$, $C_3$-$C_7$-cycloalkyl, —$C_0$-$C_6$alkyl$R_{21}$, —$SC_1$-$C_6$alkyl or $C_1$-$C_6$ alkyl optionally substituted with halo or cyano, wherein each aryl, heteroaryl, cycloalkyl, or heterocyclyl substituent is further optionally substituted with 1-3 groups independently selected from halo, $CF_3$, $C_1$-$C_6$ alkyl, $C_1$-$C_6$ haloalkoxy, $NR_{13}R_{14}$ and $C_1$-$C_6$ alkoxy;

$R_3$ is H Or $C_1$-$C_6$ alkyl;

or $R_2$ and $R_3$ together with the nitrogen to which they are attached form a 4-7 membered heterocyclyl or heteroaryl group containing up to three heteroatoms independently selected from O, N, and S, and wherein the heterocyclyl or heteroaryl group is optionally substituted with one or two of halo or $C_1$-$C_6$ alkyl;

$R_{2a}$ is aryl or $C_0$-$C_6$ alkyl-heteroaryl, wherein the aryl and heteroaryl are optionally substituted with aryl, —$N(R_{13})$—$C(O)$—$C_3$-$C_7$ cycloalkyl or —$C(O)$ $NR_{13}R_{14}$;

$R_{13}$ and $R_{14}$ are independently H or $C_1$-$C_6$ alkyl;

$R_{15}$ and $R_{16}$ are independently H, $C_1$-$C_6$ alkyl, heteroaryl, or heterocyclyl, or $R_{15}$ and $R_{16}$ together with the nitrogen to which they are attached form a 4-7 membered heterocyclyl or heteroaryl group wherein one or two ring carbons are each optionally replaced with a heteroatom independently selected from O, N, and S, and wherein each heterocyclyl or heteroaryl group is optionally substituted with one or two moieties independently selected from halo, $C_1$-$C_6$ alkyl, or —$C(O)O$—$C_1$-$C_6$ alkyl;

$R_{21}$ is heterocyclyl, aryl, heteroaryl, or $C_3$-$C_7$ cycloalkyl, and wherein alkyl, aryl, heteroaryl, $C_3$-$C_7$ cycloalkyl, and heterocyclyl are optionally substituted with one or two moieties independently selected from halo, —$S(O)_2$—$C_0$-$C_1$ alkyl, —$C(O)$—$C_0$-$C_1$ alkyl, —$C(O)$—H, —$C_0$-$C_1$ alkyl-aryl, $C_1$-$C_6$ alkyl, $NR_{13}R_{14}$, and heterocyclyl;

n is 0-6;

provided that when V is $NH_2$, X, Y and Z are not simultaneously H.

In another embodiment, the compound of formula I is that wherein V is $NHR_1$.

In another embodiment, the compound of formula I is that wherein Z is $NR_2R_3$.

In another embodiment, the compound of formula I is that wherein V is $NHR_1$, and Z is $NR_2R_3$.

The Compound of Formula II is of the following formula:

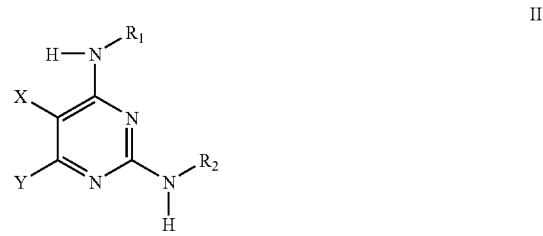

II or a pharmaceutically acceptable salt, hydrate, or prodrug thereof, wherein, $R_1$ is H, CN, halo, —$NR_{13}R_{14}$, $C(O)NR_{13}R_{14}$, $C_1$-$C_6$ alkyl, —$C(O)$—$C_1$-$C_6$ alkyl, —$C_0$-$C_6$ alkyl-$R_{20}$, wherein $R_{20}$ is aryl, heteroaryl, heterocyclyl, or a 5-12 membered fused bicyclical or tricyclic saturated, partially saturated, or unsaturated ring system containing 0-4 ring atoms selected from N, O, and S, wherein aryl, heteroaryl, $C_3$-$C_7$ heterocyclyl, or the 5-12 membered ring system are optionally substituted with one, two, or three groups independently selected from $C_1$-$C_6$ alkyl, and —$C_0$-$C_6$ alkyl-$R_{21}$;

X is H, halo, $C_0$-$C_6$ alkyl, $NO_2$, mono-, di-, or ti-halo substituted methyl, $NR_{13}R_{14}$, $C(O)O$—$C_0$-$C_6$ alkyl, or $N(R_{13})$—$C(O)$—$C_1$-$C_6$ alkyl;

Y is H, halo, OH, $C_1$-$C_6$ alkyl, $NR_{15}R_{16}$, $C_1$-$C_6$ alkoxy, —$N(R_{13})$—$(CH_2)_n$—$NR_{15}R_{16}$, —$C(O)O$—$C_1$-$C_6$ alkyl, —O—$(CH_2)_n$—$NR_{15}R_{16}$, —$C(O)$—$C_0$-$C_6$ alkyl, —$C_0$-$C_6$-alkyl-$R_{21}$, —O—$R_{21}$, —$C(O)$—$R_{21}$, —O—$(CH_2)_n$—$R_{21}$, —$C(O)$—$NR_{13}R_{14}$, —$C(O)$—$N(R_{13})$-aryl, —$C(O)$—$N(R_{13})$—$(CH_2)_n$—$NR_{15}R_{16}$, —$C(O)$—N$(R_{13})$—$(CH_2)_n$-aryl, —$C(O)$—$N(R_{13})$—$(CH_2)_n$-heterocyclyl;

or X and Y together with the atoms to which they are attached form a 4-7 membered heterocyclyl or heteroaryl group containing one or two heteroatoms independently selected from O, N, and S, wherein the heterocyclyl or heteroaryl group is optionally substituted with one or two moieties independently selected from halo, $C_1$-$C_6$ alkyl, aryl-$C_1$-$C_6$ alkyl-, aryl-$(CH_2)_n$—O—$(CH_2)_n$-aryl-, arylOH, $C_3$-$C_7$ cycloalkyl, heterocyclyl, -aryl-$N(R_{13})C(O)$—$C_3$-$C_7$ cycloalkyl-$C(O)$—$N(R_{14})$-aryl, and a group of the formula -L-M-Q, wherein L is a bond or $C_3$-$C_7$ cycloalkyl, M is $C_1$-$C_6$ alkyl, $C_2$-$C_6$ alkenyl, or $C_2$-$C_6$ alkynyl, Q is $NR_{13}R_{14}$, $N(R_{13})C(O)$—$C_1$-$C_6$ alkyl, heterocyclyl, or a saturated fused bicyclic ring containing one or two heteroatoms independently selected from O, N, and S, wherein each aryl, heteroaryl, or heterocyclyl substituent on the group formed by X and Y is optionally further substituted with one or two moieties independently selected from halo, $C(O)O$—$(CH_2)_n$-phenyl, and $C(O)$—$C_1$-$C_6$ alkyl;

$R_2$ is —$C_0$-$C_6$ alkyl, —$C_1$-$C_6$ alkyl-$NR_{13}R_{14}$, —$C(O)$-aryl, —$C_0$-$C_6$-alkyl-aryl, —$C_0$-$C_6$-alkyl-heteroaryl, —$C_0$-$C_6$-alkyl-$(C_3$-$C_7$-cycloalkyl), —$C_0$-$C_6$-alkyl-heterocyclyl, or —$C_0$-$C_6$ alkyl-5-12 membered fused bicyclic or tricyclic saturated, partially saturated, or unsaturated ring system containing 0-4 ring atoms selected from N, O, and S, wherein each alkyl is optionally substituted with phenyl, and
each aryl, heteroaryl, $C_3$-$C_7$ cycloalkyl, heterocyclyl, or 5-12 membered ring system is optionally substituted with one, two, or three groups independently selected from halo, mono-, di-, or tri-halo substituted methyl or methoxy, CN, $NO_2$, $NR_{13}R_{14}$, $C(O)O$—$C_1$-$C_6$ alkyl, $N(R_{13})C(O)$—$C_1$-$C_6$ alkyl, —$SO_2NR_{13}R_{14}$, —O—C(O)—$NR_{13}R_{14}$, —$C_0$-$C_6$ alkyl-$C(O)NR_{15}R_{16}$, $C_1$-$C_6$ alkoxy, $C_1$-$C_6$ thioalkoxy, —O—$(CH_2)_n$—$NR_{15}R_{16}$, —$C_1$-$C_6$ alkyl-$NR_{13}R_{14}$, —$N(R_{13})$—$C(O)$—$C_1$-$C_6$ alkyl, —$N(R_{13})$—C(O)-aryl, —$C_0$-$C_6$ alkyl-C(O)—$N(R_{13})$—$(CH_2)_n$—$NR_{15}R_{16}$, —$C_0$-$C_6$ alkyl-C(O)—$N(R_{13})$—$(CH_2)_n$-aryl, —O—$(CH_2)_n$—$C(O)$—$N(R_{13})$—$(CH_2)_n$—$NR_{15}R_{16}$, —O—$(CH_2)_n$—$C(O)$—$NR_{15}R_{16}$, —$C_0$-$C_6$ alkyl-C(O)—$N(R_{13})$—$(CH_2)_n$—O—$C_1$-$C_6$ alkyl, —$C_0$-$C_6$ alkyl-$N(R_{13})$—$C(O)O$—$C_1$-$C_6$ alkyl, —$C_0$-$C_6$alkyl-C(O)-heterocyclyl, —$C_0$-$C_6$alkyl-C(O)-heteroaryl, —$C_0$-$C_6$alkyl-C(O)-aryl, —$C_0$-$C_6$-alkyl-$R_{21}$, aryloxy, —O—$(CH_2)_n$—$R_{21}$, —$SO_2$-heterocyclyl, $N(R_{13})$—C(O)—$C_3$-$C_7$-cycloalkyl, —$C_0$-$C_6$alkyl C(O) O—$R_{21}$, $C_3$-$C_7$-cycloalkyl, —$C_0$-$C_6$alkyl$R_{21}$, —$SC_1$-$C_6$alkyl or $C_1$-$C_6$ alkyl optionally substituted with halo or cyano,
wherein each aryl, heteroaryl, cycloalkyl, or heterocyclyl substituent is further optionally substituted with 1-3 groups independently selected from halo, mono-, di-, or tri-halo substituted methyl, $C_1$-$C_6$ alkyl, $C_1$-$C_6$ haloalkoxy, $NR_{13}R_{14}$ and $C_1$-$C_6$ alkoxy;
$R_{13}$ and $R_{14}$ are independently H or $C_1$-$C_6$ alkyl, or $R_{13}$ and $R_{14}$ together with the nitrogen to which they are attached form a 4-7 membered heterocyclyl or heteroaryl group wherein one or two ring carbons are each optionally replaced with a heteroatom independently selected from O, N, and S, and wherein each heterocyclyl or heteroaryl group is optionally substituted with one or two of halo, $C_1$-$C_6$ alkyl, or $C_1$-$C_6$ alkoxy;
$R_{15}$ and $R_{16}$ are independently H, $C_1$-$C_6$ alkyl, heteroaryl, or heterocyclyl, or $R_{15}$ and $R_{16}$ together with the nitrogen to which they are attached form a 4-7 membered heterocyclyl or heteroaryl group wherein one or two ring carbons are each optionally replaced with a heteroatom independently selected from O, N, and S, and wherein each heterocyclyl or heteroaryl group is optionally substituted with one or two of halo, $C_1$-$C_6$ alkyl, or —$C(O)O$—$C_1$-$C_6$ alkyl;
$R_{21}$ is heterocyclyl, aryl, heteroaryl, or $C_3$-$C_7$ cycloalkyl, and wherein alkyl, aryl, heteroaryl, $C_3$-$C_7$ cycloalkyl, and heterocyclyl are optionally substituted with one or two moieties independently selected from halo, $C_1$-$C_6$ alkyl, $NR_{13}R_{14}$, and heterocyclyl; and
n is 1-6.

In another embodiment of the invention, the compound is according to formula II where X is H, $C_1$-$C_6$ alkyl, or halo.

In another embodiment of the compound according to formula II, X is H or halo.

In another embodiment of the compound according to formula II, X is halo. In another embodiment, the halo is Cl or Br. In another embodiment, the halo is Br.

In another embodiment of the compound according to formula II, Y is H, halo, $C_1$-$C_6$ alkyl, $C_1$-$C_6$ alkoxy, $NR_{15}R_{16}$, —$C(O)O$—$C_1$-$C_6$ alkyl, —O—$(CH_2)_n$—$NR_{15}R_{16}$, —$N(R_{13})$—$(CH_2)_n$—$NR_{15}R_{16}$, —O—$R_{21}$, —O—$(CH_2)_n$—$R_{21}$, or aryl.

In another embodiment of the compound according to formula II, Y is H.

In another preferred embodiment of the compound according to formula II, Y is halo. In another embodiment, the halo is Cl or Br. In another embodiment, the halo is Br.

In another embodiment of the compound according to formula II, Y is $C_1$-$C_6$ alkyl, preferably $C_1$-$C_3$ alkyl, more preferably methyl.

In another embodiment of the compound according to formula II, $R_1$ is aryl or heteroaryl optionally substituted with one, two, or three groups independently selected from $C_1$-$C_6$ alkyl, $C_3$-$C_7$ cycloalkyl, aryl, and heteroaryl.

In another embodiment of the compound according to formula II, $R_1$ is heteroaryl, optionally substituted with one, two, or three groups independently selected from $C_1$-$C_6$ alkyl, $C_3$-$C_7$ cycloalkyl, aryl, and heteroaryl.

In another embodiment of the compound according to formula II, $R_1$ is pyrazolyl or isoxazolyl, optionally substituted with one, two, or three groups independently selected from $C_1$-$C_6$ alkyl, $C_3$-$C_7$ cycloalkyl, aryl, and heteroaryl.

In another embodiment of the compound according to formula II, $R_2$ is aryl or —$C_1$-$C_6$-alkyl-heteroaryl, wherein aryl or heteroaryl are optionally substituted as defined above for compounds of formula II.

In another embodiment of the compound according to formula II, $R_2$ is $C_1$-$C_6$-alkyl-heteroaryl, optionally substituted as defined above for compounds of formula II. In another embodiment, $R_2$ is $C_1$-$C_2$-isoxazolyl, optionally substituted with aryl, heterocyclyl, or $C_1$-$C_6$ alkyl.

In another embodiment of the compound according to formula II, $R_2$ is aryl, optionally substituted as defined above for compounds of formula II. In another embodiment, $R_2$ is phenyl, optionally substituted with —O—$(CH_2)_n$—$NR_{15}R_{16}$, $NR_{13}R_{14}$, —$C_0$-$C_6$ alkyl-$C(O)NR_{15}R_{16}$, —$C_0$-$C_6$ alkyl-C(O)—$N(R_{13})$—$(CH_2)_n$—$NR_{15}R_{16}$, $N(R_{13})C(O)$—$C_1$-$C_6$ alkyl, halo, —$C_1$-$C_6$ alkyl-$NR_{13}R_{14}$, $C_1$-$C_6$ alkoxy, or heterocyclyl.

The Compound of Formula III is of the following formula:

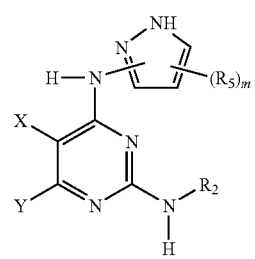

III or a pharmaceutically acceptable salt, hydrate, or prodrug thereof, wherein,
m is 1 or 2;
$R_5$ at each occurrence is independently H, $C_1$-$C_6$ alkyl, $C_3$-$C_7$ cycloalkyl, aryl, or heteroaryl;
X is H, halo, $C_1$-$C_6$ alkyl, $NO_2$, mono-, di-, or tri-halo substituted methyl, $NR_{13}R_{14}$, $C(O)O$—$C_1$-$C_6$ alkyl, or $N(R_{13})$—$C(O)$—$C_1$-$C_6$ alkyl;
Y is H, halo, OH, $C_1$-$C_6$ alkyl, $NR_{15}R_{16}$, $C_1$-$C_6$ alkoxy, —$N(R_{13})$—$(CH_2)_n$—$NR_{15}R_{16}$, —$C(O)O$—$C_1$-$C_6$ alkyl, —O—$(CH_2)_n$—$NR_{15}R_{16}$, —C(O)—$C_1$-$C_6$ alkyl, —$C_0$-$C_6$-alkyl-$R_{21}$, —O—$R_{21}$, —C(O)—$R_{21}$, —O—$(CH_2)_n$—$R_{21}$, —C(O)—$NR_{13}R_{14}$, —C(O)—$N(R_{13})$-aryl, —C(O)—$N(R_{13})$—$(CH_2)_n$—$NR_{15}R_{16}$, C(O)—$N(R_{13})$—$(CH_2)_n$-aryl, —C(O)—$N(R_{13})$—$(CH_2)_n$-heterocyclyl;
or X and Y together with the atoms to which they are attached form a 4-7 membered heterocyclyl or heteroaryl group containing one or two heteroatoms independently selected from O, N, and S, wherein the heterocyclyl or heteroaryl group is optionally substituted with one or two moieties independently selected from halo, $C_1$-$C_6$ alkyl, aryl-$C_1$-$C_6$ alkyl-, aryl-$(CH_2)_n$—O-aryl-, $C_3$-$C_7$ cycloalkyl, heterocyclyl, -aryl-$N(R_{13})C(O)$—$C_3$-$C_7$ cycloalkyl-$C(O)$—$N(R_{14})$-aryl, and a group of the formula -L-M-Q, wherein L is a bond or $C_3$-$C_7$ cycloalkyl, M is $C_1$-$C_6$ alkyl, $C_2$-$C_6$ alkenyl, or $C_2$-$C_6$ alkynyl, Q is $NR_{13}R_{14}$, $N(R_{13})C(O)$—$C_1$-$C_6$ alkyl, heterocyclyl, or a saturated fused bicyclic ring containing one or two heteroatoms independently selected from O, N, and S, wherein each aryl, heteroaryl, or heterocyclyl substituent on the group formed by X and Y is optionally further substituted with one or two moieties independently selected from halo, $C(O)O$—$(CH_2)_n$-phenyl, and $C(O)$—$C_1$-$C_6$ alkyl;

$R_2$ is —$C_1$-$C_6$ alkyl, —$C_1$-$C_6$ alkyl-$NR_{13}R_{14}$, —$C(O)$-aryl, —$C_0$-$C_6$-alkyl-aryl, —$C_0$-$C_6$-alkyl-heteroaryl, —$C_0$-$C_6$-alkyl-($C_3$-$C_7$-cycloalkyl), —$C_0$-$C_6$-alkyl-heterocyclyl, or —$C_0$-$C_6$ alkyl-5-12 membered fused bicyclic or tricyclic saturated, partially saturated, or unsaturated ring system containing 0-4 ring atoms selected from N, O, and S, wherein each alkyl is optionally substituted with phenyl, and each aryl, heteroaryl, $C_3$-$C_7$ cycloalkyl, heterocyclyl, or 5-12 membered ring system is optionally substituted with one, two, or three groups independently selected from halo, mono-, di-, or tri-halo substituted methyl or methoxy, CN, $NO_2$, $NR_{13}R_{14}$, $C(O)O$—$C_1$-$C_6$ alkyl, $N(R_{13})C(O)$—$C_1$-$C_6$ alkyl, —$SO_2NR_{13}R_{14}$, —O—C(O)—$NR_{13}R_{14}$, —$C_0$-$C_6$ alkyl-$C(O)NR_{15}R_{16}$, $C_1$-$C_6$ alkoxy, $C_1$-$C_6$ thioalkoxy, —O—$(CH_2)_n$—$NR_{15}R_{16}$, —$C_1$-$C_6$ alkyl-$NR_{13}R_{14}$, —$N(R_{13})$—$C(O)$—$C_1$-$C_6$ alkyl, —$N(R_{13})$—$C(O)$-aryl, —$C_0$-$C_6$ alkyl-$C(O)$—$N(R_{13})$—$(CH_2)_n$—$NR_{15}R_{16}$, —$C_0$-$C_6$ alkyl-$C(O)$—$N(R_{13})$—$(CH_2)_n$-aryl, —O—$(CH_2)_n$—$C(O)$—$N(R_{13})$—$(CH_2)_n$—$NR_{15}R_{16}$, —O—$(CH_2)_n$—$C(O)$—$NR_{15}R_{16}$, —$C_0$-$C_6$ alkyl-$C(O)$—$N(R_{13})$—$(CH_2)_n$—O—$C_1$-$C_6$ alkyl, —$C_0$-$C_6$ alkyl-$N(R_{13})$—$C(O)O$—$C_1$-$C_6$ alkyl, —$C_0$-$C_6$alkyl-$C(O)$-heterocyclyl, —$C_0$-$C_6$alkyl-$C(O)$-heteroaryl, —$C_0$-$C_6$alkyl-$C(O)$-aryl, —$C_0$-$C_6$-alkyl-$R_{21}$, aryloxy, —O—$(CH_2)_n$—$R_{21}$, —$SO_2$-heterocyclyl, $N(R_{13})$—$C(O)$—$C_3$-$C_7$-cycloalkyl, or $C_1$-$C_6$ alkyl optionally substituted with halo or cyano, wherein each aryl, heteroaryl, cycloalkyl, or heterocyclyl substituent is further optionally substituted with 1-3 groups independently selected from halo, mono-, di-, or tri-halo substituted methyl, $C_1$-$C_6$ alkyl, and $C_1$-$C_6$ alkoxy;

$R_{13}$ and $R_{14}$ are independently H or $C_1$-$C_6$ alkyl, or $R_{13}$ and $R_{14}$ together with the nitrogen to which they are attached form a 4-7 membered heterocyclyl or heteroaryl group wherein one or two ring carbons are each optionally replaced with a heteroatom independently selected from O, N, and S, and wherein each heterocyclyl or heteroaryl group is optionally substituted with one or two of halo, $C_1$-$C_6$ alkyl, or $C_1$-$C_6$ alkoxy;

$R_{15}$ and $R_{16}$ are independently H, $C_1$-$C_6$ alkyl, heteroaryl, or heterocyclyl, or $R_{15}$ and $R_{16}$ together with the nitrogen to which they are attached form a 4-7 membered heterocyclyl or heteroaryl group wherein one or two ring carbons are each optionally replaced with a heteroatom independently selected from O, N, and S, and wherein each heterocyclyl or heteroaryl group is optionally substituted with one or two moieties independently selected from halo, $C_1$-$C_6$ alkyl, and —$C(O)O$—$C_1$-$C_6$ alkyl;

$R_{21}$ is heterocyclyl, aryl, heteroaryl, or $C_3$-$C_7$ cycloalkyl, and wherein alkyl, aryl, heteroaryl, $C_3$-$C_7$ cycloalkyl, and heterocyclyl are optionally substituted with one or two moieties independently selected from halo, $C_1$-$C_6$ alkyl, $NR_{13}R_{14}$, and heterocyclyl; and n is 1-6.

In another embodiment of the compound according to formula III, X is H, $C_1$-$C_6$ alkyl, or halo.

In another embodiment of the compound according to formula III, X is H or halo.

In another embodiment of the compound according to formula III, X is halo. In another embodiment, the halo is Cl or Br. In another embodiment, the halo is Br.

In another embodiment of the compound according to formula III, Y is H, halo, $C_1$-$C_6$ alkyl, $C_1$-$C_6$ alkoxy, $NR_{15}R_{16}$, —$C(O)O$—$C_1$-$C_6$ alkyl, —O—$(CH_2)_n$—$NR_{15}R_{16}$, —$N(R_{13})$—$(CH_2)_n$—$NR_{15}R_{16}$, —O—$(CH_2)_n$—$R_{21}$, —O—$R_{21}$, or aryl.

In another embodiment of the compound according to formula III, Y is H.

In another embodiment of the compound according to formula III, Y is halo. In another embodiment, the halo is Cl or Br. In another embodiment, the halo is Br.

In another embodiment of the compound according to formula III, Y is $C_1$-$C_6$ alkyl, preferably $C_1$-$C_3$ alkyl, such as methyl.

In another embodiment of the compound according to formula III, $R_2$ is aryl or —$C_1$-$C_6$-alkyl-heteroaryl, wherein aryl or heteroaryl are optionally substituted as defined above for compounds of formula III.

In another embodiment of the compound according to formula III, $R_2$ is $C_1$-$C_6$-alkyl-heteroaryl, optionally substituted as defined above for compounds of formula III. In another embodiment, $R_2$ is $C_1$-$C_2$-isoxazolyl, optionally substituted with 1 or 2 of aryl, heterocyclyl, or $C_1$-$C_6$ alkyl.

In another embodiment of the compound according to formula III, $R_2$ is aryl, optionally substituted as defined above for compounds of formula III. In another embodiment, $R_2$ is phenyl, optionally substituted with 1 or 2 of —O—$(CH_2)_n$—$NR_{15}R_{16}$, $NR_{13}R_{14}$, —$C_0$-$C_6$ alkyl-$C(O)NR_{15}R_{16}$, —$C_0$-$C_6$ alkyl-$C(O)$—$N(R_{13})$—$(CH_2)_n$—$NR_{15}R_{16}$, $N(R_{13})C(O)$—$C_1$-$C_6$ alkyl, halo, —$C_1$-$C_6$ alkyl-$NR_{13}R_{14}$, $C_1$-$C_6$ alkoxy, or heterocyclyl.

The Compound of Formula IV is of the following formula:

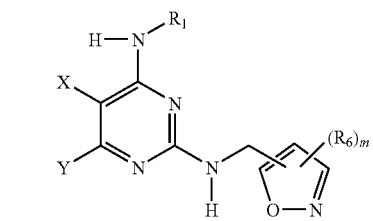

IV or a pharmaceutically acceptable salt, hydrate, or prodrug thereof, wherein, $R_1$ is H, CN, halo, —$NR_{13}R_{14}$, $C(O)NR_{13}R_{14}$, $C_1$-$C_6$ alkyl, —$C(O)$—$C_1$-$C_6$ alkyl, —$C_0$-$C_6$ alkyl-$R_{20}$, wherein $R_{20}$ is aryl, heteroaryl, heterocyclyl, or a 5-12 membered fused bicyclical or tricyclic saturated, partially saturated, or unsaturated ring system containing 0-4 ring atoms selected from N, O, and S, wherein aryl, heteroaryl, $C_3$-$C_7$ heterocyclyl, or the 5-12 membered ring system are optionally substituted with one, two, or three groups independently selected from $C_1$-$C_6$ alkyl, and —$C_0$-$C_6$ alkyl-$R_{21}$;

X is H, halo, $C_1$-$C_6$ alkyl, $NO_2$, mono-, di-, or tri-halo substituted methyl, $NR_{13}R_{14}$, C(O)O—$C_1$-$C_6$ alkyl, or $N(R_{13})$—C(O)—$C_1$-$C_6$ alkyl;

Y is H, halo, OH, $C_1$-$C_6$ alkyl, $NR_{15}R_{16}$, $C_1$-$C_6$ alkoxy, —$N(R_{13})$—$(CH_2)_n$—$NR_{15}R_{16}$, —C(O)O—$C_1$-$C_6$ alkyl, —O—$(CH_2)_n$—$NR_{15}R_{16}$, —C(O)—$C_1$-$C_6$ alkyl, —$C_0$-$C_6$-alkyl-$R_{21}$, —O—$R_{21}$, —C(O)—$R_{21}$, —O—$(CH_2)_n$—$R_{21}$, —C(O)—$NR_{13}R_{14}$, —C(O)—$N(R_{13})$-aryl, —C(O)—$N(R_{13})$—$(CH_2)_n$—$NR_{15}R_{16}$, C(O)—$N(R_{13})$—$(CH_2)$-aryl, —C(O)—$N(R_{13})$—$(CH_2)_n$-heterocyclyl;

or X and Y together with the atoms to which they are attached form a 4-7 membered heterocyclyl or heteroaryl group containing one or two heteroatoms independently selected from O, N, and S, wherein the heterocyclyl and heteroaryl group is optionally substituted with one or two moieties selected from halo, $C_1$-$C_6$ alkyl, aryl-$C_1$-$C_6$ alkyl-, aryl-$(CH_2)_n$—O-aryl-, $C_3$-$C_7$ cycloalkyl, heterocyclyl, -aryl-N$(R_{13})$C(O)—$C_3$-$C_7$ cycloalkyl-C(O)—$N(R_{14})$-aryl, and a group of the formula -L-M-Q, wherein L is a bond or $C_3$-$C_7$ cycloalkyl, M is $C_1$-$C_6$ alkyl, $C_2$-$C_6$ alkenyl, or $C_2$-$C_6$ alkynyl, Q is $NR_{13}R_{14}$, $N(R_{13})C(O)$—$C_1$-$C_6$ alkyl, heterocyclyl, or a saturated fused bicyclic ring containing one or two heteroatoms independently selected from O, N, and S, wherein each aryl, heteroaryl, and heterocyclyl substituent on the group formed by X and Y is optionally further substituted with one or two moieties selected from halo, C(O)O—$(CH_2)_n$-phenyl, and C(O)—$C_1$-$C_6$ alkyl;

$R_6$ at each occurrence is independently H, halo, mono-, di-, or tri-halo substituted methyl or methoxy, CN, $NO_2$, $NR_{13}R_{14}$, C(O)O—$C_1$-$C_6$ alkyl, $N(R_{13})C(O)$—$C_1$-$C_6$ alkyl, —$SO_2NR_{13}R_{14}$, —O—C(O)—$NR_{13}R_{14}$, —$C_0$-$C_6$ alkyl-C(O)$NR_{15}R_{16}$, $C_1$-$C_6$ alkoxy, $C_1$-$C_6$ thioalkoxy, —O—$(CH_2)_n$—$NR_{15}R_{16}$, —$C_1$-$C_6$ alkyl-$NR_{13}R_{14}$, —$N(R_{13})$—C(O)—$C_1$-$C_6$ alkyl, —$N(R_{13})$—C(O)-aryl, —$C_0$-$C_6$alkyl-C(O)—$N(R_{13})$—$(CH_2)_n$—$NR_{15}R_{16}$, —$C_0$-$C_6$ alkyl-C(O)—$N(R_{13})$—$(CH_2)_n$-aryl, —O—$(CH_2)_n$—C(O)—$N(R_{13})$—$(CH_2)_n$—$NR_{15}R_{16}$, —O—$(CH_2)_n$—C(O)—$NR_{15}R_{16}$, —$C_0$-$C_6$alkyl-C(O)—$N(R_{13})$—$(CH_2)_n$—O—$C_1$-$C_6$ alkyl, —$C_0$-$C_6$ alkyl-$N(R_{13})$—C(O)O—$C_1$-$C_6$ alkyl, —$C_0$-$C_6$alkyl-C(O)-heterocyclyl, —$C_0$-$C_6$alkyl-C(O)-heterocyclyl, —$C_0$-$C_6$alkyl-C(O)-aryl, —$C_0$-$C_6$-alkyl-$R_{21}$, aryloxy, —O—$(CH_2)_n$—$R_{21}$, —$SO_2$-heterocyclyl, $N(R_{13})$—C(O)—$C_3$-$C_7$-cycloalkyl, or $C_1$-$C_6$ alkyl optionally substituted with halo or cyano, wherein each aryl, heteroaryl, cycloalkyl, or heterocyclyl substituent is further optionally substituted with 1-3 groups independently selected from halo, mono-, di-, or tri-halo substituted methyl, $C_1$-$C_6$ alkyl, and $C_1$-$C_6$ alkoxy;

$R_{13}$ and $R_{14}$ are independently H or $C_1$-$C_6$ alkyl, or $R_{23}$ and $R_{14}$ together with the nitrogen to which they are attached form a 4-7 membered heterocyclyl or heteroaryl group wherein one or two ring carbons are each optionally replaced with a heteroatom independently selected from O, N, and S, and wherein each heterocyclyl or heteroaryl group is optionally substituted with one or two of halo, $C_1$-$C_6$ alkyl, or $C_1$-$C_6$ alkoxy;

$R_{15}$ and $R_{16}$ are independently H, $C_1$-$C_6$ alkyl, heteroaryl, or heterocyclyl, or $R_{15}$ and $R_{16}$ together with the nitrogen to which they are attached form a 4-7 membered heterocyclyl or heteroaryl group wherein one or two ring carbons are each optionally replaced with a heteroatom independently selected from O, N, and S, and wherein each heterocyclyl or heteroaryl group is optionally substituted with one or two moieties selected from halo, $C_1$-$C_6$ alkyl, or —C(O)O—$C_1$-$C_6$ alkyl;

$R_{21}$ is heterocyclyl, aryl, heteroaryl, or $C_3$-$C_7$ cycloalkyl, and wherein alkyl, aryl, heteroaryl, $C_3$-$C_7$ cycloalkyl, and heterocyclyl are optionally substituted with one or two moieties independently selected from halo, $C_1$-$C_6$ alkyl, $NR_{13}R_{14}$, and heterocyclyl; and m is 1 or 2; and n is 1-6.

In another embodiment of the compound according to formula IV, X is H, $C_1$-$C_6$ alkyl, or halo.

In another embodiment of the compound according to formula IV, X is H or halo.

In another embodiment of the compound according to formula IV, X is halo. In another embodiment, the halo is Cl or Br. In another embodiment, the halo is Br.

In another embodiment of the compound according to formula IV, Y is H, halo, $C_1$-$C_6$ alkyl, $C_1$-$C_6$ alkoxy, $NR_{15}R_{16}$, —C(O)O—$C_1$-$C_6$ alkyl, —O—$(CH_2)_n$—$NR_{15}R_{16}$, —$N(R_{13})$—$(CH_2)_n$—$NR_{15}R_{16}$, —O—$(CH_2)_n$—$R_{21}$, —O—$R_{21}$, or aryl.

In another embodiment of the compound according to formula IV, Y is H.

In another embodiment of the compound according to formula IV, Y is halo. In another embodiment, the halo is Cl or Br. In another embodiment, the halo is Br.

In another embodiment of the compound according to formula IV, Y is $C_1$-$C_6$ alkyl, including $C_1$-$C_3$ alkyl such as methyl.

In another embodiment of the compound according to formula IV, $R_1$ is aryl or heteroaryl optionally substituted with one, two, or three groups independently selected from $C_1$-$C_6$ alkyl, $C_3$-$C_7$ cycloalkyl, aryl, and heteroaryl.

In another embodiment of the compound according to formula IV, $R_1$ is heteroaryl, optionally substituted with one, two, or three groups independently selected from $C_1$-$C_6$ alkyl, $C_3$-$C_7$ cycloalkyl, aryl, and heteroaryl.

In another embodiment of the compound according to formula IV, $R_1$ is pyrazolyl or isoxazolyl, optionally substituted with one, two, or three groups independently selected from $C_1$-$C_6$ alkyl, $C_3$-$C_7$ cycloalkyl, aryl, and heteroaryl.

In another preferred embodiment of the compound according to formula IV, m is 1 and $R_6$ is aryl, heterocyclyl, or $C_1$-$C_6$ alkyl.

The Compound of Formula V is of the following formula:

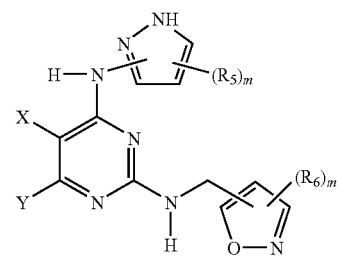

or a pharmaceutically acceptable salt, hydrate, or prodrug thereof, wherein, m is independently 1 or 2;

$R_5$ at each occurrence is independently H, $C_1$-$C_6$ alkyl, $C_3$-$C_7$ cycloalkyl, aryl, or heteroaryl; X is H, halo, $C_1$-$C_6$ alkyl, $NO_2$, mono-, di-, or tri-halo substituted methyl, $NR_{13}R_{14}$, C(O)O—$C_1$-$C_6$ alkyl, or $N(R_{13})$—C(O)—$C_1$-$C_6$ alkyl;

Y is H, halo, OH, $C_1$-$C_6$ alkyl, $NR_{15}R_{16}$, $C_1$-$C_6$ alkoxy, —$N(R_{13})$—$(CH_2)_n$—$NR_{15}R_{16}$, —C(O)O—$C_1$-$C_6$ alkyl, —O—$(CH_2)_n$—$NR_{15}R_{16}$, —C(O)—$C_1$-$C_6$ alkyl, —$C_0$-$C_6$-alkyl-$R_{21}$, —O—$R_{21}$, —C(O)—$R_{21}$, —O—$(CH_2)_n$—$R_{21}$, —C(O)—$NR_{13}R_{14}$, —C(O)—$N(R_{13})$-aryl, —C(O)—$N(R_{13})$—$(CH_2)_n$—$NR_{15}R_{16}$, C(O)—$N(R_{13})$—$(CH_2)_n$-aryl, —C(O)—$N(R_{13})$—$(CH_2)_n$-heterocyclyl;

or X and Y together with the atoms to which they are attached form a 4-7 membered heterocyclyl or heteroaryl group containing one or two heteroatoms independently selected from O, N, and S, wherein the heterocyclyl and heteroaryl group is optionally substituted with one or two moieties selected from halo, $C_1$-$C_6$ alkyl, aryl-$C_1$-$C_6$ alkyl-, aryl-$(CH_2)_n$—O-aryl-, $C_3$-$C_7$ cycloalkyl, heterocyclyl, -aryl-N$(R_{13})$C(O)—$C_3$-$C_7$ cycloalkyl-C(O)—$N(R_{14})$-aryl, and a group of the formula -L-M-Q, wherein L is a bond or $C_3$-$C_7$ cycloalkyl, M is $C_1$-$C_6$ alkyl, $C_2$-$C_6$ alkenyl, or $C_2$-$C_6$ alkynyl, Q is $NR_{13}R_{14}$, $N(R_{13})C(O)$—$C_1$-$C_6$ alkyl, heterocyclyl, or a saturated fused bicyclic ring containing one or two heteroatoms independently selected from O, N, and S, wherein each aryl, heteroaryl, or heterocyclyl substituent on the group formed by X and Y is optionally further substituted with one or two moieties selected from halo, C(O)O—$(CH_2)_n$-phenyl, and C(O)—$C_1$-$C_6$ alkyl;

$R_6$ at each occurrence is independently H, halo, mono-, di-, or tri-halo substituted methyl or methoxy, CN, $NO_2$, $NR_{13}R_{14}$, C(O)O—$C_1$-$C_6$ alkyl, $N(R_{13})C(O)$—$C_1$-$C_6$ alkyl, —$SO_2NR_{13}R_{14}$, —O—C(O)—$NR_{13}R_{14}$, —$C_0$-$C_6$ alkyl-C(O)$NR_{15}R_{16}$, $C_1$-$C_6$ alkoxy, $C_1$-$C_6$ thioalkoxy, —O—$(CH_2)_n$—$NR_{15}R_{16}$, —$C_1$-$C_6$ alkyl-$NR_{13}R_{14}$, —$N(R_{13})$—C(O)—$C_1$-$C_6$ alkyl, —$N(R_{13})$—C(O)-aryl, —$C_0$-$C_6$ alkyl-C(O)—$N(R_{13})$—$(CH_2)_n$—$NR_{15}R_{16}$, —$C_0$-$C_6$ alkyl-C(O)—$N(R_{13})$—$(CH_2)_n$-aryl, —O—$(CH_2)_n$—C(O)—$N(R_{13})$—$(CH_2)_n$—$NR_{15}R_{16}$, —O—$(CH_2)_n$—C(O)—$NR_{15}R_{16}$, —$C_0$-$C_6$ alkyl-C(O)—$N(R_{13})$—$(CH_2)_n$—O—$C_1$-$C_6$ alkyl, —$C_0$-$C_6$ alkyl-$N(R_{13})$—C(O)O—$C_1$-$C_6$ alkyl, —$C_0$-$C_6$alkyl-C(O)-heterocyclyl, —$C_0$-$C_6$alkyl-C(O)-heterocyclyl, —$C_0$-$C_6$alkyl-C(O)-aryl, —$C_0$-$C_6$-alkyl-$R_{21}$, aryloxy, —O—$(CH_2)_n$—$R_{21}$, —$SO_2$-heterocyclyl, $N(R_{13})$—C(O)—$C_3$-$C_7$-cycloalkyl, or $C_1$-$C_6$ alkyl optionally substituted with halo or cyano, wherein each aryl, heteroaryl, cycloalkyl, or heterocyclyl is optionally substituted with 1-3 groups independently selected from halo, mono-, di-, or tri-halo substituted methyl, $C_1$-$C_6$ alkyl, and $C_1$-$C_6$ alkoxy;

$R_{13}$ and $R_{14}$ are independently H or $C_1$-$C_6$ alkyl, or $R_{13}$ and $R_{14}$ together with the nitrogen to which they are attached form a 4-7 membered heterocyclyl or heteroaryl group wherein one or two ring carbons are each optionally replaced with a heteroatom independently selected from O, N, and S, and wherein each heterocyclyl or heteroaryl group is optionally substituted with one or two of halo, $C_1$-$C_6$ alkyl, or $C_1$-$C_6$ alkoxy;

$R_{15}$ and $R_{16}$ are independently H, $C_1$-$C_6$ alkyl, heteroaryl, or heterocyclyl, or $R_{15}$ and $R_{16}$ together with the nitrogen to which they are attached form a 4-7 membered heterocyclyl or heteroaryl group wherein one or two ring carbons are each optionally replaced with a heteroatom independently selected from O, N, and S, and wherein each heterocyclyl and heteroaryl group is optionally substituted with one or two moieties selected from halo, $C_1$-$C_6$ alkyl, and —C(O)O—$C_1$-$C_6$ alkyl;

$R_{21}$ is heterocyclyl, aryl, heteroaryl, or $C_3$-$C_7$ cycloalkyl, and wherein alkyl, aryl, heteroaryl, $C_3$-$C_7$ cycloalkyl, and heterocyclyl are optionally substituted with one or two moieties independently selected from halo, $C_1$-$C_6$ alkyl, $NR_{13}R_{14}$, and heterocyclyl; and n is 1-6.

In another embodiment of the compound according to formula V, X is H, $C_1$-$C_6$ alkyl, or halo.

In another embodiment of the compound according to formula V, X is H or halo.

In another embodiment of the compound according to formula V, X is halo. In another embodiment, the halo is Cl or Br. In another embodiment, the halo is Br.

In another embodiment of the compound according to formula V, Y is H, halo, $C_1$-$C_6$ alkyl, $C_1$-$C_6$ alkoxy, $NR_{15}R_{16}$, —C(O)O—$C_1$-$C_6$ alkyl, —O—$(CH_2)_n$—$NR_{15}R_{16}$, —$N(R_{13})$—$(CH_2)_n$—$NR_{15}R_{16}$, —O—$(CH_2)$—$R_{21}$, —O—$R_{21}$, or aryl.

In another embodiment of the compound according to formula V, Y is H.

In another embodiment of the compound according to formula V, Y is halo. In another embodiment, the halo is Cl or Br. In another embodiment, the halo is Br.

In another embodiment of the compound according to formula V, Y is $C_1$-$C_6$ alkyl, preferably $C_1$-$C_3$ alkyl, more preferably methyl.

In another embodiment of the compound according to formula V, m is 1 and $R_6$ is aryl, heterocyclyl, or $C_1$-$C_6$ alkyl.

In another embodiment of the compound according to Formula I,

V is $NR_1R_{1a}$, $R_1$ is —$C_0$-$C_6$ alkyl-$R_{20}$, wherein $R_{20}$ heteroaryl, wherein the heteroaryl is optionally substituted with one, two, or three groups independently selected from $C_1$-$C_6$ alkyl, and —$C_0$-$C_6$ alkyl-$R_{21}$;

$R_{1a}$ is H;

X is H, or halo;

Y is H, $C_1$-$C_6$ alkyl, $NR_{15}R_{16}$, $C_0$-$C_6$ alkyl-$NR_{15}R_{16}$, —$N(R_{13})$—$(CH_2)_n$—$NR_{15}R_{16}$, —O—$(CH_2)_n$—$NR_{15}R_{16}$, —$C_0$-$C_6$-alkyl-$R_{21}$, —O—$R_{21}$ or —O—$(CH_2)_n$—$R_{21}$;

Z is $NR_2R_3$, or —O—$R_{2a}$, wherein $R_2$ is —$C_0$-$C_6$-alkyl-heteroaryl, wherein the heteroaryl is optionally substituted with one, two, or three groups independently selected from —$C_0$-$C_6$-alkyl-$R_{21}$ or $C_1$-$C_6$ alkyl;

$R_3$ is H;

$R_{2a}$ is $C_0$-$C_6$ alkyl-heteroaryl, wherein the heteroaryl is optionally substituted with aryl;

$R_{13}$ is H;

$R_{15}$ and $R_{16}$ are independently H, $C_1$-$C_6$ alkyl or heterocyclyl optionally substituted with $C_1$-$C_6$ alkyl;

$R_{21}$ is heterocyclyl, aryl, heteroaryl, or $C_3$-$C_7$ cycloalkyl, and wherein alkyl, aryl, heteroaryl, $C_3$-$C_7$ cycloalkyl, and heterocyclyl are optionally substituted with one or two moieties independently selected from halo, —$S(O)_2$—$C_0$-$C_1$ alkyl, —C(O)—$C_0$-$C_1$ alkyl, —C(O)—H, —$C_0$-$C_1$ alkyl-aryl, $C_1$-$C_6$ alkyl or $NR_{13}R_{14}$; and n is 1-4.

In another embodiment of the compound according to formula I, Z is $NR_2R_3$, wherein $R_2$ is —$C_1$-$C_3$-alkyl-heteroaryl, wherein the heteroaryl is optionally substituted with $R_{21}$ or $C_1$-$C_4$ alkyl. Non-limiting examples of the $C_1$-$C_4$ alkyl include methyl, propyl or isopropyl. Also preferred are compounds wherein the $R_{21}$ is heteroaryl or aryl wherein the heteroaryl and aryl are optionally substituted with halo or $NH_2$. Preferably, the halo is fluoro.

In another embodiment of the compound according to formula I, Z is —O—$R_2R_3$, wherein $R_2$ is $C_1$-$C_2$ alkyl-heteroaryl, wherein the heteroaryl is optionally substituted with phenyl.

In another embodiment of the compound according to formula I, $R_1$ is heteroaryl optionally substituted with $C_1$-$C_4$ alkyl or $R_{2n}$. In another embodiment, the $C_1$-$C_4$ alkyl is methyl, propyl, isopropyl. In another embodiment, $R_{21}$ is $C_3$-$C_4$ cycloalkyl such as cyclopropyl.

In another embodiment of the compound according to formula I, X is chloro.

In another embodiment of the compound according to formula I, Y is $C_1$-$C_4$ alkyl, $NR_{15}R_{16}$, $C_1$-$C_4$ alkyl-$NR_{15}R_{16}$, —N(H)—$(CH_2)_{2-3}$—$NR_{15}R_{16}$, —O—$(CH_2)_2$—$NR_{15}R_{16}$, —$R_{21}$, —O—$R_{21}$ or —O—$(CH_2)_2$—$R_{21}$. In another embodiment, $R_{15}$ and $R_{16}$ are independently H, $C_1$-$C_4$ alkyl or heterocyclyl optionally substituted with $C_1$-$C_3$ alkyl. In another embodiment, $R_{15}$ and $R_{16}$ are independently methyl, ethyl, propyl, heterocyclyl optionally substituted with methyl, ethyl or propyl. In another embodiment, $R_{21}$ is heterocyclyl optionally substituted with one or two moieties independently selected from —$S(O)_2$—$C_1$-$C_3$ alkyl, —C(O)—$C_1$-$C_3$ alkyl, —C(O)—H, $C_1$-$C_2$ alkyl-aryl, or $C_1$-$C_4$ alkyl. In another embodiment, $R_{21}$ is optionally substituted with one or two moieties independently selected from —$S(O)_2$—$CH_3$, —C(O)—$CH_3$, —$CH_2$-phenyl, methyl, ethyl or propyl.

The Compound of formula VI is of the following formula:

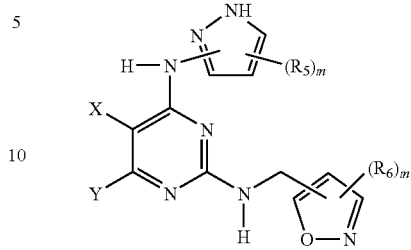

VI wherein,
m is 1 or 2 or 3;
$R_5$ is $C_1$-$C_6$ alkyl or —$C_0$-$C_6$ alkyl-$R_{21}$;
X is H, or halo;
Y is —$C_0$-$C_6$-alkyl-$R_{21}$;
$R_6$ is —$C_0$-$C_6$-alkyl-$R_2$, or $C_1$-$C_6$ alkyl;
$R_{21}$ is heterocyclyl, aryl, heteroaryl, or $C_3$-$C_7$ cycloalkyl, and wherein alkyl, aryl, heteroaryl, $C_3$-$C_7$ cycloalkyl, and heterocyclyl are optionally substituted with one or two moieties independently selected from halo, —$S(O)_2$—$C_0$-$C_1$ alkyl, —C(O)—$C_0$-$C_1$ alkyl, —C(O)—H, —$C_0$-$C_1$ alkyl-aryl, $C_1$-$C_6$ alkyl or $NR_{13}R_{14}$.

In another embodiment of the compound according to formula VI, Y is heterocyclyl optionally substituted with $C_1$-$C_3$ alkyl, X is H or halo, $R_5$ is $C_3$-$C_4$ cycloalkyl and $R_6$ is $C_1$-$C_4$ alkyl. In another embodiment, Y is heterocyclyl optionally substituted with methyl, ethyl, propyl or isopropyl, X is H, $R_5$ is cyclopropyl and $R_6$ is methyl, ethyl, propyl or isopropyl.

In another embodiment, the compound is selected from compounds listed in Tables 1 and 1a, or a pharmaceutically acceptable salt, hydrate, or prodrug thereof.

TABLE 1

"Abs" refers to absolute stereochemistry.

| Entry | Structure |
|---|---|
| 1 | 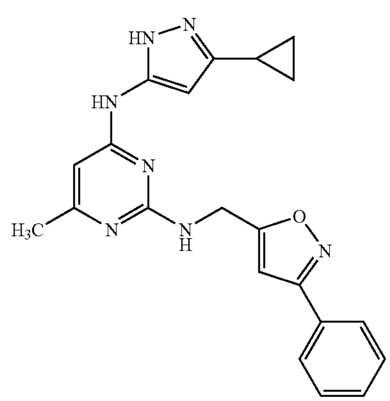 |

TABLE 1-continued
2
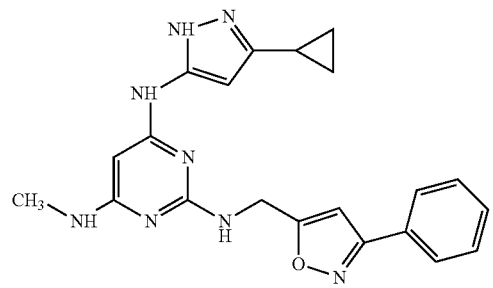
3
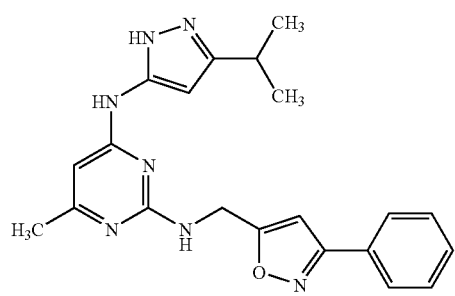
4
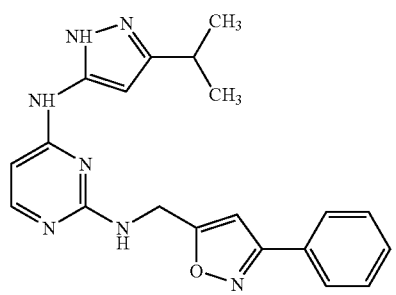
5
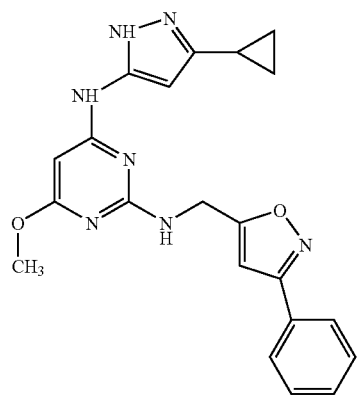

TABLE 1-continued
| | |
|---|---|
| 6 | 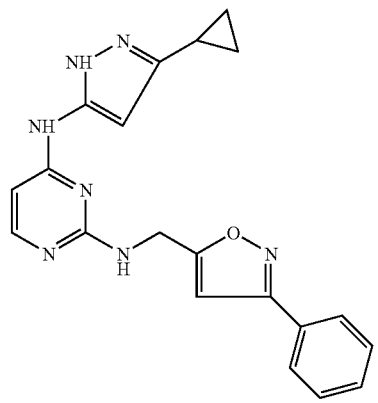 |
| 7 | 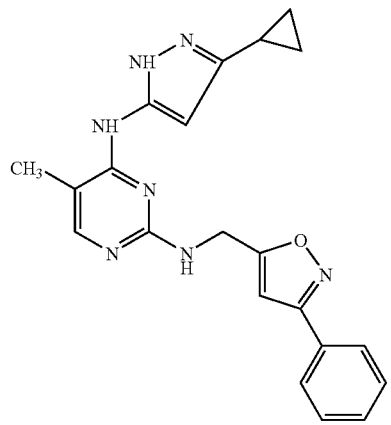 |
| 8 | 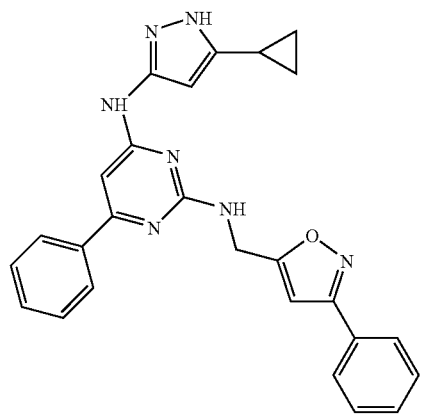 |
| 9 | 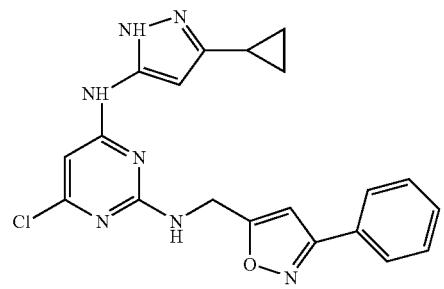 |

TABLE 1-continued
| | |
|---|---|
| 10 | 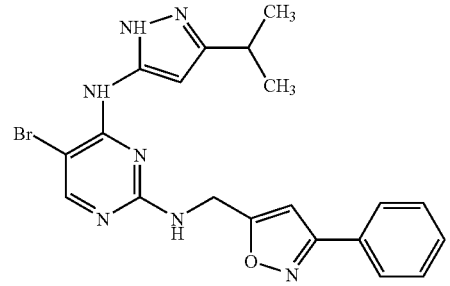 |
| 11 | 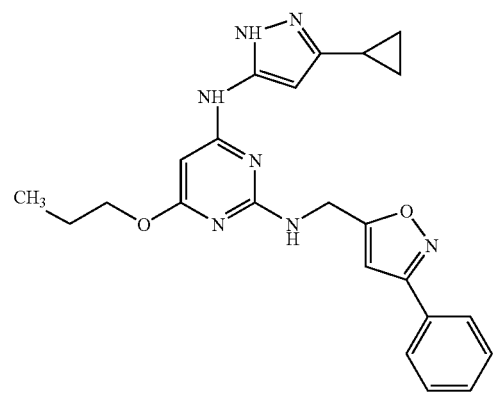 |
| 12 | 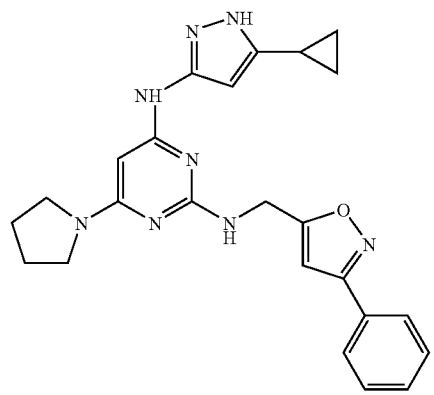 |
| 13 | 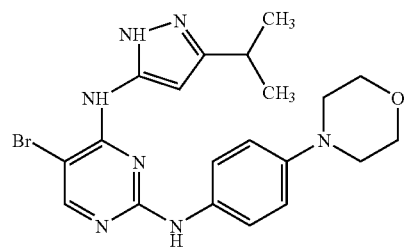 |

TABLE 1-continued
| | |
|---|---|
| 14 | 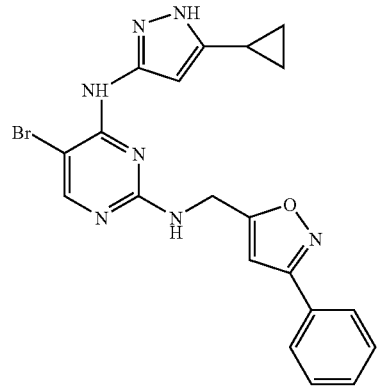 |
| 15 | 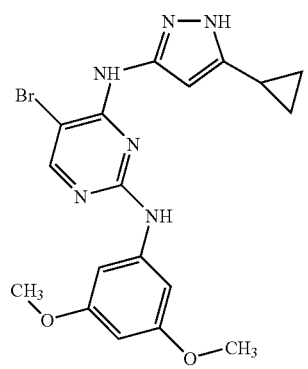 |
| 16 | 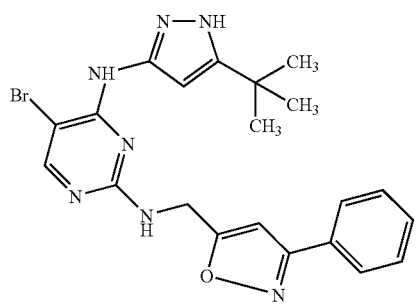 |
| 17 | 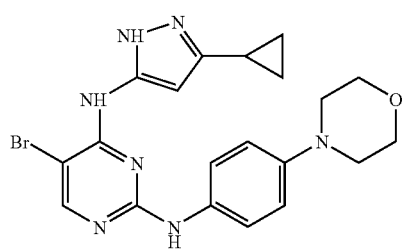 |
| 18 | 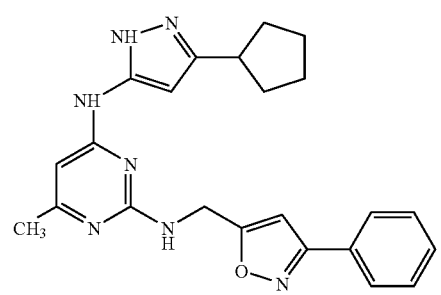 |

TABLE 1-continued
| | |
|---|---|
| 19 | 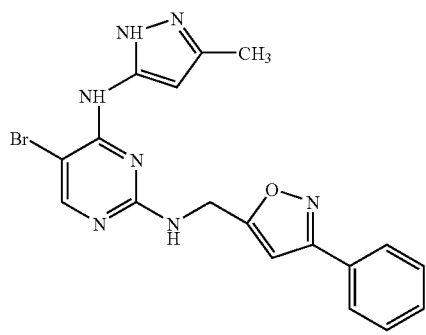 |
| 20 | 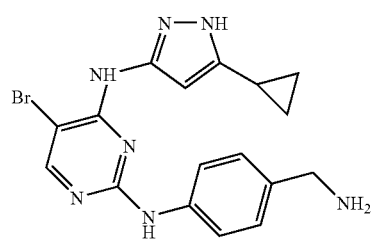 |
| 21 | 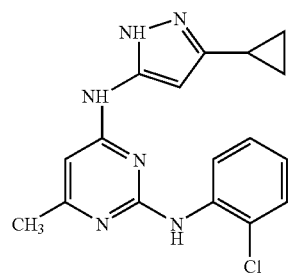 |
| 22 | 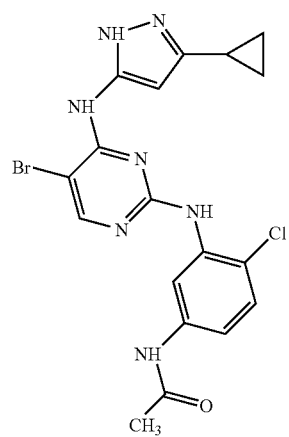 |
| 23 | 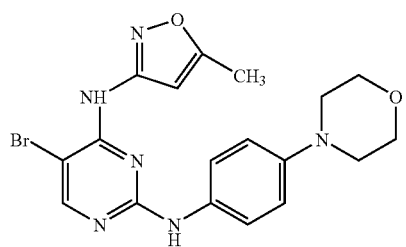 |

TABLE 1-continued
| 24 | 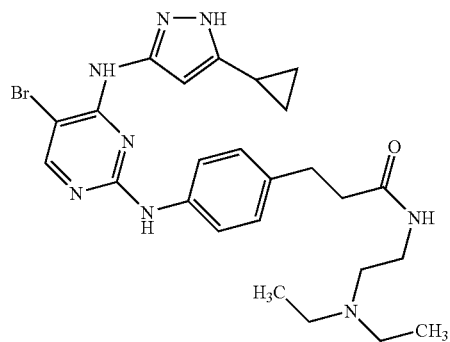 |
| --- | --- |
| 25 | 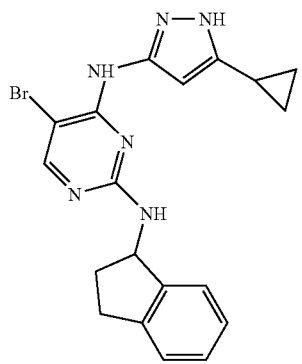 |
| 26 | 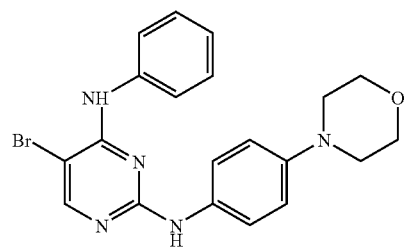 |
| 27 | 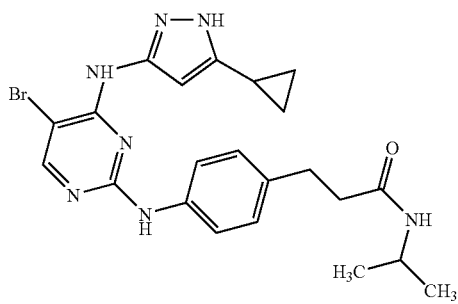 |
| 28 | 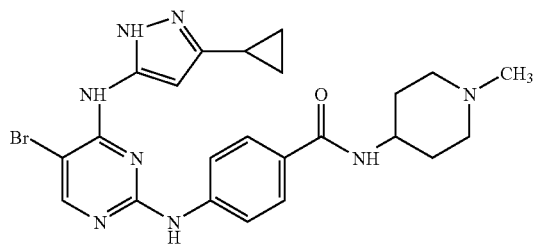 |

TABLE 1-continued
29 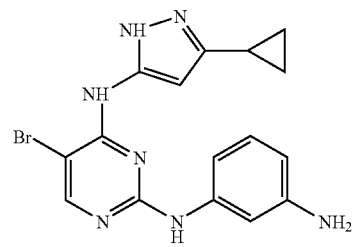
30 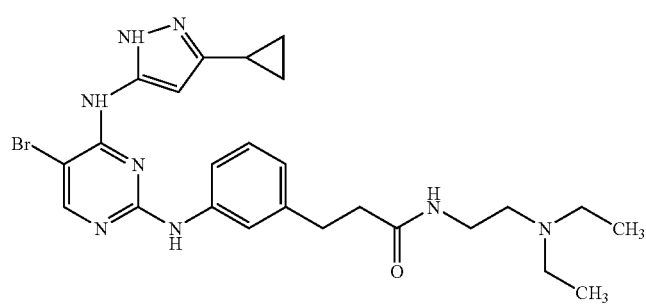
31 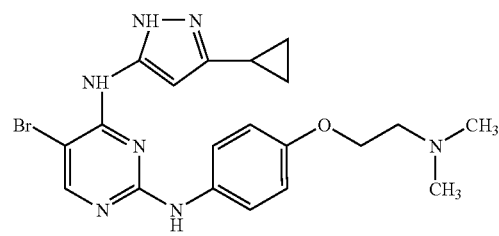
32 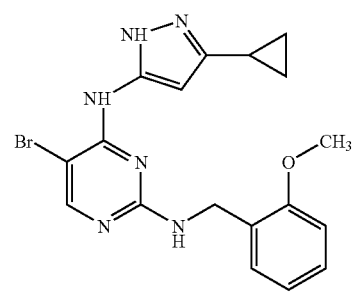
33 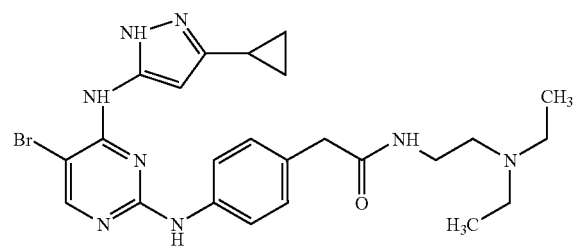

TABLE 1-continued
| | |
|---|---|
| 34 | 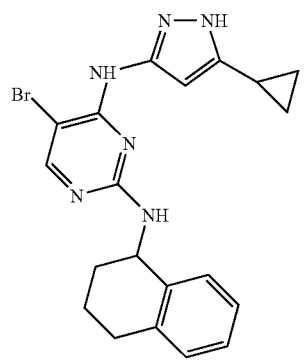 |
| 35 | 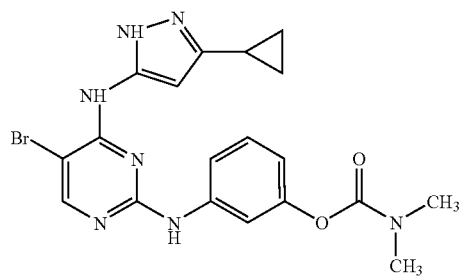 |
| 36 | 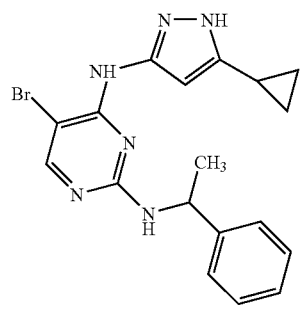 |
| 37 | 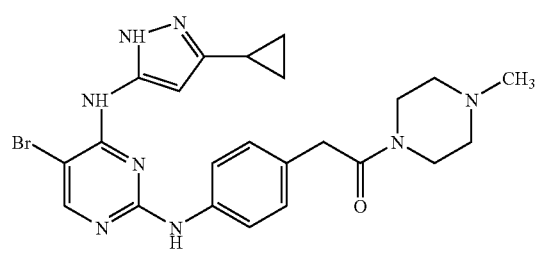 |
| 38 | 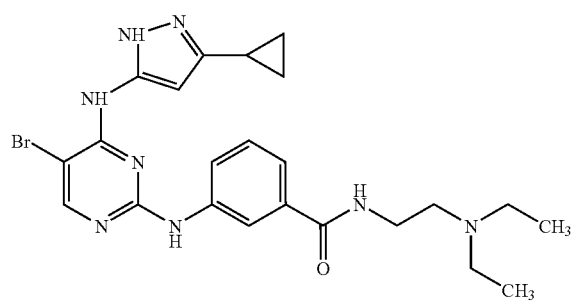 |

TABLE 1-continued
| 39 | 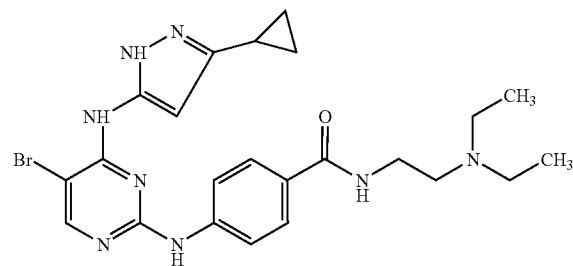 |
| --- | --- |
| 40 | 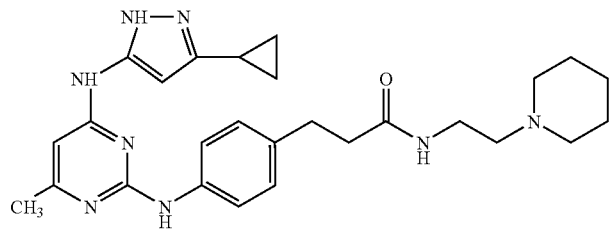 |
| 41 | 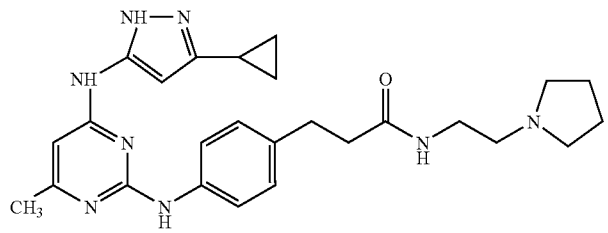 |
| 42 | 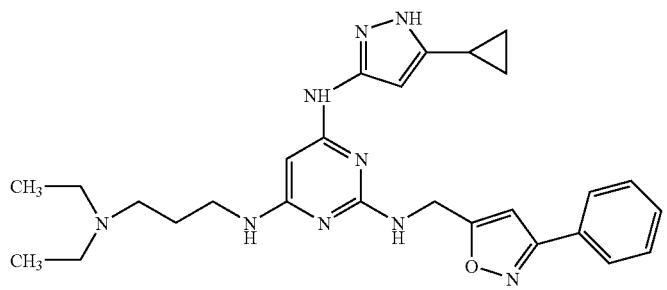 |
| 43 | 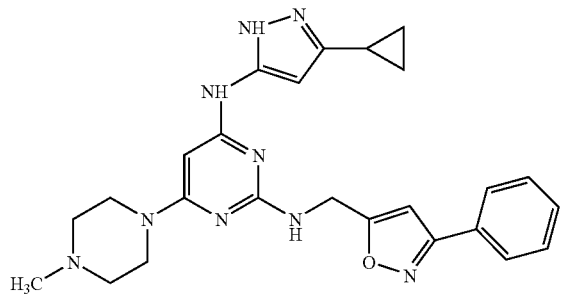 |
| 44 | 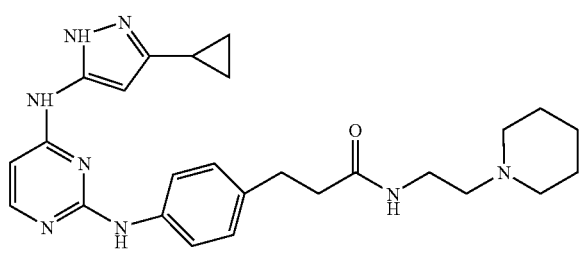 |

TABLE 1-continued
| 45 | 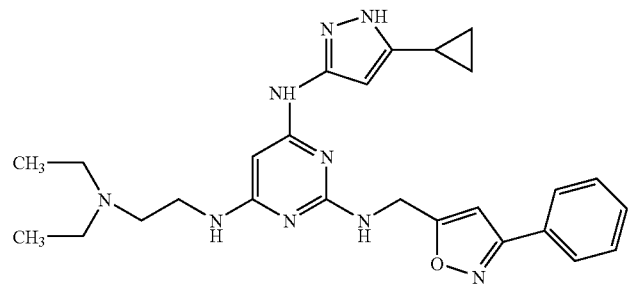 |
| 46 | 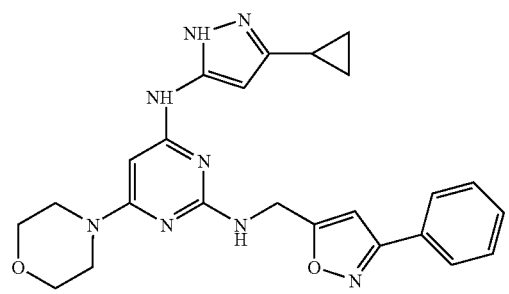 |
| 47 | 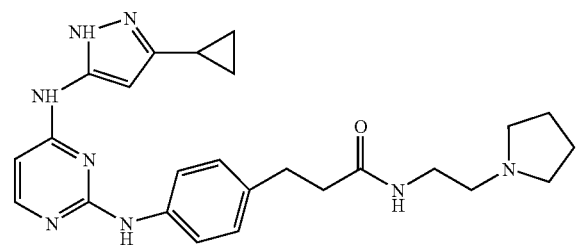 |
| 48 | 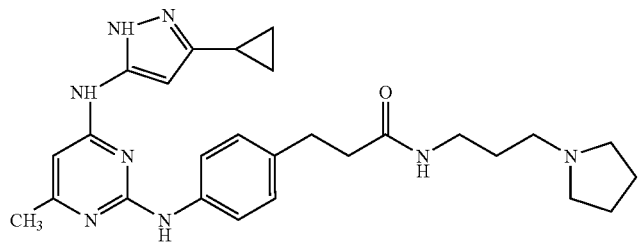 |
| 49 | 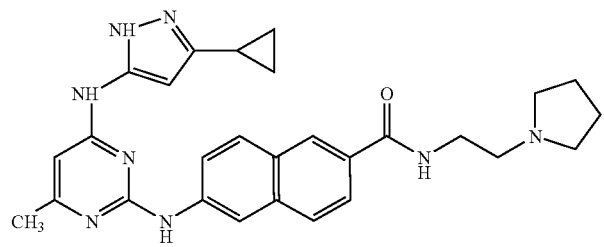 |

TABLE 1-continued
| 50 | 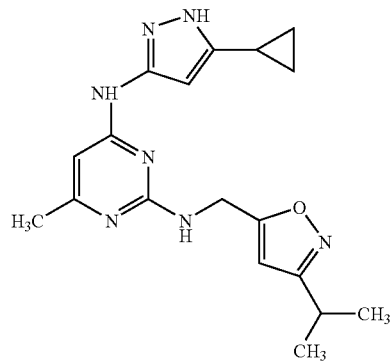 |
| --- | --- |
| 51 | 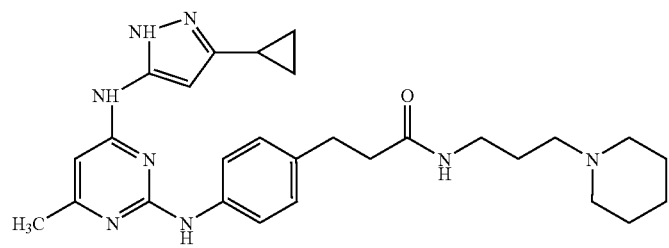 |
| 52 | 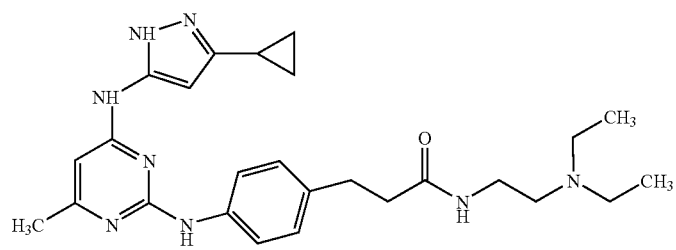 |
| 53 | 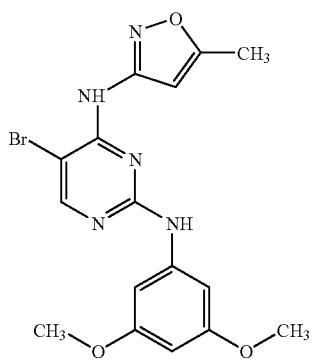 |
| 54 | 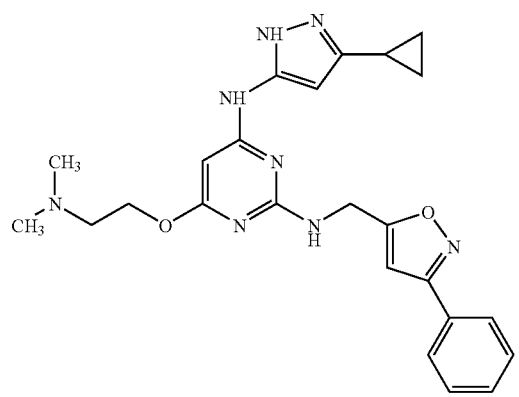 |

TABLE 1-continued
| 55 | 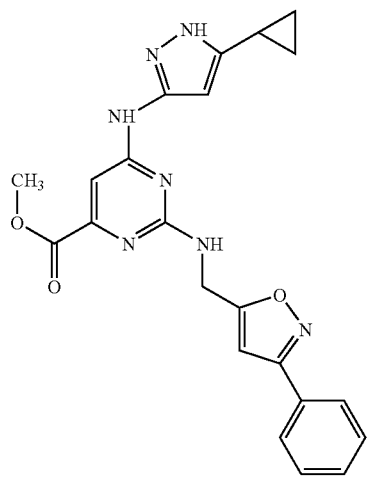 |
| 56 | 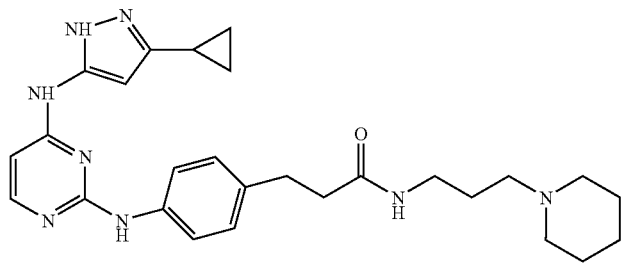 |
| 57 | 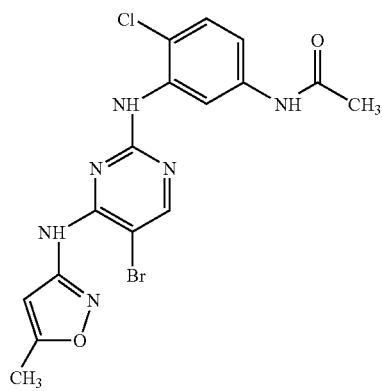 |
| 58 | 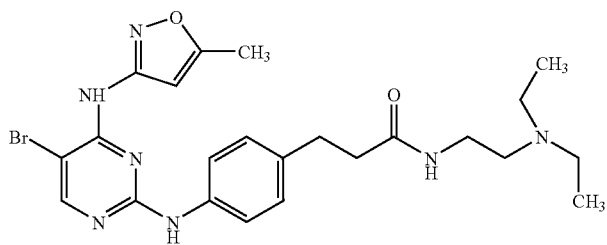 |
| 59 | 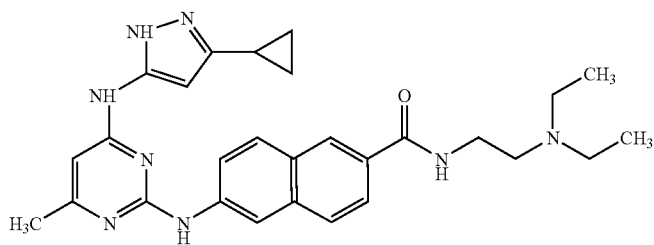 |

TABLE 1-continued
| | |
|---|---|
| 60 | 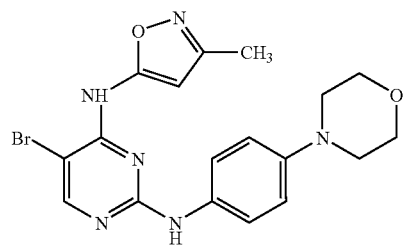 |
| 61 | 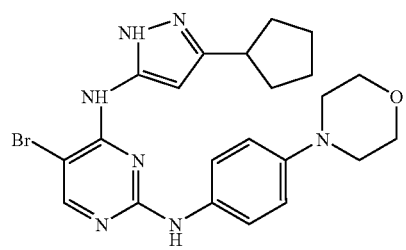 |
| 62 | 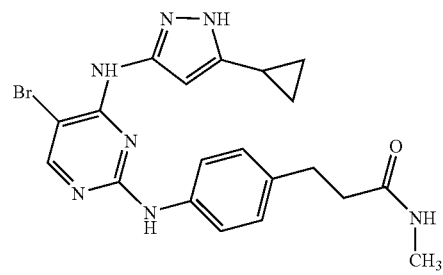 |
| 63 | 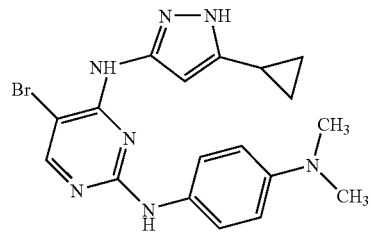 |
| 64 | 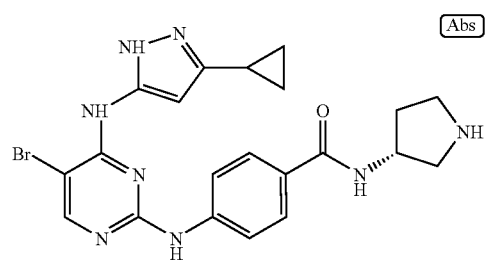 |

TABLE 1-continued
65 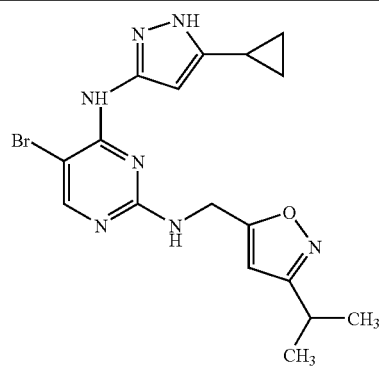
66 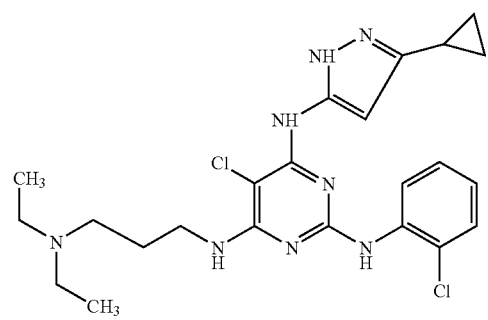
67 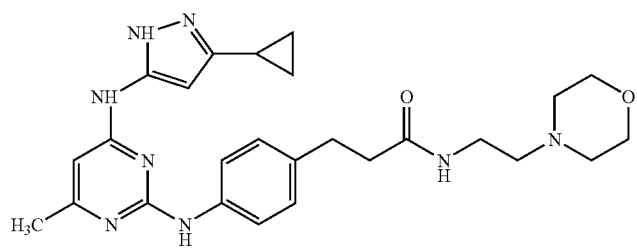
68 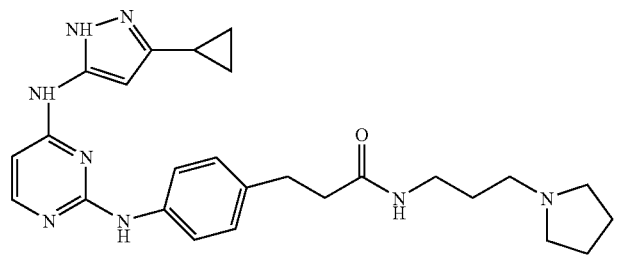
69 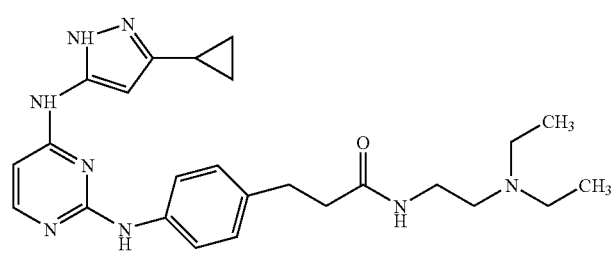

TABLE 1-continued
| | |
|---|---|
| 70 | 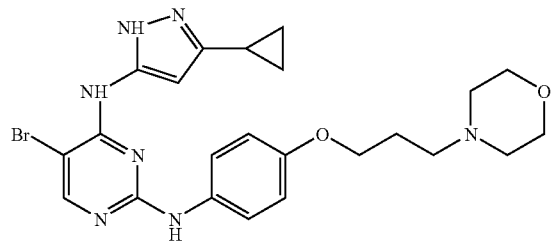 |
| 71 | 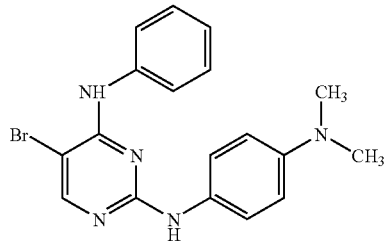 |
| 72 | 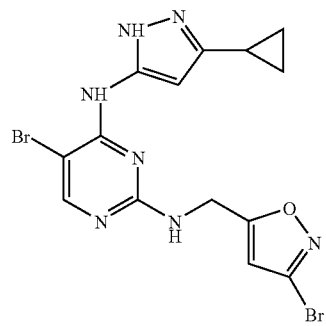 |
| 73 | 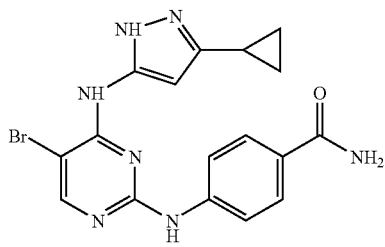 |
| 74 | 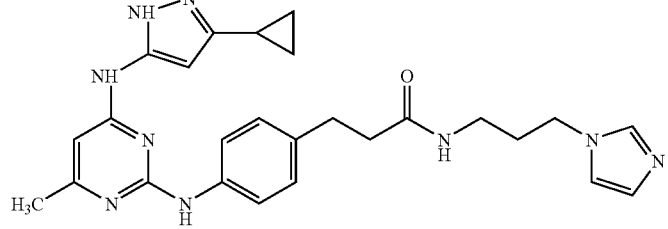 |
| 75 | 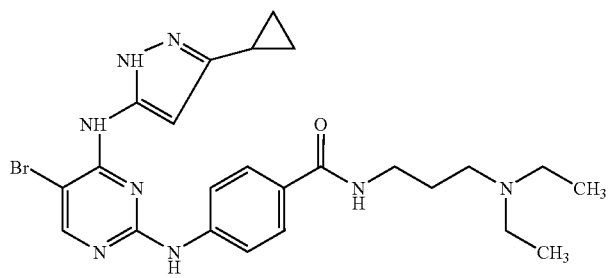 |

TABLE 1-continued
| | |
|---|---|
| 76 | 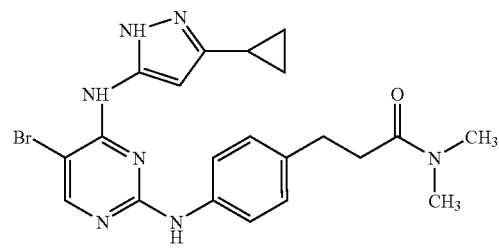 |
| 77 | 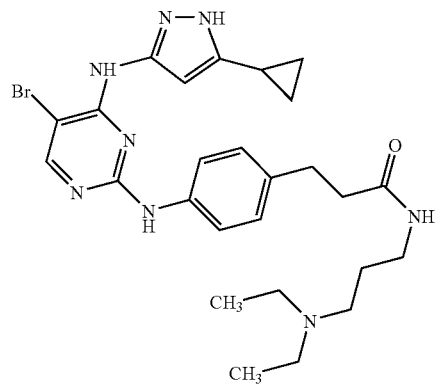 |
| 78 | 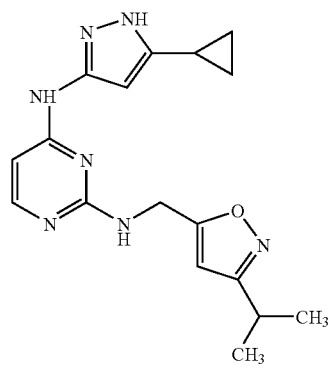 |
| 79 | 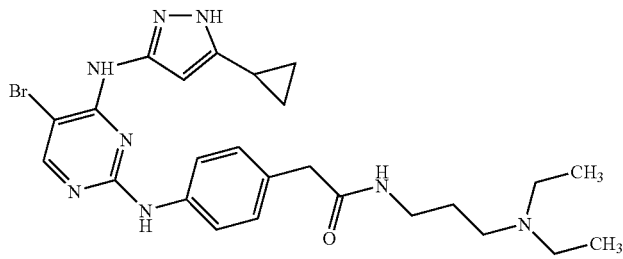 |
| 80 | 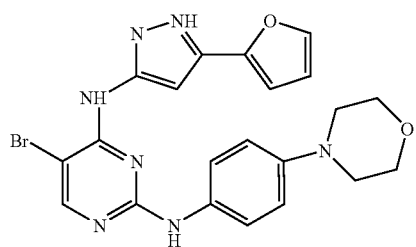 |

TABLE 1-continued
| 81 | 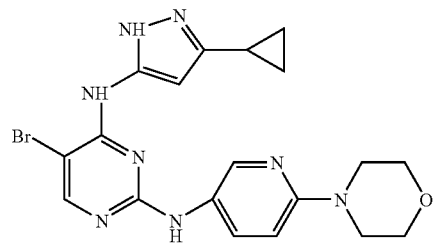 |
| 82 | 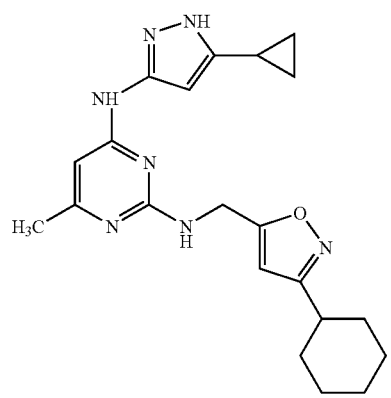 |
| 83 | 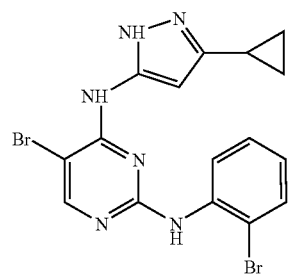 |
| 84 | 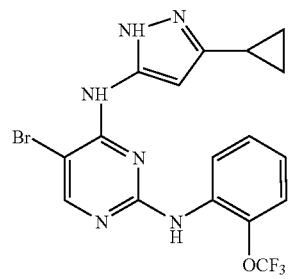 |
| 85 | 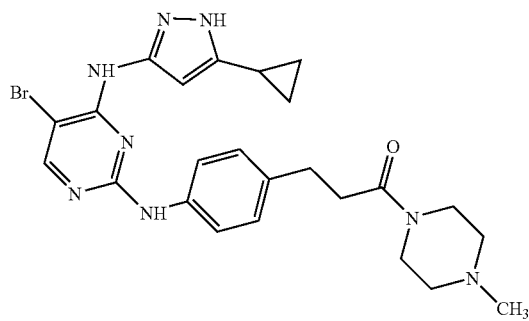 |

TABLE 1-continued
| | |
|---|---|
| 86 | 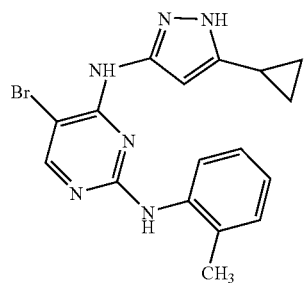 |
| 87 | 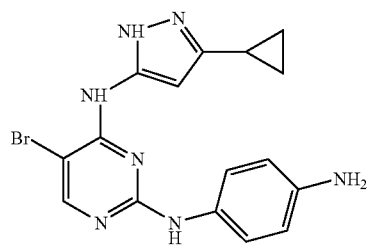 |
| 88 | 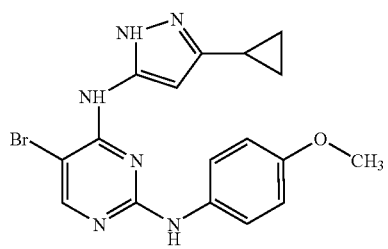 |
| 89 | [Abs] 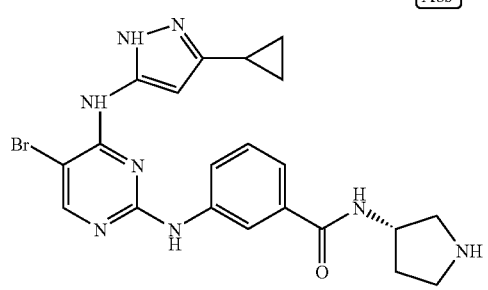 |
| 90 | 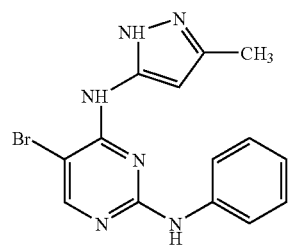 |
| 91 | 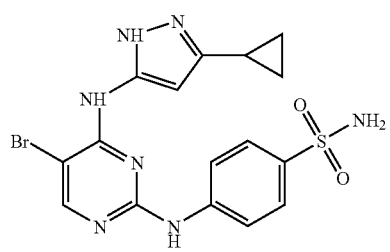 |

TABLE 1-continued
92
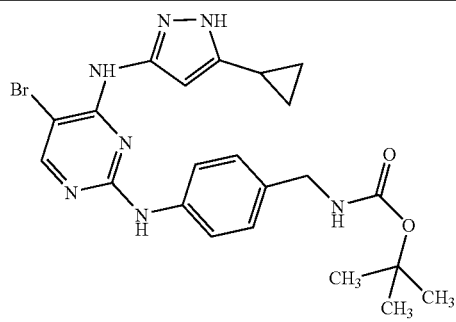
93
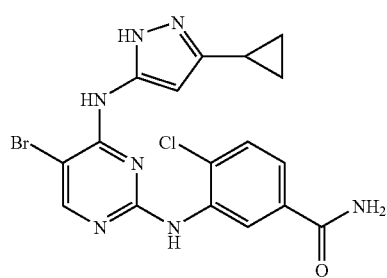
94
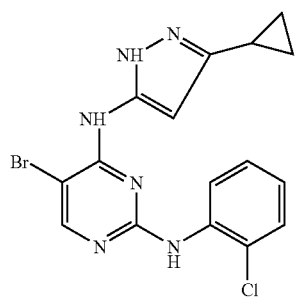
95
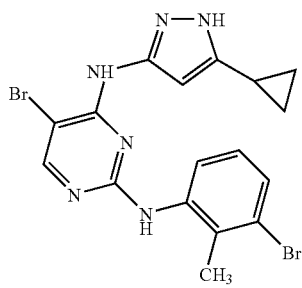
96
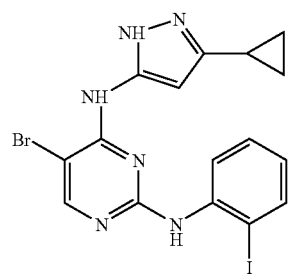

TABLE 1-continued
| 97 | 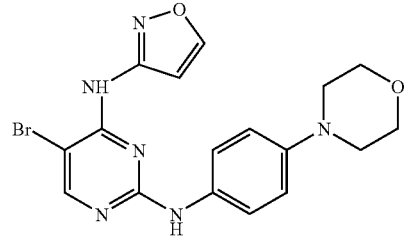 |
| --- | --- |
| 98 | 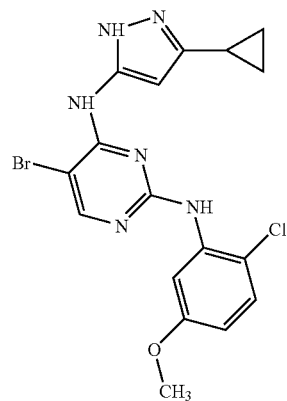 |
| 99 | 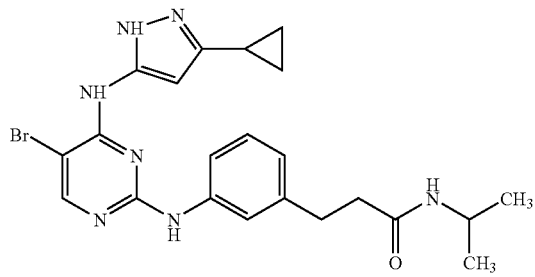 |
| 100 | 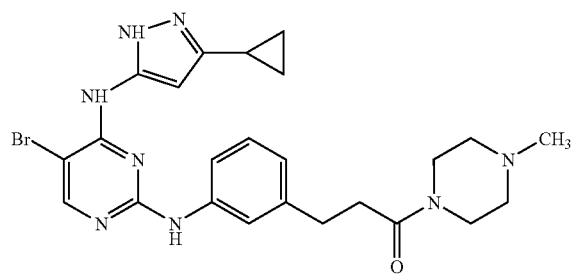 |
| 101 | 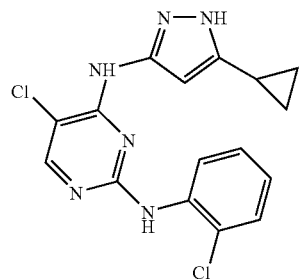 |

TABLE 1-continued
| 102 | 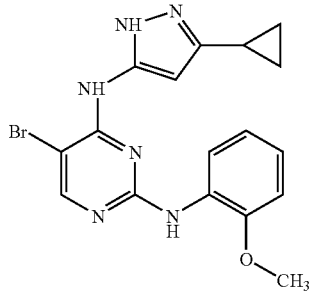 |
| --- | --- |
| 103 | 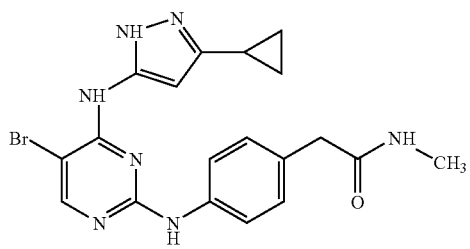 |
| 104 | 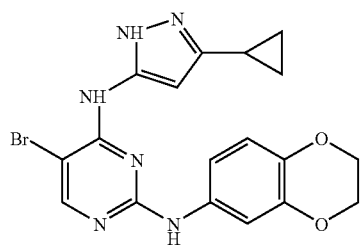 |
| 105 | 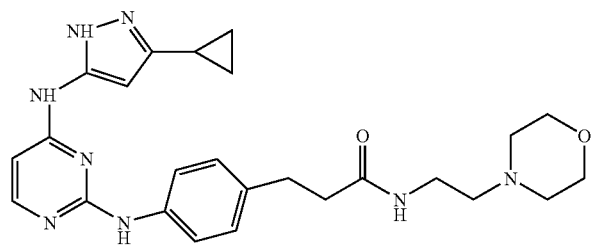 |
| 106 | 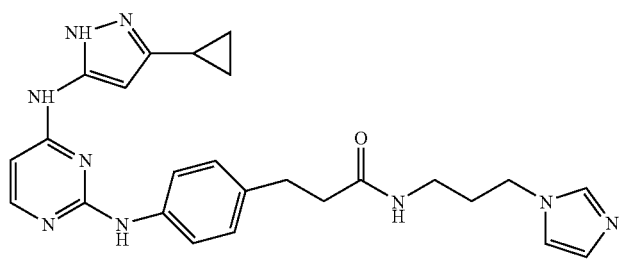 |
| 107 | 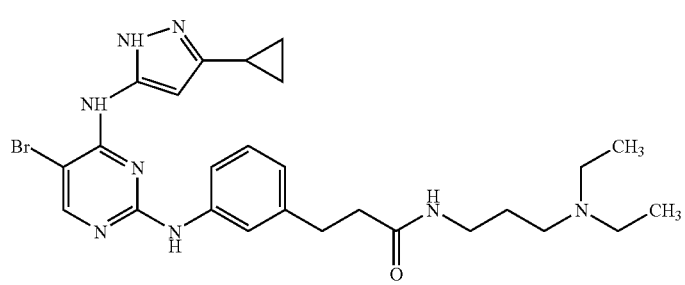 |

TABLE 1-continued
| 108 | 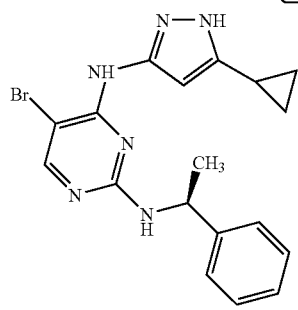 |
| --- | --- |
| 109 | 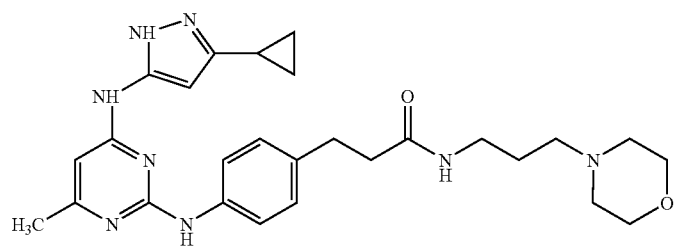 |
| 110 | 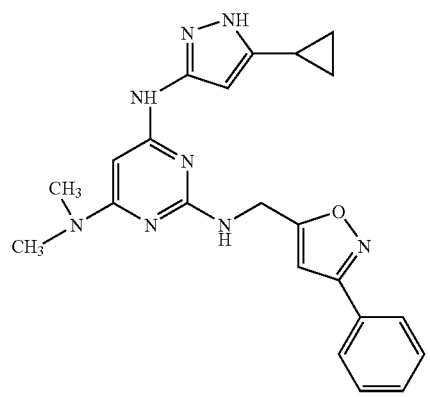 |
| 111 | 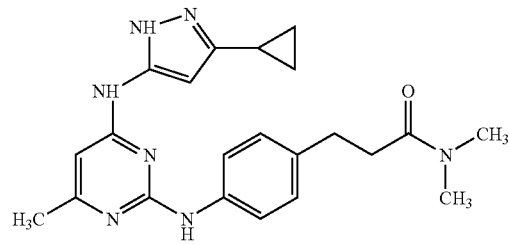 |
| 112 | 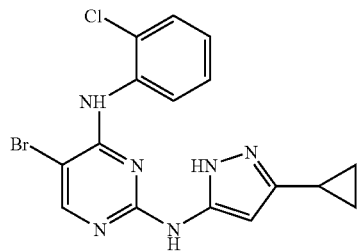 |

TABLE 1-continued
| | |
|---|---|
| 113 | 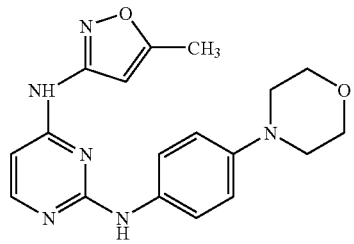 |
| 114 | 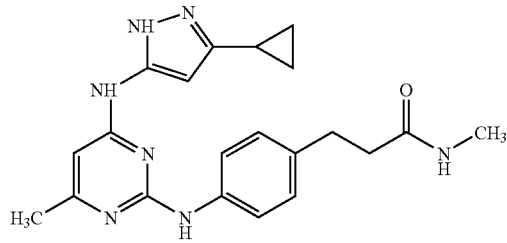 |
| 115 | 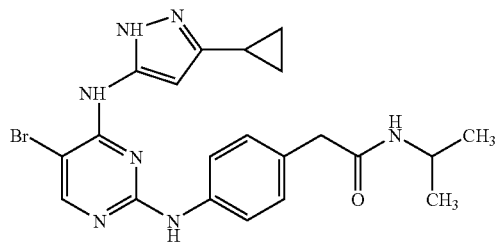 |
| 116 | 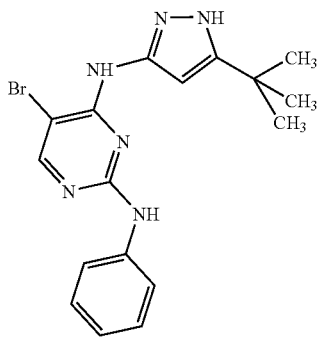 |
| 117 | 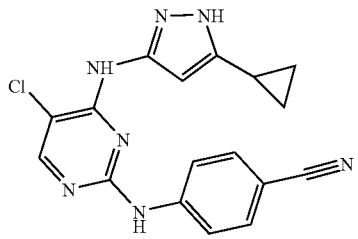 |
| 118 | 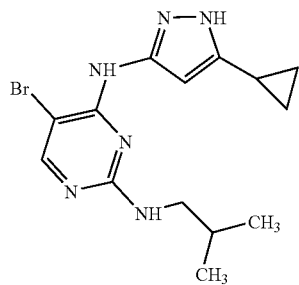 |

TABLE 1-continued
| | |
|---|---|
| 119 | 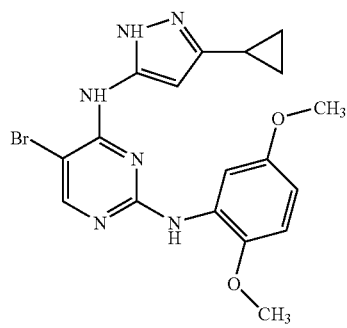 |
| 120 | 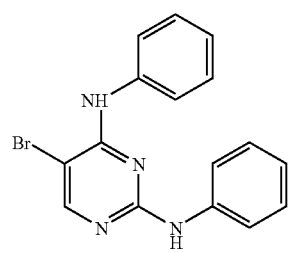 |
| 121 | 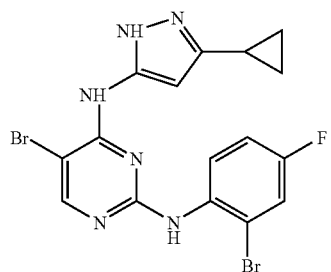 |
| 122 | 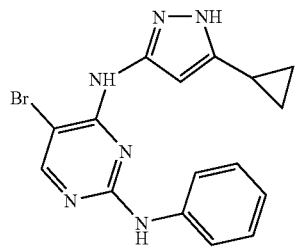 |
| 123 | 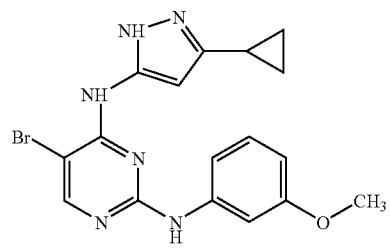 |
| 124 | 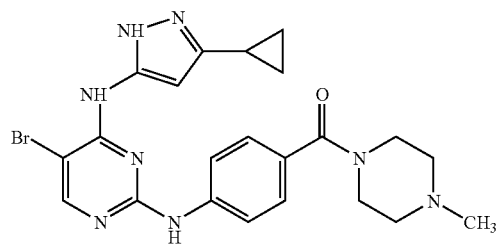 |

TABLE 1-continued
| 125 | 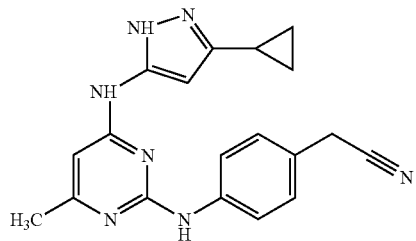 |
| 126 | 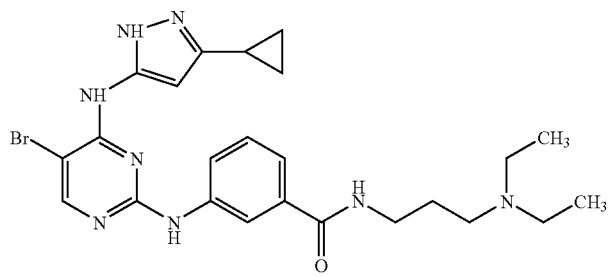 |
| 127 | 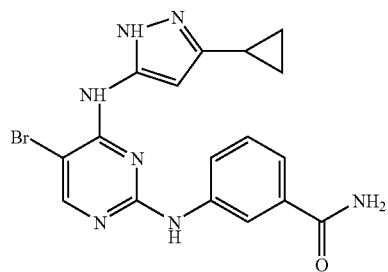 |
| 128 | 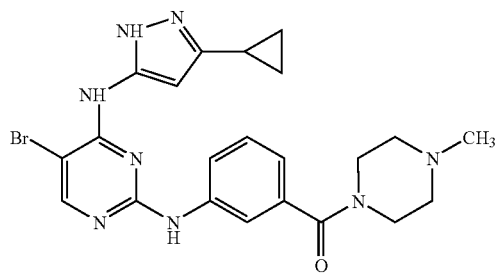 |
| 129 | 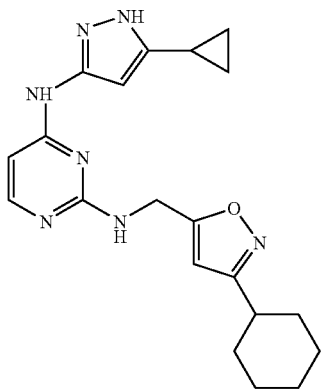 |

TABLE 1-continued
| 130 | 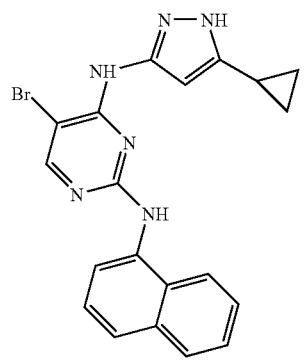 |
| 131 | 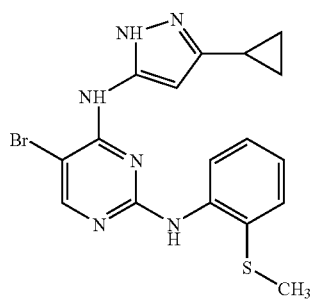 |
| 132 | 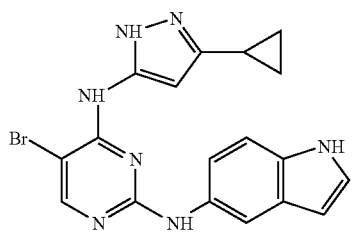 |
| 133 | 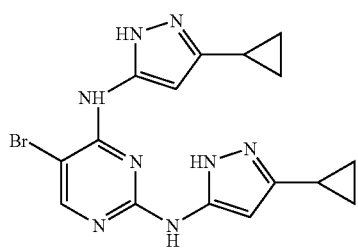 |
| 134 | 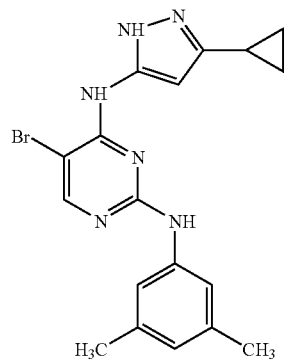 |

TABLE 1-continued
| | |
|---|---|
| 135 | 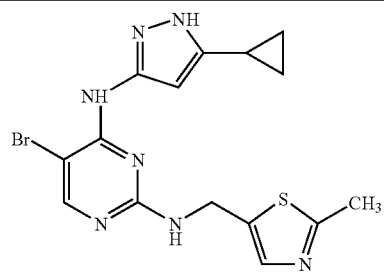 |
| 136 | 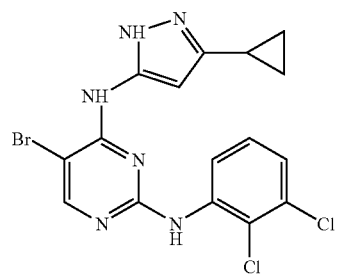 |
| 137 | 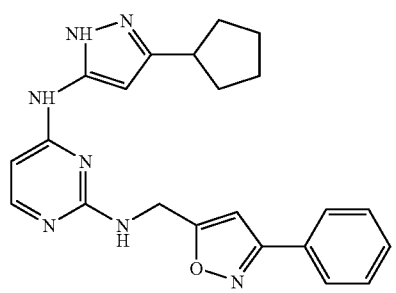 |
| 138 | 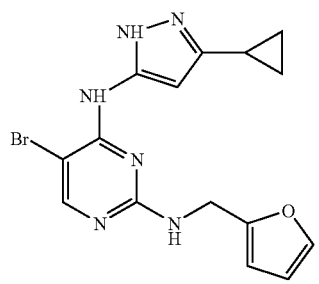 |
| 139 | 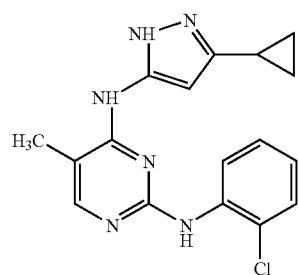 |

TABLE 1-continued
| 140 | 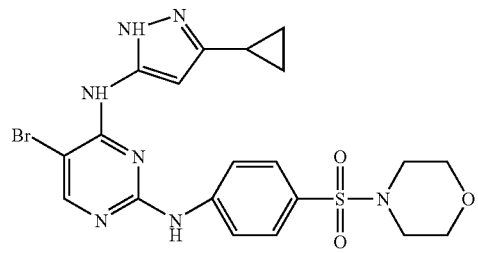 |
| --- | --- |
| 141 | 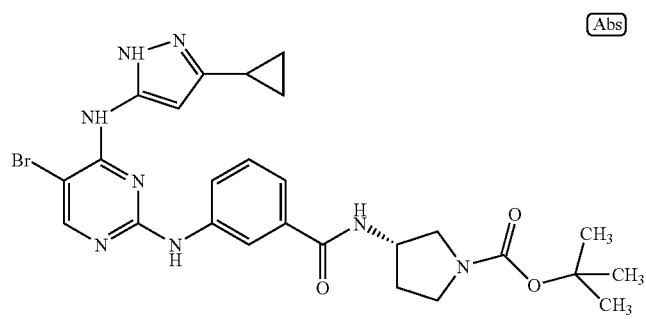 Abs |
| 142 | 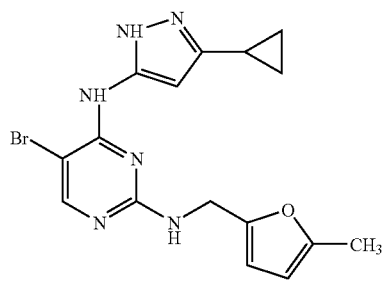 |
| 143 | 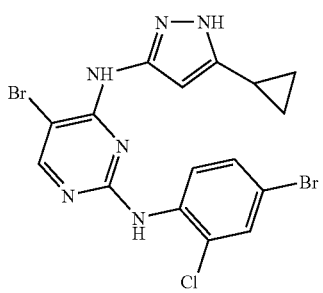 |
| 144 | 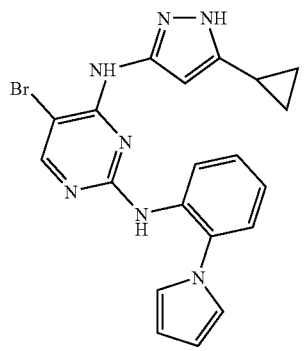 |

TABLE 1-continued
| 145 | 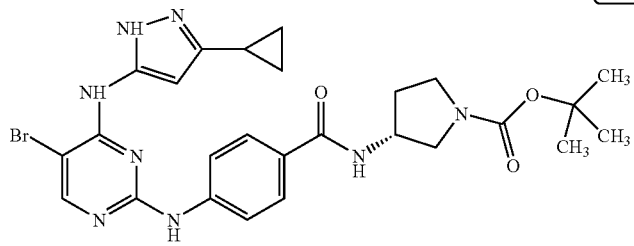 Abs |
|---|---|
| 146 | 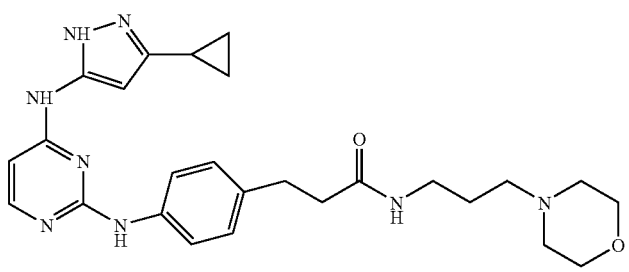 |
| 147 | 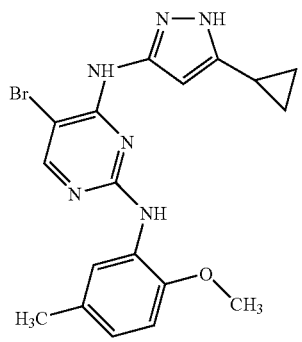 |
| 148 | 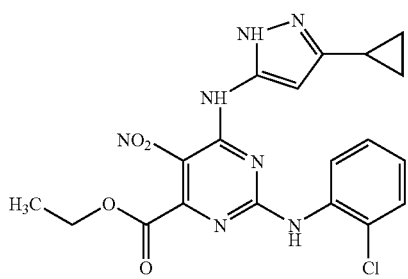 |
| 149 | 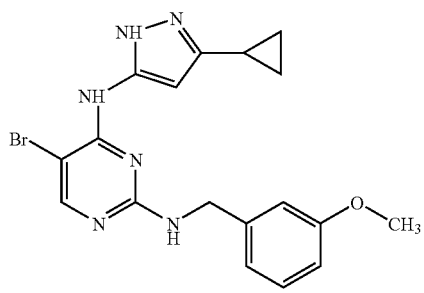 |

TABLE 1-continued
| 150 | 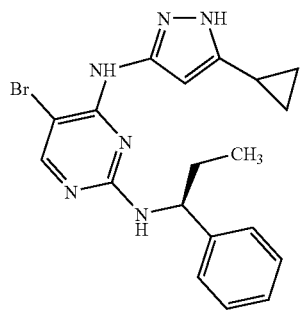 |
| --- | --- |
| 151 | 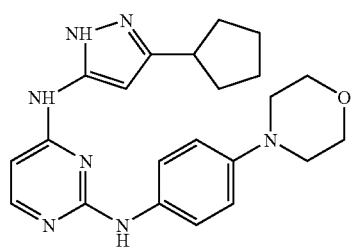 |
| 152 | 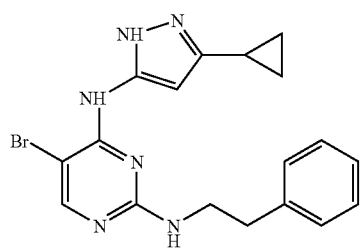 |
| 153 | 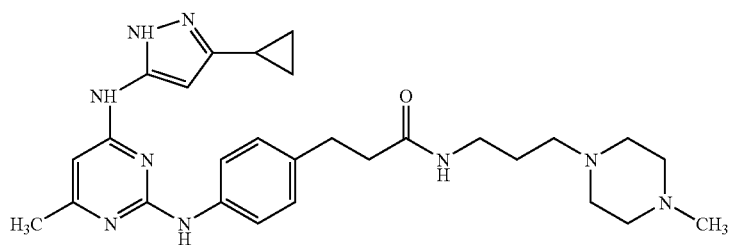 |
| 154 | 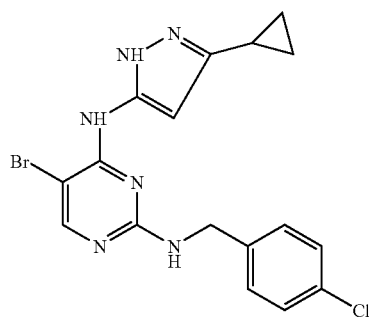 |

TABLE 1-continued
| 155 | 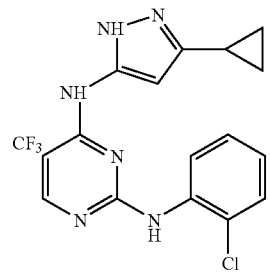 |
| 156 | 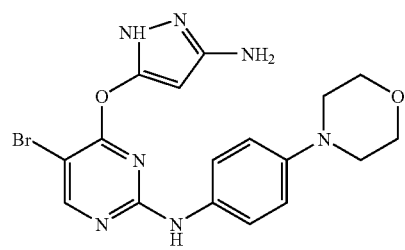 |
| 157 | 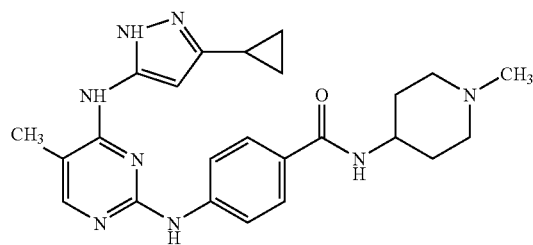 |
| 158 | 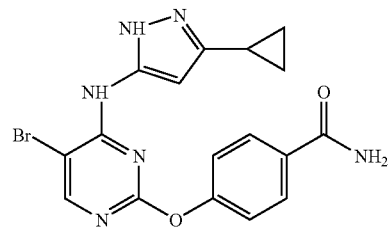 |
| 159 | 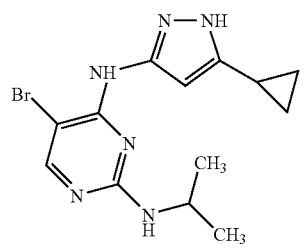 |
| 160 | 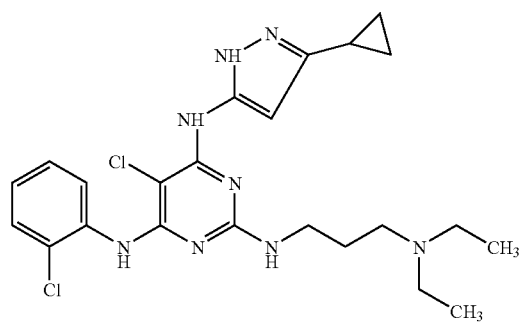 |

TABLE 1-continued
| | |
|---|---|
| 161 | 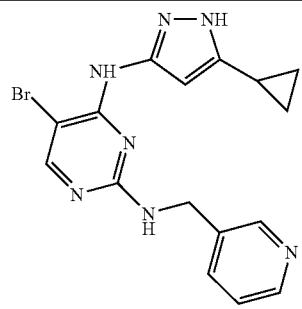 |
| 162 | 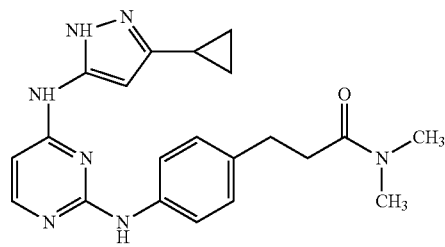 |
| 163 | 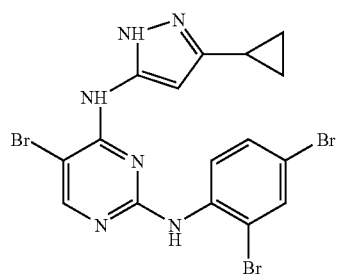 |
| 164 | 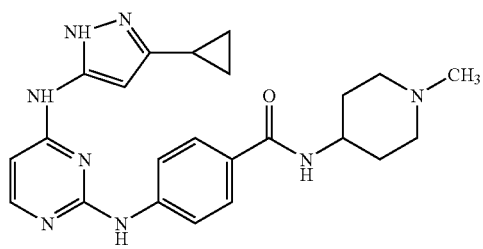 |
| 165 | 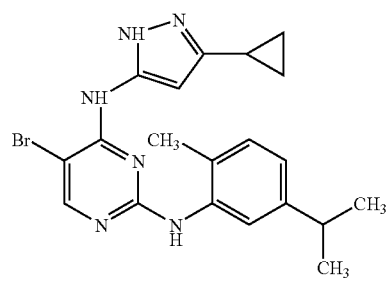 |
| 166 | 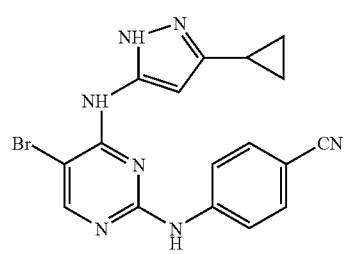 |

TABLE 1-continued
167 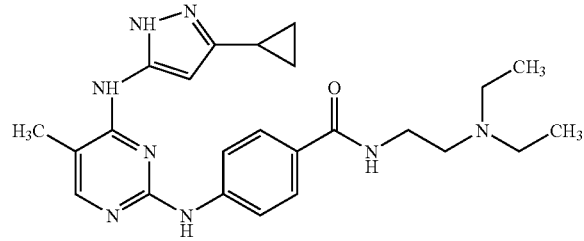
168 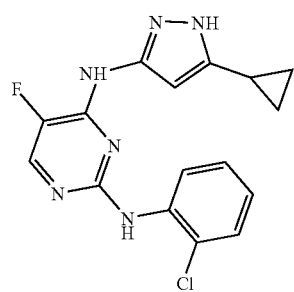
169 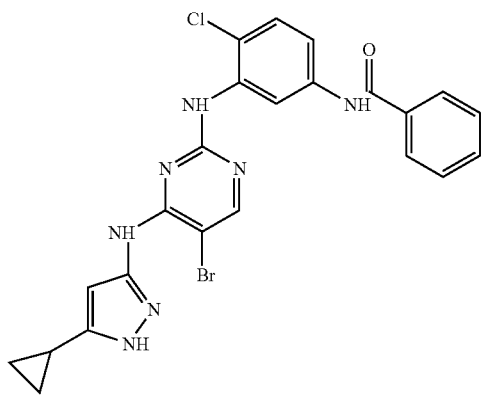
170 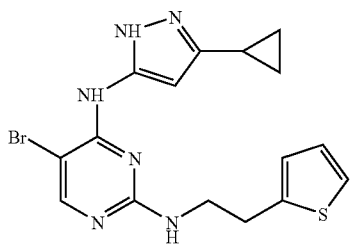
171 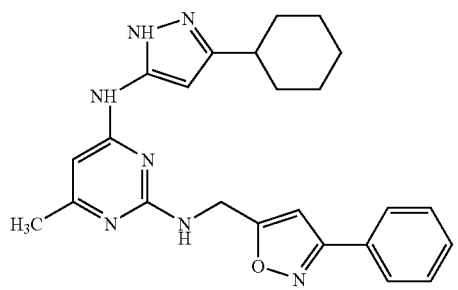

TABLE 1-continued
| | |
|---|---|
| 172 | 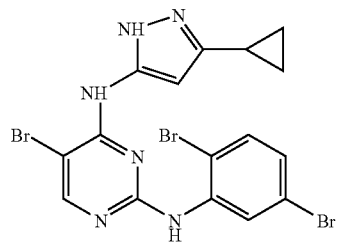 |
| 173 | 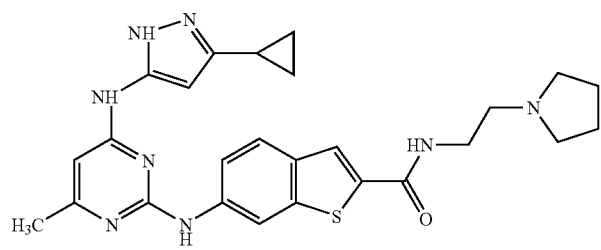 |
| 174 | 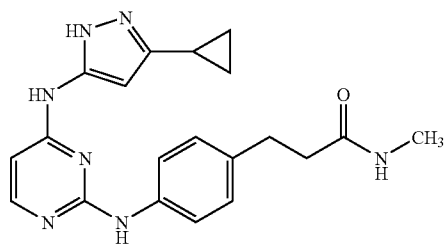 |
| 175 | 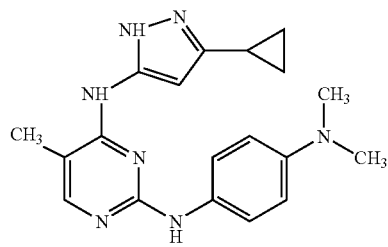 |
| 176 | 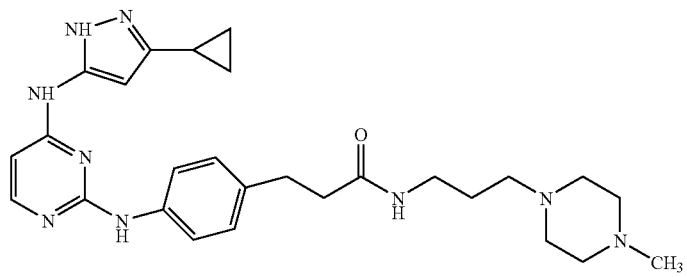 |

TABLE 1-continued
| 177 | 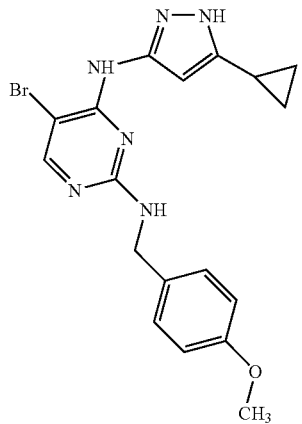 |
| --- | --- |
| 178 | 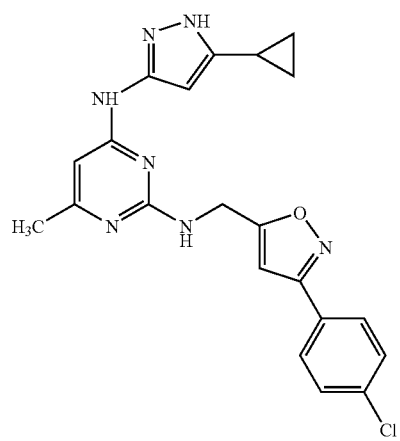 |
| 179 | 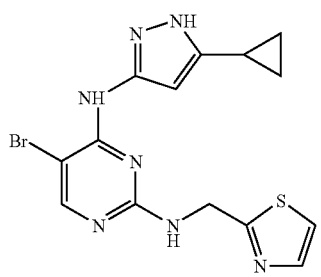 |
| 180 | 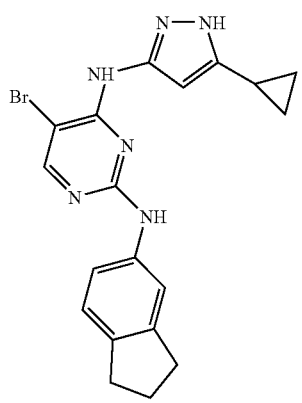 |

TABLE 1-continued
| 181 | 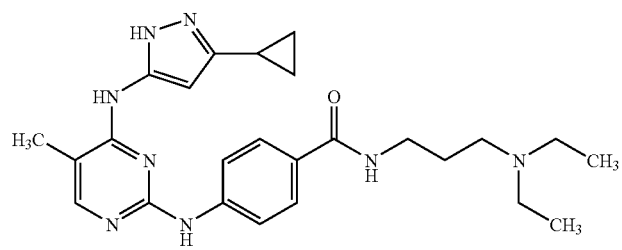 |
| 182 | 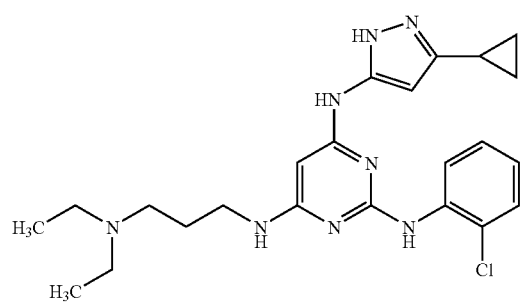 |
| 183 | 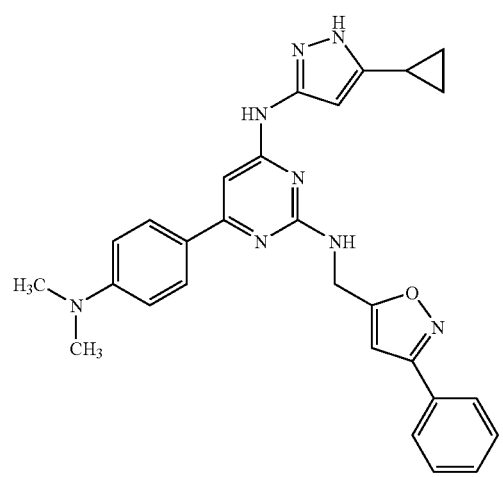 |
| 184 | 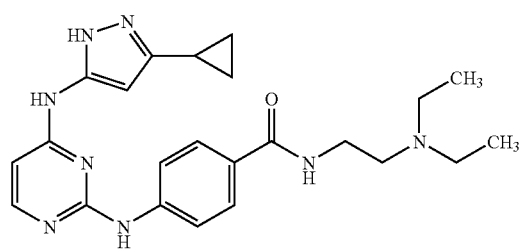 |
| 185 | 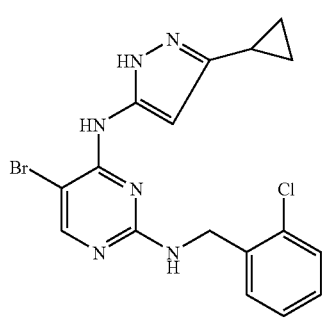 |

TABLE 1-continued
| 186 | 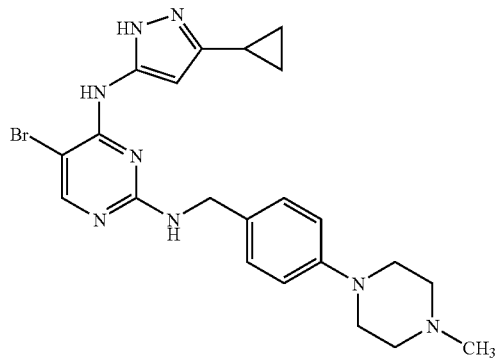 |
| 187 | 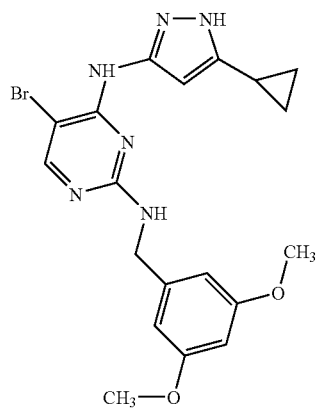 |
| 188 | 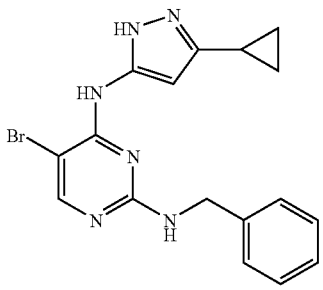 |
| 189 | 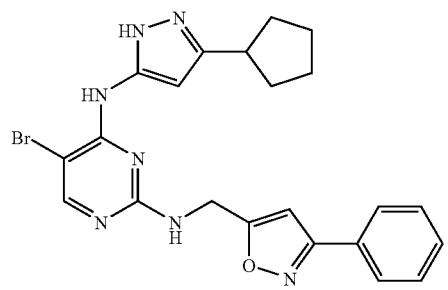 |

TABLE 1-continued
| | |
|---|---|
| 190 | 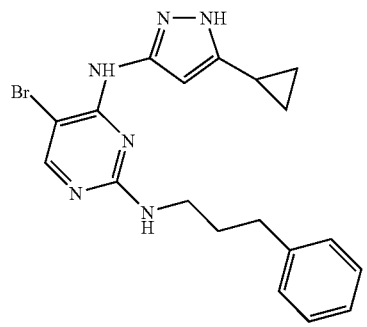 |
| 191 | 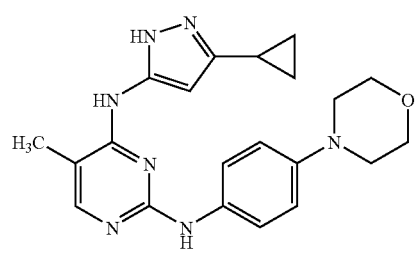 |
| 192 | 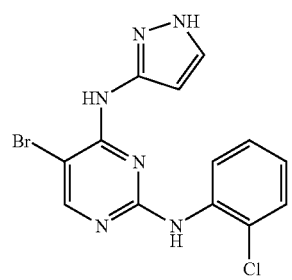 |
| 193 | 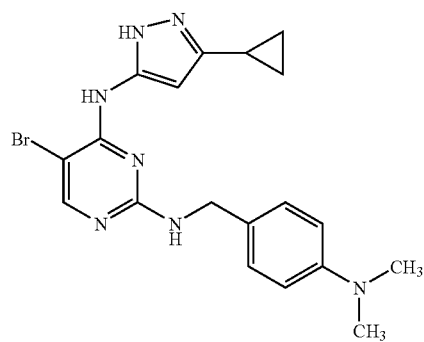 |
| 194 | 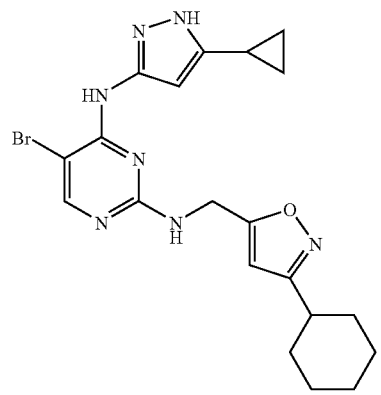 |

TABLE 1-continued
| 195 | 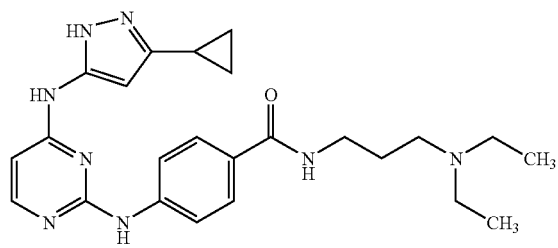 |
| 196 | 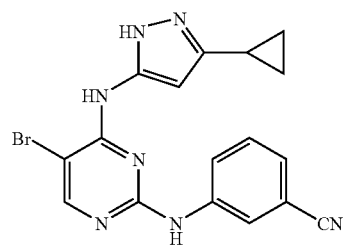 |
| 197 | 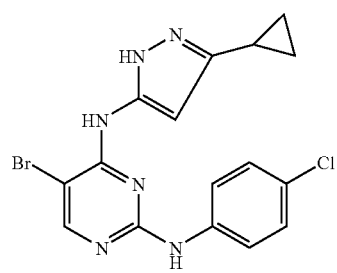 |
| 198 | 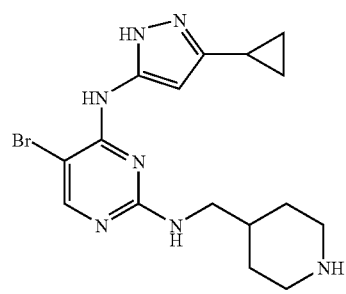 |
| 199 | 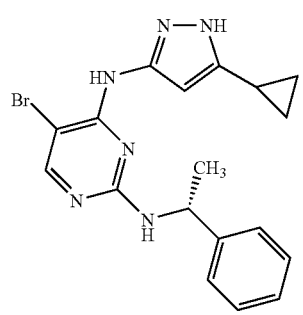 |

TABLE 1-continued
| | |
|---|---|
| 200 | 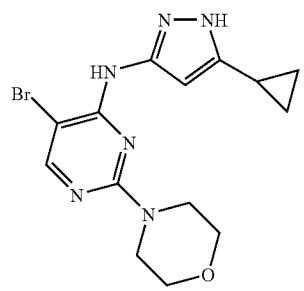 |
| 201 | 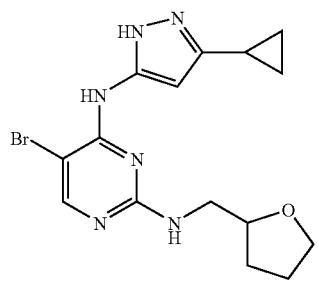 |
| 202 | 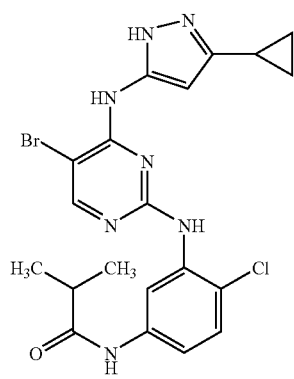 |
| 203 | 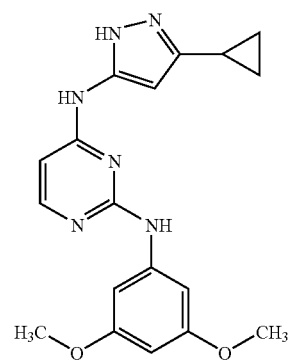 |
| 204 | 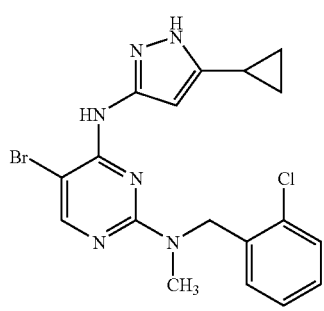 |

TABLE 1-continued
| 205 | 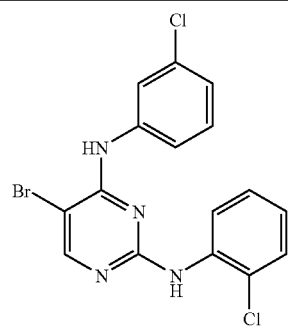 |
| --- | --- |
| 206 | 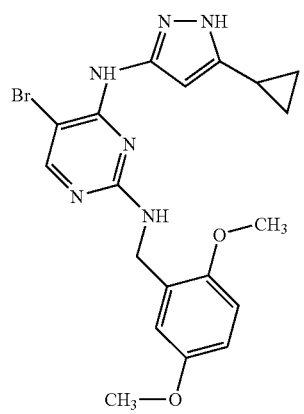 |
| 207 | 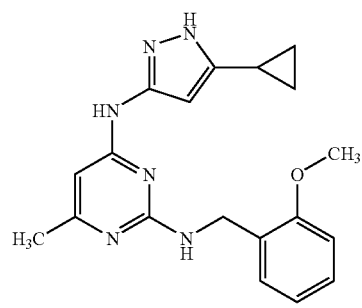 |
| 208 | 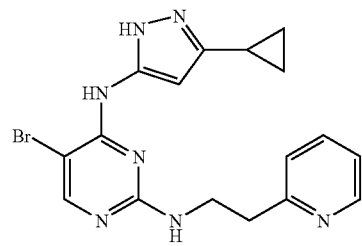 |
| 209 | 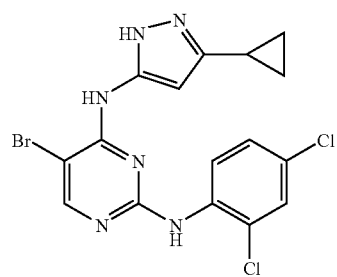 |

TABLE 1-continued
| 210 | 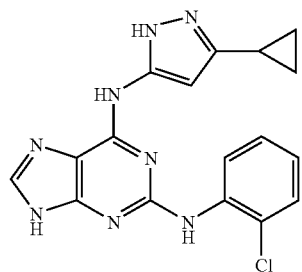 |
| --- | --- |
| 211 | 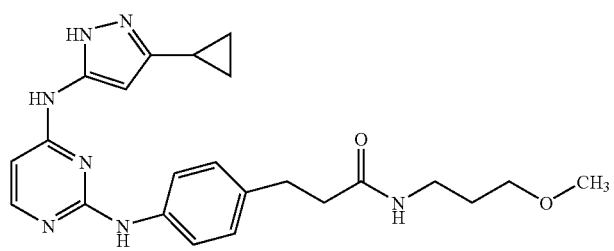 |
| 212 | 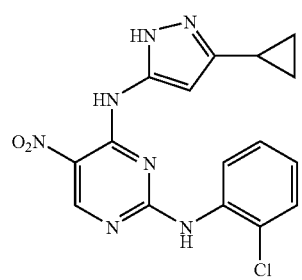 |
| 213 | 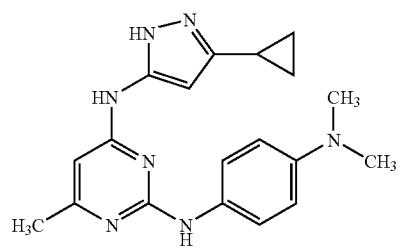 |
| 214 | 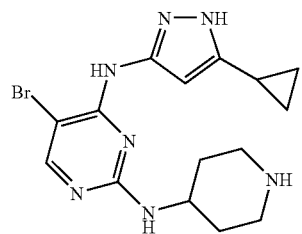 |
| 215 | 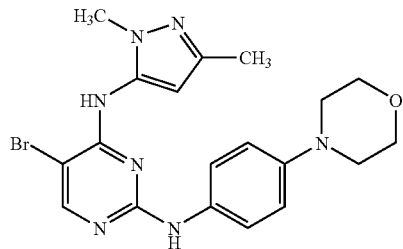 |

TABLE 1-continued
216 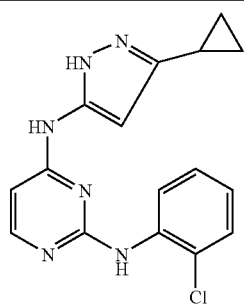
217 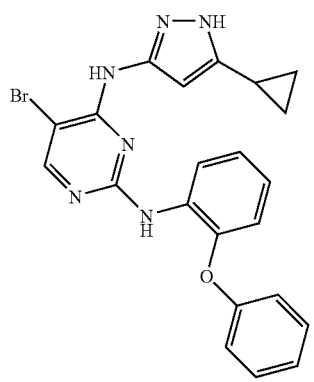
218 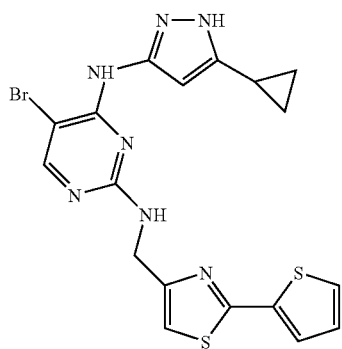
219 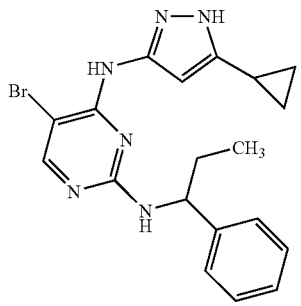
220 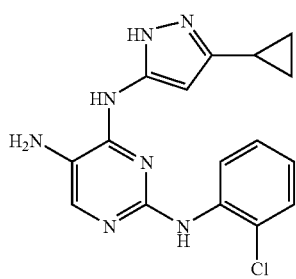

TABLE 1-continued
| | |
|---|---|
| 221 | 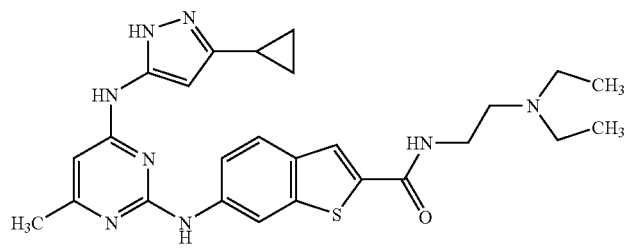 |
| 222 | 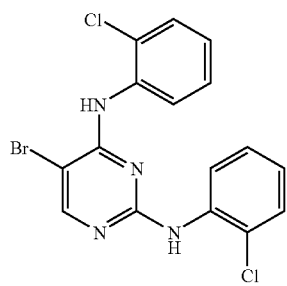 |
| 223 | 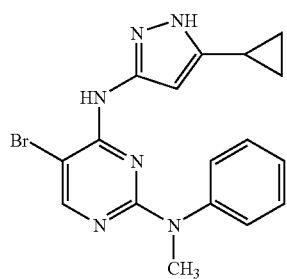 |
| 224 | 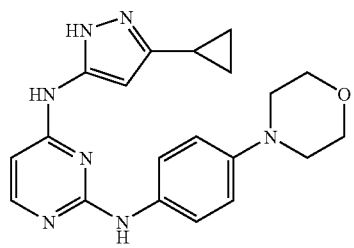 |
| 225 | 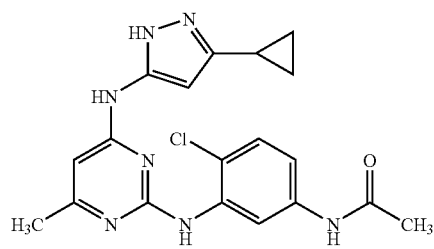 |
| 226 | 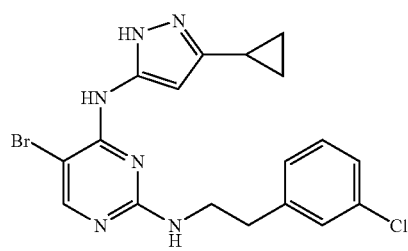 |

TABLE 1-continued
| | |
|---|---|
| 227 | 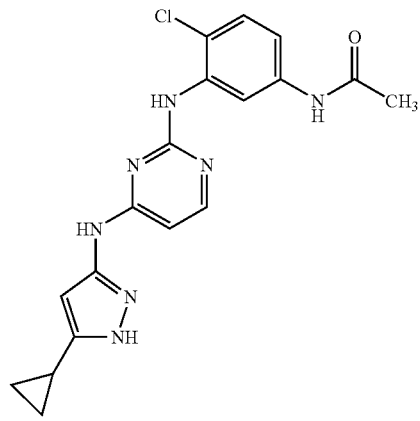 |
| 228 | 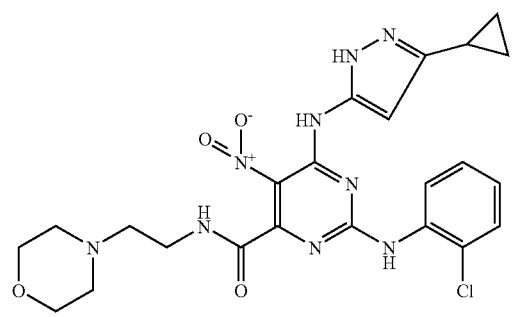 |
| 229 | 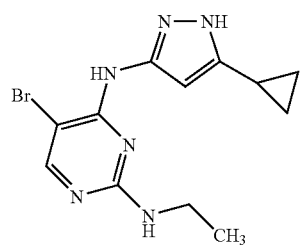 |
| 230 | 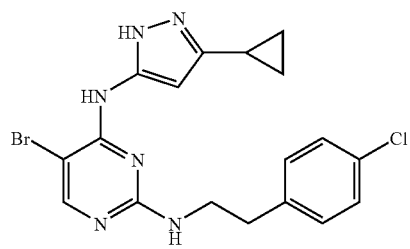 |
| 231 | 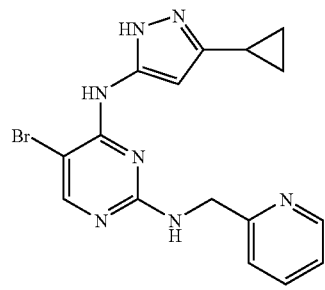 |

TABLE 1-continued
| 232 | 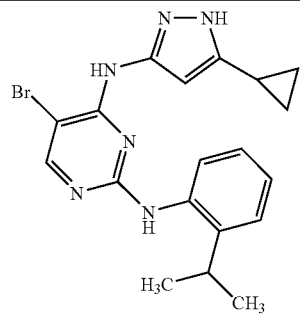 |
| --- | --- |
| 233 | 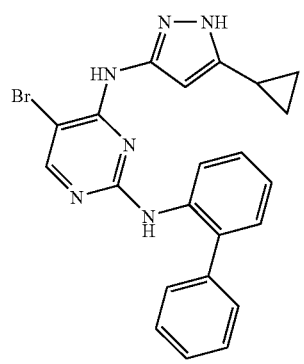 |
| 234 | 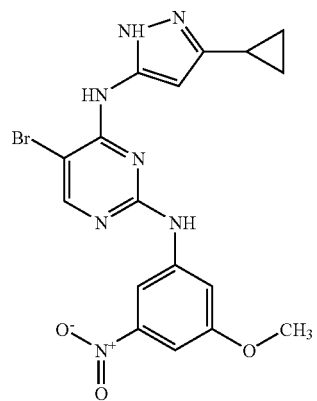 |
| 235 | 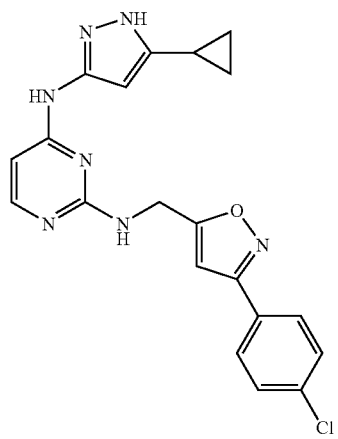 |

TABLE 1-continued
| | |
|---|---|
| 236 | 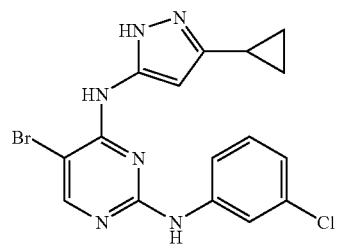 |
| 237 | 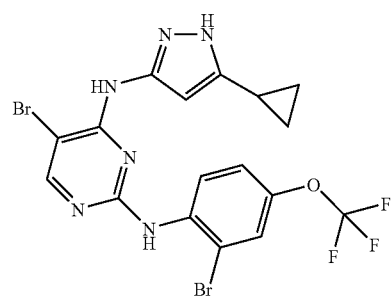 |
| 238 | 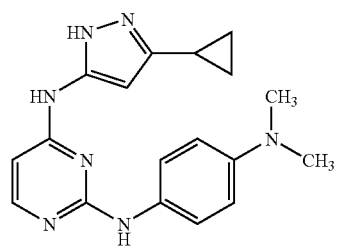 |
| 239 | 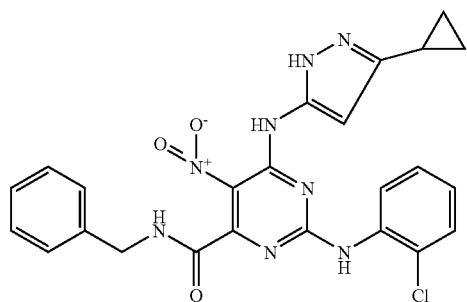 |
| 240 | 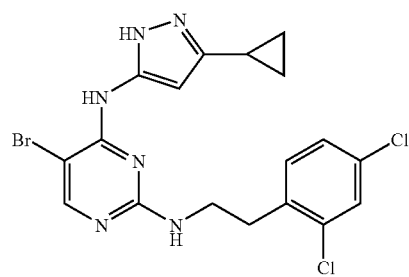 |

TABLE 1-continued
| 241 | 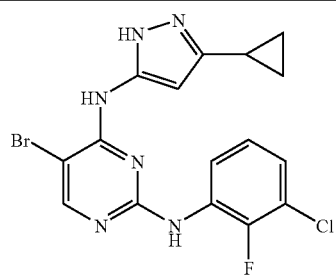 |
| 242 | 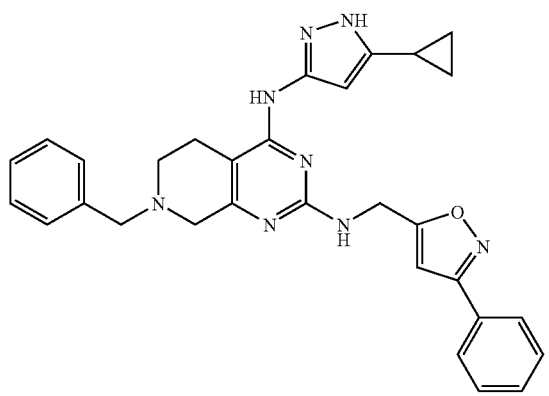 |
| 243 | 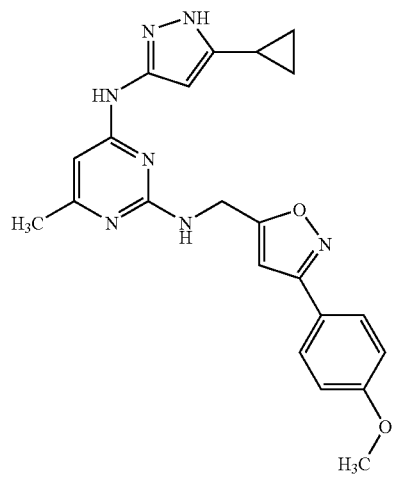 |
| 244 | 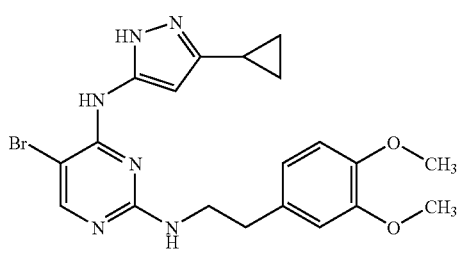 |

TABLE 1-continued
245 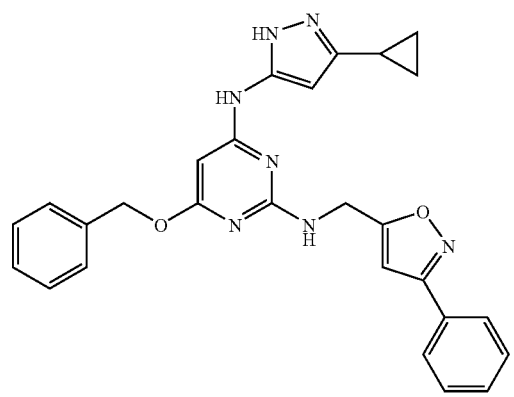
246 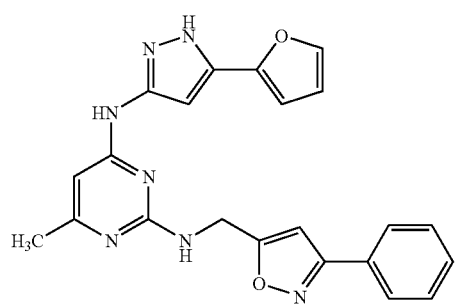
247 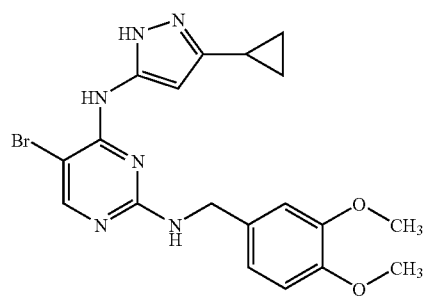
248 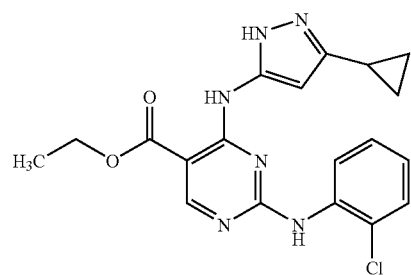
249 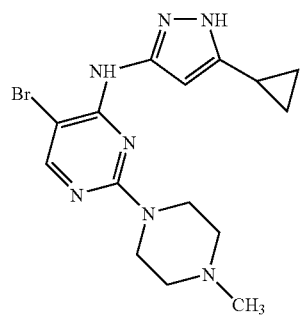

TABLE 1-continued
| 250 | 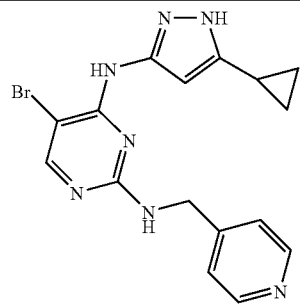 |
| --- | --- |
| 251 | 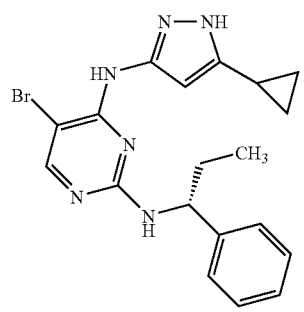 |
| 252 | 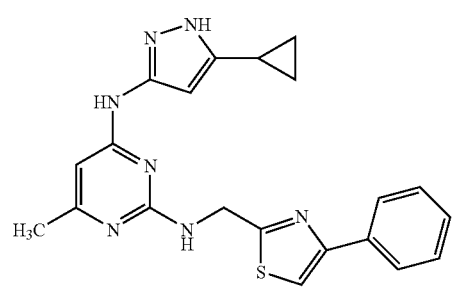 |
| 253 | 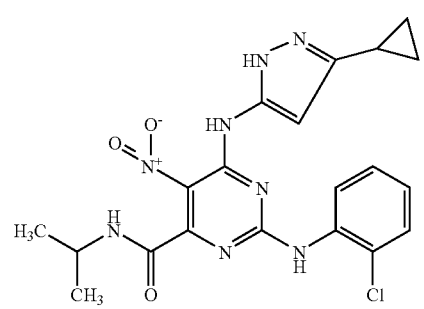 |
| 254 | 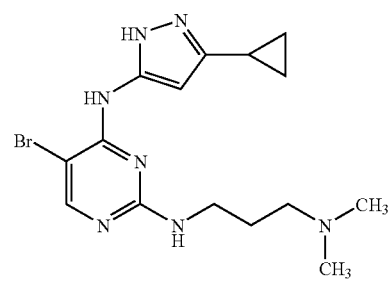 |

TABLE 1-continued
| | |
|---|---|
| 255 | 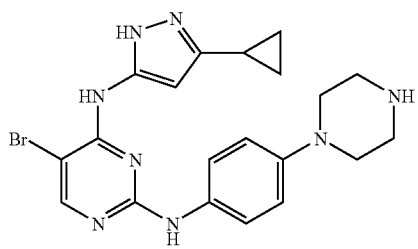 |
| 256 | 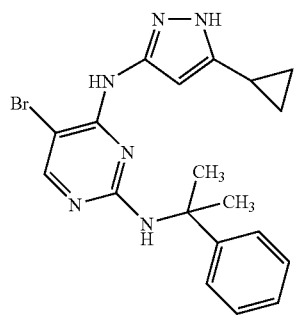 |
| 257 | 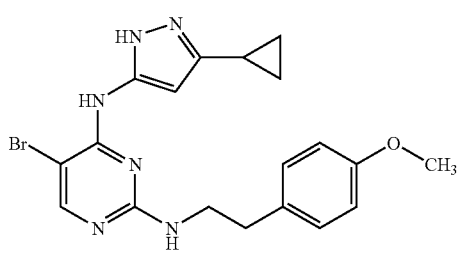 |
| 258 | 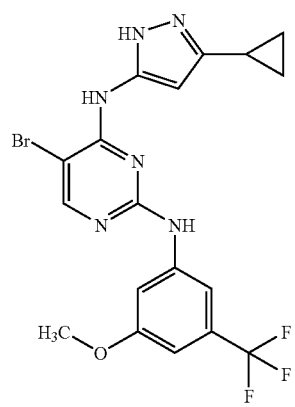 |
| 259 | 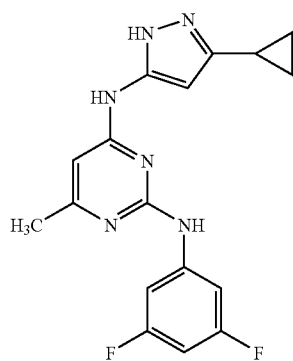 |

TABLE 1-continued
| 260 | 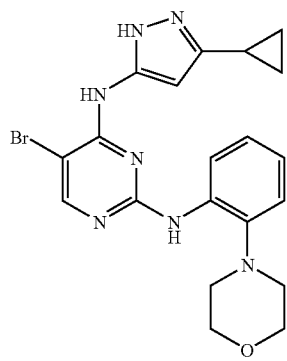 |
| --- | --- |
| 261 | 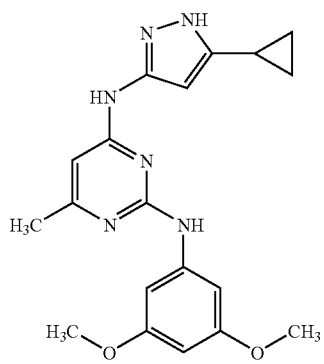 |
| 262 | 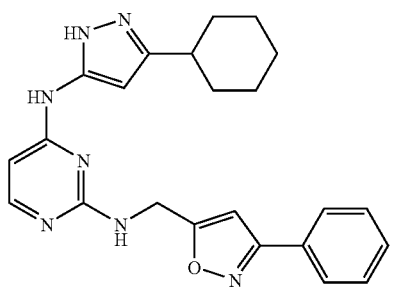 |
| 263 | 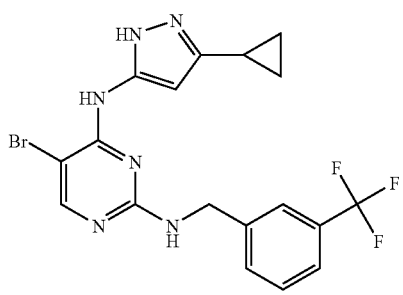 |
| 264 | 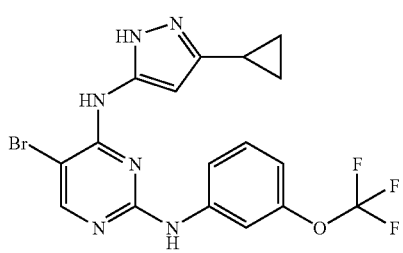 |

TABLE 1-continued
265 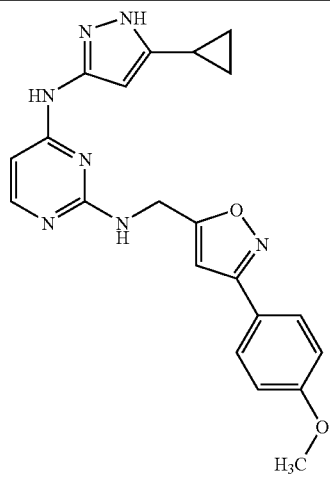
266 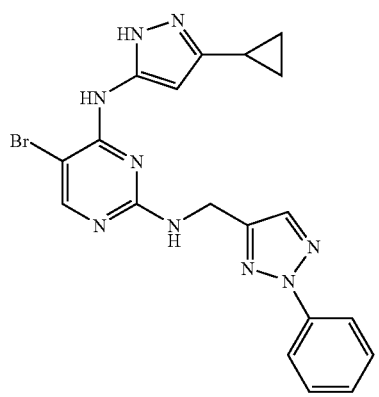
267 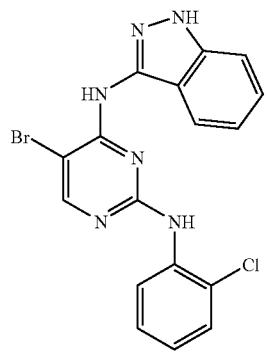
268 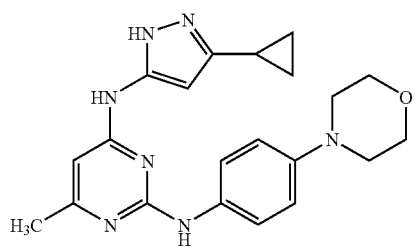

TABLE 1-continued
| 269 | 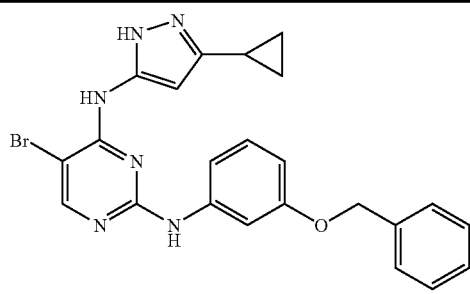 |
| --- | --- |
| 270 | 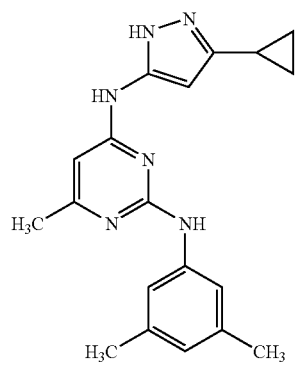 |
| 271 | 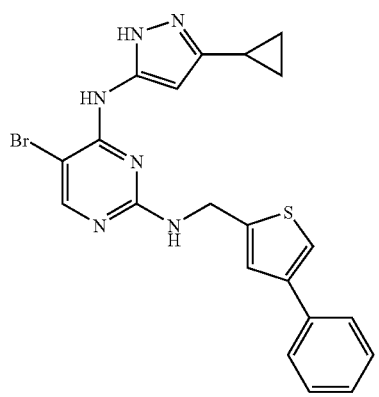 |
| 272 | 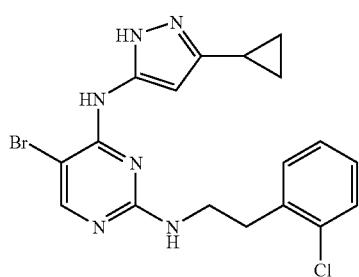 |
| 273 | 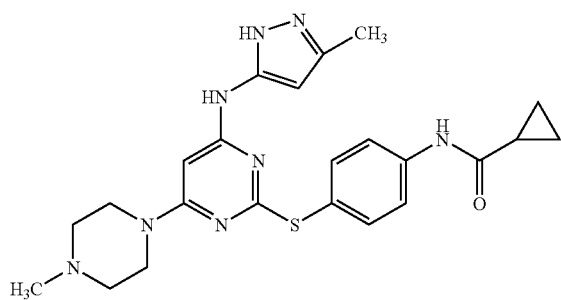 |

TABLE 1-continued
274 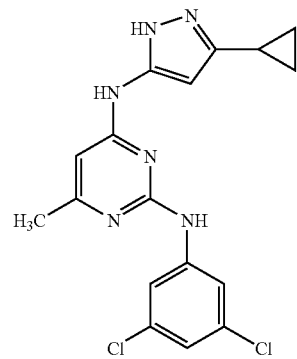
275 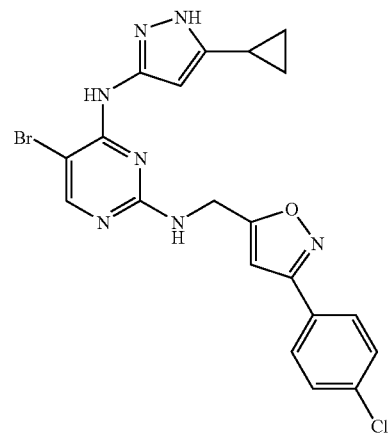
276 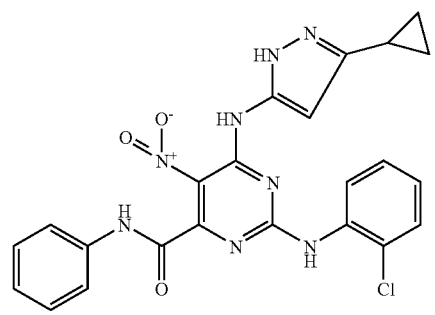
277 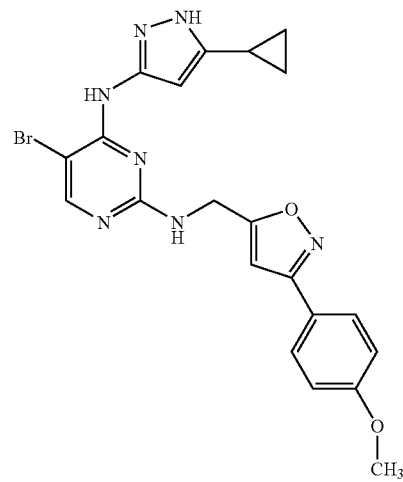

TABLE 1-continued
| | |
|---|---|
| 278 | 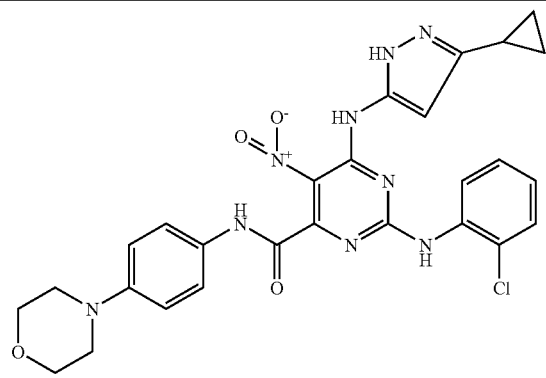 |
| 279 | 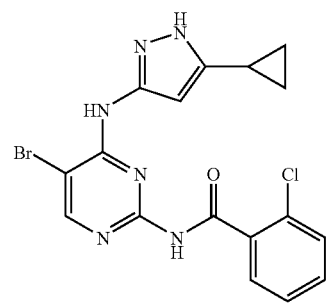 |
| 280 | 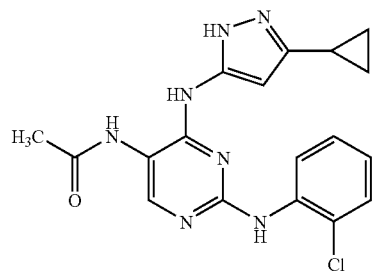 |
| 281 | 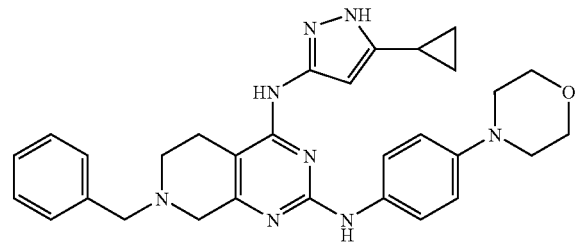 |
| 282 | 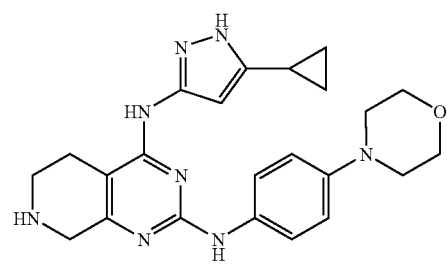 |

TABLE 1-continued
283 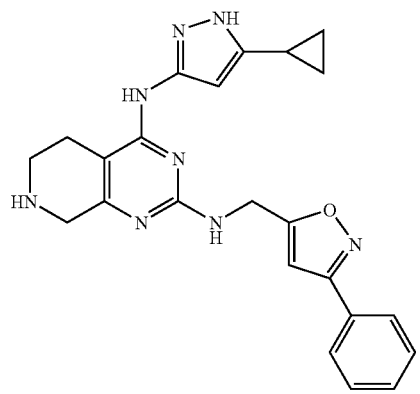
284 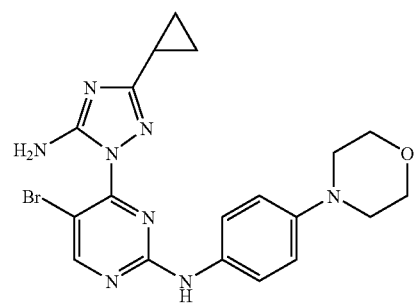
285 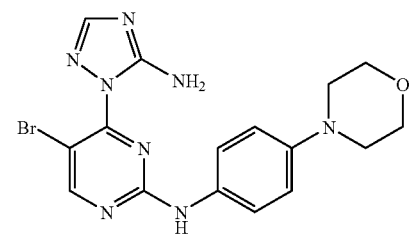
286 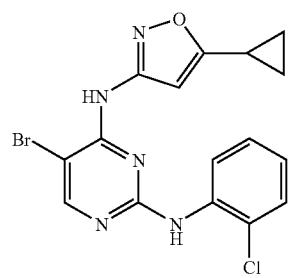
287 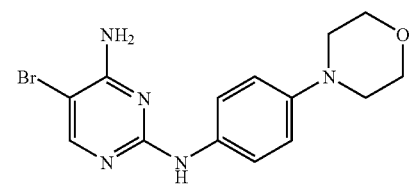

TABLE 1-continued
288 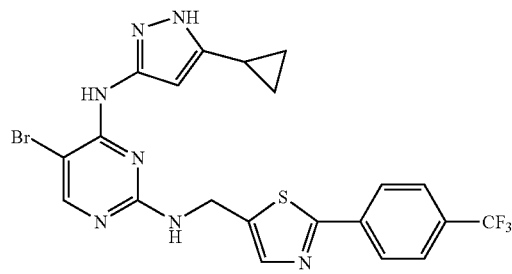
289 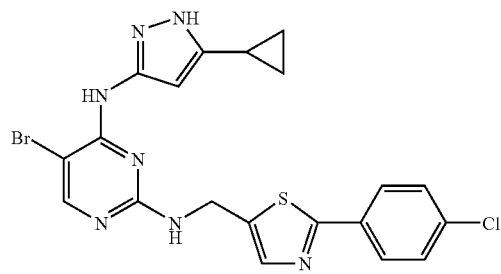
290 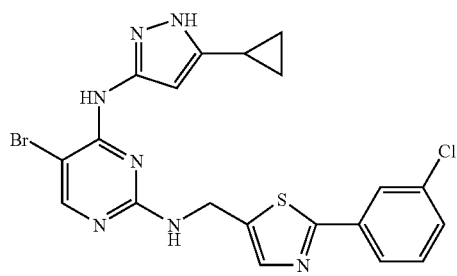
291 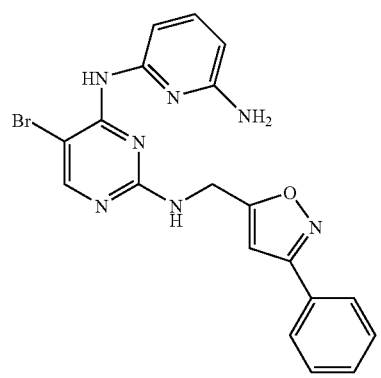
292 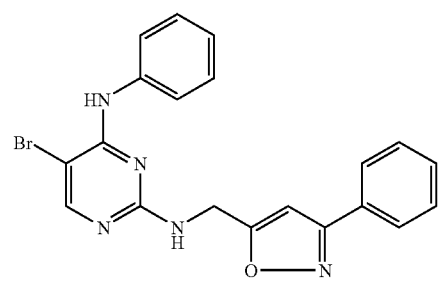

TABLE 1-continued
| | |
|---|---|
| 293 | 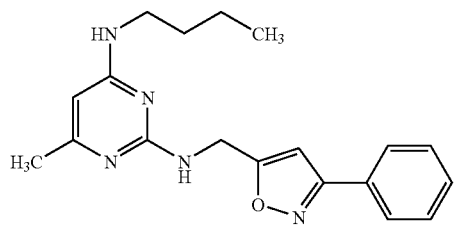 |
| 294 | 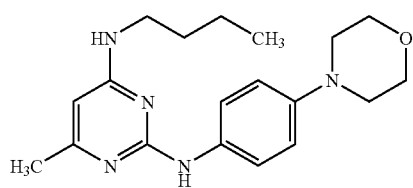 |
| 295 | 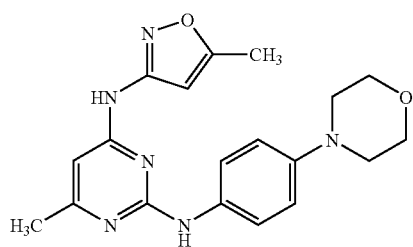 |
| 296 | 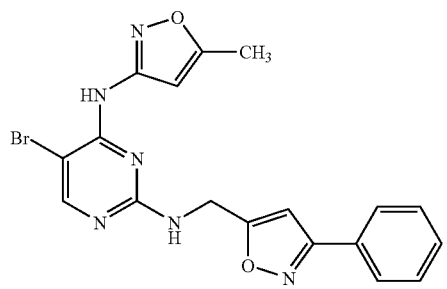 |
| 297 | 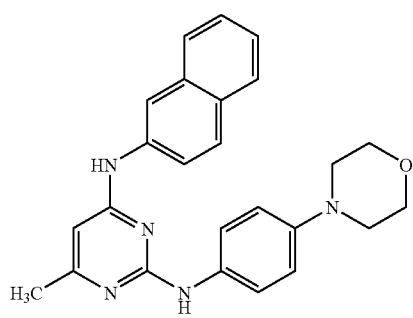 |

TABLE 1-continued
| | |
|---|---|
| 298 | 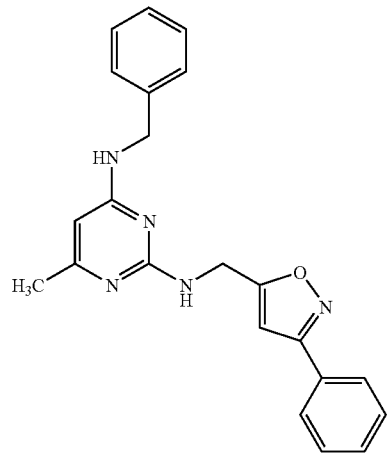 |
| 299 | 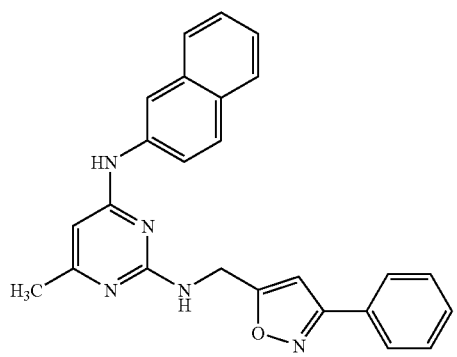 |
| 300 | 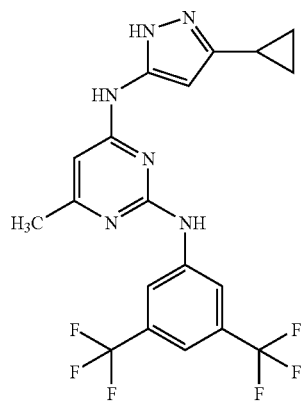 |
| 301 | 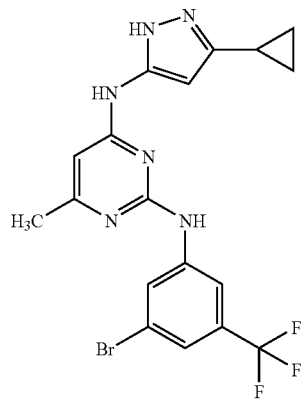 |

TABLE 1-continued
| 302 | 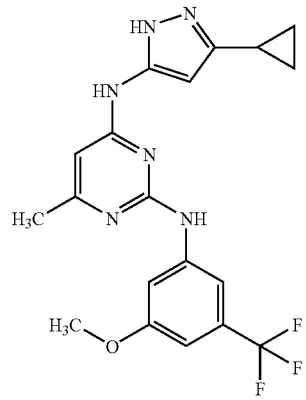 |
| --- | --- |
| 303 | 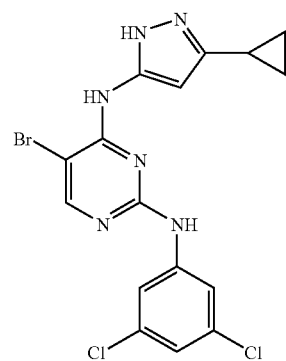 |
| 304 | 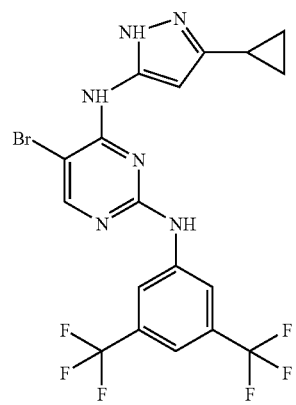 |
| 305 | 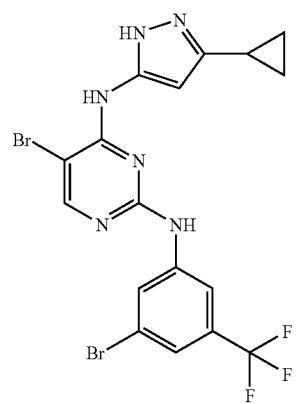 |

TABLE 1-continued
306 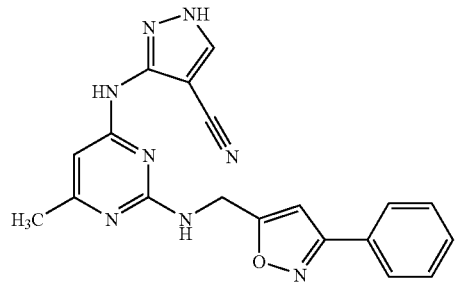
307 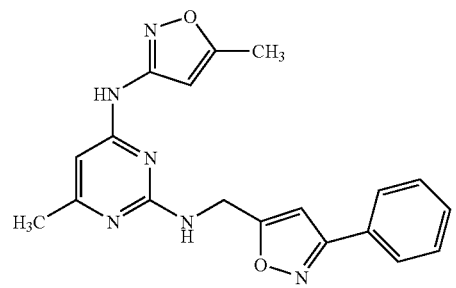
308 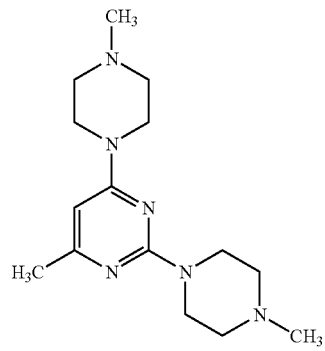
309 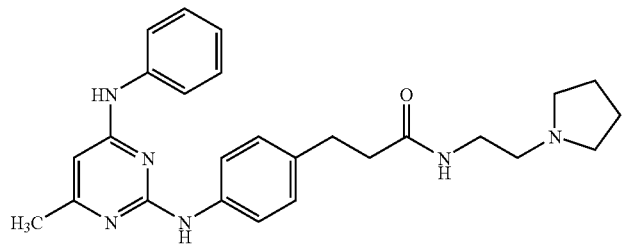
310 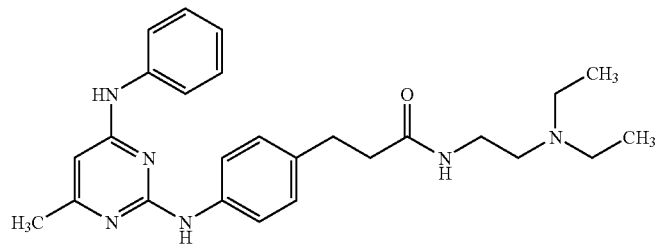

TABLE 1-continued
| 311 | 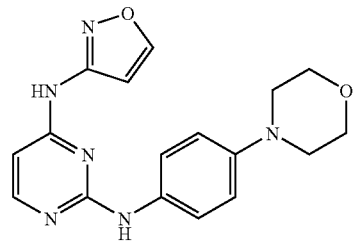 |
| 312 | 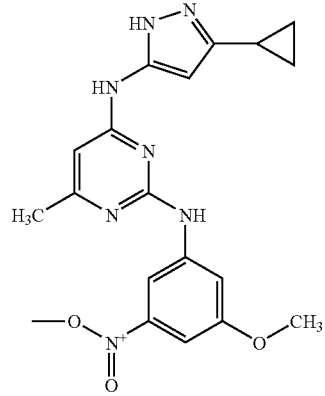 |
| 313 | 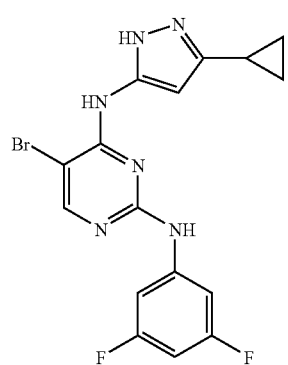 |
| 314 | 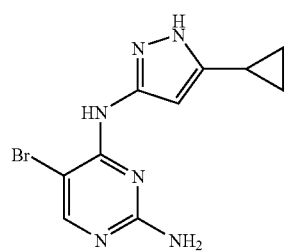 |
| 315 | 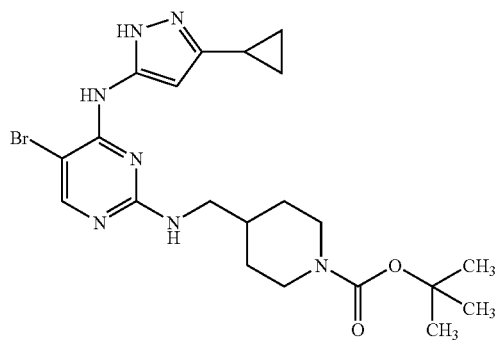 |

TABLE 1-continued
| | |
|---|---|
| 316 | 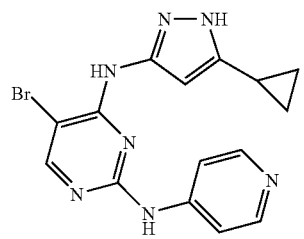 |
| 317 | 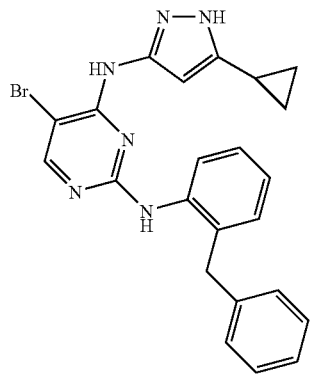 |
| 318 | 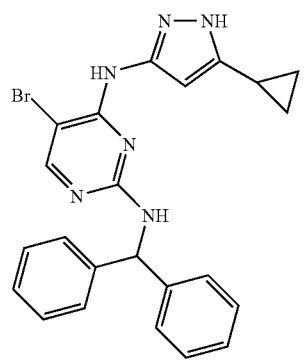 |
| 319 | 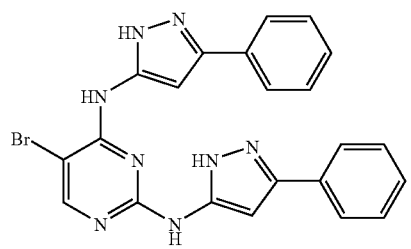 |
| 320 | 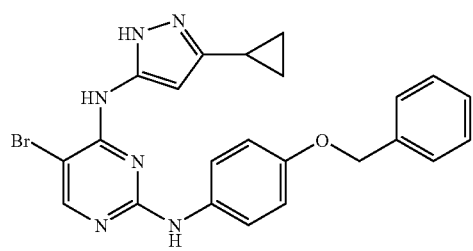 |

TABLE 1-continued
| 321 | 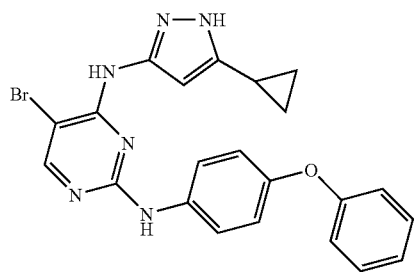 |
| 322 | 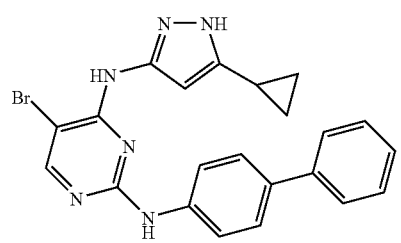 |
| 323 | 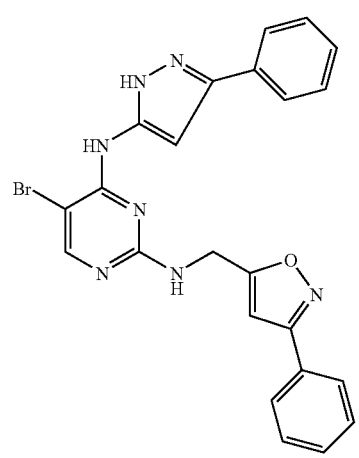 |
| 324 | 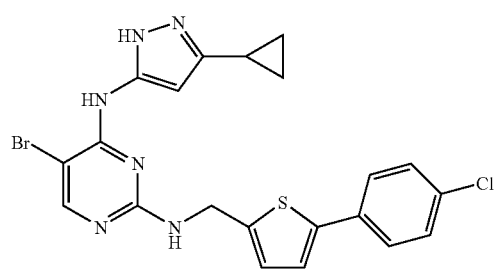 |
| 325 | 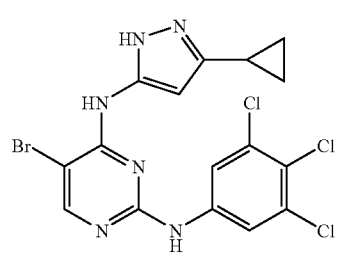 |

TABLE 1-continued
326
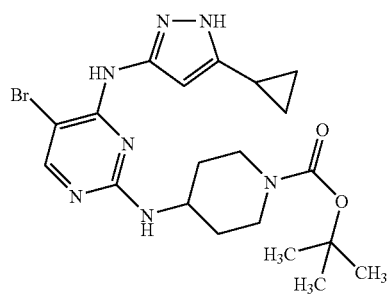
327
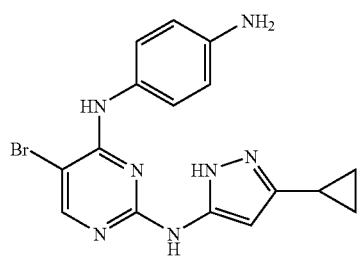
328
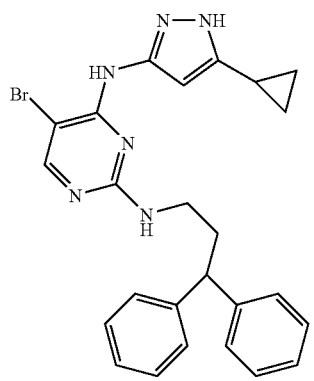
329
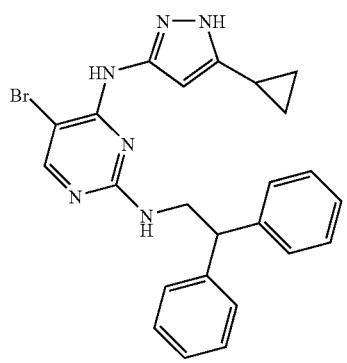
330
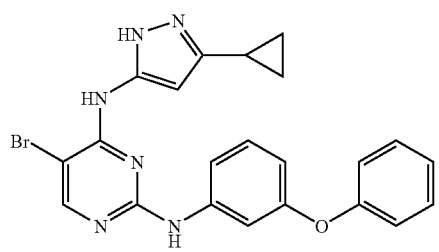

TABLE 1-continued
| | |
|---|---|
| 331 | 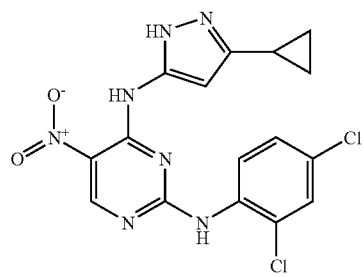 |
| 332 | 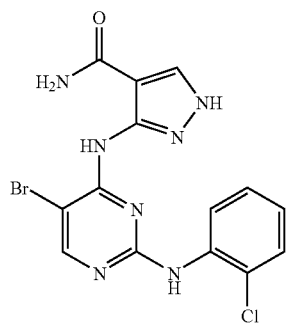 |
| 333 | 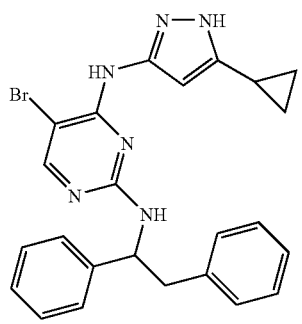 |
| 334 | 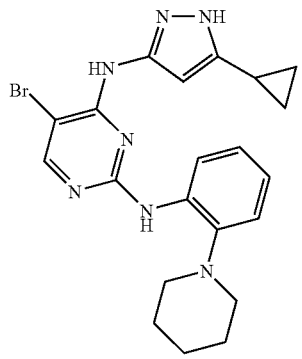 |
| 335 | 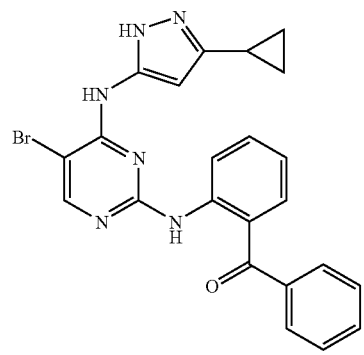 |

TABLE 1-continued
336
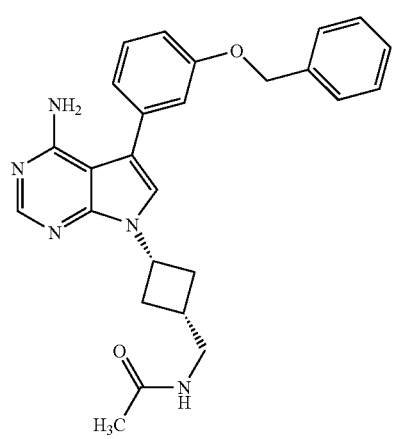
337
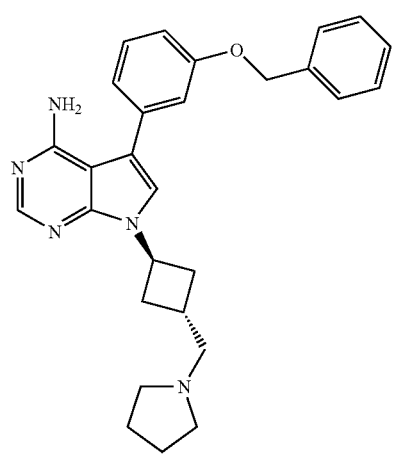
338
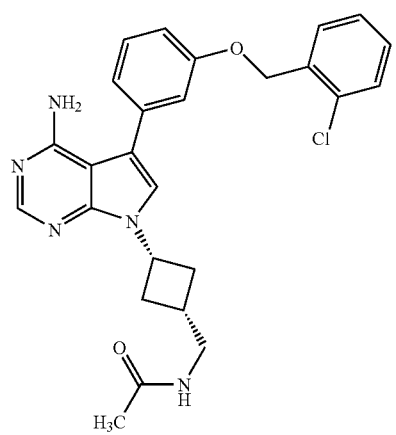

TABLE 1-continued
| | |
|---|---|
| 339 | 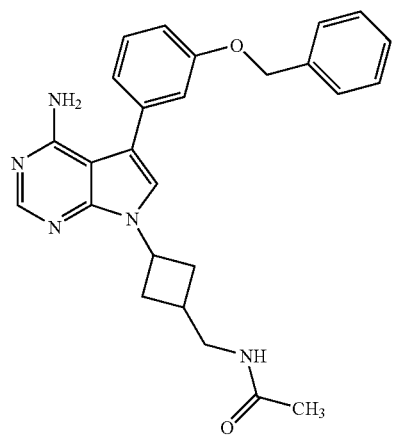 |
| 340 | 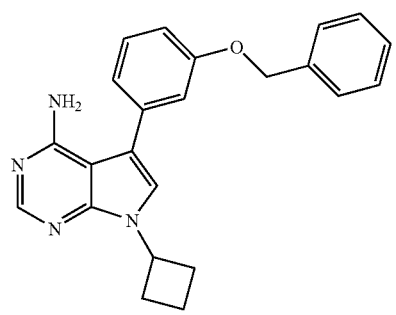 |
| 341 | 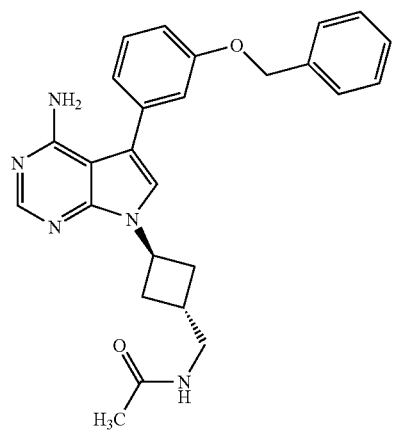 |
| 342 | 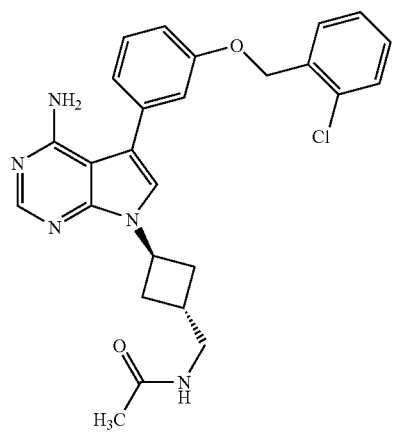 |

TABLE 1-continued
343
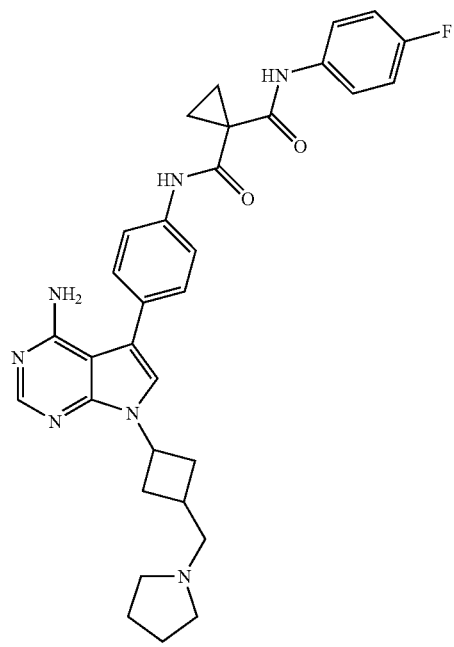
344
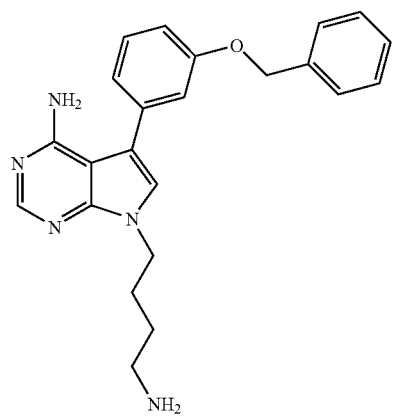
345
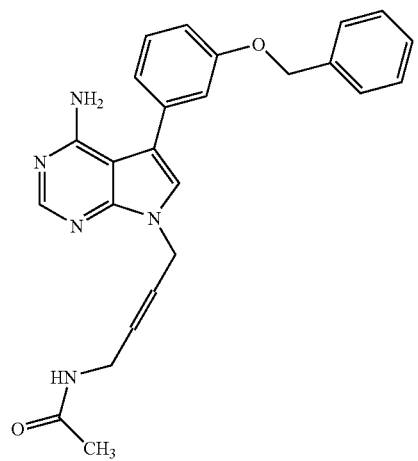

TABLE 1-continued
346
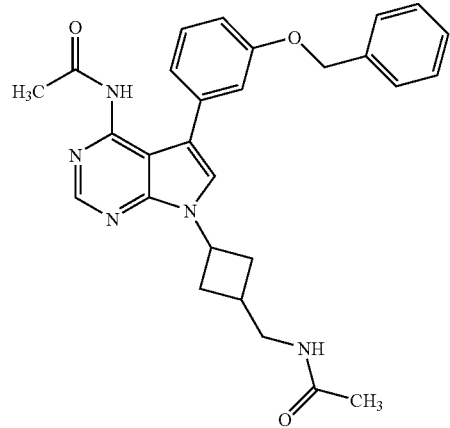
347
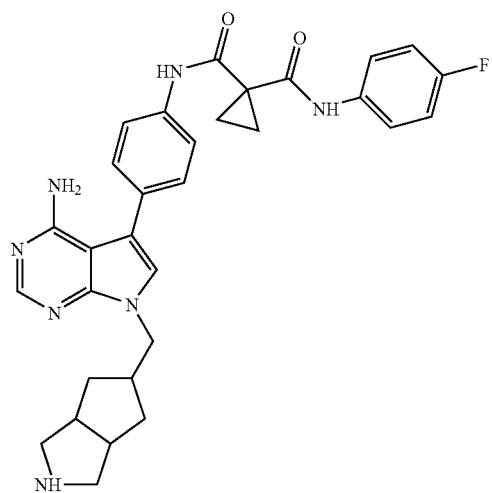
348
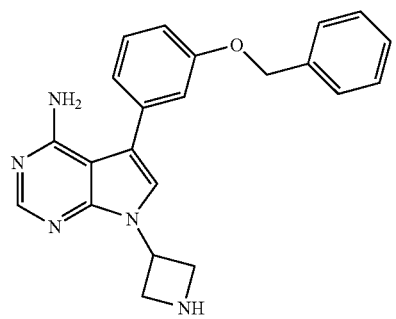

TABLE 1-continued
349 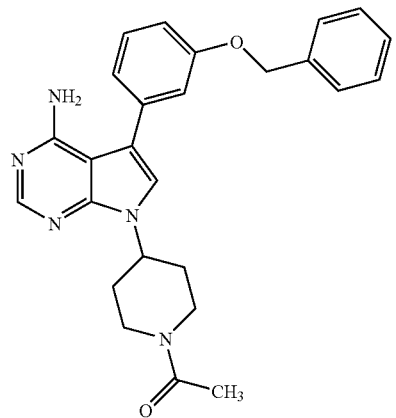
350 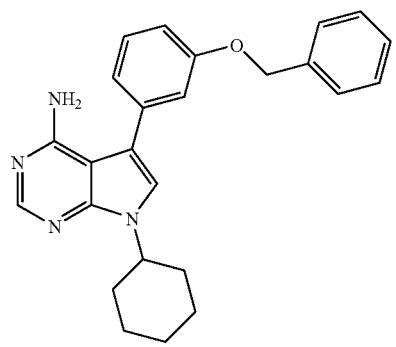
351 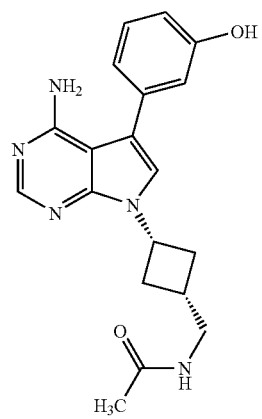
352 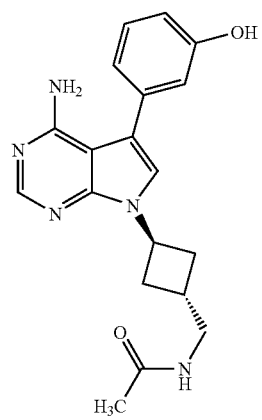

TABLE 1-continued
353
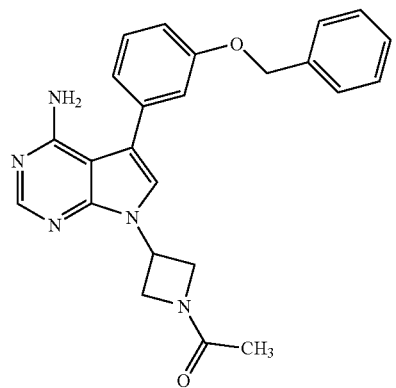
354
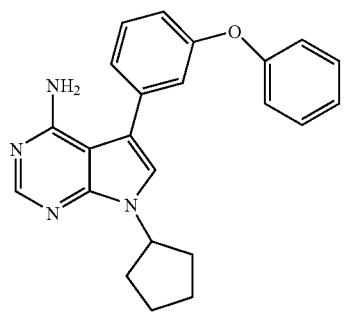
355
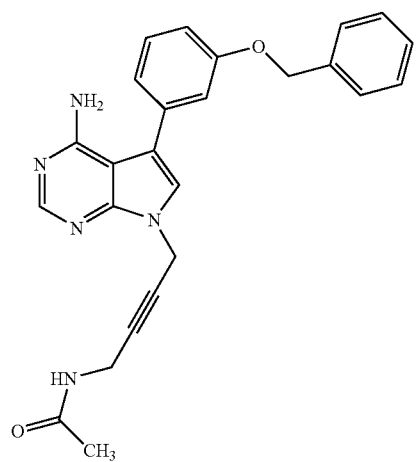

TABLE 1-continued
356
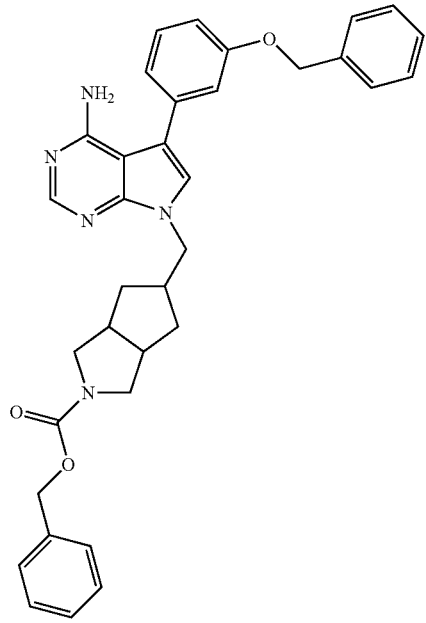
357
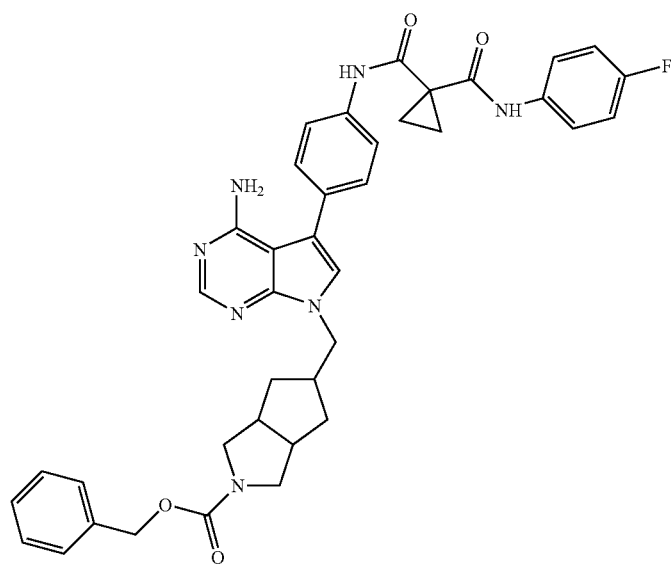
358
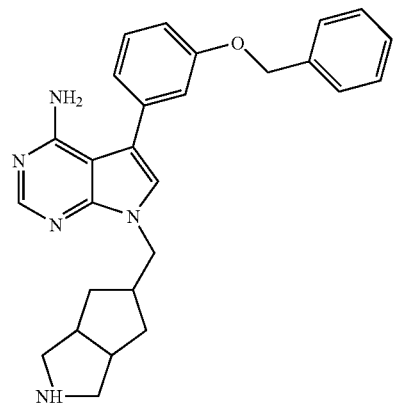

TABLE 1-continued
495
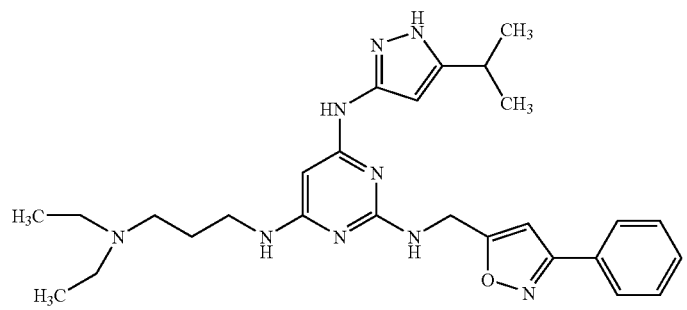
496
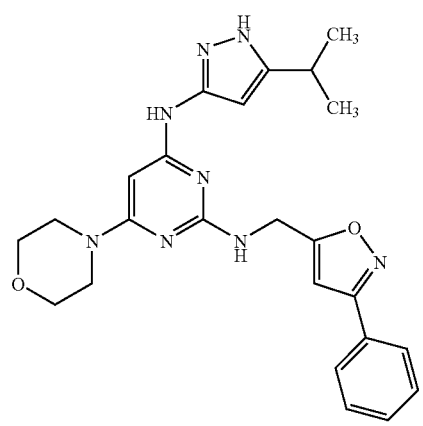
497
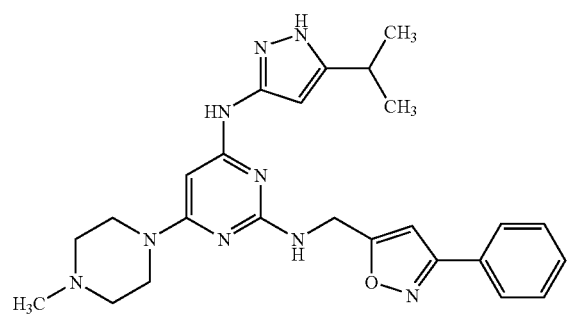
498
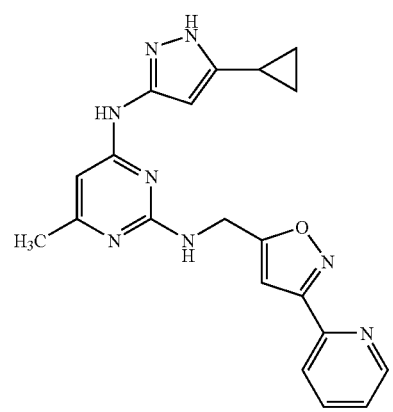

TABLE 1-continued
499
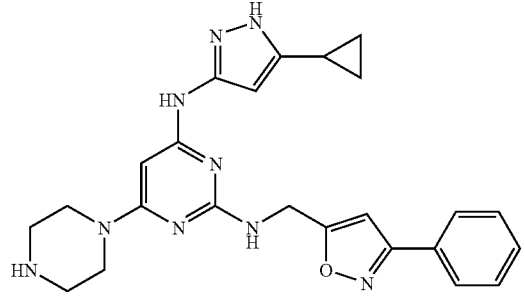
500
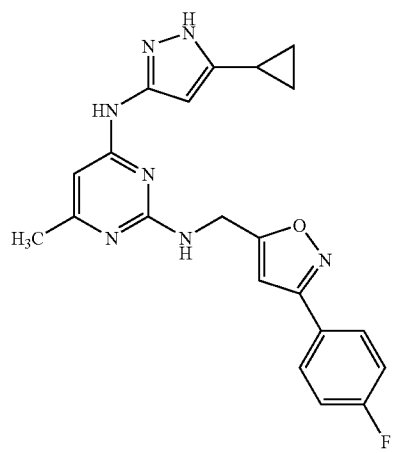
501
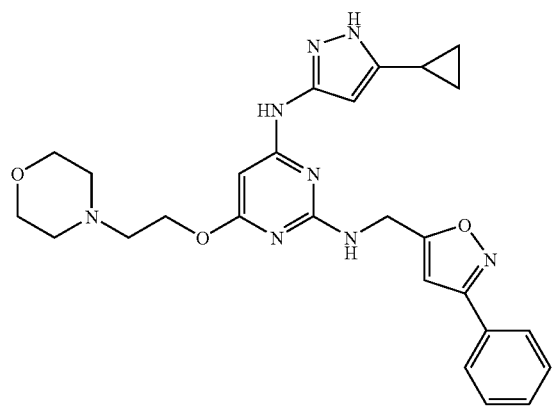
502 Chiral
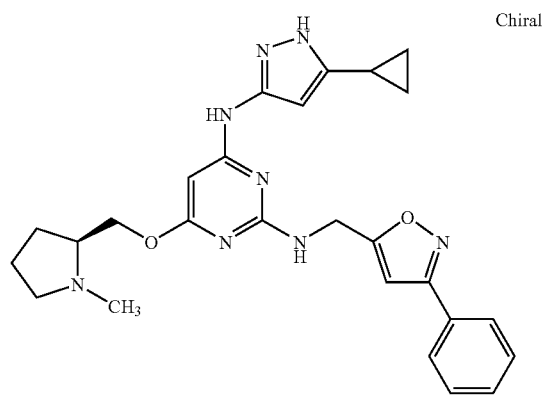

TABLE 1-continued
503 Chiral
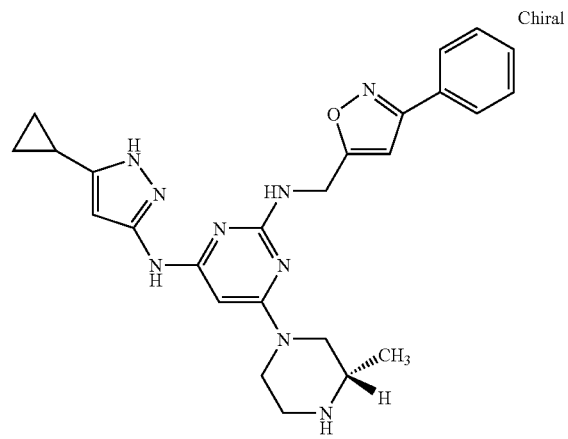
504
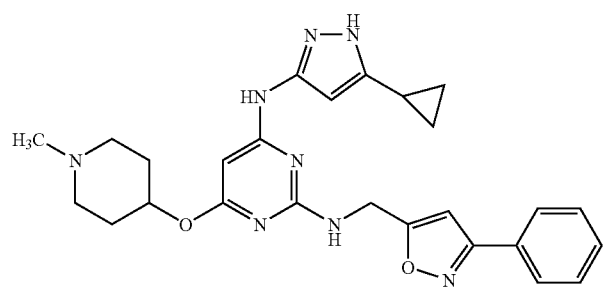
505
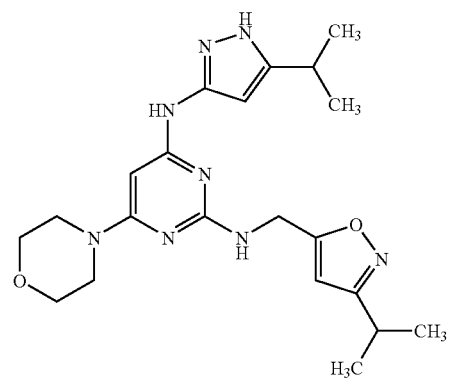
506
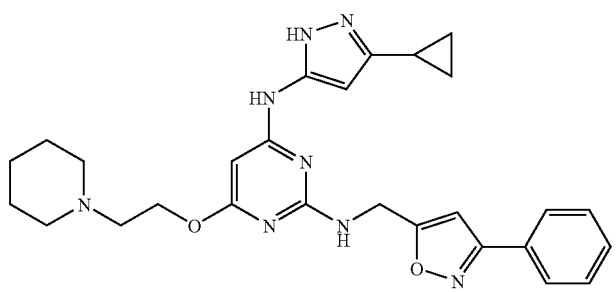

TABLE 1-continued
| 507 | 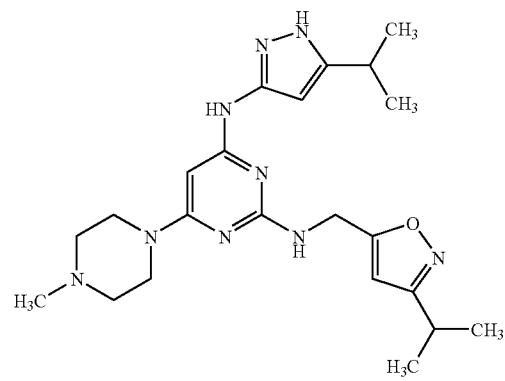 |
| --- | --- |
| 508 | 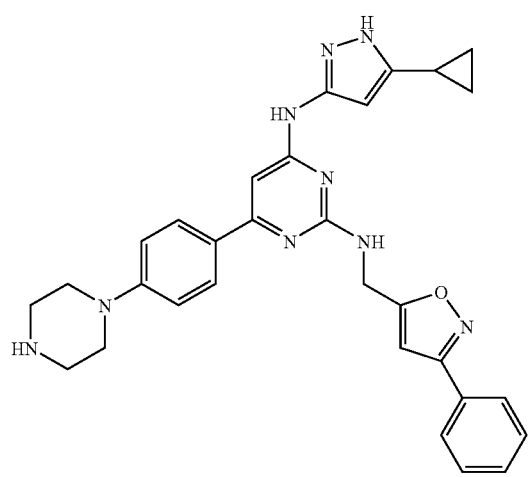 |
| 509 | 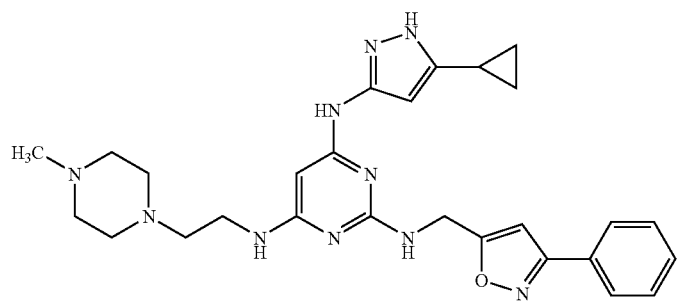 |
| 510 | 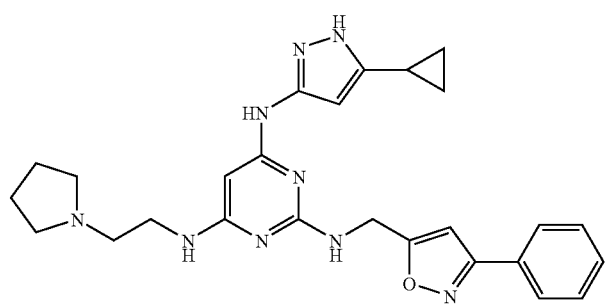 |

TABLE 1-continued
| | | |
|---|---|---|
| 511 | 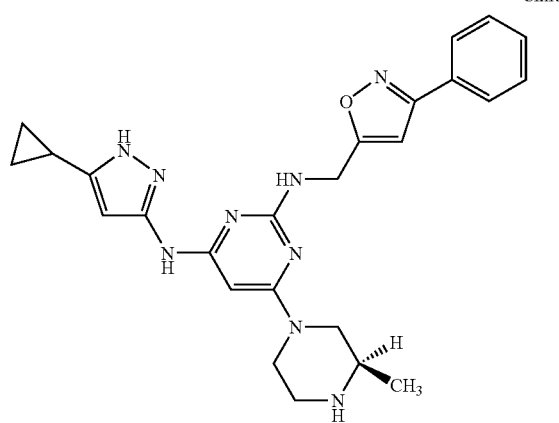 | Chiral |
| 512 | 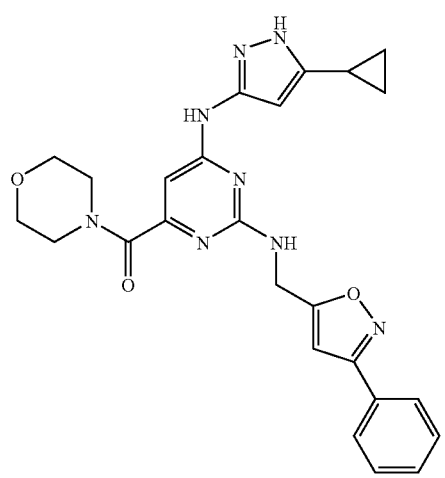 | |
| 513 | 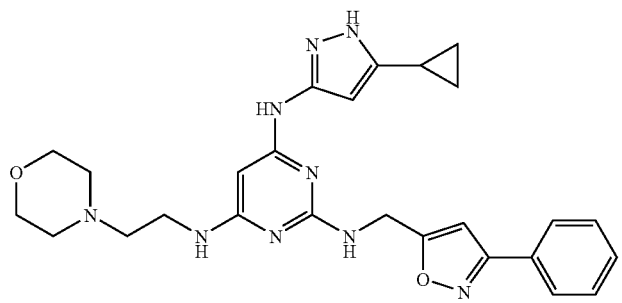 | |
| 514 | 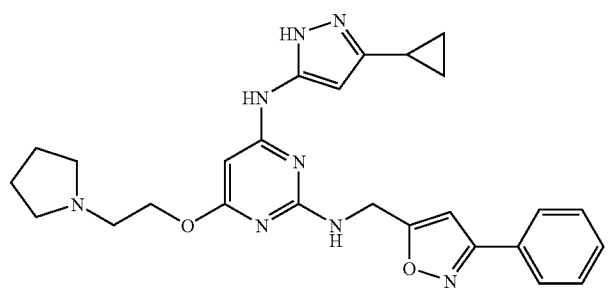 | |

TABLE 1-continued
515 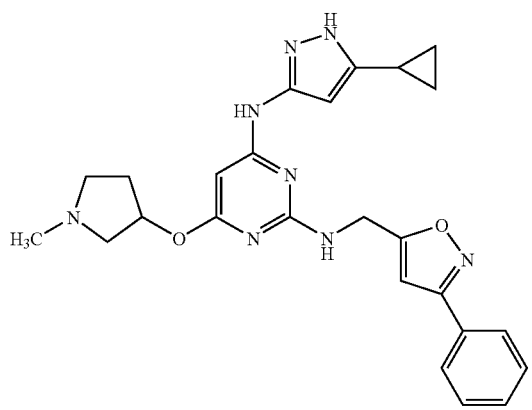
516 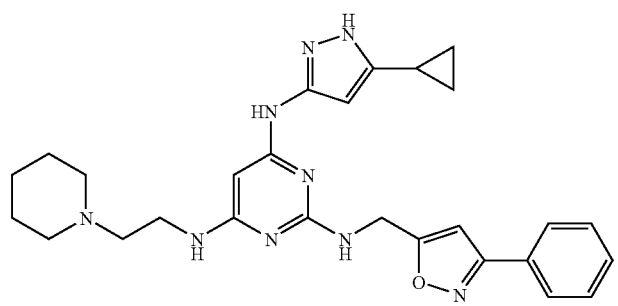
517 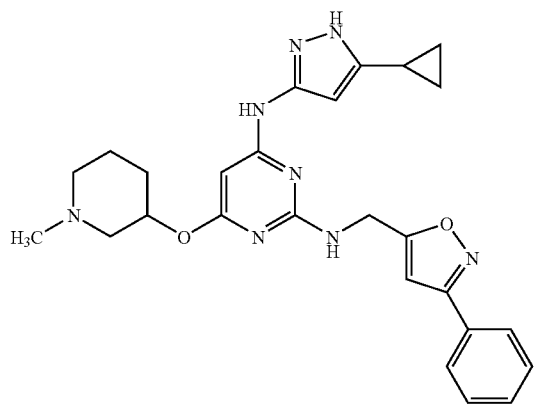
518 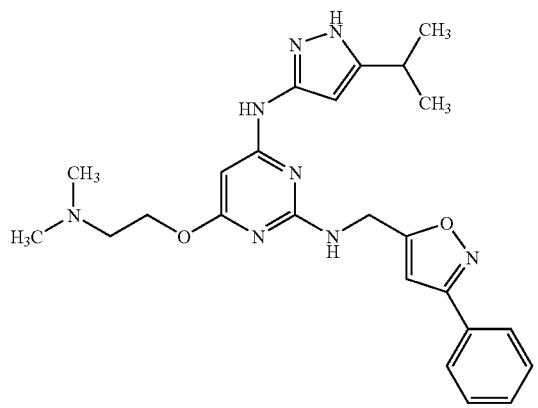

TABLE 1-continued
| | |
|---|---|
| 519 | 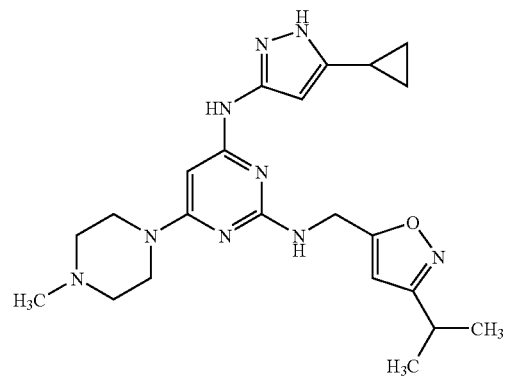 |
| 520 | 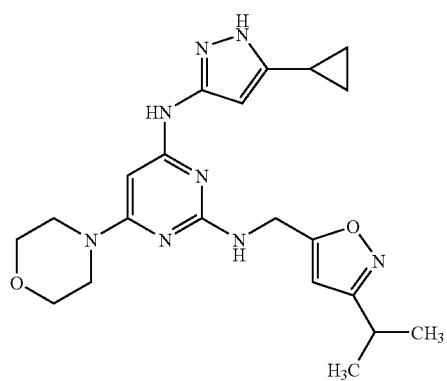 |
| 521 | 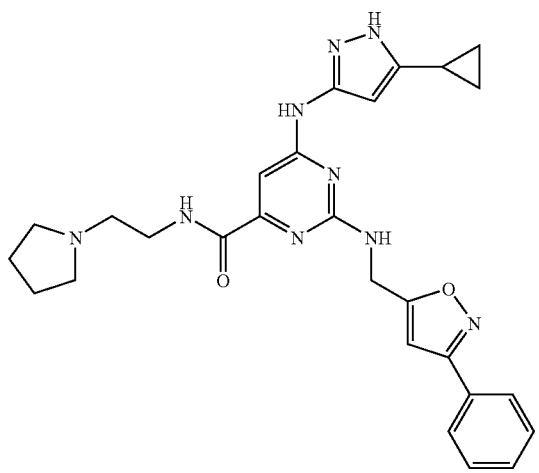 |
| 522 | 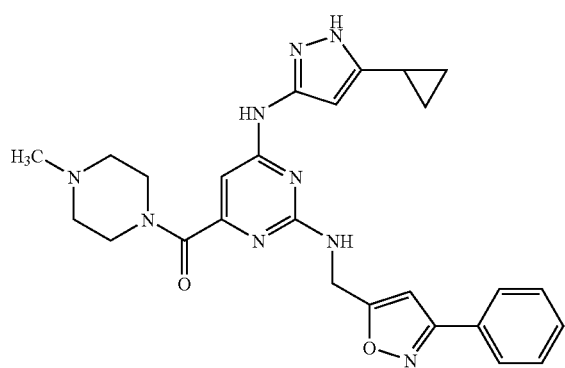 |

TABLE 1-continued
| | |
|---|---|
| 523 | 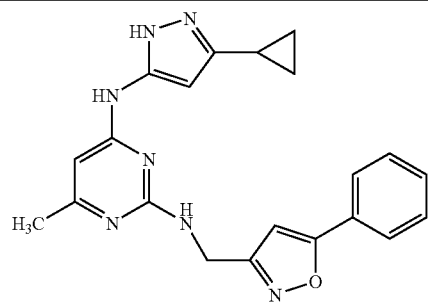 |
| 524 | 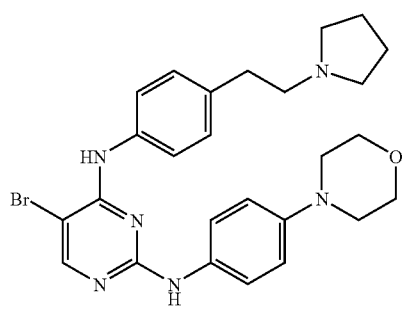 |
| 525 | 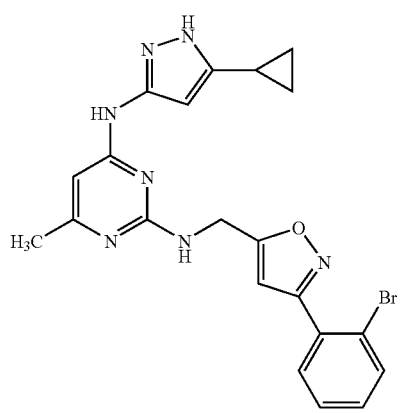 |
| 526 | 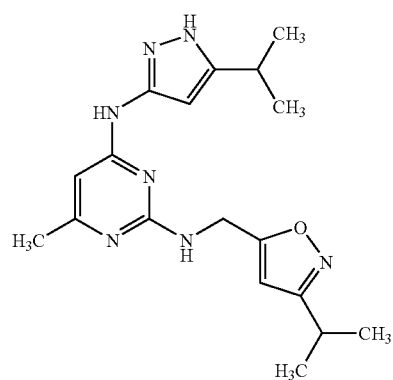 |

TABLE 1-continued
527
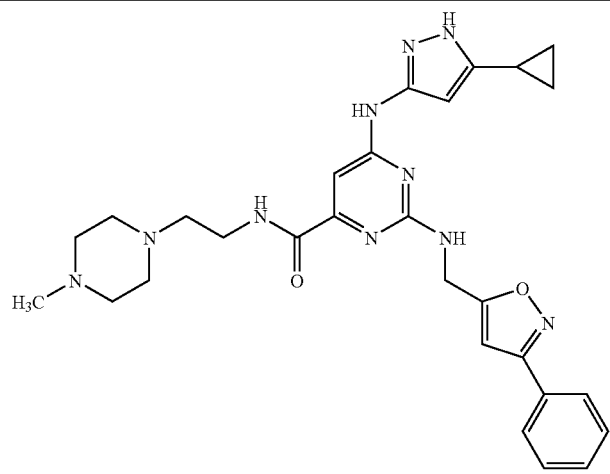
528
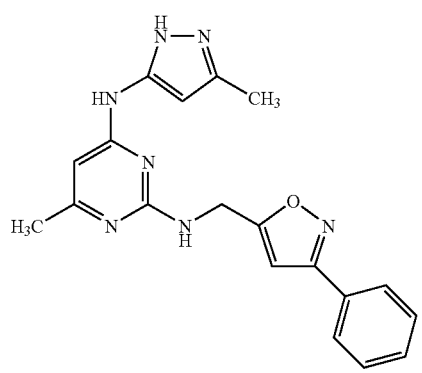
529
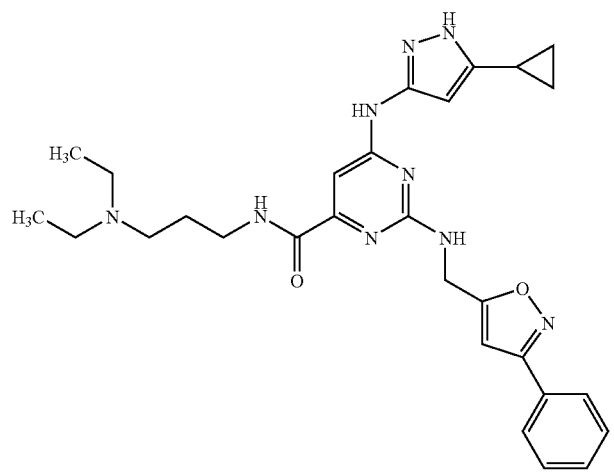

US 8,222,256 B2
TABLE 1-continued
530 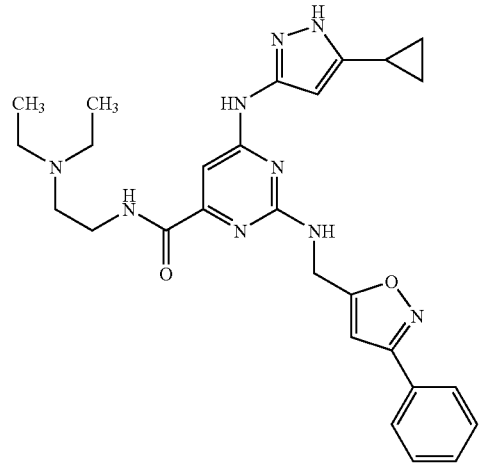
531 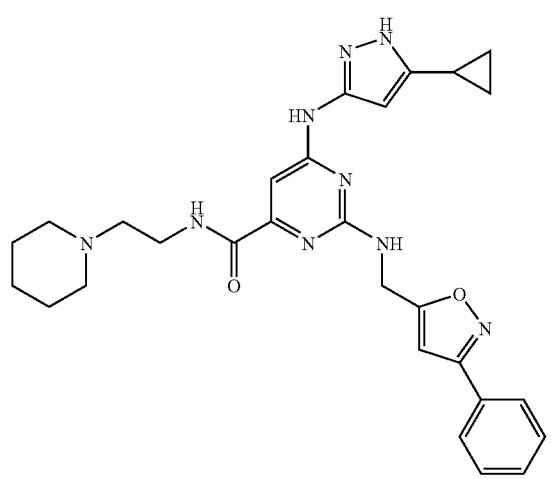
532 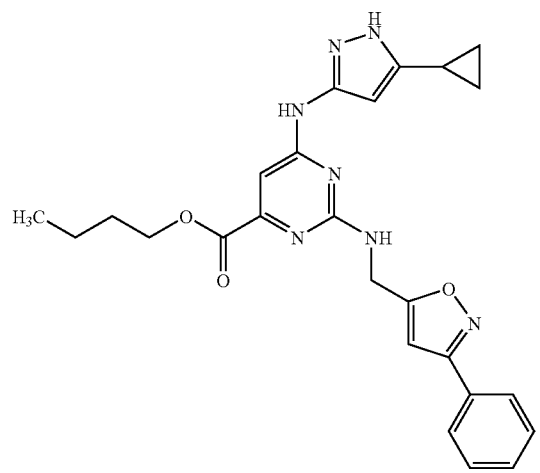

TABLE 1-continued
533 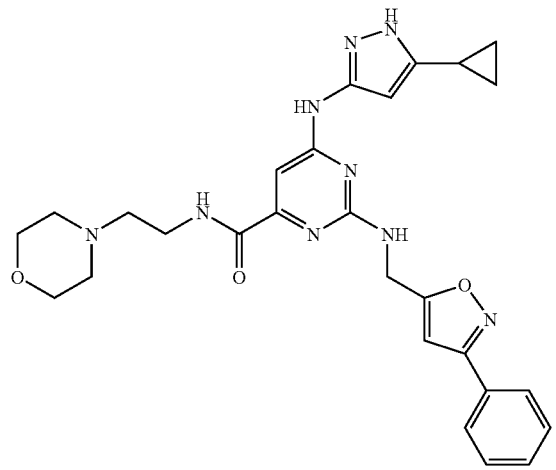
534 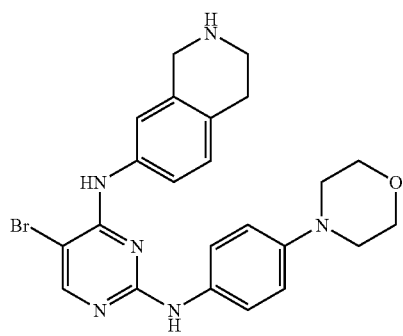
535 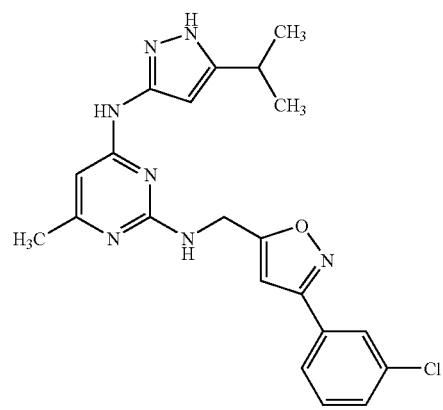
536 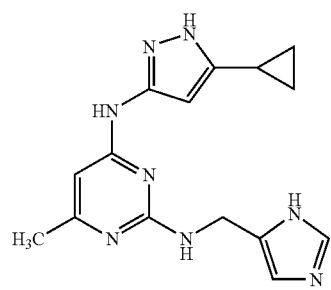

| | |
|---|---|
| 537 | 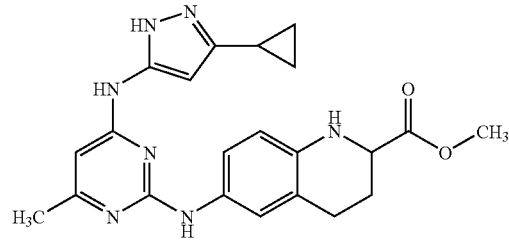 |
| 538 | 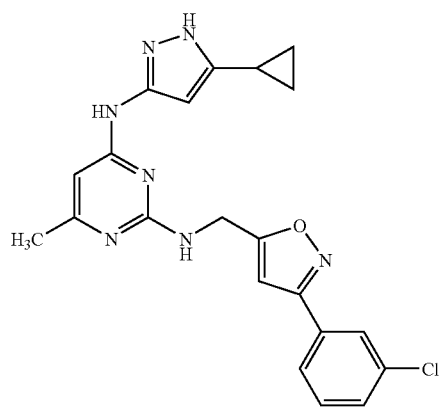 |
| 539 | 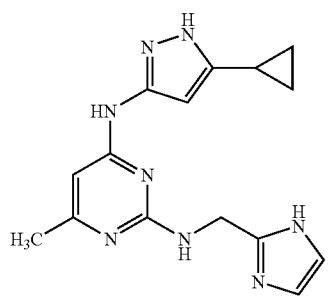 |
| 540 | 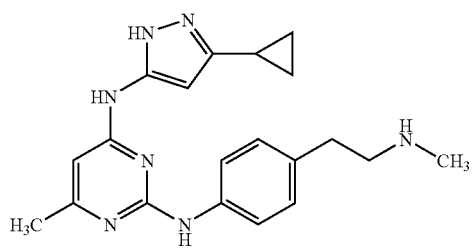 |
| 541 | 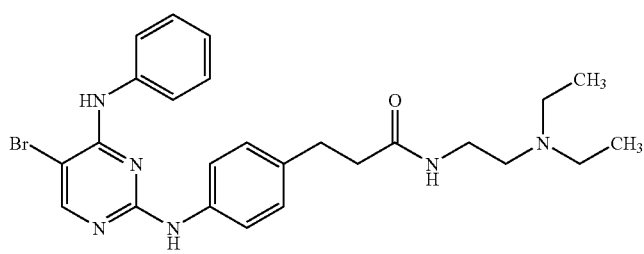 |

TABLE 1-continued
| | |
|---|---|
| 542 | 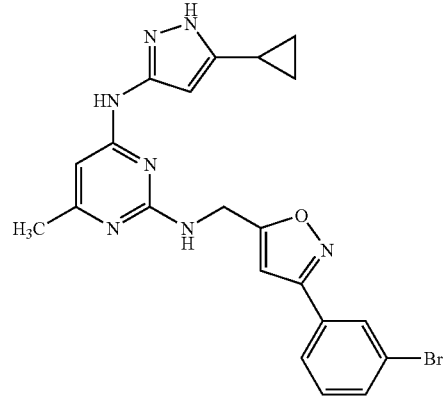 |
| 543 | 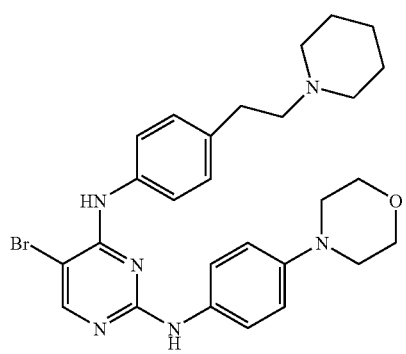 |
| 544 | 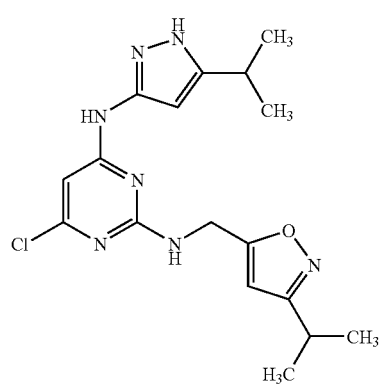 |
| 545 | 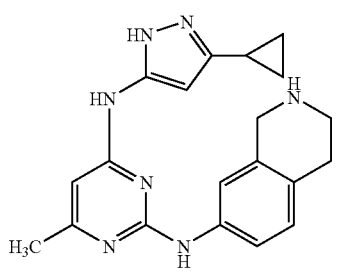 |

TABLE 1-continued
546 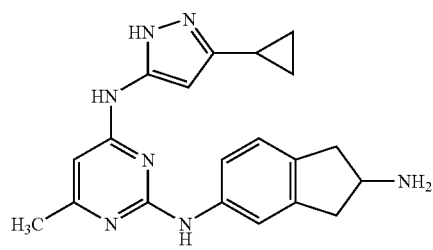
547 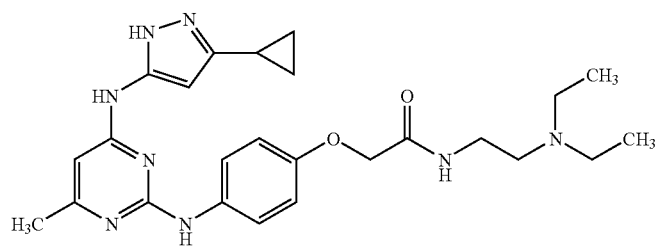
548 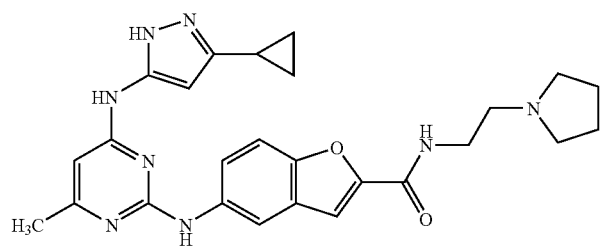
549 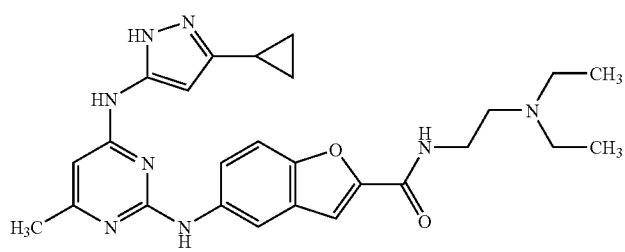
550 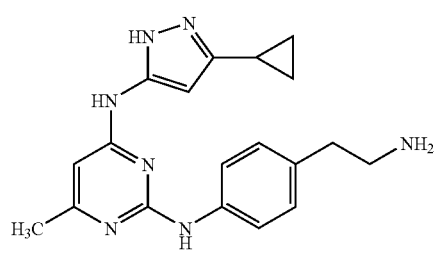
551 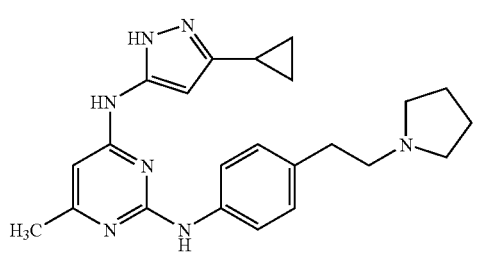

TABLE 1-continued
552 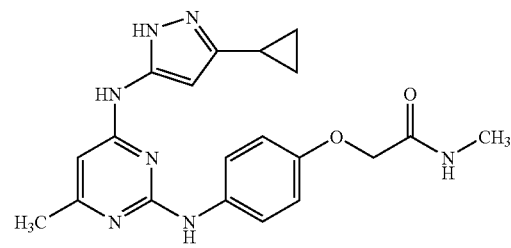
553 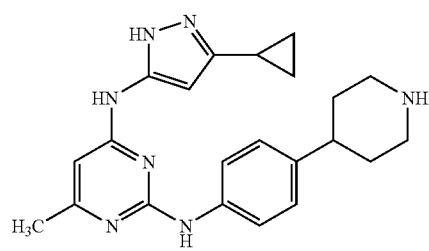
554 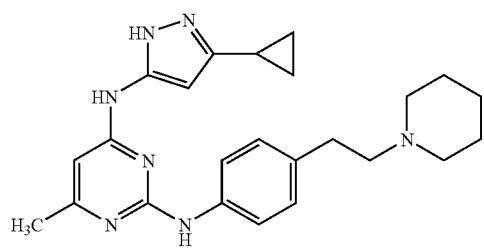
555 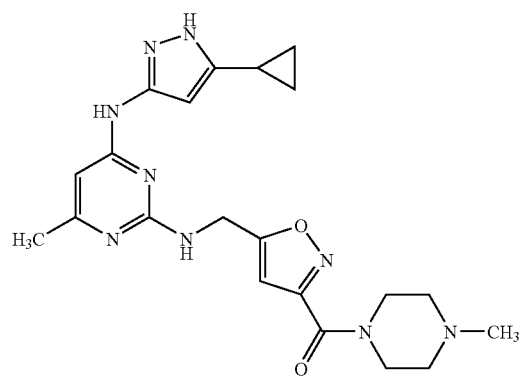
556 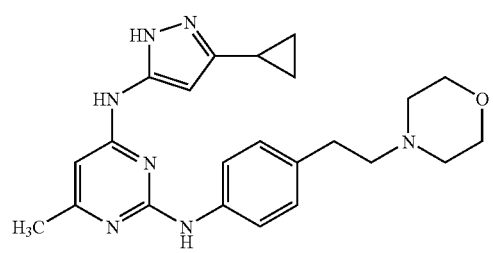

TABLE 1-continued
| 557 | 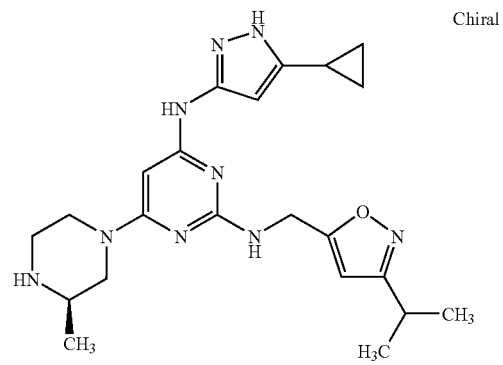 Chiral |
| 558 | 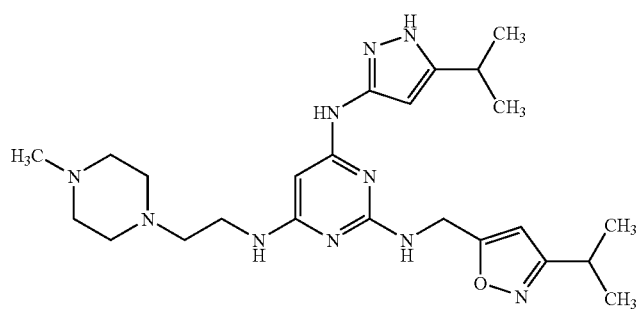 |
| 559 | 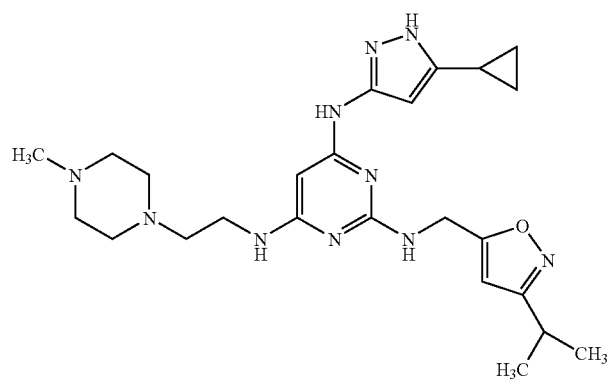 |
| 560 | 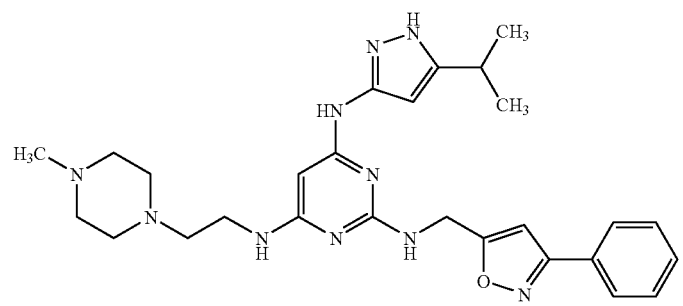 |

TABLE 1-continued
| 561 | 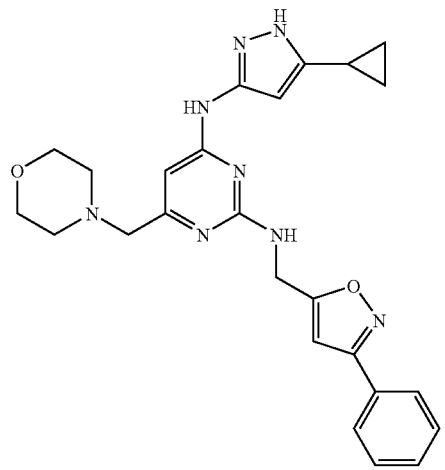 |
| --- | --- |
| 562 | 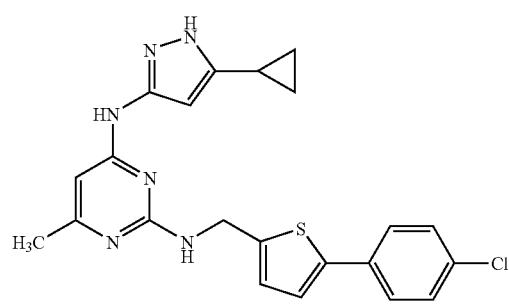 |
| 563 | 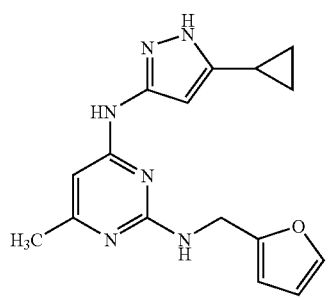 |
| 564 | 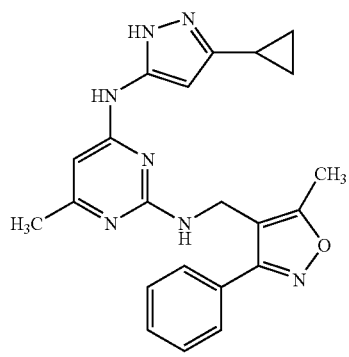 |

TABLE 1-continued
| | |
|---|---|
| 565 | 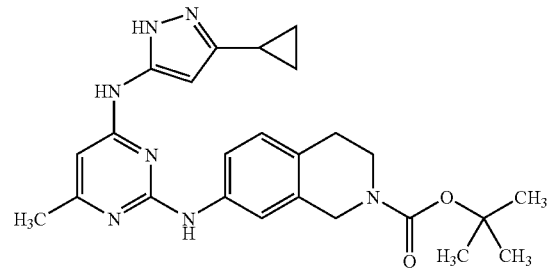 |
| 566 | 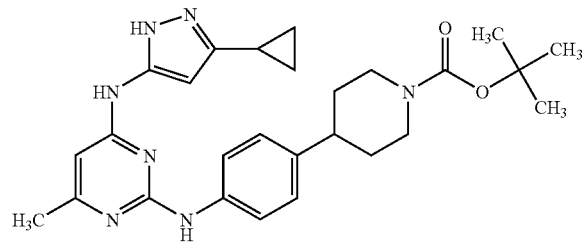 |
| 567 | 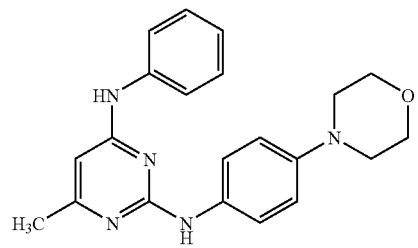 |
| 568 | 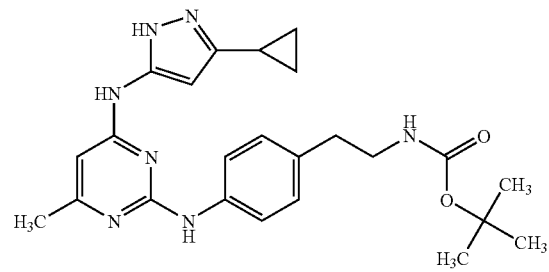 |
| 569 | 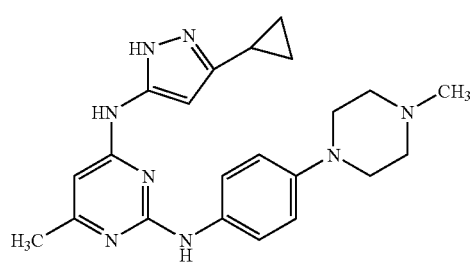 |
| 570 | 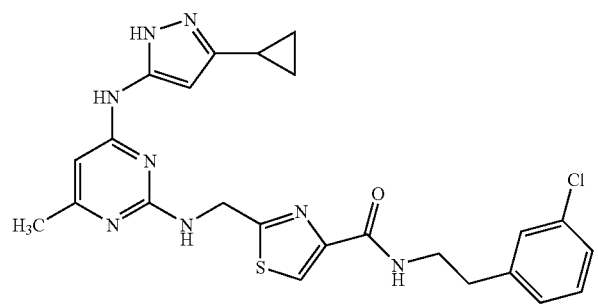 |

TABLE 1-continued
| Cmpd No. | Structure | IUPAC Name |
|---|---|---|
| 571 | 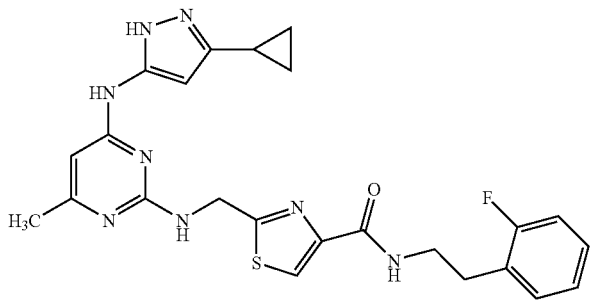 | |
| 572 | 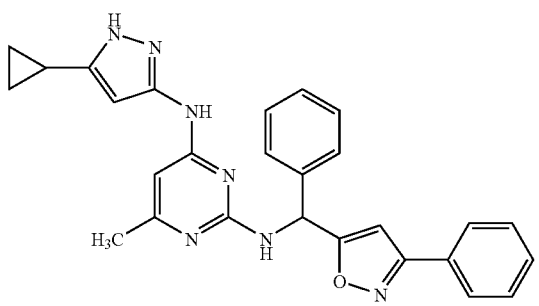 | |
| 573 | 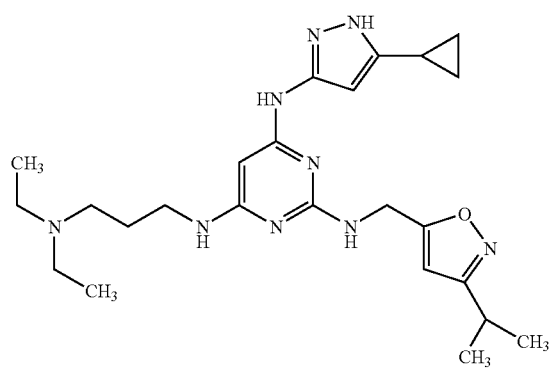 | $N^4$-(5-cyclopropyl-1H-pyrazol-3-yl)-$N^6$-[3-(diethylamino)propyl]-$N^2$-{[3-(1-methylethyl)isoxazol-5-yl]methyl}pyrimidine-2,4,6-triamine |
| 574 | 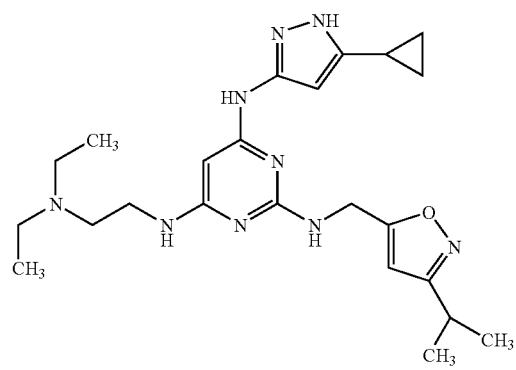 | $N^4$-(5-cyclopropyl-1H-pyrazol-3-yl)-$N^6$-[2-(diethylamino)ethyl]-$N^2$-{[3-(1-methylethyl)isoxazol-5-yl]methyl}pyrimidine-2,4,6-triamine |

| | | |
|---|---|---|
| 575 | 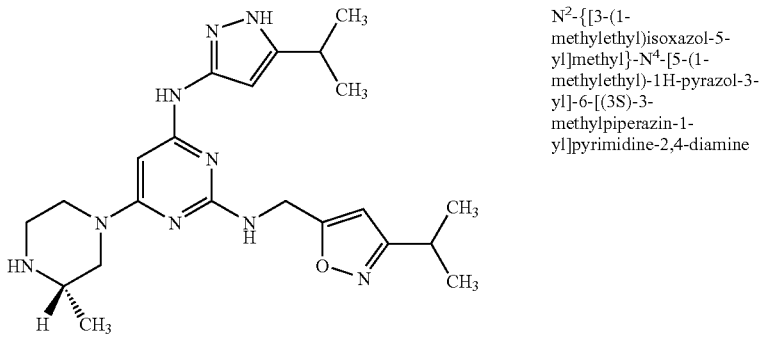 | $N^2$-{[3-(1-methylethyl)isoxazol-5-yl]methyl}-$N^4$-[5-(1-methylethyl)-1H-pyrazol-3-yl]-6-[(3S)-3-methylpiperazin-1-yl]pyrimidine-2,4-diamine |
| 576 | 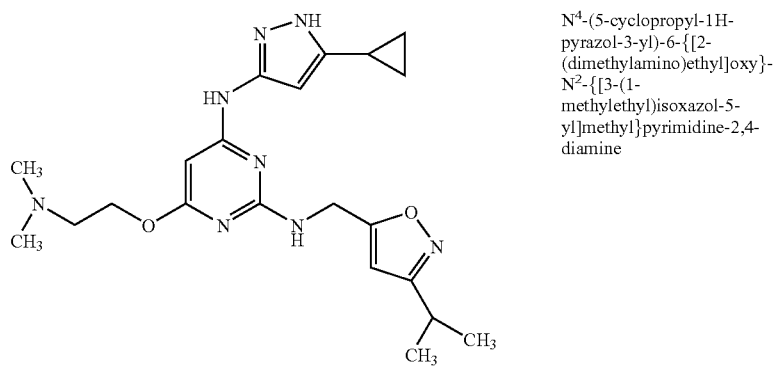 | $N^4$-(5-cyclopropyl-1H-pyrazol-3-yl)-6-{[2-(dimethylamino)ethyl]oxy}-$N^2$-{[3-(1-methylethyl)isoxazol-5-yl]methyl}pyrimidine-2,4-diamine |
| 577 | 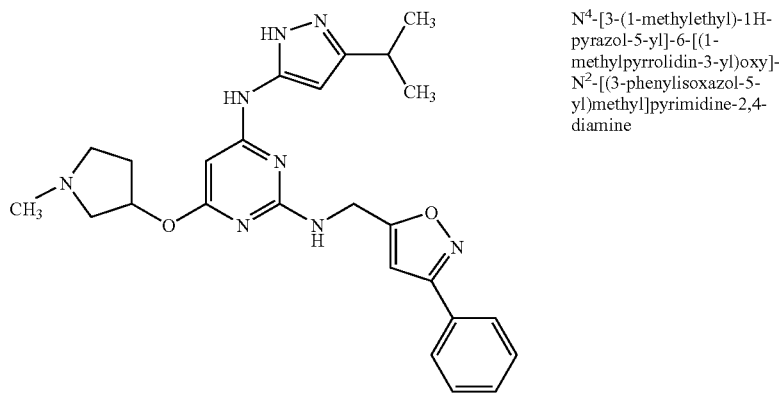 | $N^4$-[3-(1-methylethyl)-1H-pyrazol-5-yl]-6-[(1-methylpyrrolidin-3-yl)oxy]-$N^2$-[(3-phenylisoxazol-5-yl)methyl]pyrimidine-2,4-diamine |
| 578 | 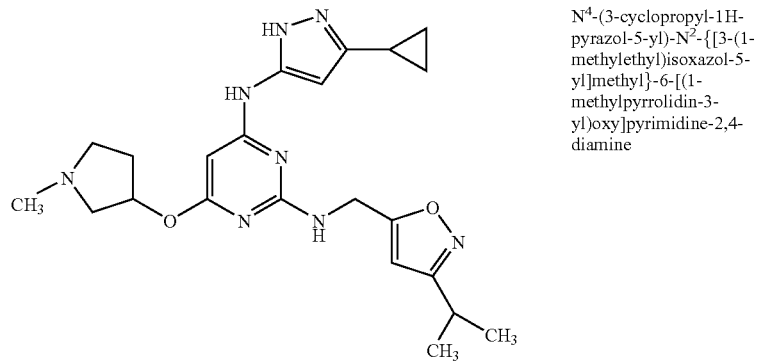 | $N^4$-(3-cyclopropyl-1H-pyrazol-5-yl)-$N^2$-{[3-(1-methylethyl)isoxazol-5-yl]methyl}-6-[(1-methylpyrrolidin-3-yl)oxy]pyrimidine-2,4-diamine |

TABLE 1-continued

| | | |
|---|---|---|
| 579 | 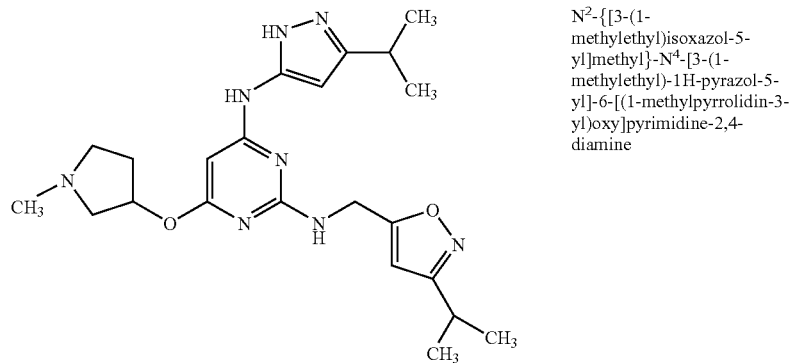 | $N^2$-{[3-(1-methylethyl)isoxazol-5-yl]methyl}-$N^4$-[3-(1-methylethyl)-1H-pyrazol-5-yl]-6-[(1-methylpyrrolidin-3-yl)oxy]pyrimidine-2,4-diamine |
| 580 | 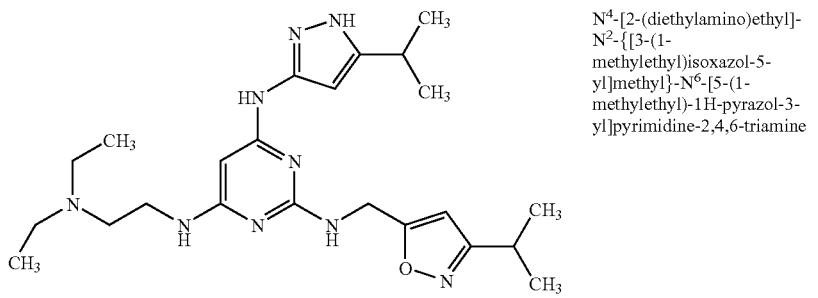 | $N^4$-[2-(diethylamino)ethyl]-$N^2$-{[3-(1-methylethyl)isoxazol-5-yl]methyl}-$N^6$-[5-(1-methylethyl)-1H-pyrazol-3-yl]pyrimidine-2,4,6-triamine |
| 581 | 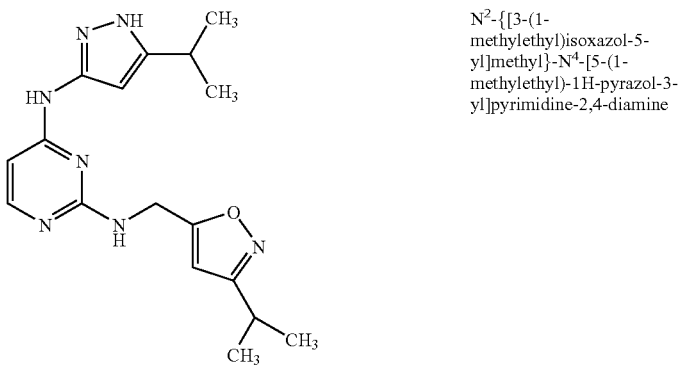 | $N^2$-{[3-(1-methylethyl)isoxazol-5-yl]methyl}-$N^4$-[5-(1-methylethyl)-1H-pyrazol-3-yl]pyrimidine-2,4-diamine |
| 582 | 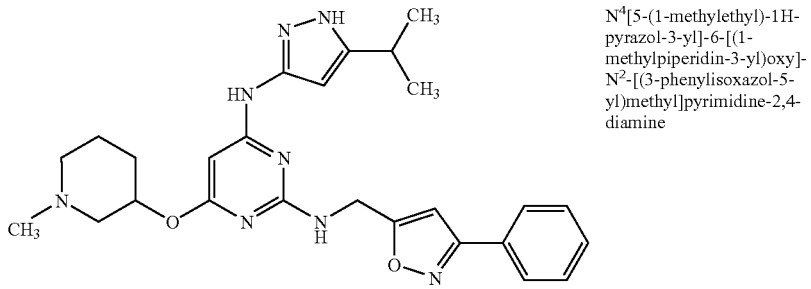 | $N^4$[5-(1-methylethyl)-1H-pyrazol-3-yl]-6-[(1-methylpiperidin-3-yl)oxy]-$N^2$-[(3-phenylisoxazol-5-yl)methyl]pyrimidine-2,4-diamine |
| 583 | 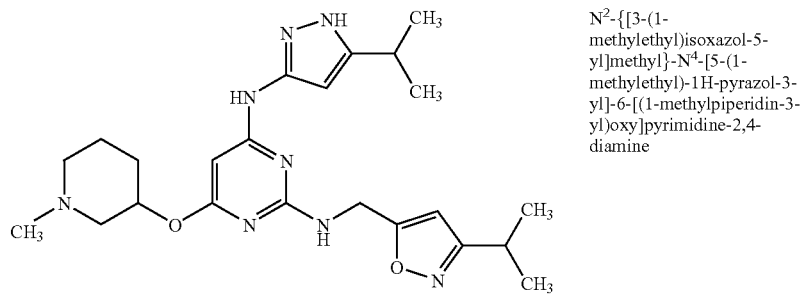 | $N^2$-{[3-(1-methylethyl)isoxazol-5-yl]methyl}-$N^4$-[5-(1-methylethyl)-1H-pyrazol-3-yl]-6-[(1-methylpiperidin-3-yl)oxy]pyrimidine-2,4-diamine |

TABLE 1-continued

| | | |
|---|---|---|
| 584 | 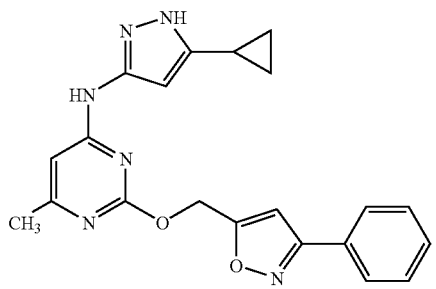 | N-(5-cyclopropyl-1H-pyrazol-3-yl)-6-methyl-2-{[(3-phenylisoxazol-5-yl)methyl]oxy}pyrimidin-4-amine |
| 585 | 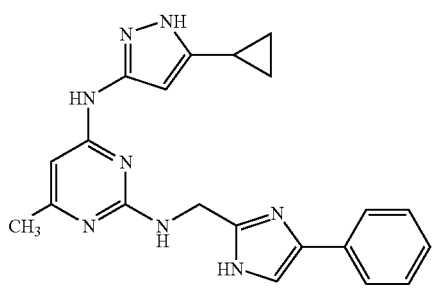 | $N^4$-(5-cyclopropyl-1H-pyrazol-3-yl)-6-methyl-$N^2$-[(4-phenyl-1H-imidazol-2-yl)methyl]pyrimidine-2,4-diamine |
| 586 | 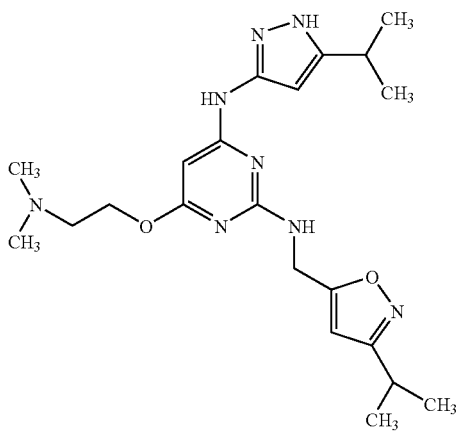 | 6-{[2-(dimethylamino)ethyl]oxy}-$N^2$-{[3-(1-methylethyl)isoxazol-5-yl]methyl}-$N^4$-[5-(1-methylethyl)-1H-pyrazol-3-yl]pyrimidine-2,4-diamine |
| 587 | 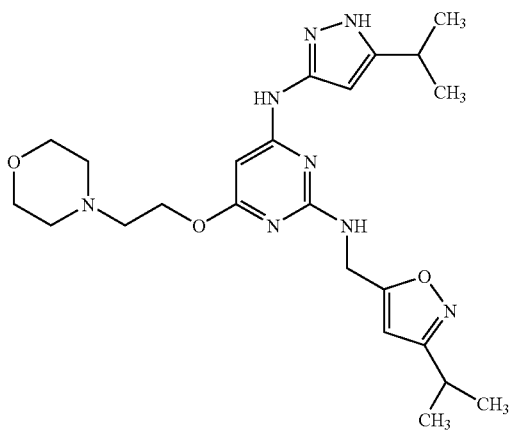 | $N^2$-{[3-(1-methylethyl)isoxazol-5-yl]methyl}-$N^4$-[5-(1-methylethyl)-1H-pyrazol-3-yl]-6-[(2-morpholin-4-ylethyl)oxy]pyrimidine-2,4-diamine |

TABLE 1-continued

| 588 | 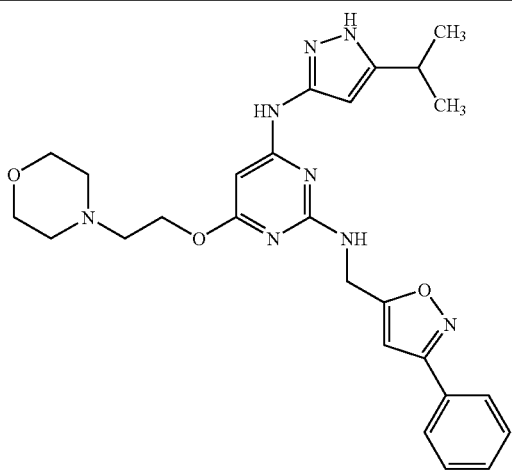 | $N^4$-[5-(1-methylethyl)-1H-pyrazol-3-yl]-6-[(2-morpholin-4-ylethyl)oxy]-$N^2$-[(3-phenylisoxazol-5-yl)methyl]pyrimidine-2,4-diamine |
| --- | --- | --- |
| 589 | 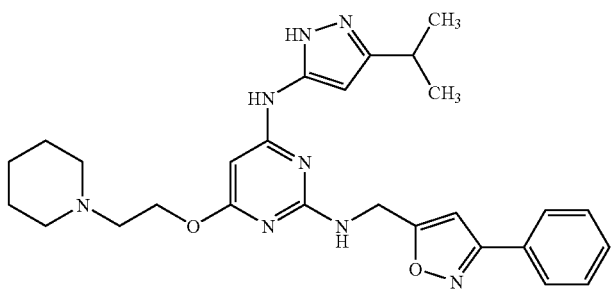 | $N^4$-[3-(1-methylethyl)-1H-pyrazol-5-yl]-$N^2$-[(3-phenylisoxazol-5-yl)methyl]-6-[(2-piperidin-1-ylethyl)oxy]pyrimidine-2,4-diamine |
| 590 | 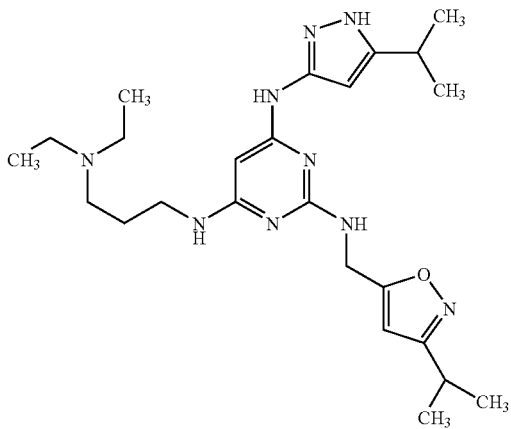 | $N^4$-[3-(diethylamino)propyl]-$N^2$-{[3-(1-methylethyl)isoxazol-5-yl]methyl}-$N^6$-[5-(1-methylethyl)-1H-pyrazol-3-yl]pyrimidine-2,4,6-triamine |
| 591 | 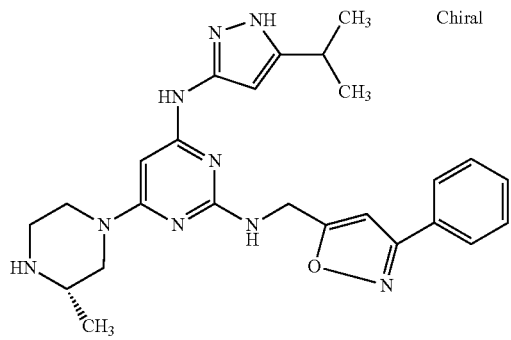 Chiral | $N^4$-[5-(1-methylethyl)-1H-pyrazol-3-yl]-6-[(3S)-3-methylpiperazin-1-yl]-$N^2$-[(3-phenylisoxazol-5-yl)methy]pyrimidine-2,4-diamine |

| | | |
|---|---|---|
| 592 | 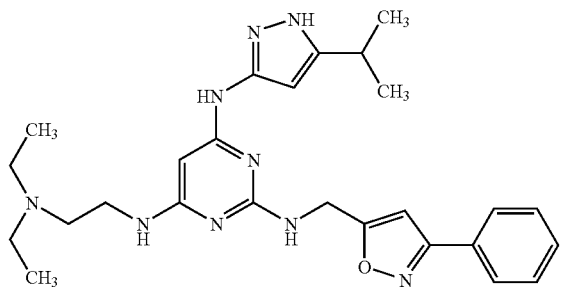 | $N^4$-[2-(diethylamino)ethyl]-$N^6$-[5-(1-methylethyl)-1H-pyrazol-3-yl]-$N^2$-[(3-phenylisoxazol-5-yl)methyl]pyrimidine-2,4,6-triamine |
| 593 | 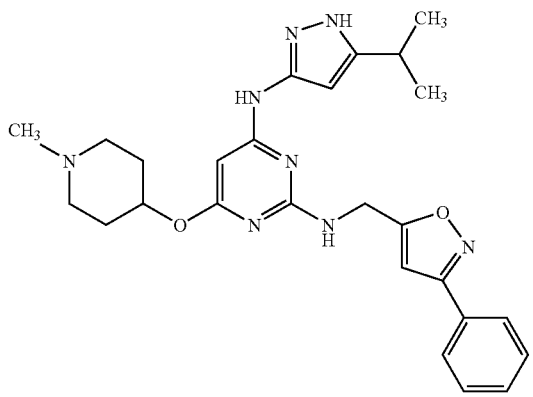 | $N^4$-[5-(1-methylethyl)-1H-pyrazol-3-yl]-6-[(1-methylpiperidin-4-yl)oxy]-$N^2$-[(3-phenylisoxazol-5-yl)methyl]pyrimidine-2,4-diamine |
| 594 | 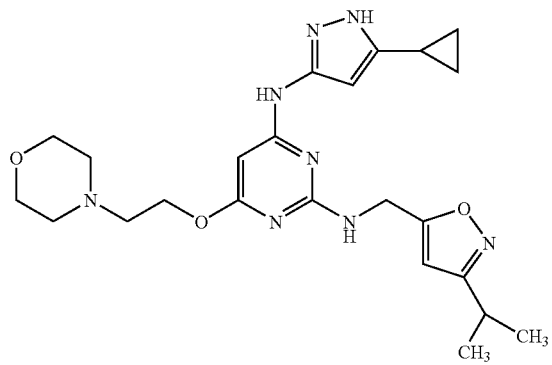 | $N^4$-(5-cyclopropyl-1H-pyrazol-3-yl)-$N^2$-{[3-(1-methylethyl)isoxazol-5-yl]methyl}-6-[(2-morpholin-4-ylethyl)oxy]pyrimidine-2,4-diamine |
| 595 | 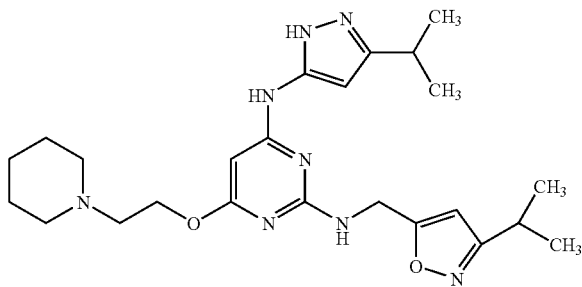 | $N^2$-{[3-(1-methylethyl)isoxazol-5-yl]methyl}-$N^4$-[3-(1-methylethyl)-1H-pyrazol-5-yl]-6-[(2-piperidin-1-ylethyl)oxy]pyrimidine-2,4-diamine |
| 596 | 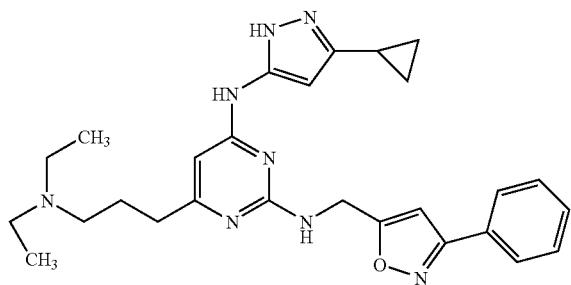 | $N^4$-(3-cyclopropyl-1H-pyrazol-5-yl)-6-[3-(diethylamino)propyl]-$N^2$-[(3-phenylisoxazol-5-yl)methyl]pyrimidine-2,4-diamine |

TABLE 1-continued

| 597 | 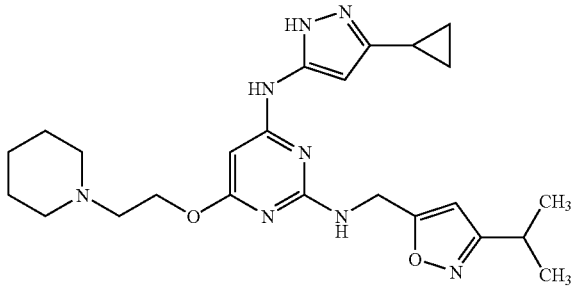 | $N^4$-(5-cyclopropyl-1H-pyrazol-3-yl)-$N^2$-{[3-(1-methylethyl)isoxazol-5-yl]methyl}-6-[(2-piperidin-1-ylethyl)oxy]pyrimidine-2,4-diamine |
| --- | --- | --- |
| 598 | 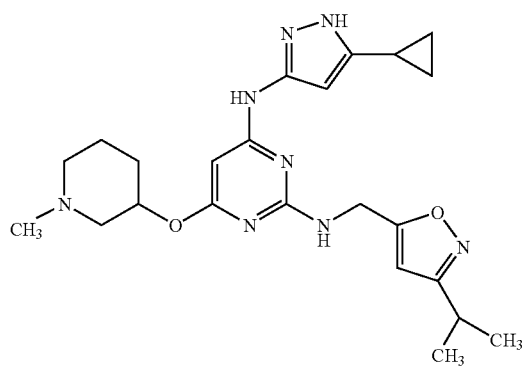 | $N^4$-(5-cyclopropyl-1H-pyrazol-3-yl)-$N^2$-{[3-(1-methylethyl)isoxazol-5-yl]methyl}-6-[(1-methylpiperidin-3-yl)oxy]pyrimidine-2,4-diamine |
| 599 | 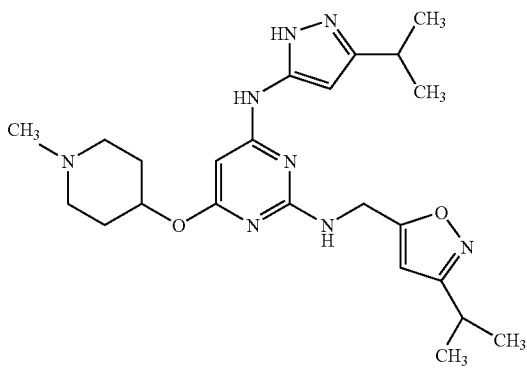 | $N^2${[3-(1-methylethyl)isoxazol-5-yl]methyl}-$N^4$-[3-(1-methylethyl)-1H-pyrazol-5-yl]-6-[(1-methylpiperidin-4-yl)oxy]pyrimidine-2,4-diamine |
| 600 | 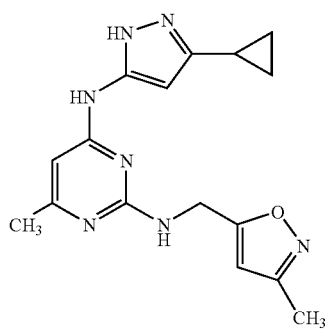 | $N^4$-(3-cyclopropyl-1H-pyrazol-5-yl)-6-methyl-$N^2$-[(3-methylisoxazol-5-yl)methyl]pyrimidine-2,4-diamine |

TABLE 1-continued

| | | |
|---|---|---|
| 601 | 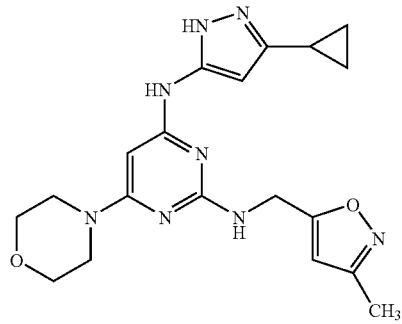 | N4-(3-cyclopropyl-1H-pyrazol-5-yl)-N2-[(3-methylisoxazol-5-yl)methyl]-6-morpholin-4-ylpyrimidine-2,4-diamine |
| 602 | 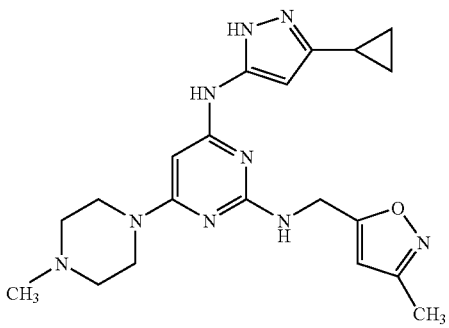 | N4-(3-cyclopropyl-1H-pyrazol-5-yl)-N2-[(3-methylisoxazol-5-yl)methyl]-6-(4-methylpiperazin-1-yl)pyrimidine-2,4-diamine |
| 603 | 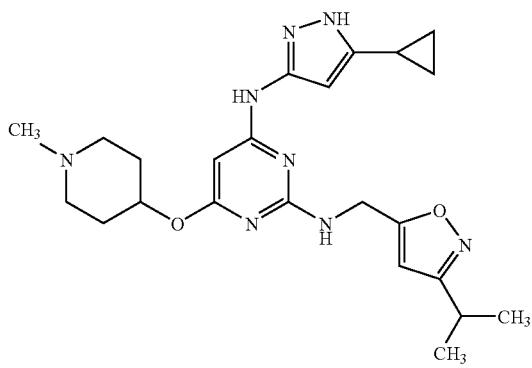 | N4-(5-cyclopropyl-1H-pyrazol-3-yl)-N2-{[3-(1-methylethyl)isoxazol-5-yl]methyl}-6-[(1-methylpiperidin-4-yl)oxy]pyrimidine-2,4-diamine |
| 604 | 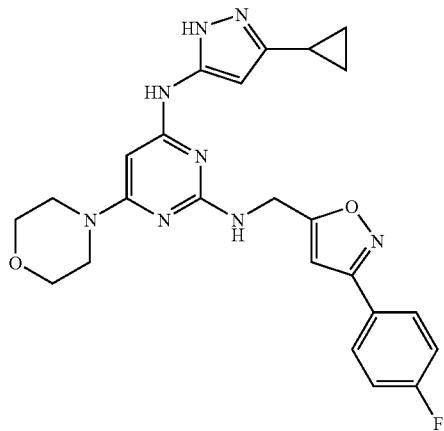 | N4-(3-cyclopropyl-1H-pyrazol-5-yl)-N2-{[3-(4-fluorophenyl)isoxazol-5-yl]methyl}-6-morpholin-4-ylpyrimidine-2,4-diamine |

TABLE 1-continued
| | | |
|---|---|---|
| 605 | 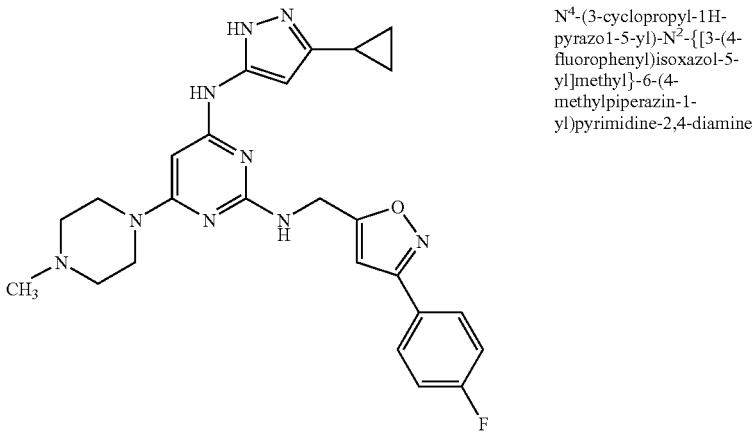 | N[4]-(3-cyclopropyl-1H-pyrazol-5-yl)-N[2]-{[3-(4-fluorophenyl)isoxazol-5-yl]methyl}-6-(4-methylpiperazin-1-yl)pyrimidine-2,4-diamine |
| 606 | 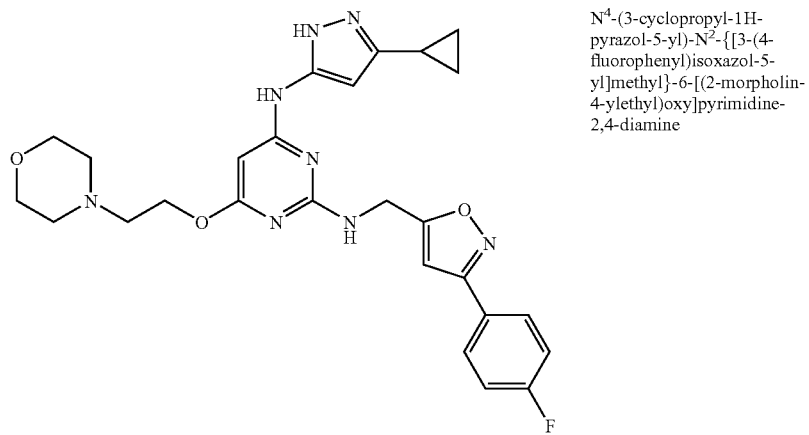 | N[4]-(3-cyclopropyl-1H-pyrazol-5-yl)-N[2]-{[3-(4-fluorophenyl)isoxazol-5-yl]methyl}-6-[(2-morpholin-4-ylethyl)oxy]pyrimidine-2,4-diamine |
| 607 | 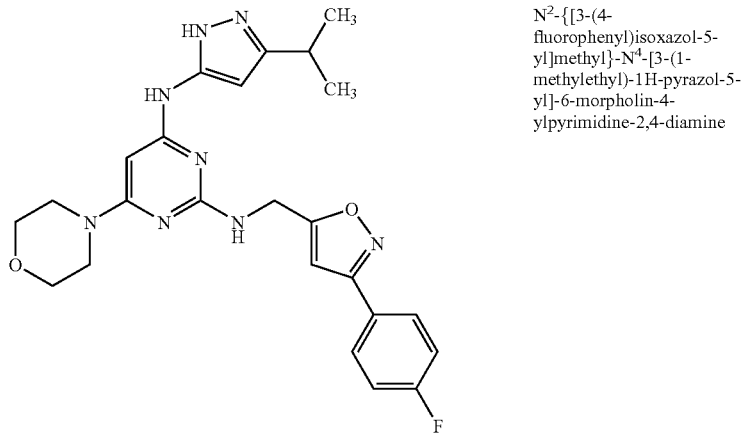 | N[2]-{[3-(4-fluorophenyl)isoxazol-5-yl]methyl}-N[4]-[3-(1-methylethyl)-1H-pyrazol-5-yl]-6-morpholin-4-ylpyrimidine-2,4-diamine |

TABLE 1-continued

| | | |
|---|---|---|
| 608 | 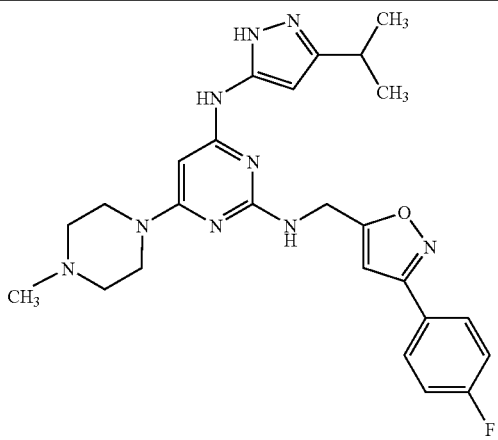 | N²-{[3-(4-fluorophenyl)isoxazol-5-yl]methyl}-N⁴-[3-(1-methylethyl)-1H-pyrazol-5-yl]-6-(4-methylpiperazin-1-yl)pyrimidine-2,4-diamine |
| 609 | 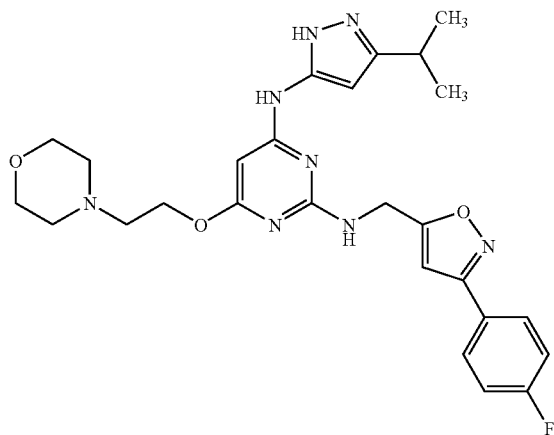 | N²-{[3-(4-fluorophenyl)isoxazol-5-yl]methyl}-N⁴-[3-(1-methylethyl)-1H-pyrazol-5-yl]-6-[(2-morpholin-4-ylethyl)oxy]pyrimidine-2,4-diamine |
| 610 | 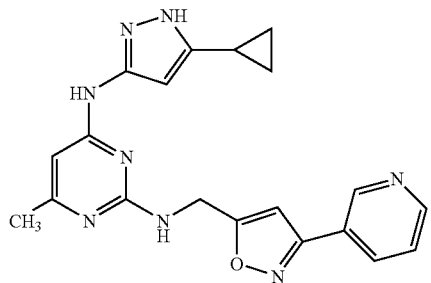 | N⁴-(5-cyclopropyl-1H-pyrazol-3-yl)-6-methyl-N²-[(3-pyridin-3-ylisoxazol-5-yl)methyl]pyrimidine-2,4-diamine |
| 611 | 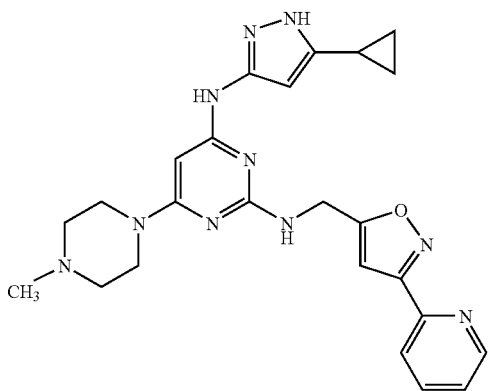 | N⁴-(5-cyclopropyl-1H-pyrazol-3-yl)-6-(4-methylpiperazin-1-yl)-N²-[(3-pyridin-2-ylisoxazol-5-yl)methyl]pyrimidine-2,4-diamine |

TABLE 1-continued

| 612 | 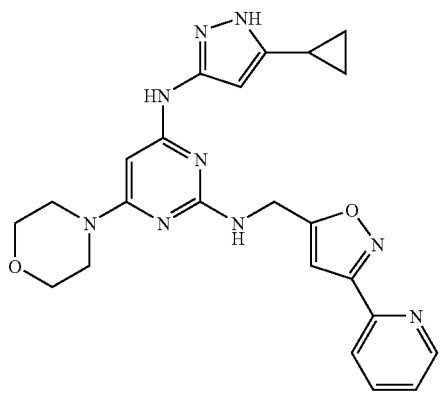 | N4-(5-cyclopropyl-1H-pyrazol-3-yl)-6-morpholin-4-yl-N2-[(3-pyridin-2-ylisoxazol-5-yl)methyl]pyrimidine-2,4-diamine |
| 613 | 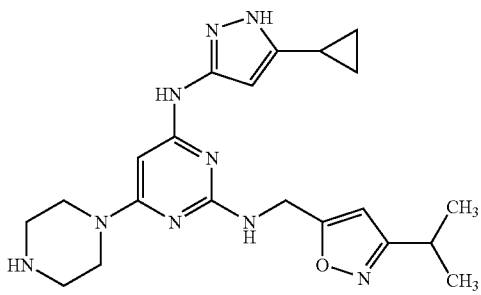 | N4-(5-cyclopropyl-1H-pyrazol-3-yl)-N2-{[3-(1-methylethyl)isoxazol-5-yl]methyl}-6-piperazin-1-ylpyrimidine-2,4-diamine |
| 614 | 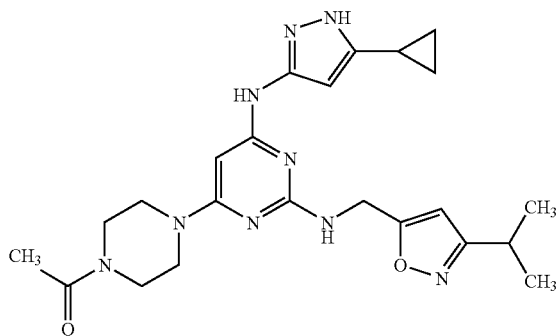 | 6-(4-acetylpiperazin-1-yl)-N4-(5-cyclopropyl-1H-pyrazol-3-yl)-N2-{[3-(1-methylethyl)isoxazol-5-yl]methyl}pyrimidine-2,4-diamine |
| 615 | 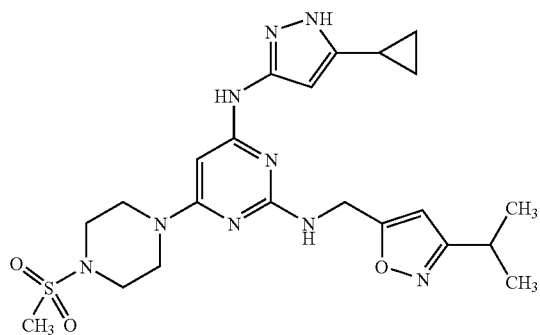 | N4-(5-cyclopropyl-1H-pyrazol-3-yl)-N2-{[3-(1 methylethyl)isoxazol-5-yl]methyl}-6-[4-(methylsulfonyl)piperazin-1-yl]pyrimidine-2,4-diamine |

| | | |
|---|---|---|
| 616 | 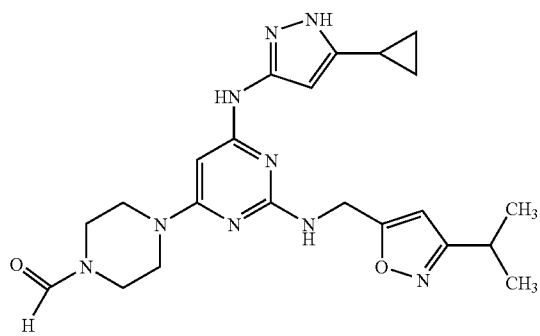 | 4-{6-[(5-cyclopropyl-1H-pyrazol-3-yl)amino]-2-({[3-(1-methylethyl)isoxazol-5-yl]methyl}amino)pyrimidin-4-yl}piperazine-1-carbaldehyde |
| 617 | 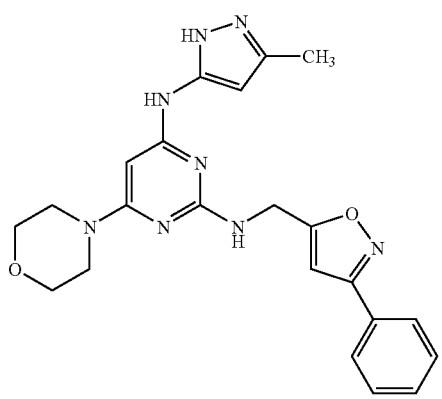 | $N^4$-(3-methyl-1H-pyrazol-5-yl)-6-morpholin-4-yl-$N^2$-[(3-phenylisoxazol-5-yl)methyl]pyrimidine-2,4-diamine |
| 618 | 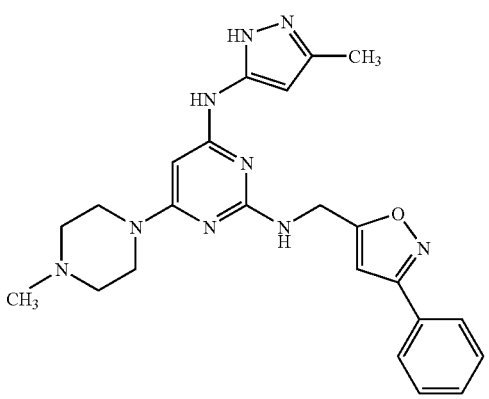 | 6-(4-methylpiperazin-1-yl)-$N^4$-(3-methyl-1H-pyrazol-5-yl)-$N^2$-[(3-phenylisoxazol-5-yl)methyl]pyrimidine-2,4-diamine |
| 619 | 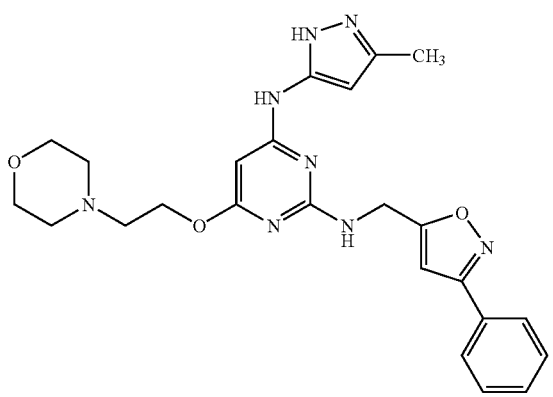 | $N^4$-(3-methyl-1H-1-pyrazol-5-yl)-6-[(2-morpholin-4-ylethyl)oxy]$N^2$-[(3-phenylisoxazol-5-yl)methyl]pyrimidine-2,4-diamine |

| | | |
|---|---|---|
| 620 | 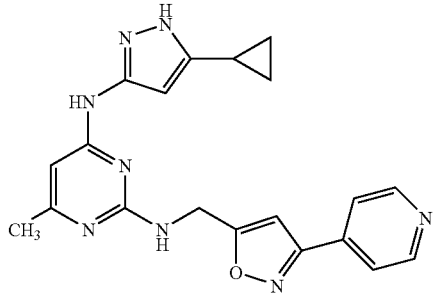 | $N^4$-(5-cyclopropyl-1H-pyrazol-3-yl)-6-methyl-$N^2$-[(3-pyridin-4-ylisoxazol-5-yl)methyl]pyrimidine-2,4-diamine |
| 621 | 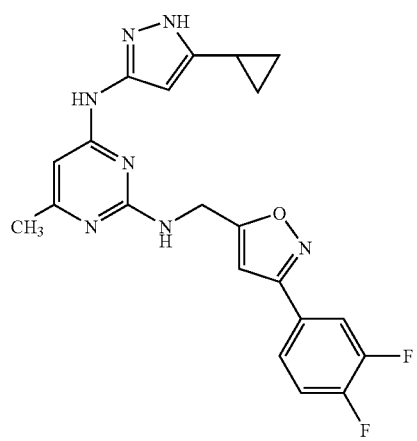 | $N^4$-(5-cyclopropyl-1H-pyrazol-3-yl)-$N^2$-{[3-(3,4-difluorophenyl)isoxazol-5-yl]methyl}-6-methylpyrimidine-2,4-diamine |
| 622 | 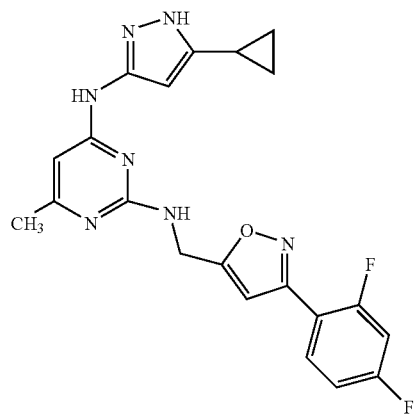 | $N^4$-(5-cyclopropyl-1H-pyrazol-3-yl)-$N^2$-([3-(2,4-difluorophenyl)isoxazol-5-yl]methyl}-6-methylpyrimidine-2,4-diamine |
| 623 | 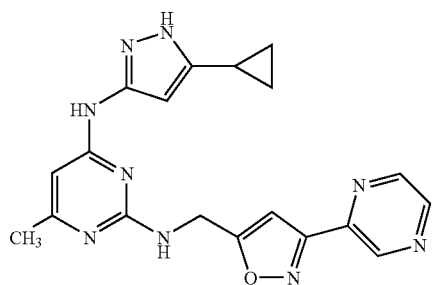 | $N^4$-(5-cyclopropyl-1H-pyrazol-3-yl)-6-methyl-$N^2$-[(3-pyrazin-2-ylisoxazol-5-yl)methyl]pyrimidine-2,4-diamine |

TABLE 1-continued

| | | |
|---|---|---|
| 624 | 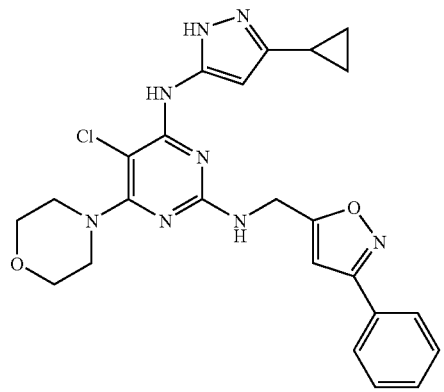 | 5-chloro-$N^4$-(3-cyclopropyl-1H-pyrazol-5-yl)-6-morpholin-4-yl-$N^2$-[(3-phenylisoxazol-5-yl)methyl]pyrimidine-2,4-diamine |
| 625 | 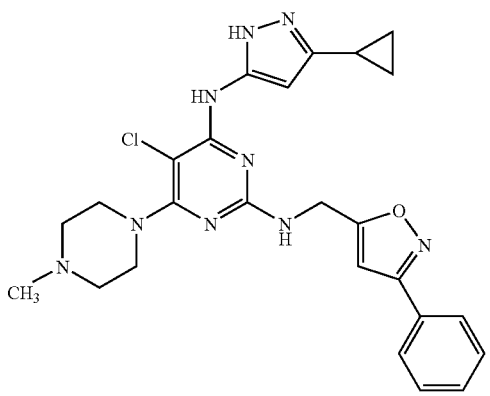 | 5-chloro-$N^4$-(3-cyclopropyl-1H-pyrazol-5-yl)-6-(4-methylpiperazin-1-yl)-$N^2$-[(3-phenylisoxazol-5-yl)methyl]pyrimidine-2,4-diamine |
| 626 | 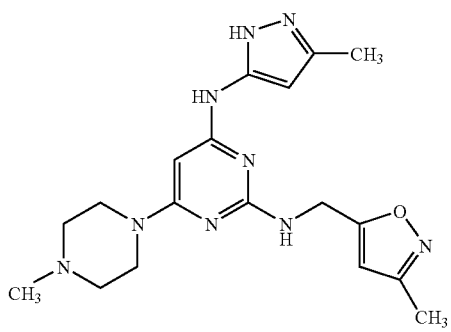 | $N^2$-{(3-methylisoxazol-5-yl)methyl]-6-(4-methylpiperazin-1-yl)-$N^4$-(3-methyl-1H-pyrazol-5-yl)pyrimidine-2,4-diamine |
| 627 | 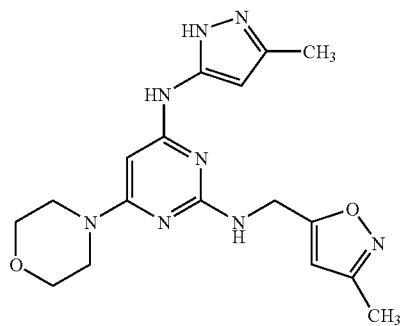 | $N^2$-[(3-methylisoxazol-5-yl)methyl]-$N^4$-(3-methyl-1H-pyrazol-5-yl)-6-morpholin-4-ylpyrimidine-2,4-diamine |

| 628 | 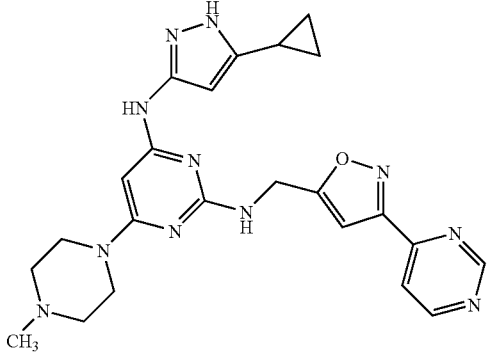 | $N^4$-(5-cyclopropyl-1H-pyrazol-3-yl)-6-(4-methylpiperazin-1-yl)-$N^2$-[(3-pyrimidin-4-ylisoxazol-5-ylmethyl]pyrimidine-2,4-diamine |
|---|---|---|
| 629 | 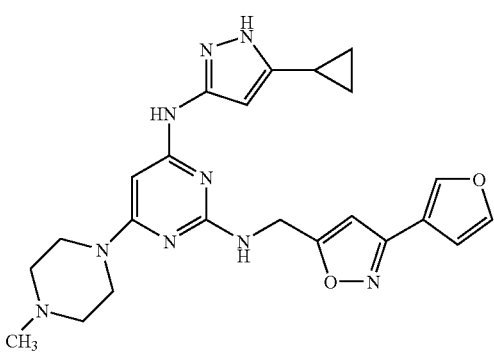 | $N^4$-(5-cyclopropyl-1H-pyrazol-3-yl)-$N^2$-[(3-furan-3-ylisoxazol-5-yl)methyl[-6-(4-methylpiperazin-1-yl)pyrimidine-2,4-diamine |
| 630 Chiral | 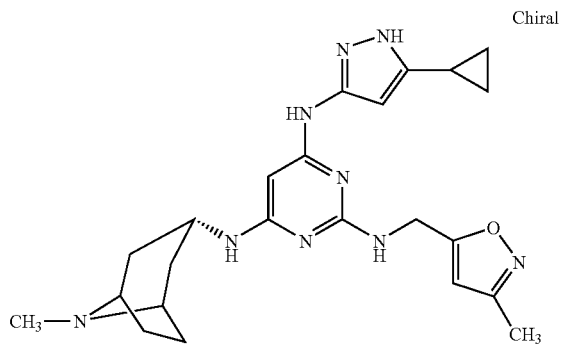 | $N^4$-(5-cyclopropyl-1H-pyrazol-3-yl)-N-(8-methyl-8-azabicyclo[3.2.1]oct-3-yl)-$N^2$-[(3-methylisoxazol-5-yl)methyl]pyrimidine-2,4,6-triamine |
| 631 | 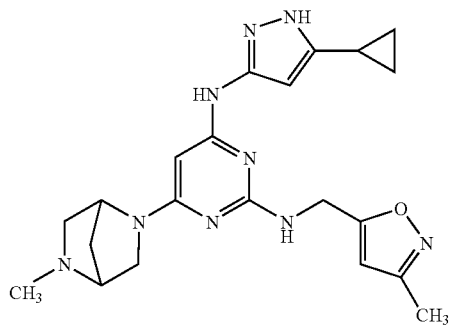 | $N^4$-(5-cyclopropyl-1H-pyrazol-3-yl)-6-(5-methyl-2,5-diazabicyclo[2.2.1]hept-2-yl)-$N^2$-[(3-methylisoxazol-5-yl)methyl]pyrimidine-2,4-diamine |

TABLE 1-continued

| | | |
|---|---|---|
| 632 | 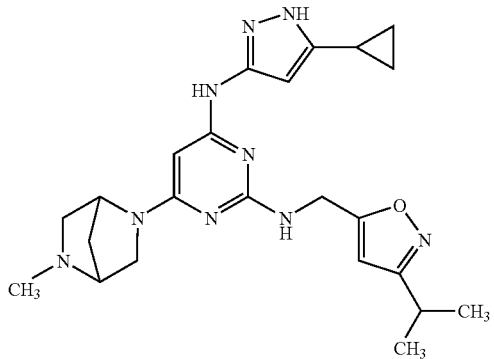 | N4-(5-cyclopropyl-1H-pyrazol-3-yl)-6-(5-methyl-2,5-diazabicyclo[2.2.1]hept-2-yl)-N2-{[3-(1-methylethyl)isoxazol-5-yl]methyl}pyrimidine-2,4-diamine |
| 633 | 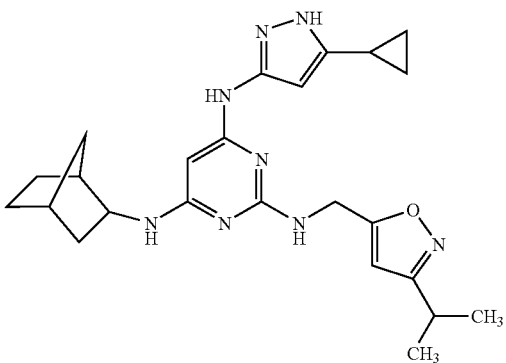 | N4-bicyclo[2.2.1]hept-2-yl-N6-(5-cyclopropyl-1H-pyrazol-3-yl)-N2-{[3-(1-methylethyl)isoxazol-5-yl]methyl}pyrimidine-2,4,6-triamine |
| 634 | 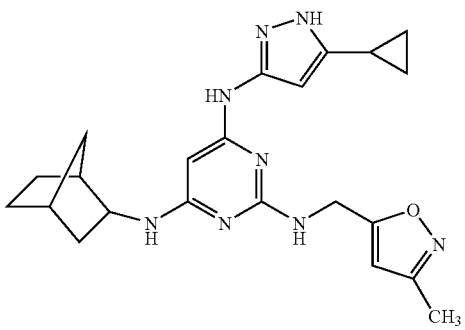 | N4-bicyclo[2.2.1]hept-2-yl-N6-(5-cyclopropyl-1H-pyrazol-3-yl)-N2-[(3-methylisoxazol-5-yl)methyl]pyrimidine-2,4,6-triamine |
| 635 | 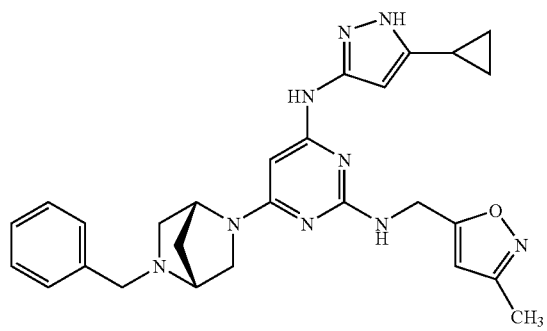 | N4-(5-cyclopropyl-1H-pyrazol-3-yl)-N2-[(3-methylisoxazol-5-yl)methyl]-6-[(1R,4R)-5-(phenylmethyl)-2,5-diazabicyclo[2.2.1]hept-2-yl]pyrimidine-2,4-diamine |

TABLE 1-continued

| | | |
|---|---|---|
| 636 | 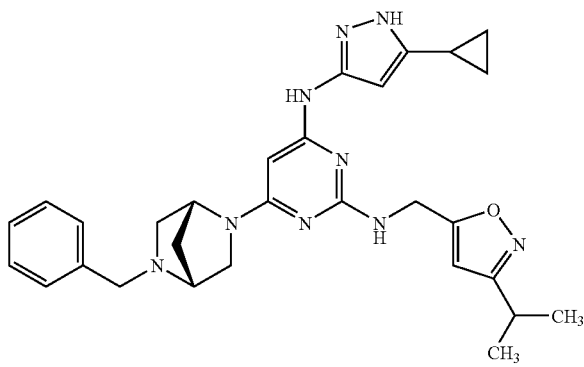 | $N^4$-(5-cyclopropyl-1H-pyrazol-3-yl)-$N^2$-{[3-(1-methylethyl)isoxazol-5-yl]methyl}-6-[(1R,4R)-5-(phenylmethyl)-2,5-diazabicyclo[2.2.1]hept-2-yl]pyrimidine-2,4-diamine |
| 637 | 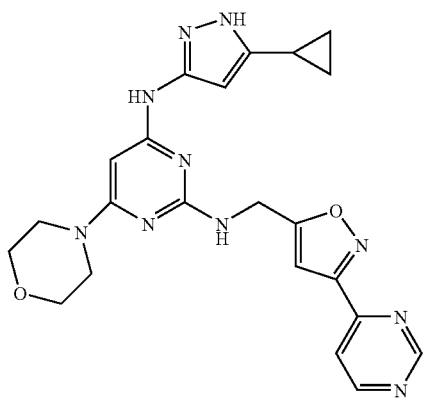 | $N^4$-(5-cyclopropyl-1H-pyrazol-3-yl)-6-morpholin-4-yl-$N^2$-[(3-pyrimidin-4-ylisoxazol-5-yl)methyl]pyrimidine-2,4-diamine |
| 638 | 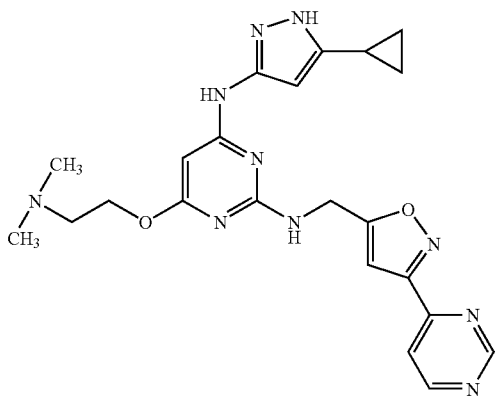 | $N^4$-(5-cyclopropyl-1H-pyrazol-3-yl)-6-{[2-(dimethylamino)ethyl]oxy}-$N^2$-[(3-pyrimidin-4-ylisoxazol-5-yl)methyl]pyrimidine-2,4-diamine |
| 639 | 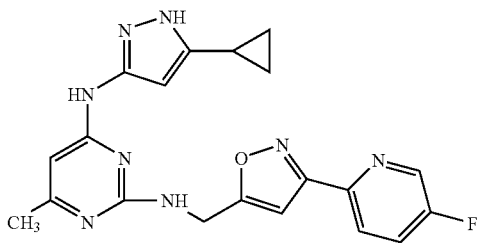 | $N^4$-(5-cyclopropyl-1H-pyrazol-3-yl)-$N^2$-{[3-(5-fluoropyridin-2-yl)isoxazol-5-yl]methyl}-6-methylpyrimidine-2,4-diamine |

TABLE 1-continued

| | | |
|---|---|---|
| 640 | 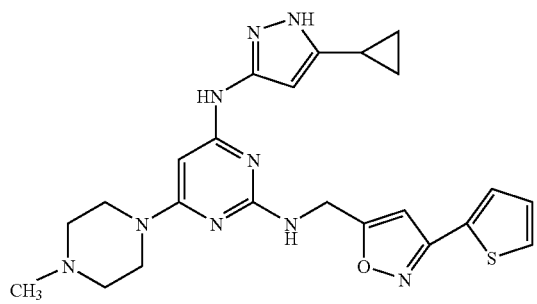 | $N^4$-(5-cyclopropyl-1H-pyrazol-3-yl)-6-(4-methylpiperazin-1-yl)-$N^2$-{[3-(2-thienyl)isoxazol-5-yl]methyl}pyrimidine-2,4-diamine |
| 641 | 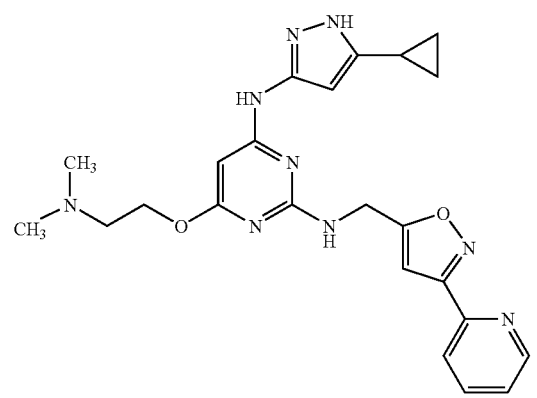 | $N^4$-(5-cyclopropyl-1H-pyrazol-3-yl)-6-{[2-(dimethylamino)ethyl]oxy}-$N^2$-[(3-pyridin-2-ylisoxazol-5-yl)methyl]pyrimidine-2,4-diamine |
| 642 | 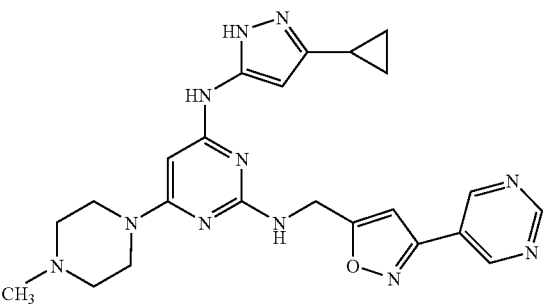 | $N^4$-(3-cyclopropyl-1H-pyrazol-5-yl)-6-(4-methylpiperazin-1-yl)-$N^2$-[(3-pyrimidin-5-ylisoxazol-5-yl)methyl]pyrimidine-2,4-diamine |
| 643 | 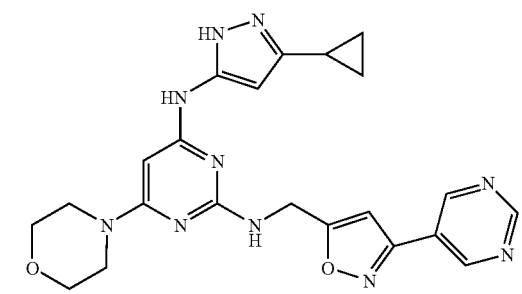 | $N^4$-(3-cyclopropyl-1H-pyrazol-5-yl)-6-morpholin-4-yl-$N^2$-[(3-pyrimidin-5-ylisoxazol-5-yl)methyl]pyrimidine-2,4-diamine |

TABLE 1-continued

| 644 | 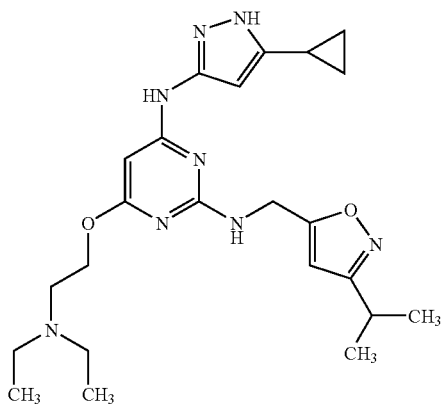 | $N^4$-(5-cyclopropyl-1H-pyrazol-3-yl)-6-{[2-(diethylamino)ethyl]oxy}-$N^2$-{[3-(1-methylethyl)isoxazol-5-yl]methyl}pyrimidine-2,4-diamine |
| --- | --- | --- |
| 645 | 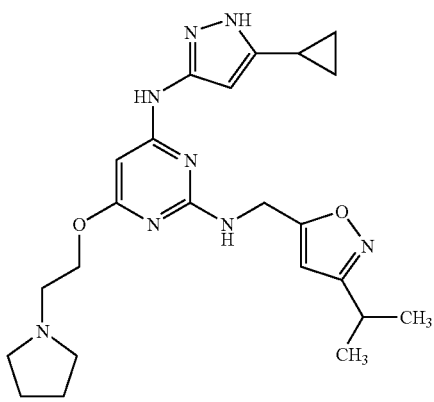 | $N^4$-(5-cyclopropyl-1H-pyrazol-3-yl)-$N^2$-{[3-(1-methylethyl)isoxazol-5-yl]methyl}-6-[(2-pyrrolidin-1-ylethyl)oxy]pyrimidine-2,4-diamine |
| 646 | 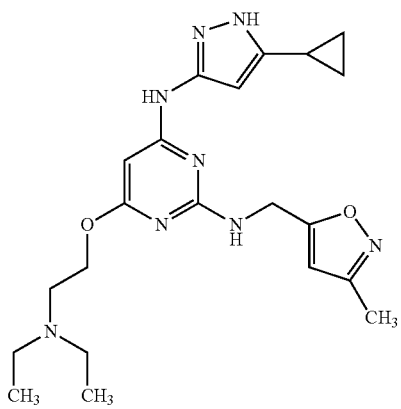 | $N^4$-(5-cyclopropyl-1H-pyrazol-3-yl)-6-{[2-(diethylamino)ethyl]oxy}-$N^2$-[(3-methylisoxazol-5-yl)methyl]pyrimidine-2,4-diamine |
| 647 | 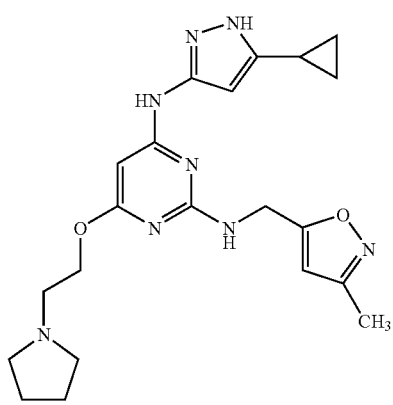 | $N^4$-(5-cyclopropyl-1H-pyrazol-3-yl)-$N^2$-[(3-methylisoxazol-5-yl)methyl]-6-[(2-pyrrolidin-1-ylethyl)oxy]pyrimidine-2,4-diamine |

TABLE 1-continued

| | | |
|---|---|---|
| 648 | 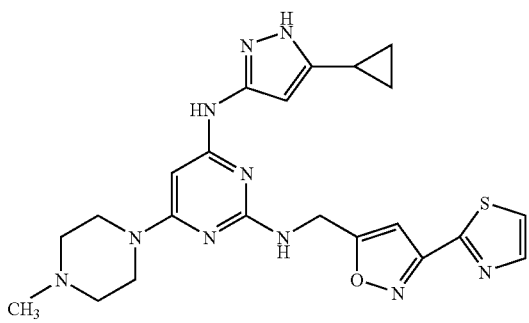 | $N^4$-(5-cyclopropyl-1H-pyrazol-3-yl)-6-(4-methylpiperazin-1-yl)-$N^2$-{[3-(1,3-thiazol-2-yl)isoxazol-5-yl]methyl}pyrimidine-2,4-diamine |
| 649 | 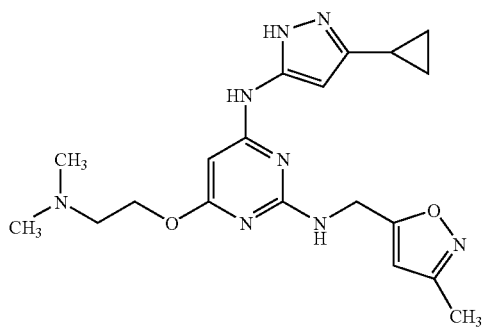 | $N^4$-(3-cyclopropyl-1H-pyrazol-5-yl)-6-[2-(dimethylamino)ethoxy]-$N^2$-[(3-methylisoxazol-5-yl)methyl]pyrimidine-2,4-diamine |
| 650 | 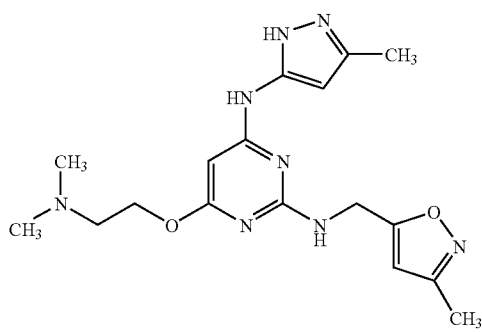 | 6-{[2-(dimethylamino)ethyl]oxy}-$N^2$-[(3-methylisoxazol-5-yl)methy]-$N^4$-(3-methyl-1H-pyrazol-5-yl)pyrimidine-2,4-diamine |
| 651 | 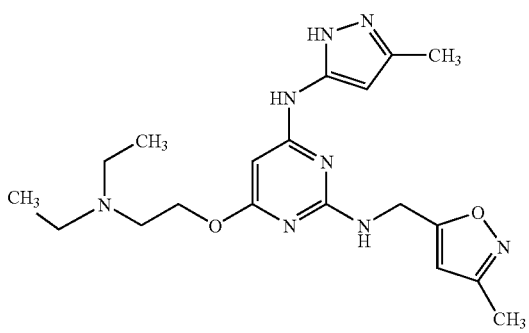 | 6-{[2-(diethylamino)ethyl]oxy}-$N^2$-[(3-methylisoxazol-5-yl)methyl]-$N^4$-(3-methyl-1H-pyrazol-5-yl)pyrimidine-2,4-diamine |
| 652 | 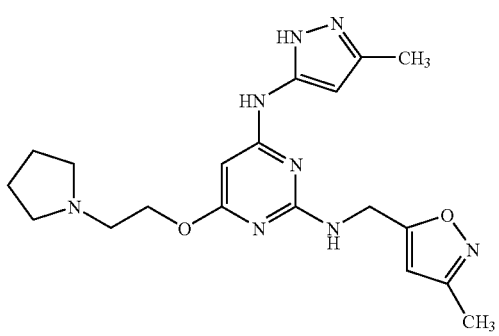 | $N^2$-[(3-methylisoxazol-5-yl)methyl]-$N^4$-(3-methyl-1H-pyrazol-5-yl)-6-[(2-pyrrolidin-1-ylethyl)oxy]pyrimidine-2,4-diamine |

| # | Structure | Name |
|---|---|---|
| 653 | 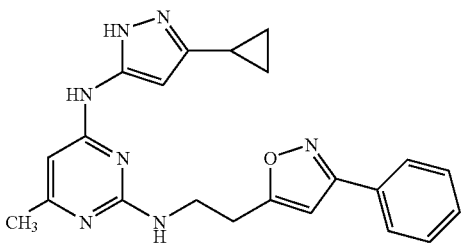 | $N^4$-(3-cyclopropyl-1H-pyrazol-5-yl)-6-methyl-$N^2$-[2-(3-phenylisoxazol-5-yl)ethyl]pyrimidine-2,4-diamine |
| 654 | 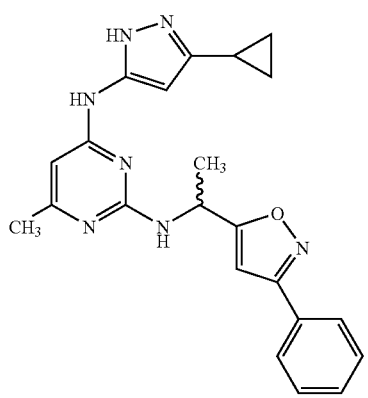 | $N^4$-(3-cyclopropyl-1H-pyrazol-5-yl)-6-methyl-$N^2$-[1-(3-phenylisoxazol-5-yl)ethyl]pyrimidine-2,4-diamine |
| 655 | 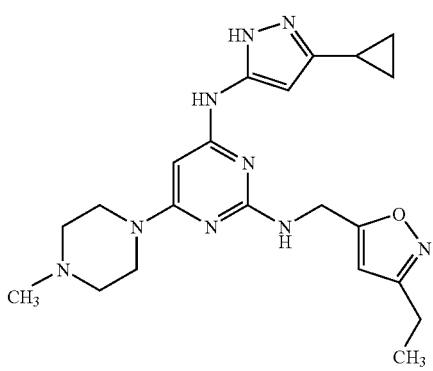 | $N^4$-(3-cyclopropyl-1H-pyrazol-5-yl)-$N^2$-[(3-ethylisoxazol-5-yl)methyl]-6-(4-methylpiperazin-1-yl)pyrimidine-2,4-diamine |
| 656 | 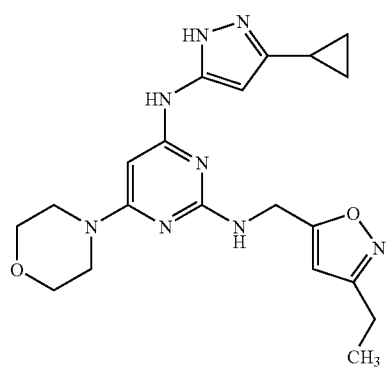 | $N^4$-(3-cyclopropyl-1H-pyrazol-5-yl)-$N^2$-[(3-ethylisoxazol-5-yl)methyl]-6-morpholin-4-ylpyrimidine-2,4-diamine |

| | | |
|---|---|---|
| 657 | 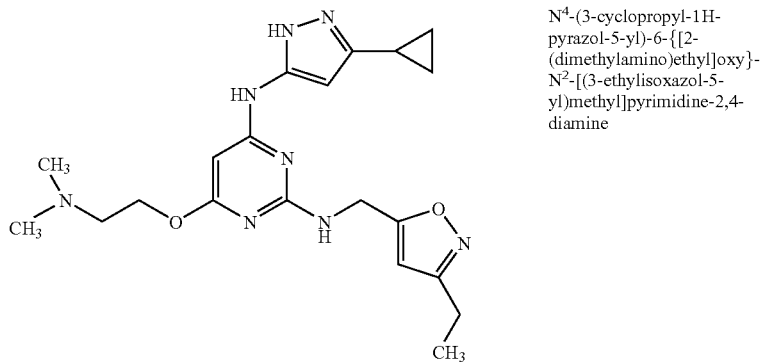 | $N^4$-(3-cyclopropyl-1H-pyrazol-5-yl)-6-{[2-(dimethylamino)ethyl]oxy}-$N^2$-[(3-ethylisoxazol-5-yl)methyl]pyrimidine-2,4-diamine |
| 658 | 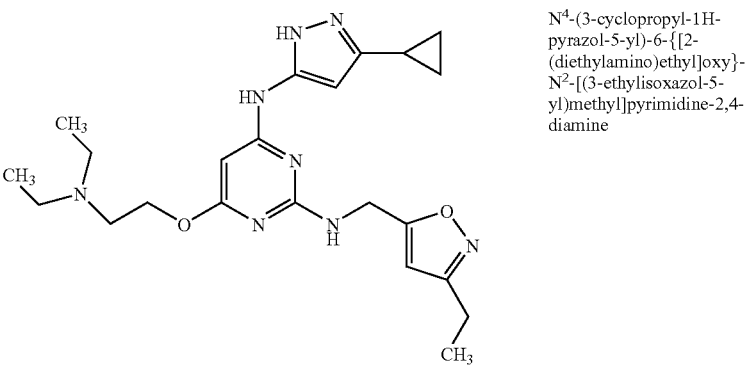 | $N^4$-(3-cyclopropyl-1H-pyrazol-5-yl)-6-{[2-(diethylamino)ethyl]oxy}-$N^2$-[(3-ethylisoxazol-5-yl)methyl]pyrimidine-2,4-diamine |
| 659 | 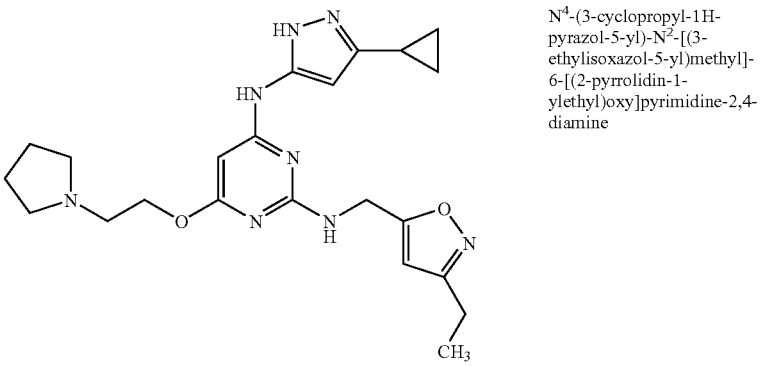 | $N^4$-(3-cyclopropyl-1H-pyrazol-5-yl)-$N^2$-[(3-ethylisoxazol-5-yl)methyl]-6-[(2-pyrrolidin-1-ylethyl)oxy]pyrimidine-2,4-diamine |
| 660 | 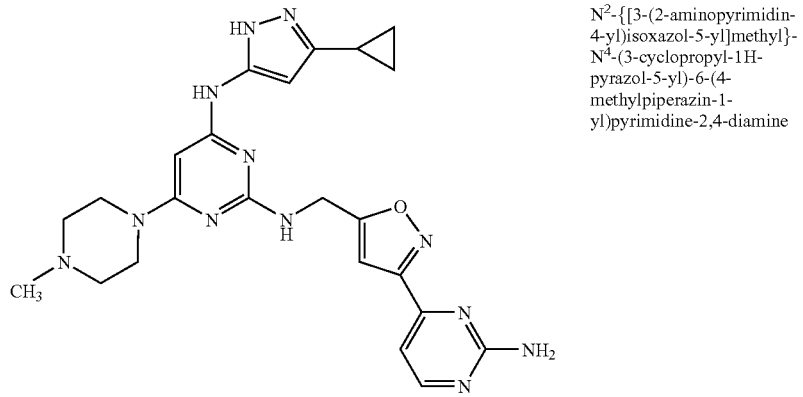 | $N^2$-{[3-(2-aminopyrimidin-4-yl)isoxazol-5-yl]methyl}-$N^4$-(3-cyclopropyl-1H-pyrazol-5-yl)-6-(4-methylpiperazin-1-yl)pyrimidine-2,4-diamine |

TABLE 1-continued

| | | |
|---|---|---|
| 661 | 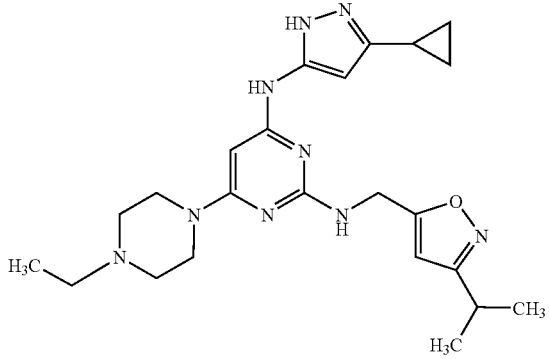 | $N^4$-(3-cyclopropyl-1H-pyrazol-5-yl)-6-(4-ethylpiperazin-1-yl)-$N^2$-{[3-(1-methylethyl)isoxazol-5-yl]methyl)pyrimidine-2,4-diamine |
| 662 | 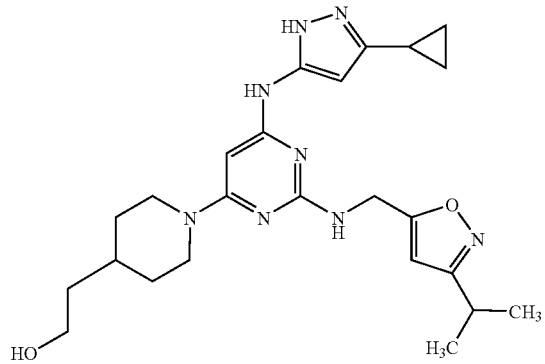 | 2-(1-{6-[(3-cyclopropyl-1H-pyrazol-5-yl)amino]-2-({[3-(1-methylethyl)isoxazol-5-yl]methyl}amino)pyrimidin-4-yl}piperidin-4-yl)ethanol |
| 663 | 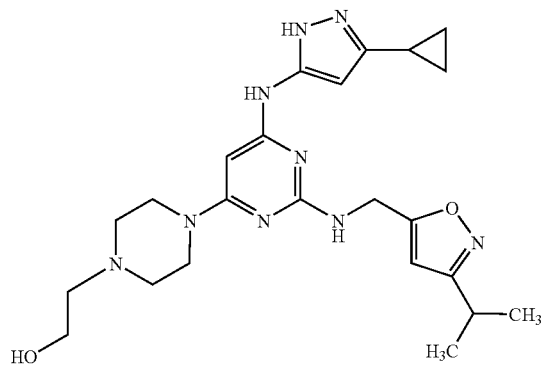 | 2-(4-{6-[(3-cyclopropyl-1H-pyrazol-5-yl)amino]-2-({[3-(1-methylethyl)isoxazol-5-yl]methyl}amino)pyrimidin-4-yl}piperazin-1-yl)ethanol |

DEFINITIONS

As used in the present specification, the following words and phrases are generally intended to have the meanings as set forth below, except to the extent that the context in which they are used indicates otherwise or they are expressly defined to mean something different.

The symbol "-" means a single bond, "=" means a double bond, "≡" means a triple bond, "⸺" means a single or double bond. The symbol "∿" refers to a group on a double-bond as occupying either position on the terminus of a double bond to which the symbol is attached; that is, the geometry, E- or Z-, of the double bond is ambiguous. When a group is depicted removed from its parent formula, the "∼" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

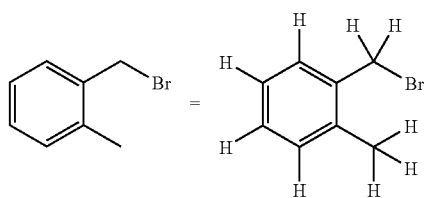

If a group "R" is depicted as "floating" on a ring system, as for example in the formula:

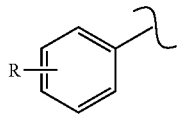

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

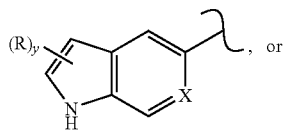

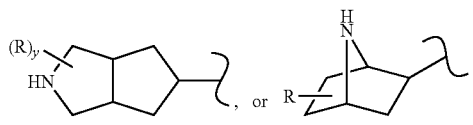

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals —CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

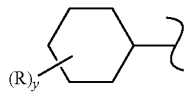

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. A "$C_0$" alkyl (as in "$C_0$-$C_6$-alkyl") is a covalent bond. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, nor-bornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl.

"Alkylene" refers to straight or branched chain divalent group consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent group consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent group consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above groups, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl group with a vinyl substituent at the 2-position of said group.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —OCH$_2$CH$_2$OCH$_3$, and glycol ethers such as polyethyleneglycol and —O(CH$_2$CH$_2$O)$_x$CH$_3$, where x is an integer of between about two and about twenty, in another example, between about two and about ten, and in a further example between about two and about five. Another exemplary substituted alkoxy group is hydroxyalkoxy or —OCH$_2$(CH$_2$)$_y$OH, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the group found on the α-carbon of an α-amino acid as defined above, for example, hydrogen (for glycine), methyl (for alanine), benzyl (for phenylalanine), and the like.

"Amino" refers to the group —NH$_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, and furanyl-oxy-sulfonamino.

"Aryl" refers to aromatic six- to fourteen-membered carbocyclic ring, for example, benzene, naphthalene, indane, tetralin, fluorene and the like, univalent substituents. As univalent substituents, the aforementioned ring examples are named, phenyl, naphthyl, indanyl, tetralinyl, and fluorenyl.

"Arylene" generically refers to any aryl that has at least two groups attached thereto. For a more specific example, "phenylene" refers to a divalent phenyl ring group. A phenylene, thus may have more than two groups attached, but is defined by a minimum of two non-hydrogen groups attached thereto.

"Arylalkyl" refers to a residue in which an aryl moiety is attached to a parent structure via one of an alkylene, alkylidene, or alkylidyne group. Examples include benzyl, phenethyl, phenylvinyl, phenylallyl and the like, Both the aryl and the corresponding alkylene, alkylidene, or alkylidyne group portion of an arylalkyl group may be optionally substituted. "Lower arylalkyl" refers to an arylalkyl where the "alkyl" portion of the group has one to six carbons; this can also be referred to as C$_{1-6}$ arylalkyl.

"Exo-alkenyl" refers to a double bond that emanates from an annular carbon, and is not within the ring system, for example the double bond depicted in the formula below.

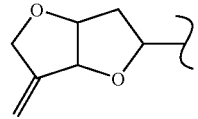

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A Spiro ring system is not a fused-polycyclic by this definition, but fused polycyclic ring systems of the invention may themselves have Spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl groups that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring group. A pyridylene, thus may have more than two groups attached, but is defined by a minimum of two non-hydrogen groups attached thereto.

"Heteroatom" refers to O, S, N, or P.

"Heterocyclyl" refers to a stable three- to fifteen-membered ring substituent that consists of carbon atoms and from one to five heteroatoms selected from the group consisting of nitrogen, phosphorus, oxygen and sulfur. For purposes of this invention, the heterocyclyl substituent may be a monocyclic, bicyclic or tricyclic ring system, which may include fused or bridged ring systems as well as spirocyclic systems; and the nitrogen, phosphorus, carbon or sulfur atoms in the heterocyclyl group may be optionally oxidized to various oxidation states. In a specific example, the group —S(O)$_{0-2}$—, refers to —S-(sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring substituent may be partially or fully saturated or aromatic. Examples of heterocyclyl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl group. A heteroalicyclic may contain unsaturation, but is not aromatic.

"Heteroaryl" refers specifically to an aromatic heterocyclyl group.

"Heterocyclylalkyl" refers to a residue in which a heterocyclyl is attached to a parent structure via one of an alkylene, alkylidene, or alkylidyne group. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl and the corresponding alkylene, alkylidene, or alkylidyne portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic, and "heteroarylalkyl" refers specifically to a heterocyclylalkyl where the heterocyclyl portion of the group is aromatic Such terms may be described in more than one way, for example, "lower heterocyclylalkyl" and "heterocyclyl $C_{1-6}$alkyl" are equivalent terms. Additionally, for simplicity, the number of annular atoms (including heteroatoms) in a heterocycle may be denoted as "$C_x$-$C_y$" (as in "$C_x$-$C_y$-heterocyclyl" and "$C_x$-$C_y$-heteroaryl" (and the like)), where x and y are integers, So, for example, $C_5$-$C_{14}$-heterocyclyl refers to a 5 to 14 membered ring system having at least one heteroatom and not a ring system containing 5 to 14 annular carbon atoms.

Preferred heterocyclyls and heteroaryls include, but are not limited to, acridinyl, azocinyl, benzimidazolyl, benzofuranyl, benzothiophenyl, benzoxazolyl, benzthiazolyl, benztriazolyl, pyridothiazolyl, benzisoxazolyl, benzisothiazolyl, benzimidazolonyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term, for example in the term "optionally substituted aryl$C_{1-8}$ alkyl," optional substitution may occur on both the "$C_{1-8}$ alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitutions is presented below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic

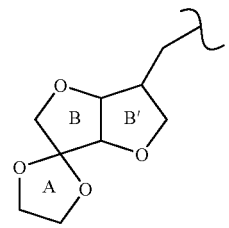

"Substituted" alkyl, aryl, and heterocyclyl, refer respectively to alkyl, aryl, and heterocyclyl, one or more (for example up to about five, in another example, up to about three) hydrogen atoms are replaced by a substituent independently selected from: optionally substituted alkyl (for example, fluoromethyl), optionally substituted aryl (for example, 4-hydroxyphenyl), optionally substituted arylalkyl (for example, 1-phenyl-ethyl), optionally substituted heterocyclylalkyl (for example, 1-pyridin-3-yl-ethyl), optionally substituted heterocyclyl (for example, 5-chloro-pyridin-3-yl or 1-methyl-piperidin-4-yl), optionally substituted alkoxy, alkylenedioxy (for example methylenedioxy), optionally substituted amino (for example, alkylamino and dialkylamino), optionally substituted amidino, optionally substituted aryloxy (for example, phenoxy), optionally substituted arylalkyloxy (for example, benzyloxy), carboxy (—CO$_2$H), carboalkoxy (that is, acyloxy or —OC(=O)R), carboxyalkyl (that is, esters or —CO$_2$R), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S(O$_2$)—H, —S(O$_2$)-(optionally substituted alkyl), —S(O$_2$)-optionally substituted aryl), —S(O$_2$)-(optionally substituted heterocyclyl), —S(O$_2$)-(optionally substituted alkoxy), —S(O$_2$)-optionally substituted aryloxy), and —S(O$_2$)— (optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent group, for example, —OCH$_2$—, then it is understood that either of the two partners may be bound to the particular group at one end, and the other partner is necessarily bound to the other end of the particular group, unless stated explicitly otherwise. Stated another way, divalent groups are not to be construed as limited to the depicted orientation, for example "—OCH$_2$-" is meant to mean not only "—OCH$_2$-" as drawn, but also "—CH$_2$O—."

In addition to the preferred embodiments recited hereinabove, also preferred are embodiments comprising combinations of preferred embodiments.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, harnartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defomians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma], vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dennatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference).

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was under-taken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

GENERAL ADMINISTRATION

Administration of the compounds of Formula I, II, III, IV, and VI, in pure form or in an appropriate pharmaceutical composition, as well as any additional chemotherapeutic agent described herein, (herein after referred to as "active agents," "active agent(s)" or "active agent") can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyoplilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and an active agent, and, in addition, may include other medicinal agents, pharmaceutical agents, carriers, adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition described herein may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active agent is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active agent(s) in a certain part of the intestinal tract in a delayed manner. Examples of embedded compositions that can be used are polymeric substances and waxes. The active agents can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., active agent(s) described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active agent(s) described herein, may contain suspending agents, as for example, ethoxylated isostearyl alcohols, polyoxyethylene sorbitol and sorbitan esters, microcrystalline cellulose; aluminum metahydroxide, bentonite, agar-agar and tragacanth, or mixtures of these substances, and the like.

Compositions for rectal administrations are, for example, suppositories that can be prepared by mixing the active agents described herein with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of the active agents described herein include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of the active agents described herein, or a pharmaceutically acceptable salt thereof, and 99% to 1% by weight of a suitable pharmaceutical excipient. In one example, the composition will be between about 5% and about 75% by weight of the active agents, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of the active agents described herein, or a pharmaceutically acceptable salt thereof, for treatment of a disease-state in accordance with the teachings of this invention.

The active agents described herein are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The active agents described herein can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

The compositions will include a conventional pharmaceutical carrier or excipient and the active agents described herein and, in addition, include other medicinal agents and pharmaceutical agents. If formulated as a fixed dose, such combination products employ the compounds of this invention within the dosage range described above and the other pharmaceutically active agent(s) within its approved dosage range. The active agents described herein may alternatively be used sequentially with known pharmaceutically acceptable agent(s) when a combination formulation is inappropriate.

SYNTHETIC EXAMPLES

The following abbreviations and terms have the indicated meanings throughout:

| Abbreviation | Meaning |
|---|---|
| Ac | Acetyl |
| ATP | adenosine triphosphate |
| BNB | 4-bromomethyl-3-nitrobenzoic acid |
| Boc | t-butyloxy carbonyl |
| Br | Broad |
| Bu | Butyl |
| ° C. | degrees Celsius |
| c- | Cyclo |
| CBZ | CarboBenZoxy = benzyloxycarbonyl |
| D | Doublet |
| Dd | doublet of doublet |
| Dt | doublet of triplet |
| DBU | Diazabicyclo[5.4.0]undec-7-ene |
| DCM | dichloromethane = methylene chloride = $CH_2Cl_2$ |
| DCE | Dichloroethylene |
| DEAD | diethyl azodicarboxylate |
| DIC | Diisopropylcarbodiimide |
| DIEA | N,N-diisopropylethyl amine |
| DMAP | 4-N,N-dimethylaminopyridine |
| DMF | N,N-dimethylformamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | Ethyl |
| Fmoc | 9-fluorenylmethoxycarbonyl |
| G | gram(s) |
| GC | gas chromatography |
| h or hr | hour(s) |
| HATU | 0-(7-Azabenzotriazol-1-yl)-1,1,3,3-tetramethyluronium hexafluorophosphate |
| HMDS | Hexamethyldisilazane |
| HOAc | acetic acid |
| HOBt | Hydroxybenzotriazole |
| HPLC | high pressure liquid chromatography |
| L | liter(s) |
| M | molar or molarity |
| M | Multiplet |
| Me | Methyl |
| mesyl | Methanesulfonyl |
| Mg | milligram(s) |
| MHz | megahertz (frequency) |
| Min | minute(s) |
| mL | milliliter(s) |
| mM | Millimolar |
| mmol | millimole(s) |
| Mol | mole(s) |
| MS | mass spectral analysis |
| MTBE | methyl t-butyl ether |

| Abbreviation | Meaning |
|---|---|
| N | normal or normality |
| NBS | N-bromosuccinimide |
| NCS | N-chlorosuccinimide |
| nM | Nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | Phenyl |
| PhOH | Phenol |
| PfP | Pentafluorophenol |
| PfPy | Pentafluoropyridine |
| PPTS | Pyridinium p-toluenesulfonate |
| Py | Pyridine |
| PyBroP | bromo-tris-pyrrolidino-phosphonium hexafluorophosphate |
| Q | Quartet |
| RT | Room temperature |
| Sat'd | Saturated |
| S | Singlet |
| s- | Secondary |
| t- | Tertiary |
| t or tr | Triplet |
| TBDMS | t-butyldimethylsilyl |
| TES | Triethylsilyl |
| TFA | trifluoroacetic acid |
| THF | Tetrahydrofuran |
| TMOF | trimethyl orthoformate |
| TMS | Trimethylsilyl |
| tosyl | p-toluenesulfonyl |
| Trt | Triphenylmethyl |
| μL | microliter(s) |
| μM | Micromole(s) or micromolar |

The compounds in Table 1 can be made by the synthetic examples and schemes described in WO 2006/074057, which is incorporated herein by reference, and in the Examples below. If the specific example of making an individual compound in Table 1 is not set forth in this specification, the skilled artisan will be able to make the necessary substitutions in reactants and/or reagents arrive at these compounds.

The Examples below serve to more fully describe the manner of making and using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety. Generally, but not necessarily, each example set out below describes a multi-step synthesis.

Example 1

$N^4$-(5-Isopropyl-1H-pyrazol-3-yl)-$N^6$-[2-(4-methylpiperazin-1-yl)ethyl]-$N^2$-(3-phenylisoxazol-5-ylmethyl)-pyrimidine-2,4,6-triamine

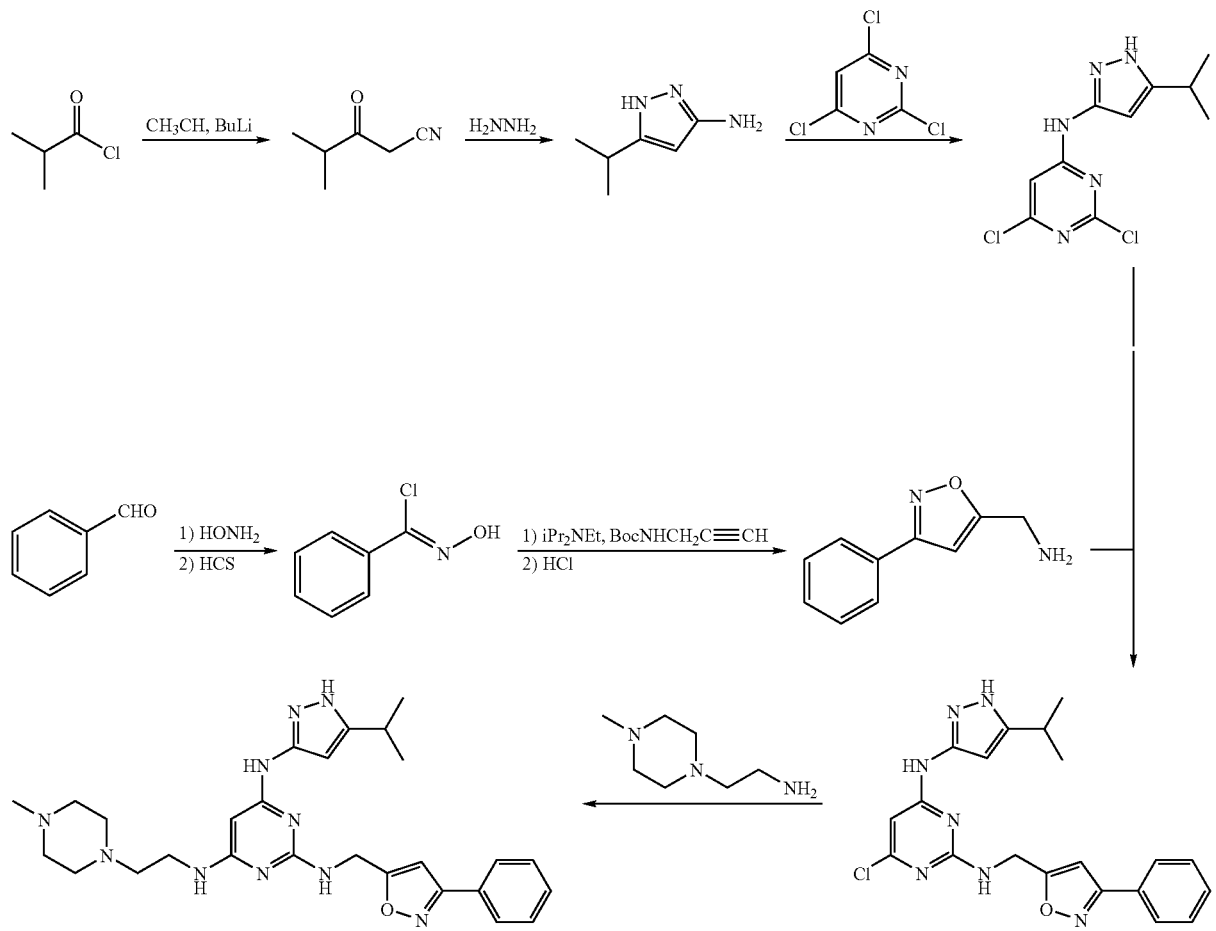

4-Methyl-3-oxopentanenitrile. A solution of acetonitrile (25.2 mL, 480 mmol) in THF (300 mL) was cooled to −78° C. in a dry ice/acetone bath, and n-butyllithium (255 mL, 1.6 M in hexanes, 408 mmol) was added dropwise. The solution was stirred at −78° C. for 2 h and isobutyril chloride (25.2 mL, 240 mmol) was added dropwise. The reaction was maintained at −78° C. for 1 h, allowed to warm to room temperature for 2 h and then stored in a refrigerator overnight. The reaction was quenched with 3 N HCl, extracted with ether, washed with water and brine and dried over sodium sulfate. The solvent was removed on a rotary evaporator to give the desired product (25 g, 94%) as a light brown oil that was used without further purification.

5-Isopropyl-1H-pyrazol-3-ylamine. A solution of 4-methyl-3-oxopentanenitrile (25 g, 225 mmol) and hydrazine (6.75 mL, 215 mmol) in ethanol (250 mL) was stirred at room temperature for 3 h, at which point LC/MS indicated exclusively product remained. The mixture was concentrated on a rotary evaporator followed by under high vacuum to give the desired product (27.8 g, 99%) as a yellow semisolid that was used without further purification.

2,6-Dichloropyrimidin-4-yl-(5-isopropyl-1H-pyrazol-3-yl)-amine. A mixture of 2,4,6-trichloropyrimidine (1.8 g, 9.8 mmol), 5-isopropyl-1H-pyrazol-3-ylamine (1.25 g, 10.0 mmol), diisopropylethylamine (3 mL, 18 mmol) and 1-butanol (10 mL) was heated to 80° C. for 2 h, at which point LC/MS indicated that the reaction was complete. The solvents were removed on a rotary evaporator and the paste was treated with ethyl acetate. The organic solution was washed with water and brine and dried over magnesium sulfate. The residue was concentrated on a rotary evaporator, and the pale yellow solid that remained was purified via flash chromatography to yield the desired product (2.3 g, 70%) as an off white solid.

3-Phenylisoxazol-5-ylmethylamine. A solution of 20% (w/v) sodium hydroxide (100 mL) was cooled to 0° C. and a solution of hydroxylamine hydrochloride (39.3 g, 565 mmol) in water (80 mL) was added. The mixture was stirred at 0° C. for 20 min and a solution of benzaldehyde (50.0 g, 471 mmol) was added such that the temperature was maintained below 0° C. The cold reaction was stirred for an additional 2 h and then extracted with ethyl acetate. The combined organic layers were washed with brine, dried over sodium sulfate and concentrated to give 56.4 g (99%) of a yellow oil. This residue was taken up in dichloromethane (1 L) containing DMF (20 mL) and cooled to 0° C. in an ice bath. N-Chlorosuccinimide (62.2 g, 466 mmol) was added slowly such that the temperature was maintained at 0° C. until addition was complete, then the reaction was allowed to warm to room temperature for 2 h. The mixture was stirred with water (500 mL) for 15 min, then the layers separated and the aqueous phase extracted with dichloromethane. The combined organic extracts were washed with water, 10% lithium chloride and brine, then dried over sodium sulfate. The solvent was removed on a rotary evaporator to give a yellow oil (64.5 g, 89%) that was dissolved in THF (300 mL). This solution was added dropwise to a solution of N-Boc-propargylamine (53.8 g, 347 mmol) in THF (1 L) that had been cooled to 0° C. Upon completion of addition, the solution was allowed to warm to room temperature and stirred overnight. The solution was concentrated on a rotary evaporator and taken up in dichloromethane (500 mL). The organic solution was washed with water and brine, dried over sodium sulfate and concentrated on a rotary evaporator to give a yellow oil that was taken up in 4N HCl in dioxane (500 mL). The mixture was stirred at room temperature and over time formed a white suspension. The suspension was diluted with dichloromethane (2 L) and stirred at room temperature overnight. The solid that had formed was collected by filtration, dissolved in methanol and made basic with 2N sodium hydroxide. The basic solution was extracted with ethyl acetate and the organic layers were dried over sodium sulfate and concentrated on a rotary evaporator to give a yellow oil that solidified overnight. The solid was stirred with hexanes, then filtered, washed with hexanes and dried to give the desired product (44.5 g, 74%) as a light yellow solid.

6-Chloro-$N^4$-(5-isopropyl-1H-pyrazol-3-yl)-$N^2$-(3-phenylisoxazol-5-ylmethyl)-pyrimidine-2,4-diamine. To a solution of 2,6-dichloropyrimidin-4-yl-(5-isopropyl-1H-pyrazol-3-yl)-amine (19.44 g, 71.7 mmol) in 1-butanol (200 mL) was added diisopropylethylamine (23.7 mL, 143 mmol) and 3-phenylisoxazol-5-ylmethylamine (15.0 g, 86.1 mmol). The mixture was stirred at 90° C. for 30 h, then concentrated on a rotary evaporator. The residue was taken up in 100 mL of methanol and boiled until the volume reached around 50 mL. The solution was allowed to cool to room temperature and then placed in the refrigerator overnight. The solid that formed was collected by filtration, while the filtrate was concentrated on a rotary evaporator, heated to boiling in methanol and cooled overnight in the refrigerator. This solid was collected and the filtrate was subjected to methanol recrystallization a third time. The three solids were combined to give the desired product (13.1 g, 45%) as a white solid.

$N^4$-(5-Isopropyl-1H-pyrazol-3-yl)-$N^6$-[2-(4-methylpiperazin-1-yl)ethyl]-$N^2$-(3-phenylisoxazol-5-ylmethyl)-pyrimidine-2,4,6-triamine. A mixture of 6-chloro-$N^4$-(5-isopropyl-1H-pyrazol-3-yl)-$N^2$-(3-phenylisoxazol-5-ylmethyl)-pyrimidine-2,4-diamine (250 mg, 0.611 mmol) and 2-(4-methylpiperazin-1-yl)-ethylamine (500 mg, 3.50 mmol) in 1-butanol (2 mL) was heated to 180° C. in a 50 mL sealed tube. The mixture was heated for 1 h, then cooled to room temperature and diluted with methanol (10 mL). The mixture thus obtained was purified via preparative reverse phase HPLC to give the desired product (93 mg, 29%) as a white solid.

$^1$H-NMR (400 MHz, $d_6$-CDCl$_3$): δ 7.8 (m, 2H), 7.4 (m, 3H), 6.5 (s, 1H), 5.9 (s, 1H), 5.2 (s, 1H), 4.8 (m, 2H), 3.5 (br s, 2H), 2.8 (m, 1H), 2.5 (m, 10H), 2.4 (s, 3H), 1.2 (m, 6H); MS (EI) for $C_{27}H_{36}N_{10}O$: 517.3 (MH$^+$).

Example 2

$N^4$-(5-Cyclopropyl-1H-pyrazol-3-yl)-6-methyl-$N^2$-(3-phenylisoxazol-5-ylmethyl)-pyrimidine-2,4,6-triamine

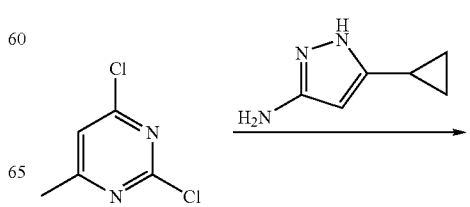

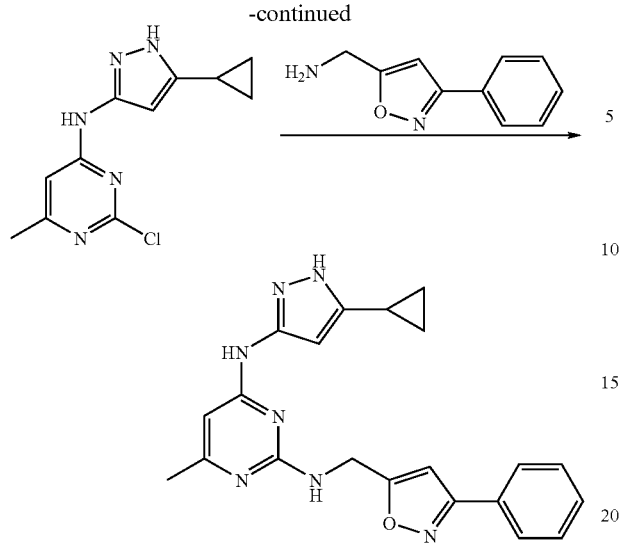

2-Chloro-6-methylpyrimidin-4-yl-(5-cyclopropyl-1H-pyrazol-3-yl)-amine. A mixture of 2,4-dichloro-6-methylpyrimidine (30.0 g, 184 mmol), 5-cyclopropyl-1H-pyrazol-3-ylamine (22.6 g, 184 mmol) and diisopropylethylamine (46 mL, 278 mmol) in 1-butanol (50 mL) was heated to 60° C. for 65 h. The reaction was cooled to room temperature and diluted with ethyl acetate. The mixture was washed with 2 N sodium hydroxide, water and brine, then dried over sodium sulfate and concentrated on a rotary evaporator. The residue was treated with a small amount of acetonitrile, sonicated and then triturated with ether until a solid was formed. The solid was collected by filtration to give the desired product (23.0 g, 50%) as a yellow solid.

$N^4$-(5-Cyclopropyl-1H-pyrazol-3-yl)-6-methyl-$N^2$-(3-phenylisoxazol-5-ylmethyl)-pyrimidine-2,4,6-triamine. A mixture of 2-chloro-6-methylpyrimidin-4-yl-(5-cyclopropyl-1H-pyrazol-3-yl)-amine (1.9 g, 7.6 mmol), 3-phenylisoxazol-5-ylmethylamine (1.7 g, 9.9 mmol) and diisopropylethylamine (1.8 mL, 11 mmol) in 1-butanol (30 mL) was heated to 160° C. in a 50 mL sealed tube for 8 h. The hot mixture was filtered to give the desired product (1.7 g, 58%) as a white solid.

$^1$H-NMR (400 MHz, $d_6$-DMSO): δ 11.8 (s, 1H), 9.2 (s, 1H), 7.8 (d, 2H), 7.45 (t, 3H), 7.25 (br s, 1H), 6.75 (s, 1H), 6.2 (br s, 1H), 4.65 (d, 2H), 2.1 (s, 3H), 1.8 (m, 1H), 0.9 (br d, 2H), 0.6 (br s, 2H); MS (EI) for $C_{21}H_{21}N_7O$: 388.5 (MH$^+$).

Example 3

5-Bromo-$N^4$-(5-cyclopropyl-1H-pyrazol-3-yl)-$N^2$-(4-dimethylaminobenzyl)-pyrimidine-2,4-diamine

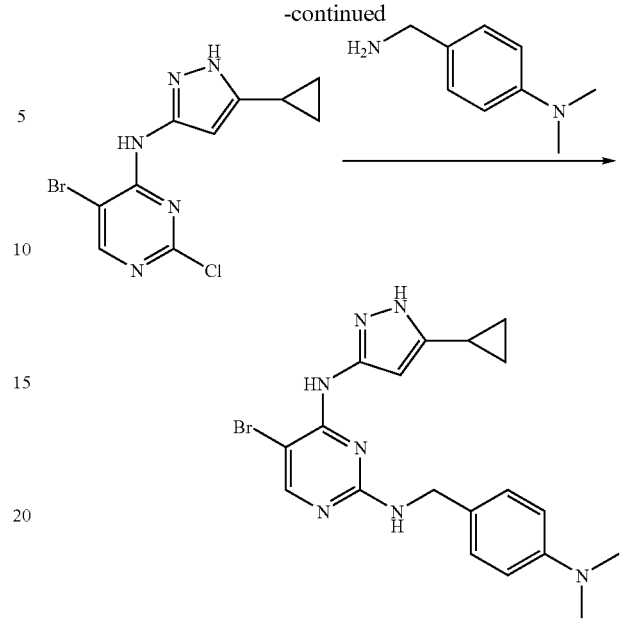

5-Bromo-2-chloropyrimidin-4-yl-(5-cyclopropyl-1H-pyrazol-3-yl)-amine. A mixture of 5-bromo-2,4-dichloropyrimidine (15.4 g, 67.6 mmol), 5-cyclopropyl-1H-pyrazol-3-ylamine (10.0 g, 81.3 mmol) and diisopropylethylamine (17 μL, 102 mmol) in 1-butanol (150 mL) was heated to 80° C. for 1 h. The solid that formed was collected by filtration and washed with acetonitrile to give the desired product (15.8 g, 75%) as a white solid.

5-Bromo-$N^4$-(5-cyclopropyl-1H-pyrazol-3-yl)-$N^2$-(4-dimethylaminobenzyl)-pyrimidine-2,4-diamine. A mixture of 5-bromo-2-chloropyrimidin-4-yl-(5-cyclopropyl-1H-pyrazol-3-yl)-amine (313 mg, 1.00 mmol) and 4-dimethylaminobenzylamine (225 mg, 1.5 mmol) in 1-butanol (20 mL) was heated to 170° C. in a 50 mL sealed tube for 3 h. The mixture was cooled and diluted with ethyl acetate. The organic layer was washed with 2 N sodium hydroxide, water and brine and dried over sodium sulfate. The solution was concentrated, redissolved in DMF and purified by preparative reverse phase HPLC to give the desired product (124 mg, 29%) as a white solid.

$^1$H-NMR (400 MHz, $d_6$-DMSO): δ 12.1 (s, 1H), 8.0 (br s, 1H), 7.2 (d, 2H), 6.6 (d, 2H), 4.4 (d, 2H), 2.8 (s, 6H), 1.8 (s, 1H), 1.0-0.6 (m, 4H); MS (EI) for $C_{19}H_{22}N_7Br$: 430.3 (MH$^+$).

Example 4

$N^4$-(5-Cyclopropyl-1H-pyrazol-3-yl)-6-morpholin-4-yl-$N^2$-(3-phenylisoxazol-5-ylmethyl)-pyrimidine-2,4-diamine

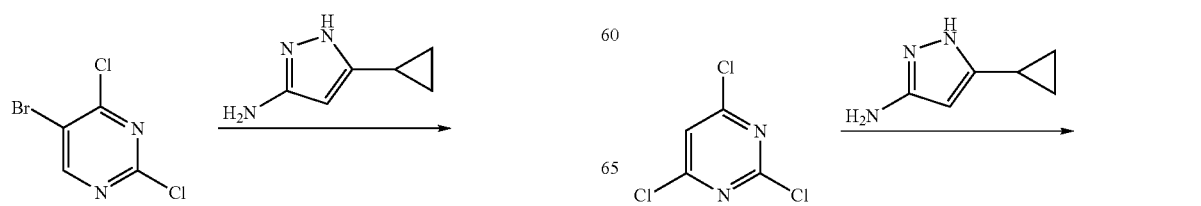

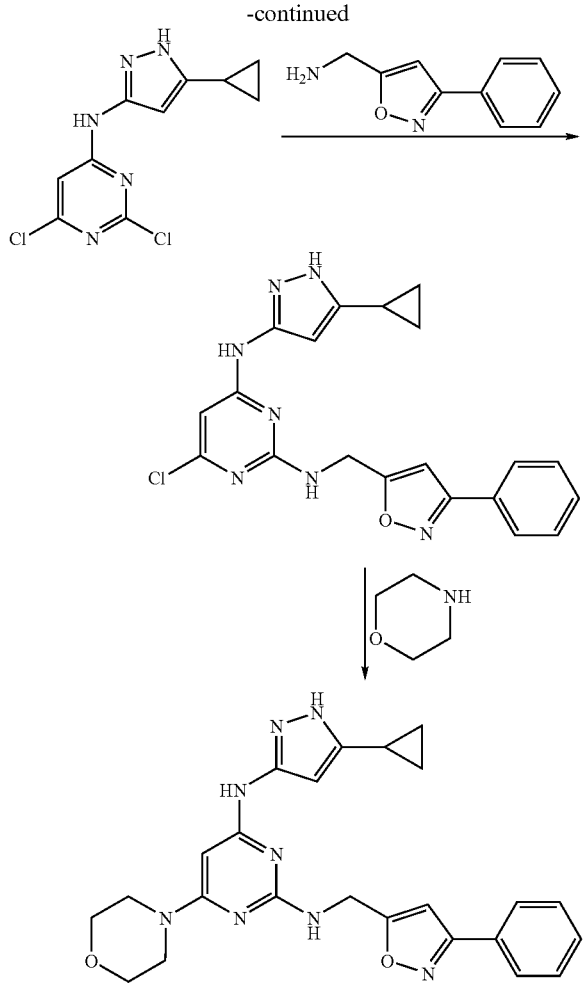

2,6-Dichloropyrimidin-4-yl-(5-cyclopropyl-1H-pyrazol-3-yl)-amine. A mixture of 2,4,6-trichloropyrimidine (30 g, 163 mmol), 5-cyclopropyl-1H-pyrazol-3-ylamine (20 g, 163 mmol), diisopropylethylamine (50 mL, 300 mmol) and 1-butanol (100 mL) was heated to 80° C. for 2 h. The solvents were removed on a rotary evaporator and the residue was taken up in ethyl acetate. The organic solution was washed with water and brine and dried over magnesium sulfate. The residue was concentrated on a rotary evaporator to give the desired product (40.7 g, 92%) as a light yellow solid.

6-Chloro-$N^4$-(5-cyclopropyl-1H-pyrazol-3-yl)-$N^2$-(3-phenylisoxazol-5-ylmethyl)-pyrimidine-2,4-diamine. To a solution of 2,6-dichloropyrimidin-4-yl-(5-cyclopropyl-1H-pyrazol-3-yl)-amine (19.3 g, 71.7 mmol) in 1-butanol (200 mL) was added diisopropylethylamine (23.7 mL, 143 mmol) and 3-phenylisoxazol-5-ylmethylamine (15.0 g, 86.1 mmol). The mixture was stirred at 90° C. for 30 h, then concentrated on a rotary evaporator. The residue was taken up in 100 mL of methanol and boiled until the volume reached around 50 mL. The solution was allowed to cool to room temperature and then placed in the refrigerator overnight. The solid that formed was collected by filtration, while the filtrate was dissolved in dichloromethane and sonicated. The solid that formed was collected and combined with the first recrystallized crop to give the desired product (17.8 g, 61%) as a white solid.

$N^4$-(5-Cyclopropyl-1H-pyrazol-3-yl)-6-morpholin-4-yl-$N^2$-(3-phenylisoxazol-5-ylmethyl)-pyrimidine-2,4-diamine. A mixture of 6-chloro-$N^4$-(5-cyclopropyl-1H-pyrazol-3-yl)-$N^2$-(3-phenylisoxazol-5-ylmethyl)-pyrimidine-2,4-diamine (8.0 g, 19.7 mmol) and morpholine (5.0 g, 57.4 mmol) was heated to 100° C. for 4 h, then concentrated on a rotary evaporator and treated with a minimal amount of methanol. The mixture was sonicated until a precipitate began to form, then water was added and the mixture was sonicated again. The solid that had formed was collected by filtration and washed with ether to give a white solid that was contaminated with excess morpholine. The solid was stirred overnight with 3 N HCl, then filtered and lyophilized to give the HCl salt of the desired product (9.3 g, 96%) as a white solid.

$^1$H NMR (400 MHz, Methanol-$d_4$) δ 7.78 (m, 2H), 7.45 (m, 3H), 6.51 (s, 1H), 5.95 (br s, 0.3H), 5.68 (br s, 0.2H), 4.68 (s, 2H), 3.68 (t, 4H), 3.46 (t, 4H), 1.85 (m, 1H), 0.91 (br s, 2H), 0.69 (br s, 2H); MS (EI) for $C_{24}H_{26}N_8O_2$: 459 (MH$^+$).

Example 5

$N^4$-(5-Cyclopropyl-2H-pyrazol-3-yl)-$N^2$-(3-isopropyl-isoxazol-5-ylmethyl)-6-(4-methyl-piperazin-1-yl)-pyrimidine-2,4-diamine

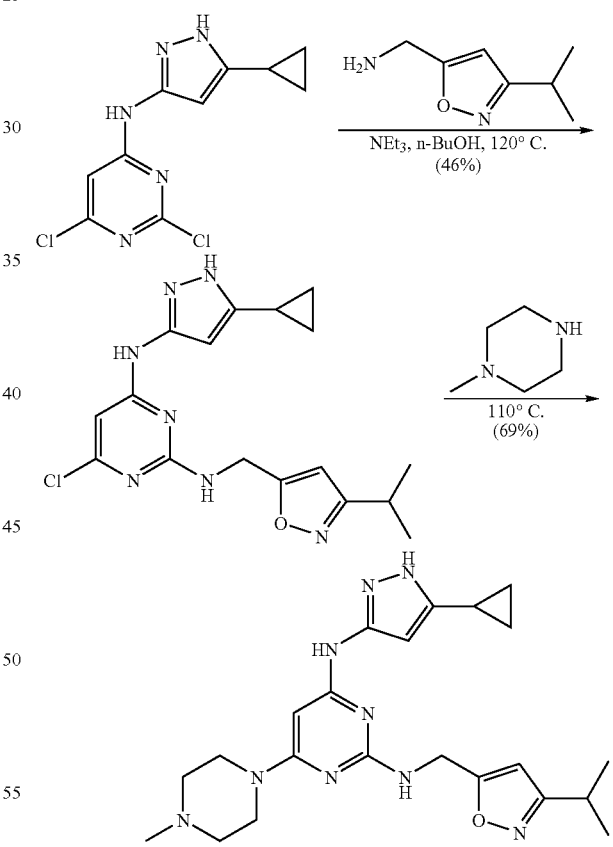

6-Chloro-$N^4$-(5-cyclopropyl-2H-pyrazol-3-yl)-$N^2$-(3-ixopropyl-isoxazol-5-ylmethyl)-pyrimidine-2,4-diamine. A mixture of 2,6-dichloropyrimidine-4-yl-(5-cyclopropyl-1H-pyrazol-3-yl)-amine (73.6 g, 274 mmol), 5-isopropyl-1H-pyrazol-3-ylamine (46.0 g, 329 mmol) and triethylamine (76.3 mL, 548 mmol) in n-butanol (1 L) was heated to 120° C. and monitored by LCMS. The reaction was complete after 16 h, at which point it was cooled to room temperature and diluted with ethyl acetate. The mixture was washed with N sodium hydroxide, water and brine, then dried over sodium sulfate and concentrated on a rotary evaporator. The residue was treated with ethyl acetate, heated to boiling and the yellow solid was collected via hot filtration and purified via recrystallization from methanol/ethyl acetate to give the product (37.7 g) as a white solid. The mother liquor was concentrated on a rotary evaporator, treated with ethyl acetate, heated to boiling and sonicated to give an additional 9.0 g of the product (46% overall yield).

$N^4$-(5-Cyclopropyl-2H-pyrazol-3-yl)-$N^2$-(3-isopropyl-isoxazol-5-ylmethyl)-6-(4-methyl-piperazin-1-yl)-pyrimidine-2,4-diamine. A mixture of 6-chloro-$N^4$-(5-cyclopropyl-2H-pyrazol-3-yl)-$N^2$-(3-ixopropyl-isoxazol-5-ylmethyl)-pyrimidine-2,4-diamine (45.5 g, 122 mmol) and 1-methylpiperazine (150 mL, 135 mmol) was heated to 110° C. for 3 h, at which time LC/MS indicated the reaction was complete. The mixture was diluted with methanol and ethyl acetate, then washed with aqueous 2 N sodium hydroxide, water, and brine. The combined organics were dried over sodium sulfate and concentrated on a rotary evaporator. The solid was treated with methanol, heated to boiling and allowed to cool to room temperature overnight. Collection of the precipitate via filtration gave the product (38.9 g) as a white solid. The mother liquor was concentrated on a rotary evaporator, diluted with methanol, heated to boiling and allowed to cool to room temperature overnight to afford a second crop (9.0 g, 90% overall yield) of the product as a white solid. The material obtained in this fashion was 98% pure by analytical HPLC. This material was then purified using preparative HPLC. The fractions that contained pure product were combined, diluted with ethyl acetate and washed with aqueous 2 N sodium hydroxide and brine and dried over sodium sulfate. Concentration on a rotary evaporator gave the product (36.7 g, 69%) as a white solid that was >99% pure by analytical HPLC.

$^1$H NMR (400 MHz, $d_6$-DMSO): δ 11.20 (s, 1H), 6.42 (s, 1H), 5.80 (s, 1H), 5.73 (s, 1H), 4.66 (d, J=5.6, 2H), 4.34 (m, 2H), 3.40 (m, 4H), 3.02 (m, 2H), 2.97 (m, 1H), 2.77 (s, 3H), 1.93 (m, 1H), 1.20 (d, J=7.2, 6H), 0.97 (m, 2H), 0.73 (m, 2H). MS (EI) for $C_{22}H_{31}N_9O$·HCl: 438 (MH$^+$).

Assays used for the Compounds in Table 1

Kinase assays were performed by measurement of incorporation of γ-$^{33}$P ATP into immobilized myelin basic protein (MBP). High binding white 384 well plates (Greiner) were coated with MBP (Sigma #M-1891) by incubation of 60 µl/well of 20 µg/ml MBP in Tris-buffered saline (TBS; 50 mM Tris pH 8.0, 138 mM NaCl, 2.7 mM KCl) for 24 hours at 4° C. Plates were washed 3× with 100 µl TBS. Kinase reactions were carried out in a total volume of 34 µl in kinase buffer (5 mM Hepes pH 7.6, 15 mM NaCl, 0.01% bovine gamma globulin (Sigma #1-5506), 10 mM MgCl$_2$, 1 mM DTT, 0.02% TritonX-100). Compound dilutions were performed in DMSO and added to assay wells to a final DMSO concentration of 1%. Each data point was measured in duplicate, and at least two duplicate assays were performed for each individual compound determination. Enzyme was added to final concentrations of 10 nM or 20 nM, for example. A mixture of unlabeled ATP and γ-$^{33}$P ATP was added to start the reaction (2×10$^6$ cpm of γ-$^{33}$P ATP per well (3000 Ci/mmole) and either 10 µM or 30 µM unlabeled ATP, typically. The reactions were carried out for 1 hour at room temperature with shaking. Plates were washed 7× with TBS, followed by the addition of 50 µl/well scintillation fluid (Wallac). Radioactivity was measured using a Wallac Trilux counter. This is only one format of such assays, various other formats are possible, as known to one of ordinary skill in the art.

The above assay procedure can be used to determine the $IC_{50}$ for inhibition and/or the inhibition constant, $K_i$. The $IC_{50}$ is defined as the concentration of compound required to reduce the enzyme activity by 50% under the conditions of the assay. Exemplary compositions have $IC_{50}$'s of, for example, less than about 100 µM, less than about 10 µM, less than about 1 µM, and further for example having $IC_{50}$'s of less than about 100 nM, and still further, for example, less than about 10 nM. The $K_i$ for a compound may be determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to equation (1) below; where V is the observed rate, $V_{max}$, is the rate of the free enzyme, $I_0$ is the inhibitor concentration, $E_0$ is the enzyme concentration, and $K_d$ is the dissociation constant of the enzyme-inhibitor complex.

$$V = V_{max}E_0\left[1 - \frac{(E_0 + I_0 + K_d) - \sqrt{(E_0 + I_0 + K_d)^2 - 4E_0 I_0}}{2E_0}\right] \quad \text{Equation (1)}$$

Kinase Specific Assays

Kinase activity and compound inhibition are investigated using one or more of the three assay formats described below. The ATP concentrations for each assay are selected to be close to the Michaelis-Menten constant ($K_M$) for each individual kinase. Dose-response experiments are performed at 10 different inhibitor concentrations in a 384-well plate format. The data are fitted to four-parameter equation (2) below; where Y is the observed signal, X is the inhibitor concentration, Min is the background signal in the absence of enzyme (0% enzyme activity), Max is the signal in the absence of inhibitor (100% enzyme activity), $IC_{50}$ is the inhibitor concentration at 50% enzyme inhibition and H represents the empirical Hill's slope to measure the cooperativity. Typically H is close to unity.

$$Y=Min+(Max-Min)/(1+(X/IC_{50})^{\wedge}H) \quad \text{Equation (2)}$$

IGF1R Kinase Assay

IGF1R kinase biochemical activity was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 3 µM ATP, 4 µM poly EY peptide and 4 nM IGF1R (baculovirus expressed human IGF1R kinase domain residues M954-C1367) in a 20 uL assay buffer (20 mM Tris-HCL pH7.5, 10 mM MgCl$_2$, 0.02% Triton X-100, 1 mM DTT, 2 mM MnCl$_2$). The mixture is incubated at ambient temperature for 2 hours after which 20 uL luciferase-luciferin mix is added and the chemiluminescent signal read using a Wallac Victor$^2$ reader. The luciferase-luciferin mix consists of 50 mM HEPES, pH 7.8, 8.5 ug/mL oxalic acid (pH 7.8), 5 (or 50)

mM DTT, 0.4% Triton X-100, 0.25 mg/mL coenzyme A, 63 uM AMP, 28 ug/mL luciferin and 40,000 units of light/mL luciferase.

Wild-Type Abl Assay

Kinase activity of wild-type Abl (ProQinase, Freiburg, Germany) and T315I Abl (Upstate, N.Y.) is measured as the percent of ATP consumed following the kinase reaction using luciferase-luciferin-coupled chemiluminescence. Reactions were conducted in 384-well white, medium binding microtiter plates (Greiner). Kinase reactions were initiated by combining test compounds, ATP, poly(Glu, Tyr) and kinase in a 20 μL volume (final concentrations: 1 μM ATP, 2 μM poly (Glu, Tyr), 10 nM wild-type Abl or S mM T315I Abl). The reaction mixture was incubated at ambient temperature for 2 h. Following the kinase reaction, a 20 μL aliquot of luciferase-luciferin mix (Promega, Madison, Wis.) was added and the chemiluminescence signal measured using a Victor2 plate reader (Perkin Elmer).

Structure Activity Relationships

Tables 2 and 3 show structure activity relationship data for selected compounds of Table 1. Inhibition is indicated as $IC_{50}$ with the following key: A=$IC_{50}$ less than 50 nM, B=$IC_{50}$ greater than 50 nM, but less than 500 nM, C=$IC_{50}$ greater than 500 nM, but less than 5000 nM, and D=$IC_{50}$ equal to or greater than 5,000 nM.

TABLE 2

| Entry | IGF 0P | IGF 3P |
|---|---|---|
| 1 | B | A |
| 2 | B | B |
| 3 | B | A |
| 4 | B | B |
| 5 | B | B |
| 6 | B | B |
| 7 | C | C |
| 8 | B | B |
| 9 | B | B |
| 10 | B | B |
| 11 | B | B |
| 12 | B | B |
| 13 | B | A |
| 14 | B | B |
| 15 | B | B |
| 16 | B | C |
| 17 | B | A |
| 18 | B | B |
| 19 | C | C |
| 20 | C | B |
| 21 | B | C |
| 22 | C | B |
| 23 | B | A |
| 24 | B | A |
| 25 | B | C |
| 26 | B | A |
| 27 | B | B |
| 28 | B | B |
| 29 | C | B |
| 30 | C | B |
| 31 | C | B |
| 32 | B | B |
| 33 | B | B |
| 34 | B | C |
| 35 | B | B |
| 36 | C | B |
| 37 | C | B |
| 38 | C | B |
| 39 | B | B |
| 40 | C | A |
| 41 | C | A |

TABLE 2-continued

| Entry | IGF 0P | IGF 3P |
|---|---|---|
| 42 | B | A |
| 43 | B | A |
| 44 | C | A |
| 45 | A | A |
| 46 | A | A |
| 47 | C | A |
| 48 | C | A |
| 49 | B | A |
| 50 | C | A |
| 51 | D | A |
| 52 | C | A |
| 53 | B | A |
| 54 | B | A |
| 55 | B | A |
| 56 | C | A |
| 57 | C | A |
| 58 | C | A |
| 59 | B | A |
| 60 | C | A |
| 61 | B | A |
| 62 | B | A |
| 63 | B | A |
| 64 | B | A |
| 65 | C | A |
| 66 | B | A |
| 67 | C | A |
| 68 | C | A |
| 69 | C | A |
| 70 | B | B |
| 71 | B | B |
| 72 | C | B |
| 73 | B | B |
| 74 | C | B |
| 75 | B | B |
| 76 | B | B |
| 77 | C | B |
| 78 | C | B |
| 79 | C | B |
| 80 | B | B |
| 81 | C | B |
| 82 | B | B |
| 83 | B | B |
| 84 | B | B |
| 85 | C | B |
| 86 | B | B |
| 87 | B | B |
| 88 | B | B |
| 89 | C | B |
| 90 | C | B |
| 91 | B | B |
| 92 | B | B |
| 93 | C | B |
| 94 | B | B |
| 95 | B | B |
| 96 | B | B |
| 97 | C | B |
| 98 | B | B |
| 99 | C | B |
| 100 | C | B |
| 101 | B | B |
| 102 | C | B |
| 103 | C | B |
| 104 | B | B |
| 105 | C | B |
| 106 | C | B |
| 107 | C | B |
| 108 | B | B |
| 109 | D | B |
| 110 | B | B |
| 111 | C | B |
| 112 | B | B |
| 113 | C | B |
| 114 | B | B |
| 115 | C | B |
| 116 | C | B |
| 117 | B | B |
| 118 | C | B |
| 119 | C | B |

TABLE 2-continued

| Entry | IGF 0P | IGF 3P |
|---|---|---|
| 120 | C | B |
| 121 | B | B |
| 122 | B | B |
| 123 | C | B |
| 124 | C | B |
| 125 | B | B |
| 126 | C | B |
| 127 | C | B |
| 128 | C | B |
| 129 | C | B |
| 130 | B | B |
| 131 | C | B |
| 132 | B | B |
| 133 | C | B |
| 134 | C | B |
| 135 | C | B |
| 136 | B | B |
| 137 | B | B |
| 138 | B | B |
| 139 | B | B |
| 140 | C | B |
| 141 | C | B |
| 142 | C | B |
| 143 | C | B |
| 144 | C | B |
| 145 | C | B |
| 146 | C | B |
| 147 | C | B |
| 148 | B | B |
| 149 | C | B |
| 150 | B | B |
| 151 | C | B |
| 152 | C | B |
| 153 | D | B |
| 154 | D | B |
| 155 | C | B |
| 156 | C | B |
| 157 | C | C |
| 158 | C | C |
| 159 | C | C |
| 160 | D | C |
| 161 | C | C |
| 162 | C | C |
| 163 | C | C |
| 164 | C | C |
| 165 | C | C |
| 166 | C | C |
| 167 | C | C |
| 168 | B | C |
| 169 | C | C |
| 170 | C | C |
| 171 | C | C |
| 172 | B | C |
| 173 | C | C |
| 174 | C | C |
| 175 | C | C |
| 176 | D | C |
| 177 | C | C |
| 178 | B | C |
| 179 | C | C |
| 180 | C | C |
| 181 | C | C |
| 182 | C | C |
| 183 | B | C |
| 184 | C | C |
| 185 | C | C |
| 186 | C | C |
| 187 | C | C |
| 188 | C | C |
| 189 | B | C |
| 190 | D | C |
| 191 | C | C |
| 192 | C | C |
| 193 | D | C |
| 194 | C | C |
| 195 | C | C |
| 196 | C | C |
| 197 | C | C |
| 198 | D | C |
| 199 | C | C |
| 200 | D | C |
| 201 | D | C |
| 202 | C | C |
| 203 | C | C |
| 204 | C | C |
| 205 | C | C |
| 206 | C | C |
| 207 | C | C |
| 208 | D | C |
| 209 | C | C |
| 210 | B | C |
| 211 | C | C |
| 212 | C | C |
| 213 | C | C |
| 214 | D | C |
| 215 | D | C |
| 216 | C | C |
| 217 | C | C |
| 218 | C | C |
| 219 | C | C |
| 220 | B | C |
| 221 | C | C |
| 222 | C | C |
| 223 | B | C |
| 224 | C | C |
| 225 | C | C |
| 226 | D | C |
| 227 | C | C |
| 228 | C | C |
| 229 | C | C |
| 230 | D | C |
| 231 | C | C |
| 232 | C | C |
| 233 | C | C |
| 234 | C | C |
| 235 | C | C |
| 236 | C | C |
| 237 | D | C |
| 238 | C | C |
| 239 | C | C |
| 240 | D | C |
| 241 | C | C |
| 242 | C | C |
| 243 | B | C |
| 244 | D | C |
| 245 | C | C |
| 246 | C | C |
| 247 | D | C |
| 248 | C | C |
| 249 | D | C |
| 250 | D | C |
| 251 | C | C |
| 252 | C | C |
| 253 | C | C |
| 254 | D | C |
| 255 | D | C |
| 256 | C | C |
| 257 | D | C |
| 258 | D | D |
| 259 | C | D |
| 260 | D | D |
| 261 | C | D |
| 262 | C | D |
| 263 | C | D |
| 264 | D | D |
| 265 | C | D |
| 266 | C | D |
| 267 | D | D |
| 268 | D | D |
| 269 | D | D |
| 270 | C | D |
| 271 | D | D |
| 272 | D | D |
| 273 | C | D |
| 274 | C | D |
| 275 | C | D |

TABLE 2-continued

| Entry | IGF 0P | IGF 3P |
|---|---|---|
| 276 | C | D |
| 277 | D | D |
| 278 | D | D |
| 279 | D | D |
| 280 | D | D |
| 281 | D | D |
| 282 | D | D |
| 283 | D | D |
| 284 | D | D |
| 285 | D | D |
| 286 | D | D |
| 287 | D | D |
| 288 | D | D |
| 289 | D | D |
| 290 | D | D |
| 291 | D | D |
| 292 | D | D |
| 293 | D | D |
| 294 | D | D |
| 295 | D | D |
| 296 | D | D |
| 297 | D | D |
| 298 | D | D |
| 299 | D | D |
| 300 | D | D |
| 301 | D | D |
| 302 | D | D |
| 303 | D | D |
| 304 | D | D |
| 305 | D | D |
| 306 | D | D |
| 307 | D | D |
| 308 | D | D |
| 309 | D | D |
| 310 | D | D |
| 311 | D | D |
| 312 | D | D |
| 313 | D | D |
| 314 | D | D |
| 315 | D | D |
| 316 | D | D |
| 317 | C | D |
| 318 | C | D |
| 319 | D | D |
| 320 | D | D |
| 321 | D | D |
| 322 | D | D |
| 323 | D | D |
| 324 | D | D |
| 325 | D | D |
| 326 | D | D |
| 327 | D | D |
| 328 | D | D |
| 329 | D | D |
| 330 | D | D |
| 331 | D | D |
| 332 | D | D |
| 333 | D | D |
| 334 | D | D |
| 335 | D | D |
| 336 | C | B |
| 337 | C | B |
| 338 | C | B |
| 339 | C | B |
| 340 | C | C |
| 341 | C | B |
| 342 | C | B |
| 343 | C | C |
| 344 | D | C |
| 345 | D | C |
| 346 | D | C |
| 347 | D | D |
| 348 | D | C |
| 349 | D | D |
| 350 | D | C |
| 351 | D | B |
| 352 | D | B |
| 353 | D | D |
| 354 | D | D |
| 355 | D | D |
| 356 | D | D |
| 357 | D | D |
| 358 | D | D |
| 495 | B | A |
| 496 | B | A |
| 497 | B | A |
| 498 | B | B |
| 499 | B | A |
| 500 | B | A |
| 501 | B | A |
| 502 | B | A |
| 503 | B | A |
| 504 | B | A |
| 505 | B | A |
| 506 | B | A |
| 507 | B | A |
| 508 | B | A |
| 509 | B | A |
| 510 | B | A |
| 511 | B | A |
| 512 | B | B |
| 513 | B | A |
| 514 | B | A |
| 515 | B | A |
| 516 | B | A |
| 517 | B | A |
| 518 | B | A |
| 519 | B | A |
| 520 | B | A |
| 521 | B | A |
| 522 | B | A |
| 523 | B | B |
| 524 | C | A |
| 525 | B | B |
| 526 | C | A |
| 527 | B | B |
| 528 | B | B |
| 529 | B | B |
| 530 | B | A |
| 531 | B | A |
| 532 | B | B |
| 533 | B | B |
| 534 | C | A |
| 535 | B | B |
| 536 | C | C |
| 537 | C | C |
| 538 | B | B |
| 539 | B | C |
| 540 | C | C |
| 541 | B | A |
| 542 | B | B |
| 543 | C | A |
| 544 | C | A |
| 545 | C | B |
| 546 | C | B |
| 547 | C | B |
| 548 | C | C |
| 549 | C | C |
| 550 | C | B |
| 551 | C | B |
| 552 | C | C |
| 553 | C | C |
| 554 | C | C |
| 555 | C | C |
| 556 | C | C |
| 557 | B | A |
| 558 | B | A |
| 559 | C | A |
| 560 | B | A |
| 561 | B | B |
| 562 | C | C |
| 563 | C | C |
| 564 | C | C |
| 565 | C | C |
| 566 | C | C |
| 567 | C | C |

TABLE 2-continued

| Entry | IGF 0P | IGF 3P |
|---|---|---|
| 568 | C | C |
| 569 | C | C |
| 570 | C | C |
| 571 | C | C |
| 572 | C | C |

TABLE 3

| Entry | IGF 0P | IGF 3P |
|---|---|---|
| 573 | B | A |
| 574 | C | A |
| 575 | B | A |
| 576 | B | A |
| 577 | B | A |
| 578 | C | A |
| 579 | C | A |
| 580 | C | A |
| 581 | C | A |
| 582 | B | A |
| 583 | Bs | A |
| 584 | B | C |
| 585 | C | C |
| 586 | B | A |
| 587 | C | A |
| 588 | B | A |
| 589 | B | A |
| 590 | B | A |
| 591 | B | A |
| 592 | B | A |
| 593 | B | A |
| 594 | C | A |
| 595 | B | A |
| 596 | B | A |
| 597 | B | A |
| 598 | B | A |
| 599 | B | A |
| 600 | B | B |
| 601 | B | A |
| 602 | B | A |
| 603 | B | A |
| 604 | B | A |
| 605 | B | A |
| 606 | B | A |
| 607 | B | A |
| 608 | B | A |
| 609 | B | A |
| 610 | B | A |
| 611 | B | A |
| 612 | B | A |
| 613 | B | A |
| 614 | B | A |
| 615 | B | A |
| 616 | B | A |
| 617 | B | A |
| 618 | B | A |
| 619 | B | B |
| 620 | B | B |
| 621 | B | A |
| 622 | B | A |
| 623 | B | A |
| 624 | B | B |
| 625 | B | B |
| 626 | C | B |
| 627 | C | B |
| 628 | B | A |
| 629 | B | A |
| 630 | B | A |
| 631 | B | A |
| 632 | B | A |
| 633 | C | A |
| 634 | B | A |
| 635 | B | A |
| 636 | B | A |
| 637 | B | A |

TABLE 3-continued

| Entry | IGF 0P | IGF 3P |
|---|---|---|
| 638 | B | A |
| 639 | C | C |
| 640 | B | A |
| 641 | B | A |
| 642 | B | A |
| 643 | B | B |
| 644 | B | A |
| 645 | B | A |
| 646 | C | A |
| 647 | B | A |
| 648 | B | A |
| 649 | B | A |
| 650 | C | C |
| 651 | C | B |
| 652 | C | B |
| 653 | C | C |
| 654 | B | B |
| 655 | B | A |
| 656 | B | A |
| 657 | B | A |
| 658 | B | A |
| 659 | B | A |
| 660 | B | B |
| 661 | B | A |
| 662 | B | A |
| 663 | B | A |

PHARMACEUTICAL COMPOSITION EXAMPLES

The following are representative pharmaceutical formulations containing a compound of Formula I, II, III, IV, V, or VI.

Tablet Formulation

The following ingredients are mixed intimately and pressed into single scored tablets.

| Ingredient | Quantity per tablet, mg |
|---|---|
| Compound of this invention | 400 |
| Cornstarch | 50 |
| croscarmellose sodium | 25 |
| Lactose | 120 |
| Magnesium stearate | 5 |

Capsule Formulation

The following ingredients are mixed intimately and loaded into a hard-shell gelatin capsule.

| Ingredient | Quantity per tablet, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

Injectable Formulation

The following ingredients are mixed to form an injectable formulation

| Ingredient | Amount |
| --- | --- |
| compound of this invention | 1.2 g |
| sodium acetate buffer solution | 0.4 M 2.0 mL |
| HCl (1 N) or NaOH (1 M) | q.s. to suitable pH |
| water (distilled, sterile) | q.s. to 20 mL |

All of the above ingredients, except water, are combined and heated to 60-70.degree. C. with stirring. A sufficient quantity of water at 60.degree. C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
| --- | --- |
| compound of this invention | 500 |
| Witepsol ® H-15 | balance |

The foregoing invention has been described in some detail by way of illustration and example, for purposes of clarity and understanding. The invention has been described with reference to various specific and preferred embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

I claim:

1. A method of treating cancer selected from colorectal cancer, non-small cell lung cancer, pancreatic cancer, prostate cancer, and chronic myelogenous leukemia comprising administering to a patient in need of said treatment a therapeutically effective amount of a compound of formula A,

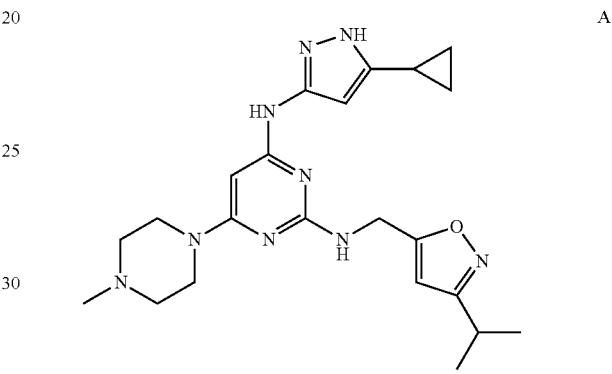

or a pharmaceutically acceptable salt or composition thereof, in combination with one or more chemotherapeutic agent(s) or anticancer therapies selected from irinotecan, fluorouracil, oxaliplatin, VEGF receptor inhibitors, EGF receptor inhibitors, paclitaxel, gemcitabine, docetaxel, cabazitaxel, nilotinib, dasatinib, and androgen deprivation therapy.

2. The method of claim 1, wherein the cancer is colorectal cancer and the one or more chemotherapeutic agent(s) is selected from irinotecan, fluorouracil, oxaliplatin, VEGF receptor inhibitors, and EFG receptor inhibitors.

3. The method of claim 1, wherein the cancer is non-small cell lung cancer and the one or more chemotherapeutic agent(s) is selected from paclitaxel, carboplatin, and VEGF receptor inhibitors.

4. The method of claim 1, wherein the cancer is pancreatic cancer and the one or more chemotherapeutic agent(s) is selected from gemcitabin and EGF receptor inhibitors.

5. The method of claim 1, wherein the cancer is prostate cancer and the one or more chemotherapeutic agent(s) or anticancer therapies is selected from docetaxel, cabazitaxel, and androgen deprivation therapy.

6. The method of claim 1, wherein the cancer is chronic myelogenous leukemia and the one or more chemotherapeutic agent(s) is selected from nilotinib and dasatinib.

* * * * *